United States Patent
Weiner et al.

(10) Patent No.: US 12,109,258 B2
(45) Date of Patent: Oct. 8, 2024

(54) SYNTHETIC MALARIA IMMUNOGENS, COMBINATIONS THEREOF, AND THEIR USE TO PREVENT AND TREAT MALARIA INFECTIONS

(71) Applicants: The Trustees of the University of Pennsylvania, Philadelphia, PA (US); Inovio Pharmaceuticals, Inc., Plymouth Meeting, PA (US); THE WISTAR INSTITUTE OF ANATOMY AND BIOLOGY, Philadelphia, PA (US); Ahmed S. I. Aly, New Orleans, LA (US)

(72) Inventors: David Weiner, Merion, PA (US); Emma Reuschel, Philadelphia, PA (US); Bernadette Ferraro, La Jolla, CA (US); Ahmed S. I. Aly, New Orleans, LA (US)

(73) Assignees: The Trustees of the University of Pennsylvania, Philadelphia, PA (US); Ahmed S.I. Aly, New Orleans, LA (US); Inovio Pharmaceuticals, Inc., Plymouth Meeting, PA (US); The Wistar Institute of Anatomy and Biology, Philadelphia, PA (US)

( * ) Notice: Subject to any disclaimer, the term of this patent is extended or adjusted under 35 U.S.C. 154(b) by 1078 days.

(21) Appl. No.: 16/302,718

(22) PCT Filed: May 19, 2017

(86) PCT No.: PCT/US2017/033617
§ 371 (c)(1),
(2) Date: Nov. 19, 2018

(87) PCT Pub. No.: WO2017/201454
PCT Pub. Date: Nov. 23, 2017

(65) Prior Publication Data
US 2019/0307870 A1     Oct. 10, 2019

Related U.S. Application Data

(60) Provisional application No. 62/338,841, filed on May 19, 2016.

(51) Int. Cl.
| | |
|---|---|
| *A61K 39/015* | (2006.01) |
| *A61K 39/00* | (2006.01) |
| *A61P 33/06* | (2006.01) |
| *C07K 14/445* | (2006.01) |

(52) U.S. Cl.
CPC ............ *A61K 39/015* (2013.01); *A61P 33/06* (2018.01); *C07K 14/445* (2013.01); *A61K 2039/53* (2013.01); *A61K 2039/55527* (2013.01); *A61K 2039/55538* (2013.01); *C07K 2319/02* (2013.01); *C07K 2319/42* (2013.01); *Y02A 50/30* (2018.01)

(58) Field of Classification Search
CPC ..................................................... A61K 39/015
See application file for complete search history.

(56) References Cited

U.S. PATENT DOCUMENTS

| | | | |
|---|---|---|---|
| 5,814,617 | A | 9/1998 | Hoffman |
| 7,521,229 | B2 | 4/2009 | Pau |
| 8,063,193 | B2* | 11/2011 | Birkenmeyer ... G01N 33/56905 536/23.7 |
| 8,765,145 | B2 | 7/2014 | Druilhe |
| 2010/0183590 | A1 | 7/2010 | Druilhe |
| 2010/0247576 | A1* | 9/2010 | Birkenmeyer .......... A61P 33/02 435/7.1 |
| 2011/0229514 | A1 | 9/2011 | Doolan |
| 2013/0171195 | A1* | 7/2013 | Charneau ............ A61K 39/015 435/320.1 |
| 2016/0158332 | A1* | 6/2016 | Srinivasan .......... A61K 39/015 424/139.1 |

FOREIGN PATENT DOCUMENTS

| | | | |
|---|---|---|---|
| EP | 2385107 | | 11/2011 |
| WO | WO 92/11868 | * | 7/1992 |
| WO | 1994028930 | | 12/1994 |
| WO | 2004043488 | | 5/2004 |
| WO | 2007027860 | | 3/2007 |
| WO | WO 2010/111220 | * | 9/2010 |
| WO | 2013082394 | | 6/2013 |
| WO | 2015052543 | | 4/2015 |

OTHER PUBLICATIONS

Krassowska et al., Biophysical Journal, 2007; 92:404-417 (Year: 2007).*
Otto et al., BMC Biology, 2014; 12(86): 1-18 (Year: 2014).*
Database Geneseq Accesssion No. AAW71319 (XP-002796583) 1 page.
Database Geneseq Accesssion No. AZP30731 (XP-002796585) 1 page.
Database Geneseq Accesssion No. AZV16553 (XP-002796584) 1 page.

* cited by examiner

*Primary Examiner* — Brian Gangle
*Assistant Examiner* — Lakia J Jackson-Tongue
(74) *Attorney, Agent, or Firm* — Riverside Law LLP

(57) ABSTRACT

Provided herein are sequences of *Plasmodium* spp. liver stage exported proteins as well as expression constructs expressing the sequences. Also provided herein are methods for generating an immune response against malaria using the expression constructs provided herein.

12 Claims, 19 Drawing Sheets
Specification includes a Sequence Listing.

| Gene Name | Size in bps | Conservation in *Plasmodium* | Confirmed Localization |
|---|---|---|---|
| EXP1/HEP17 | 510 | Yes | LS and BS |
| EXP2/HEP19 | 525 | Yes | LS, Sporozoite, BS |
| EXP23 | 810 | Yes | LS and BS |
| TMP21 | 645 | Yes | LS only |
| UIS3 | 690 | Yes | LS only |
| ICP | 1074 | Yes | LS and BS |

Figure 2

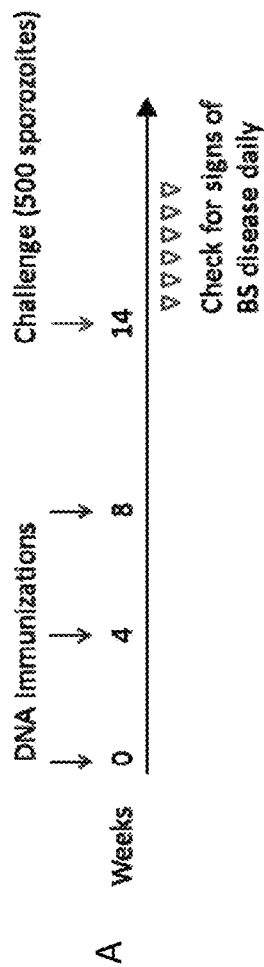
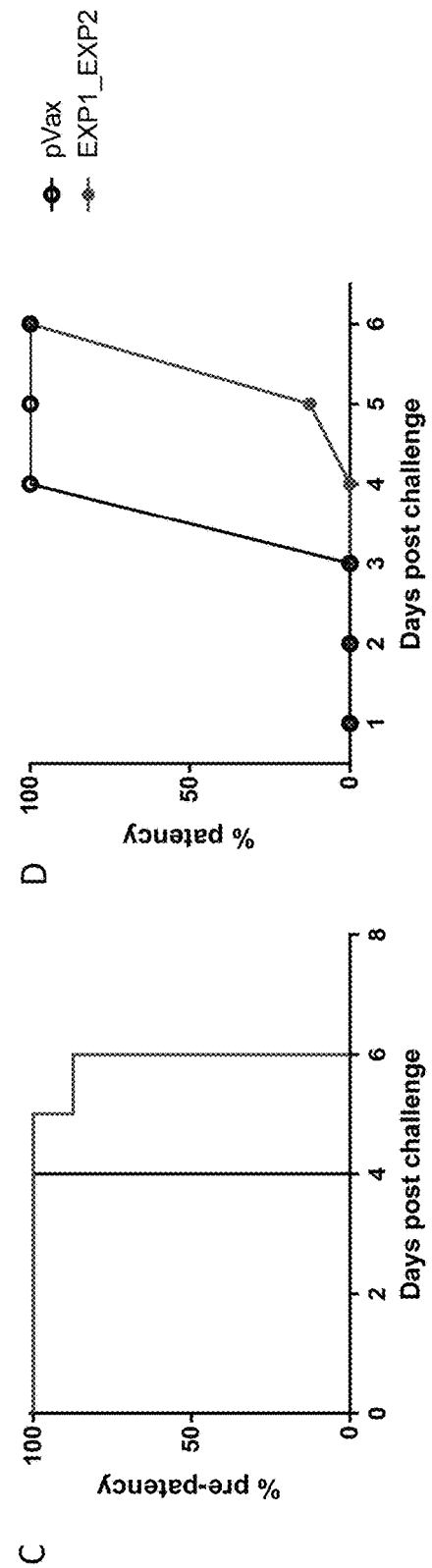
Figures 3A – 3D

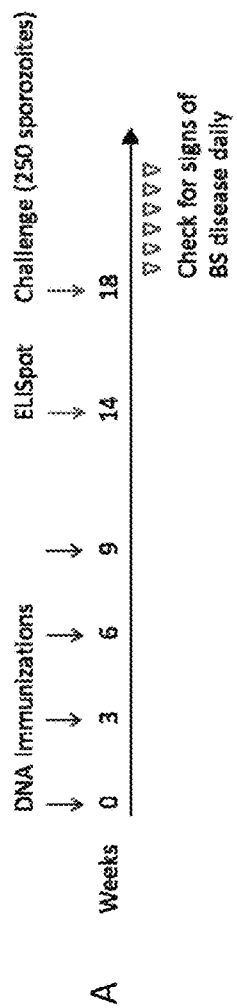
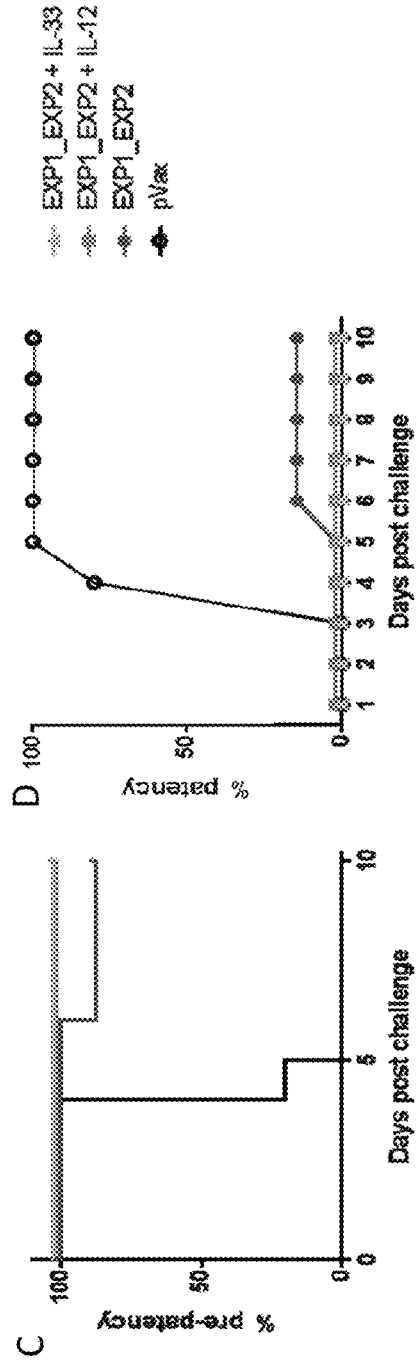
Figures 4A – 4D

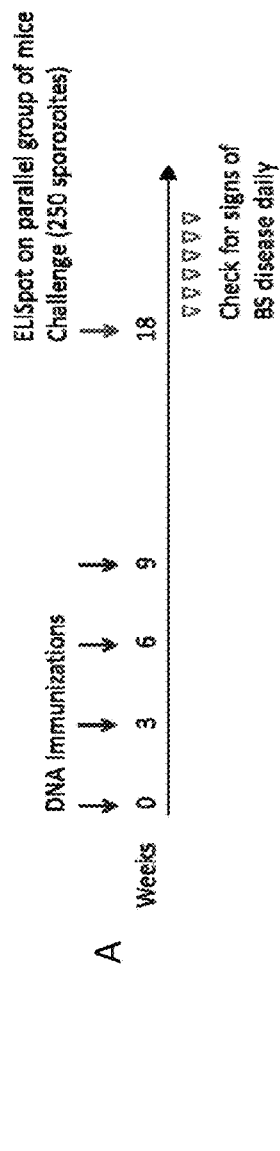

| Construct | Immunization Intervals in days | IV Challenge dose (days after last immunization) | Protected+/Challenged | Average BS pre-patency in days after IV challenge for infected mice |
|---|---|---|---|---|
| EXP1_EXP2 | 0, 21, 43, 64 | 250 (63) | 6/8 | d. 6 (for two mice) |
| EXP1_EXP2 + IL12 | 0, 21, 43, 64 | 250 (63) | 8/8 | - |
| EXP1_EXP2 + IL33 | 0, 21, 43, 64 | 250 (63) | 7/7± | - |
| EXP23 + ICP | 0, 21, 43, 64 | 250 (63) | 5/7 | d. 5.5 (for two mice) |
| EXP23 + ICP + IL12 | 0, 21, 43, 64 | 250 (63) | 7/8 | d. 7 (for one mouse= 3 days delay) |
| EXP23 + ICP + IL33 | 0, 21, 43, 64 | 250 (63) | 8/8 | - |
| TMP21 + UIS3 | 0, 21, 43, 64 | 250 (63) | 7/8 | d. 6 (for one mouse = 2 days delay) |
| TMP21 + UIS3 + IL12 | 0, 21, 43, 64 | 250 (63) | 8/8 | - |
| TMP21 + UIS3 + IL33 | 0, 21, 43, 64 | 250 (63) | 8/8 | - |
| EXP1_EXP2 + EXP23 + ICP + TMP21 + UIS3 | 0, 21, 43, 64 | 250 (63) | 6/7± | d. 6 (for one mouse= 2 days delay) |
| EXP1_EXP2 + EXP23 + ICP + TMP21 + UIS3 + IL12 | 0, 21, 43, 64 | 250 (63) | 8/8 | - |
| EXP1_EXP2 + EXP23 + ICP + TMP21 + UIS3 + IL33 | 0, 21, 43, 64 | 250 (63) | 7/7± | - |
| IL12 only | 0, 21, 43, 64 | 250 (63) | 0/4± | d. 4 (for all mice) |
| IL33 only | 0, 21, 43, 64 | 250 (63) | 0/5 | d. 4 (for all mice) |
| Control Vector | 0, 21, 43, 64 | 250 (63) | 0/5 | d. 4 (for all mice) |

+ Protection is defined as the complete absence of any BS parasites on daily blood smears for at least 10 days post challenge.
± one mouse was badly injected, and could not be reinjected and therefore excluded from the study.

Figures 7A – 7B

| Construct | Immunization Intervals in days | IV Challenge dose (days after last immunization) | Protected+ / Challenged | Average BS pre-patency in days after IV challenge for infected mice |
|---|---|---|---|---|
| EXP1_EXP2 | 1, 21, 42, 63 | 250 (60) | 7/8 | d. 6 (for just one mouse) |
| EXP1_EXP2 (IL12) | 1, 21, 42, 63 | 250 (60) | 8/8* | - |
| EXP1_EXP2 (IL33) | 1, 21, 42, 63 | 250 (60) | 8/8 | - |
| EXP1_EXP2/ CelTOS_TRAP | 1, 21, 42, 63 | 250 (60) | 6/8 | d. 6 (for just two mice) |
| EXP1_EXP2/ CelTOS_TRAP (IL12) | 1, 21, 42, 63 | 250 (60) | 6/8 | d. 6.5 (for just two mice) |
| EXP1_EXP2/ CelTOS_TRAP (IL33) | 1, 21, 42, 63 | 250 (60) | 7/8 | d. 7 (for just one mouse) |
| Control Vector | 1, 21, 42, 63 | 250 (60) | 0/5 | d. 4.6 (for all mice) |

Figure 14

| | Immunization Intervals (days) | IV Challenge dose (days after last immunization) | Average pre-patency in days after IV challenge |
|---|---|---|---|
| EXP1_EXP2 | 1, 30, 60 | 500 (45) | 5.88 (7 on day 6, 1 on day 5) |
| EXP1_EXP2/ CelTOS_TRAP | 1, 30, 60 | 500 (45) | 6 |
| CelTOS_TRAP | 1, 30, 60 | 500 (45) | 5 |
| UIS10 | 1, 30, 60 | 500 (45) | 4.75 (6 on day 5, 2 on day4) |
| SPECT1_SPECT2 | 1, 30, 60 | 500 (45) | 4.88 (7 on day 5, 1 on day 4) |
| Control Vector | 1, 30, 60 | 500 (45) | 4 |

Figure 18

SYNTHETIC MALARIA IMMUNOGENS, COMBINATIONS THEREOF, AND THEIR USE TO PREVENT AND TREAT MALARIA INFECTIONS

CROSS-REFERENCE TO RELATED APPLICATIONS

This application is the U.S. national phase application filed under 35 U.S.C. § 371 claiming benefit to International Patent Application No. PCT/US2017/033617, filed on May 19, 2017, which is entitled to priority under 35 U.S.C. § 119(e) to U.S. provisional application No. 62/338,841, filed May 19, 2016, the disclosures of which are incorporated herein by reference in their entirety.

FIELD OF THE INVENTION

The present invention relates to antigenic malaria proteins and nucleic acid molecules which encode the same; improved malaria vaccines including such proteins and/or nucleic acid molecules; and methods for using the vaccines for inducing immune responses against malaria antigens and methods of preventing malaria infection and/or treating individuals infected with malaria.

BACKGROUND OF THE INVENTION

Malaria is a mosquito-borne infectious disease caused by a eukaryotic protist of the genus *Plasmodium*. It is widespread in tropical and subtropical regions, including parts of the Americas (22 countries), Asia, and Africa. Each year, there are more than 250 million cases of malaria, killing between one and three million people, the majority of whom are young children in sub-Saharan Africa. Despite efforts to reduce transmission and increase treatment, there has been little change in which areas are at risk of this disease since 1992. Indeed, if the prevalence of malaria stays on its present upwards course, the death rate could double in the next twenty years. Precise statistics are unknown because many cases occur in rural areas where people do not have access to hospitals or the means to afford health care. As a consequence, the majority of cases are undocumented.

Five species of the *plasmodium* parasite can infect humans: the most serious forms of the disease are caused by *Plasmodium falciparum* (also referred to herein as *P. falciparum*, P.f. and PF). *P. falciparum* is a protozoan parasite, one of the species of *Plasmodium* that cause malaria in humans. It is transmitted by the female *Anopheles* mosquito. *P. falciparum* is the most dangerous of these infections as *P. falciparum* (or malignant) malaria has the highest rates of complications and mortality. As of 2006 it accounted for 91% of all 247 million human malarial infections (98% in Africa) and 90% of the deaths.

A wide variety of antimalarial drugs are available to treat malaria. In the last 5 years, treatment of *P. falciparum* infections in endemic countries has been transformed by the use of combinations of drugs containing an artemisinin derivative. Severe malaria is treated with intravenous or intramuscular quinine or, increasingly, the artemisinin derivative artesunate. Several drugs are also available to prevent malaria in travelers to malaria-endemic countries (prophylaxis). Resistance has developed to several antimalarial drugs, most notably chloroquine.

Vaccines for malaria are under development, with no completely effective vaccine yet available. The first promising studies demonstrating the potential for a malaria vaccine were performed in 1967 by immunizing mice with live, radiation-attenuated sporozoites, providing protection to about 60% of the mice upon subsequent injection with normal, viable sporozoites. Since the 1970s, there has been a considerable effort to develop similar vaccination strategies within humans. However, the current most advanced malaria vaccine candidate confers only partial protection against clinical disease. Subunit and DNA vaccines against *Plasmodium* pre-erythrocytic stages have relied substantially on targeting surface sporozoite antigens like CSP; however, these have met with limited success.

Therefore there is need in the art for novel immunogenic compositions which protect against malaria infection and/or treat infected subjects.

SUMMARY OF THE INVENTION

In one embodiment, the invention relates to an immunogenic composition comprising at least one nucleic acid molecule comprising at least one nucleotide sequence encoding at least one consensus *Plasmodium* spp. liver stage (LS) immunogen.

In one embodiment, at least one LS immunogen is selected from the group consisting of: EXP1, EXP2, EXP23, ICP, TMP21, UIS3, UIS10, SPECT1, SPECT2 and RON2.

In one embodiment the immunogenic composition encodes EXP1 and EXP2. In one embodiment the immunogenic composition comprises a nucleotide sequence encoding an amino acid sequence of SEQ ID NO:1, SEQ ID NO:17, or SEQ ID NO:32. In one embodiment the immunogenic composition comprises a nucleic acid sequence encoding an amino acid sequence comprising at least 90% of SEQ ID NO:1, at least 90% of SEQ ID NO:17, or at least 90% of SEQ ID NO:32. In one embodiment the immunogenic composition comprises a nucleic acid sequence that encodes an amino acid sequence comprising at least 90% homology to SEQ ID NO:1, at least 90% homology to SEQ ID NO:17, or at least 90% homology to SEQ ID NO:32. In one embodiment the immunogenic composition comprises a nucleotide sequence of SEQ ID NO:2, SEQ ID NO:3, SEQ ID NO: 18, SEQ ID NO: 19, SEQ ID NO:33 or SEQ ID NO:34. In one embodiment the immunogenic composition comprises at least 90% of SEQ ID NO:2, at least 90% of SEQ ID NO:3, at least 90% of SEQ ID NO:18, at least 90% of SEQ ID NO:19, at least 90% of SEQ ID NO:33, or at least 90% of SEQ ID NO:34. In one embodiment the immunogenic composition comprises a nucleotide sequence having at least 90% homology to SEQ ID NO:2, at least 90% homology to SEQ ID NO:3, at least 90% homology to SEQ ID NO:18, at least 90% homology to SEQ ID NO:19, at least 90% homology to SEQ ID NO:33, or at least 90% homology to SEQ ID NO:34.

In one embodiment the immunogenic composition encodes EXP23. In one embodiment the immunogenic composition comprises a nucleotide sequence encoding SEQ ID NO:4, SEQ ID NO:20 or SEQ ID NO:35. In one embodiment the immunogenic composition comprises a nucleic acid sequence encoding an amino acid sequence comprising at least 90% of SEQ ID NO:4, at least 90% of SEQ ID NO:20, or at least 90% of SEQ ID NO:35. In one embodiment the immunogenic composition comprises a nucleic acid sequence encoding an amino acid sequence comprising at least 90% homology to SEQ ID NO:4 at least 90% homology to SEQ ID NO:20 or at least 90% homology to SEQ ID NO:35. In one embodiment the immunogenic composition comprises a nucleotide sequence of SEQ ID NO:5, SEQ ID NO:6, SEQ ID NO:21, SEQ ID NO:22, SEQ ID NO:36 or SEQ ID NO:37 In one embodiment the immunogenic composition comprises a nucleotide sequence that comprises at least 90% of SEQ ID NO:5, at least 90% of SEQ ID NO:6, at least 90% of SEQ ID NO:21, at least 90% of SEQ ID NO:22, at least 90% of SEQ ID NO:36 or at least 90% of SEQ ID NO:37. In one embodiment the immunogenic composition comprises a nucleotide sequence having at least 90% homology to SEQ ID NO:5, at least 90% homology to SEQ ID NO:6, at least 90% homology to SEQ ID NO:21, at least 90% homology to SEQ ID NO:22, at least 90% homology to SEQ ID NO:36 or at least 90% homology to SEQ ID NO:37.

In one embodiment the immunogenic composition encodes ICP. In one embodiment the immunogenic composition comprises a nucleotide sequence encoding an amino acid sequence of SEQ ID NO:7, SEQ ID NO:23 or SEQ ID NO:38. In one embodiment the immunogenic composition comprises a nucleic acid sequence that encodes an amino acid sequence comprising at least 90% of SEQ ID NO:7, at least 90% of SEQ ID NO:23 or at least 90% of SEQ ID NO:38. In one embodiment the immunogenic composition comprises a nucleic acid sequence that encodes an amino acid sequence comprising at least 90% homology to SEQ ID NO:7, at least 90% homology to SEQ ID NO:23, or at least 90% homology to SEQ ID NO:38. In one embodiment the immunogenic composition comprises a nucleotide sequence of SEQ ID NO:8, SEQ ID NO:9, SEQ ID NO:24, SEQ ID NO:25, SEQ ID NO:39 or SEQ ID NO:40. In one embodiment the immunogenic composition comprises a nucleotide sequence comprising at least 90% of SEQ ID NO:8, at least 90% of SEQ ID NO:9, at least 90% of SEQ ID NO:24, at least 90% of SEQ ID NO:25, at least 90% of SEQ ID NO:39, or at least 90% of SEQ ID NO:40. In one embodiment the immunogenic composition comprises a nucleotide sequence comprising at least 90% homology to SEQ ID NO:8, at least 90% homology to SEQ ID NO:9, at least 90% homology to SEQ ID NO:24, at least 90% homology to SEQ ID NO:25, at least 90% homology to SEQ ID NO:39 or at least 90% homology to SEQ ID NO:40.

In one embodiment the immunogenic composition encodes TMP21. In one embodiment the immunogenic composition comprises a nucleotide sequence encoding SEQ ID NO:10, SEQ ID NO:26 or SEQ ID NO:41. In one embodiment the immunogenic composition comprises a nucleic acid sequence that encodes an amino acid sequence comprising at least 90% of SEQ ID NO:10, at least 90% of SEQ ID NO:26 or at least 90% of SEQ ID NO:41. In one embodiment the immunogenic composition comprises a nucleic acid sequence that encodes an amino acid sequence comprising at least 90% homology to SEQ ID NO:10, at least 90% homology to SEQ ID NO:26 or at least 90% homology to SEQ ID NO:41. In one embodiment the immunogenic composition comprises a nucleotide sequence of SEQ ID NO:11, SEQ ID NO:12, SEQ ID NO:27, SEQ ID NO:28, SEQ ID NO:42 or SEQ ID NO:43. In one embodiment the immunogenic composition comprises a nucleotide sequence that comprises at least 90% of SEQ ID NO:11, at least 90% of SEQ ID NO:12, at least 90% of SEQ ID NO:27, at least 90% of SEQ ID NO:28, at least 90% of SEQ ID NO:42 or at least 90% of SEQ ID NO:43. In one embodiment the immunogenic composition comprises a nucleotide sequence comprising at least 90% homology to SEQ ID NO:11, at least 90% homology to SEQ ID NO:12, at least 90% homology to SEQ ID NO:27, at least 90% homology to SEQ ID NO:28, at least 90% homology to SEQ ID NO:42 or at least 90% homology to SEQ ID NO:43.

In one embodiment the immunogenic composition encodes UIS3. In one embodiment the immunogenic composition comprises a nucleotide sequence encoding an amino acid sequence of SEQ ID NO:13, SEQ ID NO:29 or SEQ ID NO:44. In one embodiment the immunogenic composition comprises a nucleic acid sequence that encodes an amino acid sequence comprising at least 90% of SEQ ID NO:13, at least 90% of SEQ ID NO:29, or at least 90% of SEQ ID NO:44. In one embodiment the immunogenic composition comprises a nucleic acid sequence that encodes an amino acid sequence comprising at least 90% homology to SEQ ID NO:13, at least 90% homology to SEQ ID NO:29 or at least 90% homology to SEQ ID NO:44. In one embodiment the immunogenic composition comprises a nucleotide sequence of SEQ ID NO:14, SEQ ID NO:15, SEQ ID NO:30, SEQ ID NO:31, SEQ ID NO:45 or SEQ ID NO:46. In one embodiment the immunogenic composition comprises a nucleotide sequence that comprises at least 90% of SEQ ID NO:14, at least 90% of SEQ ID NO:15, at least 90% of SEQ ID NO:30, at least 90% of SEQ ID NO:31, at least 90% of SEQ ID NO:45, or at least 90% of SEQ ID NO:46. In one embodiment the immunogenic composition comprises a nucleotide sequence comprising at least 90% homology to SEQ ID NO:14, at least 90% homology to SEQ ID NO:15, at least 90% homology to SEQ ID NO:30, at least 90% homology to SEQ ID NO:31, at least 90% homology to SEQ ID NO:45, or at least 90% homology to SEQ ID NO:46.

In one embodiment the immunogenic composition encodes UIS10. In one embodiment the immunogenic composition comprises a nucleotide sequence encoding SEQ ID NO:47; a nucleic acid sequence that encoding an amino acid sequence comprising at least 90% of SEQ ID NO:47; or a nucleic acid sequence that encodes an amino acid sequence comprising at least 90% homology to SEQ ID NO:47. In one embodiment the immunogenic composition comprises a nucleotide sequence of SEQ ID NO:48 or SEQ ID NO:49. In one embodiment the immunogenic composition comprises a nucleotide sequence that comprises at least 90% of SEQ ID NO:48 or at least 90% of SEQ ID NO:49. In one embodiment the immunogenic composition comprises a nucleotide sequence comprising at least 90% homology to SEQ ID NO:48 or at least 90% homology to SEQ ID NO:49.

In one embodiment the immunogenic composition encodes SPECT1 and SPECT2. In one embodiment the immunogenic composition comprises a nucleotide sequence encoding SEQ ID NO:50, a nucleic acid sequence that encoding an amino acid sequence comprising at least 90% of SEQ ID NO:50, or a nucleic acid sequence that encodes an amino acid sequence comprising at least 90% homology to SEQ ID NO:50. In one embodiment the immunogenic composition comprises a nucleotide sequence of SEQ ID NO:51 or SEQ ID NO:52. In one embodiment the immunogenic composition comprises a nucleotide sequence that comprises at least 90% of SEQ ID NO:51 or at least 90% of SEQ ID NO:52. In one embodiment the immunogenic composition comprises a nucleotide sequence comprising at least 90% homology to SEQ ID NO:51 or at least 90% homology to SEQ ID NO:52.

In one embodiment the immunogenic composition encodes RON2. In one embodiment the immunogenic composition comprises a nucleotide sequence encoding SEQ ID NO:53, a nucleic acid sequence that encoding an amino acid sequence comprising at least 90% of SEQ ID NO:53 or a nucleic acid sequence that encodes an amino acid sequence comprising at least 90% homology to SEQ ID NO:53. In one embodiment the immunogenic composition comprises a nucleotide sequence of SEQ ID NO:54 or SEQ ID NO:55. In one embodiment the immunogenic composition comprises a nucleotide sequence that comprises at least 90% of SEQ ID NO:54 or at least 90% of SEQ ID NO:55. In one embodiment the immunogenic composition comprises a nucleotide sequence comprising at least 90% homology to SEQ ID NO:54 or a nucleotide sequence comprising at least 90% homology to SEQ ID NO:55.

In one embodiment the immunogenic composition comprises a nucleic acid sequence encoding an IgE leader sequence of SEQ ID NO:16.

In one embodiment the immunogenic composition comprises a nucleic acid sequence encoding an HA tag.

In one embodiment the immunogenic composition further comprises one or more nucleotide sequences encoding one or more of: CSP, LSA1, TRAP, CelTOS and Ama1. In one embodiment the immunogenic composition further comprises a nucleic acid sequence encoding an amino acid sequence of SEQ ID NO:56, SEQ ID NO:59, SEQ ID NO:62 or SEQ ID NO:65. In one embodiment the immunogenic composition further comprises a nucleic acid sequence of SEQ ID NO:60, SEQ ID NO:61, SEQ ID NO:63, SEQ ID NO:64, SEQ ID NO:66 or SEQ ID NO:67.

In one embodiment the immunogenic composition further comprises a nucleotide sequences that encodes IL-12, IL-15, IL-28B, IL-33 or RANTES.

In one embodiment one or more nucleotide sequences are incorporated into one or more plasmids.

In one embodiment, the invention relates to a method of immunizing a mammal against malaria comprising the step of administering an immunogenic composition comprising at least one nucleic acid molecule comprising at least one nucleotide sequence encoding at least one consensus *Plasmodium* spp. liver stage (LS) immunogen to the tissue of the mammal. In one embodiment, the method comprises the steps of a) administering the immunogenic composition to the tissue of the mammal, and b) electroporating cells of the tissue with a pulse of energy at a constant current effective to permit entry of the nucleic acid molecules into the cells. In one embodiment, the immunogenic composition is administered by intramuscular or intradermal injection.

In one embodiment, the invention relates to a nucleic acid molecule comprising one or more nucleic acid sequence that encodes one or more consensus *Plasmodium* spp. LS immunogen selected from the group consisting of: EXP1, EXP2, EXP23, ICP, TMP21, UIS3, UIS10, SPECT1, SPECT2 and RON2.

In one embodiment the nucleic acid molecule encodes EXP1 and EXP2. In one embodiment the nucleic acid molecule comprises a nucleotide sequence encoding an amino acid sequence of SEQ ID NO:1, SEQ ID NO:17, or SEQ ID NO:32. In one embodiment the nucleic acid molecule comprises a nucleic acid sequence encoding an amino acid sequence comprising at least 90% of SEQ ID NO:1, at least 90% of SEQ ID NO:17, or at least 90% of SEQ ID NO:32. In one embodiment the nucleic acid molecule comprises a nucleic acid sequence that encodes an amino acid sequence comprising at least 90% homology to SEQ ID NO:1, at least 90% homology to SEQ ID NO:17, or at least 90% homology to SEQ ID NO:32. In one embodiment the nucleic acid molecule comprises a nucleotide sequence of SEQ ID NO:2, SEQ ID NO:3, SEQ ID NO: 18, SEQ ID NO: 19, SEQ ID NO:33 or SEQ ID NO:34. In one embodiment the nucleic acid molecule comprises at least 90% of SEQ ID NO:2, at least 90% of SEQ ID NO:3, at least 90% of SEQ ID NO:18, at least 90% of SEQ ID NO:19, at least 90% of SEQ ID NO:33, or at least 90% of SEQ ID NO:34. In one embodiment the nucleic acid molecule comprises a nucleotide sequence having at least 90% homology to SEQ ID NO:2, at least 90% homology to SEQ ID NO:3, at least 90% homology to SEQ ID NO:18, at least 90% homology to SEQ ID NO:19, at least 90% homology to SEQ ID NO:33, or at least 90% homology to SEQ ID NO:34.

In one embodiment the nucleic acid molecule encodes EXP23. In one embodiment the nucleic acid molecule comprises a nucleotide sequence encoding SEQ ID NO:4, SEQ ID NO:20 or SEQ ID NO:35. In one embodiment the nucleic acid molecule comprises a nucleic acid sequence encoding an amino acid sequence comprising at least 90% of SEQ ID NO:4, at least 90% of SEQ ID NO:20, or at least 90% of SEQ ID NO:35. In one embodiment the nucleic acid molecule comprises a nucleic acid sequence encoding an amino acid sequence comprising at least 90% homology to SEQ ID NO:4 at least 90% homology to SEQ ID NO:20 or at least 90% homology to SEQ ID NO:35. In one embodiment the nucleic acid molecule comprises a nucleotide sequence of SEQ ID NO:5, SEQ ID NO:6, SEQ ID NO:21, SEQ ID NO:22, SEQ ID NO:36 or SEQ ID NO:37 In one embodiment the nucleic acid molecule comprises a nucleotide sequence that comprises at least 90% of SEQ ID NO:5, at least 90% of SEQ ID NO:6, at least 90% of SEQ ID NO:21, at least 90% of SEQ ID NO:22, at least 90% of SEQ ID NO:36 or at least 90% of SEQ ID NO:37. In one embodiment the nucleic acid molecule comprises a nucleotide sequence having at least 90% homology to SEQ ID NO:5, at least 90% homology to SEQ ID NO:6, at least 90% homology to SEQ ID NO:21, at least 90% homology to SEQ ID NO:22, at least 90% homology to SEQ ID NO:36 or at least 90% homology to SEQ ID NO:37.

In one embodiment the nucleic acid molecule encodes ICP. In one embodiment the nucleic acid molecule comprises a nucleotide sequence encoding an amino acid sequence of SEQ ID NO:7, SEQ ID NO:23 or SEQ ID NO:38. In one embodiment the nucleic acid molecule comprises a nucleic acid sequence that encodes an amino acid sequence comprising at least 90% of SEQ ID NO:7, at least 90% of SEQ ID NO:23 or at least 90% of SEQ ID NO:38. In one embodiment the nucleic acid molecule comprises a nucleic acid sequence that encodes an amino acid sequence comprising at least 90% homology to SEQ ID NO:7, at least 90% homology to SEQ ID NO:23, or at least 90% homology to SEQ ID NO:38. In one embodiment the nucleic acid molecule comprises a nucleotide sequence of SEQ ID NO:8, SEQ ID NO:9, SEQ ID NO:24, SEQ ID NO:25, SEQ ID NO:39 or SEQ ID NO:40. In one embodiment the nucleic acid molecule comprises a nucleotide sequence comprising at least 90% of SEQ ID NO:8, at least 90% of SEQ ID NO:9, at least 90% of SEQ ID NO:24, at least 90% of SEQ ID NO:25, at least 90% of SEQ ID NO:39, or at least 90% of SEQ ID NO:40. In one embodiment the nucleic acid molecule comprises a nucleotide sequence comprising at least 90% homology to SEQ ID NO:8, at least 90% homology to SEQ ID NO:9, at least 90% homology to SEQ ID NO:24, at least 90% homology to SEQ ID NO:25, at least 90% homology to SEQ ID NO:39 or at least 90% homology to SEQ ID NO:40.

In one embodiment the nucleic acid molecule encodes TMP21. In one embodiment the nucleic acid molecule comprises a nucleotide sequence encoding SEQ ID NO:10, SEQ ID NO:26 or SEQ ID NO:41. In one embodiment the nucleic acid molecule comprises a nucleic acid sequence that encodes an amino acid sequence comprising at least 90% of SEQ ID NO:10, at least 90% of SEQ ID NO:26 or at least 90% of SEQ ID NO:41. In one embodiment the nucleic acid molecule comprises a nucleic acid sequence that encodes an amino acid sequence comprising at least 90% homology to SEQ ID NO:10, at least 90% homology to SEQ ID NO:26 or at least 90% homology to SEQ ID NO:41. In one embodiment the nucleic acid molecule comprises a nucleotide sequence of SEQ ID NO:11, SEQ ID NO:12, SEQ ID NO:27, SEQ ID NO:28, SEQ ID NO:42 or SEQ ID NO:43. In one embodiment the nucleic acid molecule comprises a nucleotide sequence that comprises at least 90% of SEQ ID NO:11, at least 90% of SEQ ID NO:12, at least 90% of SEQ ID NO:27, at least 90% of SEQ ID NO:28, at least 90% of SEQ ID NO:42 or at least 90% of SEQ ID NO:43. In one embodiment the nucleic acid molecule comprises a nucleotide sequence comprising at least 90% homology to SEQ ID NO:11, at least 90% homology to SEQ ID NO:12, at least 90% homology to SEQ ID NO:27, at least 90% homology to SEQ ID NO:28, at least 90% homology to SEQ ID NO:42 or at least 90% homology to SEQ ID NO:43.

In one embodiment the nucleic acid molecule encodes UIS3. In one embodiment the nucleic acid molecule comprises a nucleotide sequence encoding an amino acid sequence of SEQ ID NO:13, SEQ ID NO:29 or SEQ ID NO:44. In one embodiment the nucleic acid molecule comprises a nucleic acid sequence that encodes an amino acid sequence comprising at least 90% of SEQ ID NO:13, at least 90% of SEQ ID NO:29, or at least 90% of SEQ ID NO:44. In one embodiment the nucleic acid molecule comprises a nucleic acid sequence that encodes an amino acid sequence comprising at least 90% homology to SEQ ID NO:13, at least 90% homology to SEQ ID NO:29 or at least 90% homology to SEQ ID NO:44. In one embodiment the nucleic acid molecule comprises a nucleotide sequence of SEQ ID NO:14, SEQ ID NO:15, SEQ ID NO:30, SEQ ID NO:31, SEQ ID NO:45 or SEQ ID NO:46. In one embodiment the nucleic acid molecule comprises a nucleotide sequence that comprises at least 90% of SEQ ID NO:14, at least 90% of SEQ ID NO:15, at least 90% of SEQ ID NO:30, at least 90% of SEQ ID NO:31, at least 90% of SEQ ID NO:45, or at least 90% of SEQ ID NO:46. In one embodiment the nucleic acid molecule comprises a nucleotide sequence comprising at least 90% homology to SEQ ID NO:14, at least 90% homology to SEQ ID NO:15, at least 90% homology to SEQ ID NO:30, at least 90% homology to SEQ ID NO:31, at least 90% homology to SEQ ID NO:45, or at least 90% homology to SEQ ID NO:46.

In one embodiment the nucleic acid molecule encodes UIS10. In one embodiment the nucleic acid molecule comprises a nucleotide sequence encoding SEQ ID NO:47; a nucleic acid sequence that encoding an amino acid sequence comprising at least 90% of SEQ ID NO:47; or a nucleic acid sequence that encodes an amino acid sequence comprising at least 90% homology to SEQ ID NO:47. In one embodiment the nucleic acid molecule comprises a nucleotide sequence of SEQ ID NO:48 or SEQ ID NO:49. In one embodiment the nucleic acid molecule comprises a nucleotide sequence that comprises at least 90% of SEQ ID NO:48 or at least 90% of SEQ ID NO:49. In one embodiment the nucleic acid molecule comprises a nucleotide sequence comprising at least 90% homology to SEQ ID NO:48 or at least 90% homology to SEQ ID NO:49.

In one embodiment the nucleic acid molecule encodes SPECT1 and SPECT2. In one embodiment the nucleic acid molecule comprises a nucleotide sequence encoding SEQ ID NO:50, a nucleic acid sequence that encoding an amino acid sequence comprising at least 90% of SEQ ID NO:50, or a nucleic acid sequence that encodes an amino acid sequence comprising at least 90% homology to SEQ ID NO:50. In one embodiment the nucleic acid molecule comprises a nucleotide sequence of SEQ ID NO:51 or SEQ ID NO:52. In one embodiment the nucleic acid molecule comprises a nucleotide sequence that comprises at least 90% of SEQ ID NO:51 or at least 90% of SEQ ID NO:52. In one embodiment the nucleic acid molecule comprises a nucleotide sequence comprising at least 90% homology to SEQ ID NO:51 or at least 90% homology to SEQ ID NO:52.

In one embodiment the nucleic acid molecule encodes RON2. In one embodiment the nucleic acid molecule comprises a nucleotide sequence encoding SEQ ID NO:53, a nucleic acid sequence that encoding an amino acid sequence comprising at least 90% of SEQ ID NO:53 or a nucleic acid sequence that encodes an amino acid sequence comprising at least 90% homology to SEQ ID NO:53. In one embodiment the nucleic acid molecule comprises a nucleotide sequence of SEQ ID NO:54 or SEQ ID NO:55. In one embodiment the nucleic acid molecule comprises a nucleotide sequence that comprises at least 90% of SEQ ID NO:54 or at least 90% of SEQ ID NO:55. In one embodiment the nucleic acid molecule comprises a nucleotide sequence comprising at least 90% homology to SEQ ID NO:54 or a nucleotide sequence comprising at least 90% homology to SEQ ID NO:55.

In one embodiment the nucleic acid molecule comprises a sequence encoding an IgE leader sequence of SEQ ID NO:16.

In one embodiment said nucleic acid molecule is a plasmid.

In one embodiment the invention relates to a nucleic acid molecule comprising one or more nucleotide sequences encoding one or more of: CSP, LSA1, TRAP, CelTOS and Ama1. In one embodiment the nucleic acid molecule further comprises a nucleic acid sequence encoding an amino acid sequence of SEQ ID NO:56, SEQ ID NO:59, SEQ ID NO:62 or SEQ ID NO:65. In one embodiment the nucleic acid molecule further comprises a nucleic acid sequence of SEQ ID NO:60, SEQ ID NO:61, SEQ ID NO:63, SEQ ID NO:64, SEQ ID NO:66 or SEQ ID NO:67. In one embodiment the nucleic acid molecule comprises a sequence encoding an IgE leader sequence of SEQ ID NO:16. In one embodiment said nucleic acid molecule is a plasmid.

BRIEF DESCRIPTION OF THE DRAWINGS

FIG. 2 depicts a list of LS exported proteins including the length of the nucleic acid sequence encoding the protein, their conservation in *Plasmodium* spp., and the stage(s) (liver stage (LS), blood stage (BS) or sporozoite stage) at which they have been identified.

FIG. 3, comprising FIG. 3A through FIG. 3D depicts increased survival in mice immunized with EXP1 and EXP2 as compared to control mice. FIG. 3A depicts a diagram of the immunization, challenge, and observation time course. FIG. 3B depicts a table showing the results of the experiment. Mice immunized with EXP1_EXP2 showed a delay in development of blood stage disease. FIG. 3C depicts the percentage of mice showing pre-patency over the course of 8 days post challenge. FIG. 3D depicts the percentage of mice showing patency over the course of 8 days post challenge.

FIG. 4, comprising FIG. 4A through FIG. 4D depicts increased survival and protection from blood stage disease in mice immunized with EXP1 and EXP2 as compared to control mice. FIG. 4A depicts a diagram of the immunization, challenge, and observation time course. FIG. 4B depicts a table showing the results of the experiment. Mice immunized with EXP1_EXP2, with and without an adjuvant of IL-12 or IL33, showed protection from development of blood stage disease. FIG. 4C depicts the percentage of mice showing pre-patency over the course of 10 days post challenge. FIG. 3D depicts the percentage of mice showing patency over the course of 10 days post challenge.

FIG. 7, comprising FIG. 7A through FIG. 7B depicts increased survival and protection from BS disease in mice immunized with various combinations of LS immunogens as compared to control mice. FIG. 7A depicts a diagram of the immunization, challenge, and observation time course. FIG. 7B depicts a table showing the results of the experiment. Mice immunized with the indicated constructs comprising combinations of LS immunogens, with and without an adjuvant of IL-12 or IL33, showed protection from development of BS disease.

FIG. 14 depicts experimental results demonstrating increased survival and protection from BS disease in mice immunized with EXP1_EXP2 alone or in combination with additional malaria immunogens CelTOS_TRAP, with or without adjuvant treatment with IL-12 or IL-33.

FIG. 18 depicts a table summarizing the results of exemplary experimental data presented in FIG. 16 and FIG. 17.

DETAILED DESCRIPTION

Figure 1:
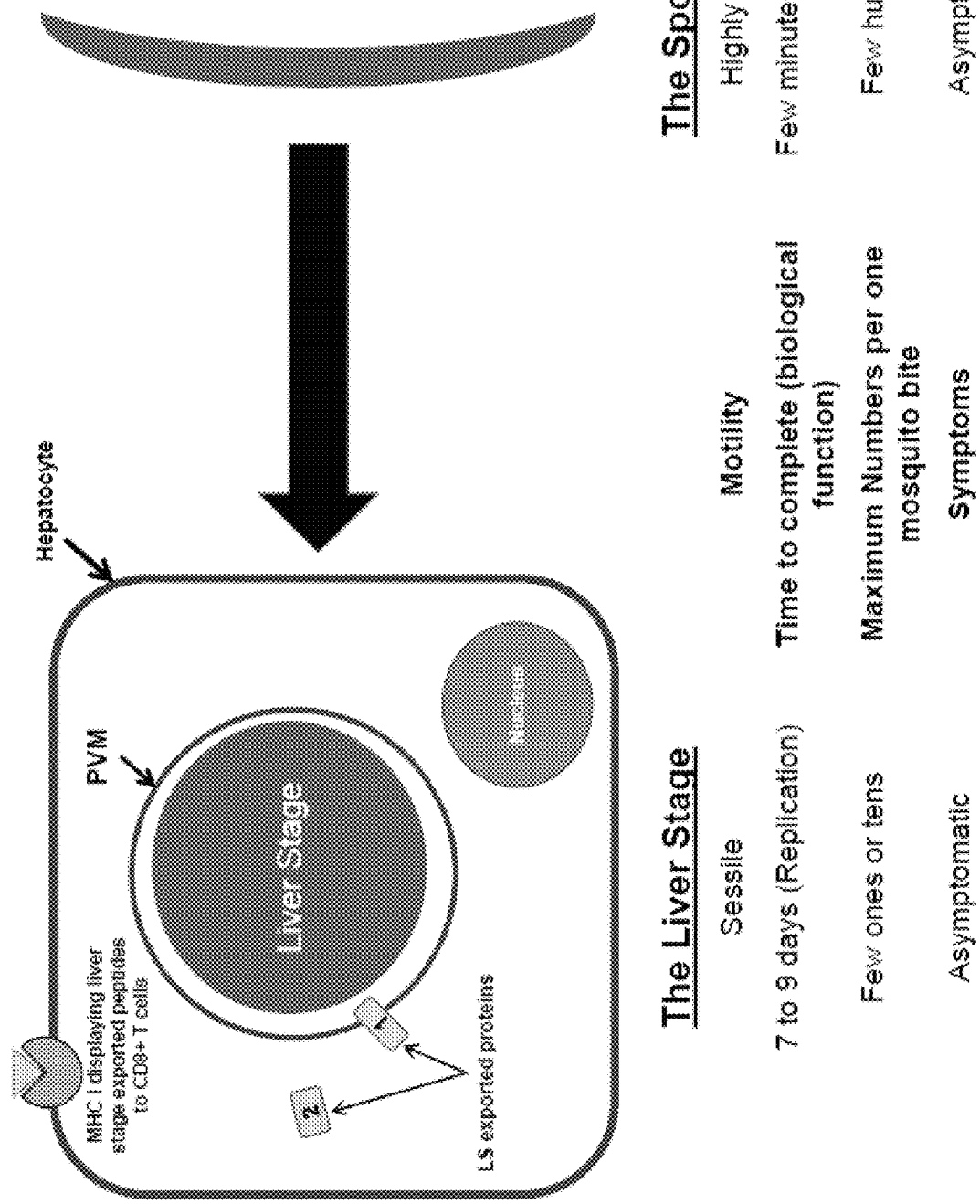
FIG. 1 depicts an illustration of the sporozoite and liver stages of *P. falciparum* infection. The liver stage (LS) exported proteins traverse the parasitophorous vacuolar membrane (PVM).
Figure 5:
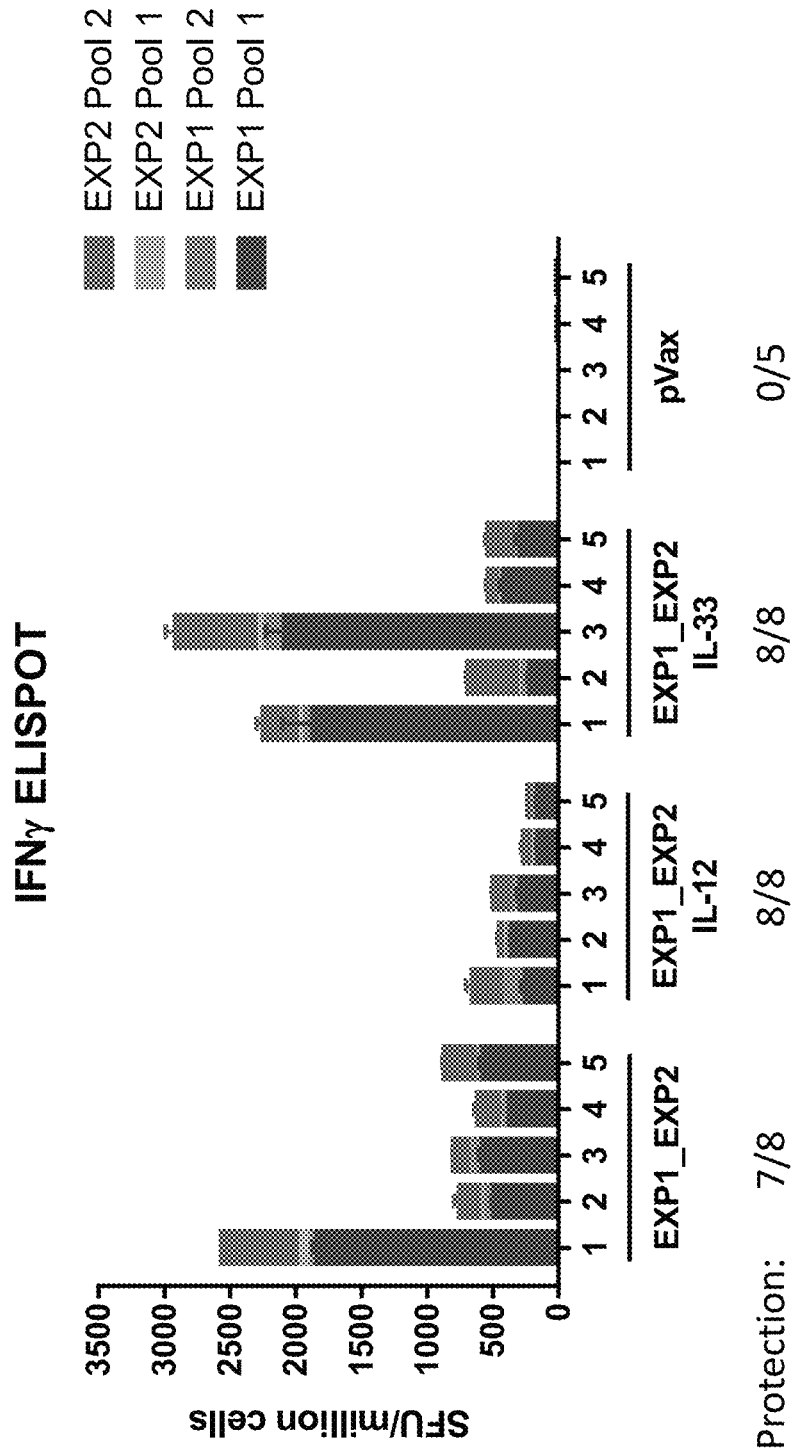
FIG. 5 depicts IFNγ ELISPOT assay results showing mice immunized with EXP1_EXP2, with and without adjuvant treatment with IL-12 or IL-33 showed an increase in immune response as compared to mice treated with control vector (pVax) 14 weeks after the first immunization.
Figure 6:
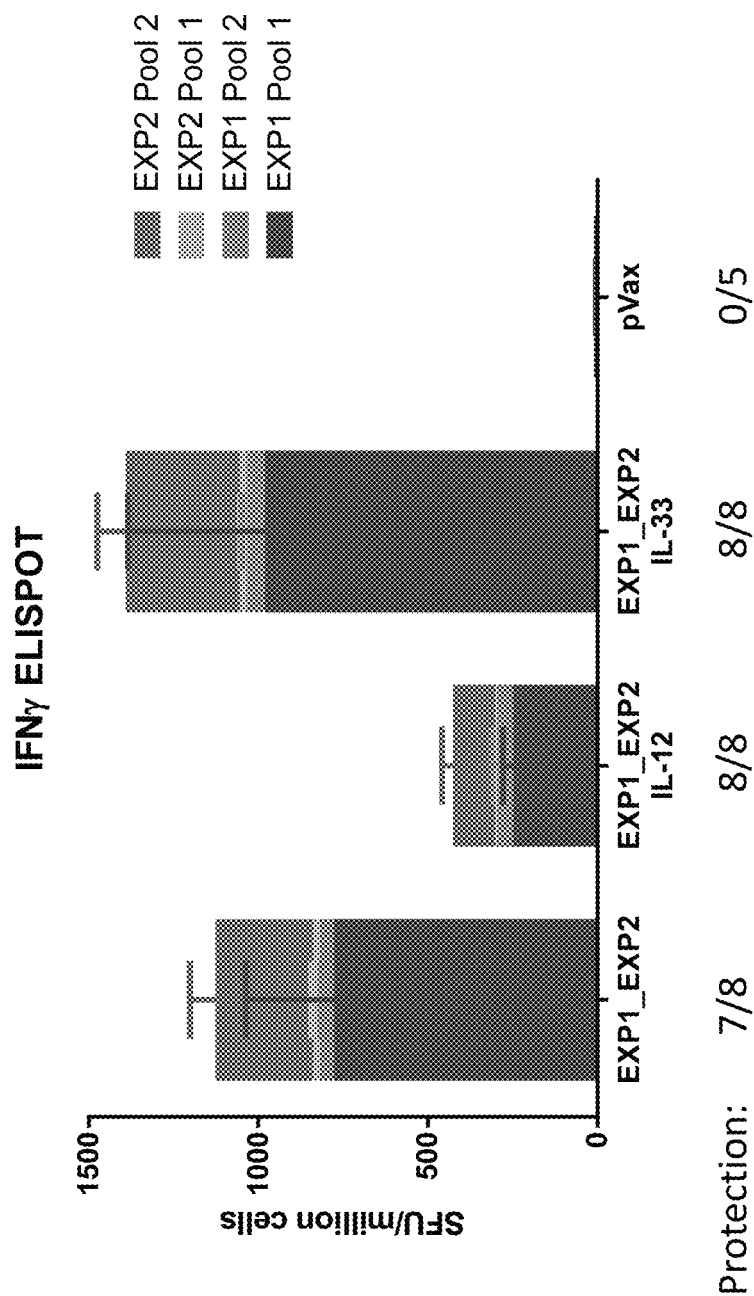
FIG. 6 depicts the average of the IFNγ ELISPOT assay results from FIG. 5, showing mice immunized with EXP1_EXP2, with and without adjuvant treatment with IL-12 or IL-33 showed an increase in immune response as compared to mice treated with control vector (pVax).

In one aspect, the invention provides compositions comprising nucleic acid and amino acid sequences for liver stage (LS) exported proteins and methods for their use as a *Plasmodium* spp. immunogenic composition. In one embodiment, the composition is a nucleic acid sequence encoding one or more LS exported protein. In one embodiment, the composition includes multiple nucleic acids encoding multiple LS exported proteins. In one embodiment, the composition is a plasmid encoding one or more LS exported protein. In one embodiment, the composition comprises multiple plasmids encoding one or more LS exported protein.

In one embodiment, the invention provides sequences that are optimized for expression in human cells. The optimized DNA sequences are preferable for treating human subjects.

Definitions

Unless otherwise defined, all technical and scientific terms used herein have the same meaning as commonly understood by one of ordinary skill in the art. In case of conflict, the present document, including definitions, will control. Exemplary methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting. The terminology used herein is for the purpose of describing particular embodiments only and is not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of" the embodiments or elements presented herein, whether explicitly set forth or not.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the DNA plasmid vaccines described herein to enhance the immunogenicity of the antigens encoded by the DNA plasmids and the encoding nucleic acid sequences described hereinafter.

"Antibody" as used herein means an antibody of classes IgG, IgM, IgA, IgD or IgE, or fragments, or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple sequences for the same gene from different organisms. Nucleic acid sequences that encode a consensus polypeptide sequence can be prepared. Vaccines comprising proteins that comprise consensus sequences and/or nucleic acid molecules that encode such proteins can be used to induce broad immunity against an antigen.

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with an antigen disclosed herein. The fragments can be DNA fragments selected from at least one of the various nucleotide sequences that encode protein fragments set forth below. Fragments can comprise at least 10%, at least 20%, at least 30%, at least 40%, at least 50%, at least 60%, at least 70%, at least 80%, at least 90%, or at least 95% of one or more of the nucleic acid sequences set forth below. In some embodiments, fragments can comprise at least 20 nucleotides or more, at least 30 nucleotides or more, at least 40 nucleotides or more, at least 50 nucleotides or more, at least 60 nucleotides or more, at least 70 nucleotides or more, at least 80 nucleotides or more, at least 90 nucleotides or more, at least 100 nucleotides or more, at least 150 nucleotides or more, at least 200 nucleotides or more, at least 250 nucleotides or more, at least 300 nucleotides or more, at least 350 nucleotides or more, at least 400 nucleotides or more, at least 450 nucleotides or more, at least 500 nucleotides or more, at least 550 nucleotides or more, at least 600 nucleotides or more, at least 650 nucleotides or more, at least 700 nucleotides or more, at least 750 nucleotides or more, at least 800 nucleotides or more, at least 850 nucleotides or more, at least 900 nucleotides or more, at least 950 nucleotides or more, or at least 1000 nucleotides or more of at least one of the nucleic acid sequences disclosed herein.

"Fragment" or "immunogenic fragment" with respect to polypeptide sequences means a polypeptide capable of eliciting an immune response in a mammal that cross reacts with an antigen disclosed herein. The fragments can be polypeptide fragments selected from at least one of the various amino acids sequences below. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 210 amino acids or more, at least 240 amino acids or more, at least 270 amino acids or more, or at least 300 amino acids or more of a protein sequence disclosed herein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the amino terminus (i.e., N terminus) of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" as used herein can mean a mammal that wants to or is in need of being immunized with the herein described vaccines. The mammal can be a human, chimpanzee, dog, cat, horse, cow, mouse, or rat.

"Substantially complementary" as used herein means that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Treatment" or "treating" as used herein can mean protecting an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. The vector can contain or include one or more heterologous nucleic acid sequences.

1. Immunogenic Composition

The present invention is directed to an immunogenic composition for use in eliciting an immune response against a *Plasmodium* ssp. In one embodiment, the immunogenic composition comprises at least one *Plasmodium* ssp. liver stage (LS) antigen. In one embodiment, the LS antigen is a consensus LS antigen, generated from multiple *Plasmodium* ssp LS antigen sequences. In one embodiment, the consensus LS antigen is capable of eliciting a broad immune response against multiple *Plasmodium* ssp.

In one embodiment, the immunogenic composition can increase the length of pre-patency by at least 1%, 5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, or more than 45% relative to the length of pre-patency in a subject that has not been immunized. In one embodiment, the immunogenic composition can reduce patency by at least 1%, 5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more than 60% after immunization relative to a subject that has not been immunized.

In one embodiment, the immunogenic composition can increase protection from *Plasmodium* ssp by at least 1%, 5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, or more than 45% relative to the protection in a population that has not been immunized.

The immunogenic composition can increase a cellular immune response in a subject administered the immunogenic composition in response to *Plasmodium* ssp challenge by about 2-fold to about 6000-fold, about 3-fold to about 6000-fold, about 4-fold to about 6000-fold, about 5-fold to about 6000-fold, about 6-fold to about 6000-fold, about 7-fold to about 6000-fold, about 8-fold to about 6000-fold, about 9-fold to about 6000-fold, about 10-fold to about 6000-fold, about 15-fold to about 6000-fold, about 10-fold to about 6000-fold, about 25-fold to about 6000-fold, about 30-fold to about 6000-fold, about 35-fold to about 6000-fold, about 40-fold to about 6000-fold, about 45-fold to about 6000-fold, about 50-fold to about 6000-fold, about 2-fold to about 5500-fold, about 2-fold to about 5000-fold, about 2-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the immunogenic composition. In some embodiments the immunogenic composition can increase the cellular immune response in the subject administered the immunogenic composition in response to *Plasmodium* ssp challenge by about 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to the cellular immune response in the subject not administered the immunogenic composition.

The immunogenic composition can increase interferon gamma (IFN-γ) levels in a subject administered the immunogenic composition in response to *Plasmodium* ssp challenge by about 2-fold to about 6000-fold, about 3-fold to about 6000-fold, about 4-fold to about 6000-fold, about 5-fold to about 6000-fold, about 6-fold to about 6000-fold, about 7-fold to about 6000-fold, about 8-fold to about 6000-fold, about 9-fold to about 6000-fold, about 10-fold to about 6000-fold, about 15-fold to about 6000-fold, about 10-fold to about 6000-fold, about 25-fold to about 6000-fold, about 30-fold to about 6000-fold, about 35-fold to about 6000-fold, about 40-fold to about 6000-fold, about 45-fold to about 6000-fold, 50-fold to about 6000-fold, about 2-fold to about 5500-fold, about 2-fold to about 5000-fold, about 2-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the immunogenic composition.

In some embodiments the immunogenic composition can increase IFN-γ levels in the subject administered the immunogenic composition in response to *Plasmodium* ssp challenge by about 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, 1000-fold, 1100-fold, 1200-fold, 1300-fold, 1400-fold, 1500-fold, 1600-fold, 1700-fold, 1800-fold, 1900-fold, 2000-fold, 2100-fold, 2200-fold, 2300-fold, 2400-fold, 2500-fold, 2600-fold, 2700-fold, 2800-fold, 2900-fold, 3000-fold, 3100-fold, 3200-fold, 3300-fold, 3400-fold, 3500-fold, 3600-fold, 3700-fold, 3800-fold, 3900-fold, 4000-fold, 4100-fold, 4200-fold, 4300-fold, 4400-fold, 4500-fold, 4600-fold, 4700-fold, 4800-fold, 4900-fold, 5000-fold, 5100-fold, 5200-fold, 5300-fold, 5400-fold, 5500-fold, 5600-fold, 5700-fold, 5800-fold, 5900-fold, or 6000-fold as compared to IFN-γ levels in the subject not administered the immunogenic composition.

The immunogenic composition can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The immunogenic composition can be an RNA of the at least one *Plasmodium* ssp. LS antigen. The RNA vaccine can be introduced into the cell.

The immunogenic composition can be an attenuated live vaccine, a vaccine using recombinant vectors to deliver antigen, subunit vaccines, and glycoprotein vaccines, for example, but not limited, the vaccines described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The immunogenic composition of the present invention can have features required of effective vaccines such as being safe so that the vaccine itself does not cause illness or death; being protective against illness; inducing neutralizing antibody; inducing protective T cell responses; and providing ease of administration, few side effects, biological stability, and low cost per dose. The vaccine can accomplish some or all of these features by containing the at least one *Plasmodium* ssp. LS antigen as discussed below.

2. *Plasmodium* ssp. LS Antigen

The synthetic consensus *Plasmodium* ssp. LS antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof. The consensus *Plasmodium* ssp. LS antigen can be a recombinant antigen. The consensus *Plasmodium* ssp. LS antigen can be a fusion antigen comprising sequences for two or more consensus *Plasmodium* ssp. LS proteins or peptides.

In one embodiment, the consensus *Plasmodium* ssp. LS antigen is derived from at least one of EXP1, EXP2, EXP23, ICP, TMP21, UIS3, UIS10, SPECT1, SPECT2 and RON2 proteins. In one embodiment, a consensus *Plasmodium* ssp. LS antigen has at least 85% and up to 99% amino acid sequence identity to a corresponding native LS antigen; at least 90% and up to 99% sequence identity; at least 93% and up to 98% sequence identity; or at least 95% and up to 99% sequence identity. In some instances the consensus *Plasmodium* ssp. LS antigen has up to 95%, 96%, 97%, 98%, 99% or 99.5% amino acid sequence identity to a corresponding native consensus *Plasmodium* ssp. LS antigen. Depending upon the *Plasmodium* ssp. LS antigen, the consensus sequence of the *Plasmodium* ssp. LS antigen can be across *Plasmodium* ssp or across multiple strains or serotypes within a *Plasmodium* ssp.

The consensus *Plasmodium* ssp. LS antigen may comprise a full length amino acid sequence of a *Plasmodium* ssp. LS antigen, a fragment thereof, a homologous variant amino acid sequence thereof, or a fragment of a homologous variant amino acid sequence. The consensus *Plasmodium* ssp. LS antigen may be operably linked to a signal peptide such as an immunoglobulin signal peptide (e.g., an IgE or IgG signal peptide). In one embodiment, the N terminal methionine of the consensus *Plasmodium* ssp. LS antigen sequence is removed and the signal peptide is N-terminally linked to the amino acid sequence of the consensus *Plasmodium* ssp. LS antigen. In some embodiments, the consensus *Plasmodium* ssp. LS antigen is operably linked to another amino acid sequences such as an HA Tag.

In some embodiment, the consensus *Plasmodium* ssp. LS antigen of the invention is optimized for increased expression. In one embodiment, the consensus *Plasmodium* ssp. LS antigen of the invention includes one or more of codon and RNA optimized for increased expression in a target species. In one embodiment, a target species is human, non-human primate, or mouse.

In one embodiment, the consensus *Plasmodium* ssp. LS antigen comprises a nucleic acid sequence that encodes an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:1, SEQ ID NO:4, SEQ ID NO:7, SEQ ID NO:10, SEQ ID NO:13, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:68, SEQ ID NO:70, SEQ ID NO:72, SEQ ID NO:74, SEQ ID NO:76, SEQ ID NO:78, SEQ ID NO:80, and SEQ ID NO:82. In one embodiment, the encoding nucleic acid sequence is a ribonucleic acid (RNA) sequence.

In one embodiment, the consensus *Plasmodium* ssp. LS antigen comprises a nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of a nucleic acid sequence as set forth in SEQ ID NO:2, SEQ ID NO:3, SEQ ID NO:5, SEQ ID NO:6, SEQ ID NO:8, SEQ ID NO:9, SEQ ID NO:11, SEQ ID NO:12, SEQ ID NO:14, SEQ ID NO:15, SEQ ID NO:18, SEQ ID NO:19, SEQ ID NO:21, SEQ ID NO:22, SEQ ID NO:24, SEQ ID NO:25, SEQ ID NO:27, SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:42, SEQ ID NO:43, SEQ ID NO:45, SEQ ID NO:46, SEQ ID NO:48, SEQ ID NO:49, SEQ ID NO:51, SEQ ID NO:52, SEQ ID NO:54, SEQ ID NO:55, SEQ ID NO:69, SEQ ID NO:71, SEQ ID NO:73, SEQ ID NO:75, SEQ ID NO:77, SEQ ID NO:79, SEQ ID NO:81, and SEQ ID NO:83. In one embodiment, the consensus *Plasmodium* ssp. LS antigen comprises a ribonucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of a ribonucleic acid sequence to a transcript of a nucleic acid sequence as set forth in SEQ ID NO:2, SEQ ID NO:3, SEQ ID NO:5, SEQ ID NO:6, SEQ ID NO:8, SEQ ID NO:9, SEQ ID NO:11, SEQ ID NO:12, SEQ ID NO:14, SEQ ID NO:15, SEQ ID NO:18, SEQ ID NO:19, SEQ ID NO:21, SEQ ID NO:22, SEQ ID NO:24, SEQ ID NO:25, SEQ ID NO:27, SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:42, SEQ ID NO:43, SEQ ID NO:45, SEQ ID NO:46, SEQ ID NO:48, SEQ ID NO:49, SEQ ID NO:51, SEQ ID NO:52, SEQ ID NO:54, SEQ ID NO:55, SEQ ID NO:69, SEQ ID NO:71, SEQ ID NO:73, SEQ ID NO:75, SEQ ID NO:77, SEQ ID NO:79, SEQ ID NO:81, and SEQ ID NO:83.

In one embodiment, the consensus *Plasmodium* ssp. LS antigen comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99%, or 100% identity over an entire length of the amino acid sequence set forth in SEQ ID NO:1, SEQ ID NO:4, SEQ ID NO:7, SEQ ID NO:10, SEQ ID NO:13, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:68, SEQ ID NO:70, SEQ ID NO:72, SEQ ID NO:74, SEQ ID NO:76, SEQ ID NO:78, SEQ ID NO:80, and SEQ ID NO:82.

Some embodiments relate to nucleic acid sequences encoding proteins homologous to the consensus *Plasmodium* ssp. LS antigen, immunogenic fragments of the consensus *Plasmodium* ssp. LS antigen, and immunogenic fragments of homologous proteins. Such nucleic acid molecules that encode immunogenic proteins that have at least 95% homology to a sequence, at least 96% homology to a sequence, at least 97% homology to a sequence, at least 98% homology to a sequence and at least 99% homology to a sequence disclosed herein can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have at least 95% homology to the nucleic acid coding sequences herein. Some embodiments relate to nucleic acid molecules that encode immunogenic proteins that have at least 96% homology to the nucleic acid coding sequences herein. Some embodiments relate to nucleic acid molecules that encode immunogenic proteins that have at least 97% homology to the nucleic acid coding sequences herein. Some embodiments relate to nucleic acid molecules that encode immunogenic proteins that have at least 98% homology to the nucleic acid coding sequences herein. Some embodiments relate to nucleic acid molecules that encode immunogenic proteins that have at least 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length consensus *Plasmodium* ssp. LS antigen, immunogenic fragment of the consensus *Plasmodium* ssp. LS antigen, and immunogenic fragments of proteins having identity to the consensus *Plasmodium* ssp. LS antigen. Such nucleic acid molecules that encode immunogenic proteins that have at least 80% identity to a full length consensus *Plasmodium* ssp. LS antigen, at least 85% identity to a full length sequence, at least 90% identity to a full length sequence, at least 91% identity to a full length sequence, at least 92% identity to a full length sequence, at least 93% identity to a full length sequence, at least 94% identity to a full length sequence, at least 95% identity to a full length sequence, at least 96% identity to a full length sequence, at least 97% identity to a full length sequence, at least 98% identity to a full length sequence, and at least 99% identity to a full length sequence disclosed herein can be provided. Likewise, nucleic acid sequences encoding the immunogenic fragments set forth herein and the immunogenic fragments of proteins with similar percent identities as indicated above to the consensus *Plasmodium* ssp. LS antigens set forth herein are also provided.

In some embodiments, the nucleic acid sequence is free of coding sequence that encodes a leader sequence. In some embodiments, the nucleic acid sequence is free of coding sequence that encodes the IgE leader.

Some embodiments relate to fragments of consensus *Plasmodium* ssp. LS antigens. Fragments can be at least 10%, at least 15%, at least 20%, at least 25%, at least 30%, at least 35%, at least 40%, at least 45%, at least 50%, at least 55% at least 60%, at least 65%, at least 70%, at least 75%, at least 80%, at least 85%, at least 90%, at least 95%, at least 96%, at least 97%, at least 98% or at least 99% of a full length sequence disclosed herein. Fragments can be at least 95%, at least 96%, at least 97%, at least 98%, or at least 99% homologous to fragments of a full length sequence disclosed herein. Fragments can be at least 80%, at least 85%, at least 90% at least 91%, at least 92%, at least 93%, at least 94%, at least 95%, at least 96%, at least 97%, at least 98%, or at least 99% identical to fragments of a full length sequence disclosed herein. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

1. EXP1 Antigen

In one embodiment, the immunogenic composition of the present invention can comprise an EXP1 antigen, a fragment thereof, a variant thereof, or a combination thereof. The nucleic acid encoding the consensus EXP1 antigen can be codon and RNA optimized for expression in humans. In one embodiment, a nucleotide sequence encodes a EXP1 antigen as set forth in SEQ ID NO:68. In one embodiment, a nucleotide sequence encodes a EXP1 antigen as set forth in SEQ ID NO:68 operably linked to an IgE leader sequence. In one embodiment, an IgE leader sequence comprises an amino acid sequence as set forth in SEQ ID NO:16. In one a nucleotide sequence encoding a consensus EXP1 antigen is set forth in SEQ ID NO:69. In one a nucleotide sequence encoding a consensus EXP1 antigen is operably linked to a sequence encoding an IgE leader.

In one embodiment, the EXP1 antigen is designed for expression in non-human primates. In one embodiment, a nucleotide sequence encoding a consensus EXP1 antigen for expression in non-human primates encodes a EXP1 antigen as set forth in SEQ ID NO:72. In one embodiment, the sequence for expression in a non-human primate is operably linked to a leader sequence having an amino acid sequence as set forth in SEQ ID NO:16. In one embodiment, a nucleotide sequence encoding a consensus EXP1 antigen for expression in non-human primates is set forth in SEQ ID NO:73. In one a nucleotide sequence encoding a consensus EXP1 antigen is operably linked to a sequence encoding an IgE leader.

In one embodiment, the EXP1 antigen is designed for expression in mice. In one embodiment, a nucleotide sequence encoding a consensus EXP1 antigen for expression in mice encodes a EXP1 antigen as set forth in SEQ ID NO:76. In one embodiment, the sequence for expression in mice is operably linked to a leader sequence having an amino acid sequence as set forth in SEQ ID NO:16. In one embodiment, a nucleotide sequence encoding a consensus EXP1 antigen for expression in mice is set forth in SEQ ID NO:77. In one a nucleotide sequence encoding a consensus EXP1 antigen is operably linked to a sequence encoding an IgE leader.

In one embodiment, the amino acid sequence of the consensus EXP1 antigen is operably linked to an HA tag. In one embodiment, the nucleic acid sequence encodes a consensus EXP1 antigen operably linked to an HA tag.

2. EXP2 Antigen

In one embodiment, the immunogenic composition of the present invention can comprise an EXP2 antigen, a fragment thereof, a variant thereof, or a combination thereof. The nucleic acid encoding the consensus EXP2 antigen can be codon and RNA optimized for expression in humans. In one embodiment, a nucleotide sequence encodes a EXP2 antigen as set forth in SEQ ID NO:70. In one embodiment, a nucleotide sequence encodes a EXP2 antigen as set forth in SEQ ID NO:70 operably linked to an IgE leader sequence. In one embodiment, an IgE leader sequence comprises an amino acid sequence as set forth in SEQ ID NO:16. In one a nucleotide sequence encoding a consensus EXP2 antigen is set forth in SEQ ID NO:71. In one a nucleotide sequence encoding a consensus EXP1 antigen is operably linked to a sequence encoding an IgE leader.

In one embodiment, the EXP2 antigen is designed for expression in non-human primates. In one embodiment, a nucleotide sequence encoding a consensus EXP2 antigen for expression in non-human primates encodes a EXP2 antigen as set forth in SEQ ID NO:74. In one embodiment, the sequence for expression in a non-human primate is operably linked to a leader sequence having an amino acid sequence as set forth in SEQ ID NO:16. In one embodiment, a nucleotide sequence encoding a consensus EXP2 antigen for expression in non-human primates is set forth in SEQ ID NO:75. In one a nucleotide sequence encoding a consensus EXP1 antigen is operably linked to a sequence encoding an IgE leader.

In one embodiment, the EXP2 antigen is designed for expression in mice. In one embodiment, a nucleotide sequence encoding a consensus EXP2 antigen for expression in mice encodes a EXP2 antigen as set forth in SEQ ID NO:78. In one embodiment, the sequence for expression in mice is operably linked to a leader sequence having an amino acid sequence as set forth in SEQ ID NO:16. In one embodiment, a nucleotide sequence encoding a consensus EXP2 antigen for expression in mice is set forth in SEQ ID NO:79. In one a nucleotide sequence encoding a consensus EXP1 antigen is operably linked to a sequence encoding an IgE leader.

In one embodiment, the amino acid sequence of the consensus EXP2 antigen is operably linked to an HA tag. In one embodiment, the nucleic acid sequence encodes a consensus EXP2 antigen operably linked to an HA tag.

3. EXP23 Antigen

In one embodiment, the immunogenic composition of the present invention can comprise an EXP23 antigen, a fragment thereof, a variant thereof, or a combination thereof. The nucleic acid encoding the consensus EXP23 antigen can be codon and RNA optimized for expression in humans. In one embodiment, a nucleotide sequence encodes a EXP23 antigen as set forth in SEQ ID NO:4. In one embodiment, a nucleotide sequence encodes a EXP23 antigen as set forth in SEQ ID NO:4 operably linked to an IgE leader sequence. In one embodiment, an IgE leader sequence comprises an amino acid sequence as set forth in SEQ ID NO:16. In one a nucleotide sequence encoding a consensus EXP23 antigen is set forth in SEQ ID NO:5. In one a nucleotide sequence encoding a consensus EXP23 antigen operably linked to a sequence encoding an IgE leader sequence is set forth in SEQ ID NO:6.

In one embodiment, the EXP23 antigen is designed for expression in non-human primates. In one embodiment, a nucleotide sequence encoding a consensus EXP23 antigen for expression in non-human primates encodes a EXP23 antigen as set forth in SEQ ID NO:20. In one embodiment, the sequence for expression in a non-human primate is operably linked to a leader sequence having an amino acid sequence as set forth in SEQ ID NO:16. In one embodiment, a nucleotide sequence encoding a consensus EXP23 antigen for expression in non-human primates is set forth in SEQ ID NO:21. In one embodiment, a nucleotide sequence encoding a consensus EXP23 antigen operably linked to a leader sequence for expression in non-human primates is set forth in SEQ ID NO:22.

In one embodiment, the EXP23 antigen is designed for expression in mice. In one embodiment, a nucleotide sequence encoding a consensus EXP23 antigen for expression in mice encodes a EXP23 antigen as set forth in SEQ ID NO:35. In one embodiment, the sequence for expression in mice is operably linked to a leader sequence having an amino acid sequence as set forth in SEQ ID NO:16. In one embodiment, a nucleotide sequence encoding a consensus EXP23 antigen for expression in mice is set forth in SEQ ID NO:36. In one embodiment, a nucleotide sequence encoding a consensus EXP23 antigen operably linked to a leader sequence for expression in mice is set forth in SEQ ID NO:37.

In one embodiment, the amino acid sequence of the consensus EXP23 antigen is operably linked to an HA tag. In one embodiment, the nucleic acid sequence encodes a consensus EXP23 antigen operably linked to an HA tag.

4. ICP Antigen

In one embodiment, the immunogenic composition of the present invention can comprise an ICP antigen, a fragment thereof, a variant thereof, or a combination thereof. The nucleic acid encoding the consensus ICP antigen can be codon and RNA optimized for expression in humans. In one embodiment, a nucleotide sequence encodes a ICP antigen as set forth in SEQ ID NO:7. In one embodiment, a nucleotide sequence encodes a ICP antigen as set forth in SEQ ID NO:7 operably linked to an IgE leader sequence. In one embodiment, an IgE leader sequence comprises an amino acid sequence as set forth in SEQ ID NO:16. In one a nucleotide sequence encoding a consensus ICP antigen is set forth in SEQ ID NO:8. In one a nucleotide sequence encoding a consensus ICP antigen operably linked to a sequence encoding an IgE leader sequence is set forth in SEQ ID NO:9.

In one embodiment, the ICP antigen is designed for expression in non-human primates. In one embodiment, a nucleotide sequence encoding a consensus ICP antigen for expression in non-human primates encodes a ICP antigen as set forth in SEQ ID NO:23. In one embodiment, the sequence for expression in a non-human primate is operably linked to a leader sequence having an amino acid sequence as set forth in SEQ ID NO:16. In one embodiment, a nucleotide sequence encoding a consensus ICP antigen for expression in non-human primates is set forth in SEQ ID NO:24. In one embodiment, a nucleotide sequence encoding a consensus ICP antigen operably linked to a leader sequence for expression in non-human primates is set forth in SEQ ID NO:25.

In one embodiment, the ICP antigen is designed for expression in mice. In one embodiment, a nucleotide sequence encoding a consensus ICP antigen for expression in mice encodes a ICP antigen as set forth in SEQ ID NO:38. In one embodiment, the sequence for expression in mice is operably linked to a leader sequence having an amino acid sequence as set forth in SEQ ID NO:16. In one embodiment, a nucleotide sequence encoding a consensus ICP antigen for expression in mice is set forth in SEQ ID NO:39. In one embodiment, a nucleotide sequence encoding a consensus ICP antigen operably linked to a leader sequence for expression in mice is set forth in SEQ ID NO:40.

In one embodiment, the amino acid sequence of the consensus ICP antigen is operably linked to an HA tag. In one embodiment, the nucleic acid sequence encodes a consensus ICP antigen operably linked to an HA tag.

5. TMP21 Antigen

In one embodiment, the immunogenic composition of the present invention can comprise a TMP21 antigen, a fragment thereof, a variant thereof, or a combination thereof. The nucleic acid encoding the consensus TMP21 antigen can be codon and RNA optimized for expression in humans. In one embodiment, a nucleotide sequence encodes a TMP21 antigen as set forth in SEQ ID NO:10. In one embodiment, a nucleotide sequence encodes a TMP21 antigen as set forth in SEQ ID NO:10 operably linked to an IgE leader sequence. In one embodiment, an IgE leader sequence comprises an amino acid sequence as set forth in SEQ ID NO:16. In one a nucleotide sequence encoding a consensus TMP21 antigen is set forth in SEQ ID NO:11. In one a nucleotide sequence encoding a consensus TMP21 antigen operably linked to a sequence encoding an IgE leader sequence is set forth in SEQ ID NO:12.

In one embodiment, the TMP21 antigen is designed for expression in non-human primates. In one embodiment, a nucleotide sequence encoding a consensus TMP21 antigen for expression in non-human primates encodes a TMP21 antigen as set forth in SEQ ID NO:26. In one embodiment, the sequence for expression in a non-human primate is operably linked to a leader sequence having an amino acid sequence as set forth in SEQ ID NO:16. In one embodiment, a nucleotide sequence encoding a consensus TMP21 antigen for expression in non-human primates is set forth in SEQ ID NO:27. In one embodiment, a nucleotide sequence encoding a consensus TMP21 antigen operably linked to a leader sequence for expression in non-human primates is set forth in SEQ ID NO:28.

In one embodiment, the TMP21 antigen is designed for expression in mice. In one embodiment, a nucleotide sequence encoding a consensus TMP21 antigen for expression in mice encodes a TMP21 antigen as set forth in SEQ ID NO:41. In one embodiment, the sequence for expression in mice is operably linked to a leader sequence having an amino acid sequence as set forth in SEQ ID NO:16. In one embodiment, a nucleotide sequence encoding a consensus TMP21 antigen for expression in mice is set forth in SEQ ID NO:42. In one embodiment, a nucleotide sequence encoding a consensus TMP21 antigen operably linked to a leader sequence for expression in mice is set forth in SEQ ID NO:43.

In one embodiment, the amino acid sequence of the consensus TMP21 antigen is operably linked to an HA tag. In one embodiment, the nucleic acid sequence encodes a consensus TMP21 antigen operably linked to an HA tag.

6. UIS3 Antigen

In one embodiment, the immunogenic composition of the present invention can comprise an UIS3 antigen, a fragment thereof, a variant thereof, or a combination thereof. The nucleic acid encoding the consensus UIS3 antigen can be codon and RNA optimized for expression in humans. In one embodiment, a nucleotide sequence encodes a UIS3 antigen as set forth in SEQ ID NO:13. In one embodiment, a nucleotide sequence encodes a UIS3 antigen as set forth in SEQ ID NO:13 operably linked to an IgE leader sequence. In one embodiment, an IgE leader sequence comprises an amino acid sequence as set forth in SEQ ID NO:16. In one a nucleotide sequence encoding a consensus UIS3 antigen is set forth in SEQ ID NO:14. In one a nucleotide sequence encoding a consensus UIS3 antigen operably linked to a sequence encoding an IgE leader sequence is set forth in SEQ ID NO:15.

In one embodiment, the UIS3 antigen is designed for expression in non-human primates. In one embodiment, a nucleotide sequence encoding a consensus UIS3 antigen for expression in non-human primates encodes a UIS3 antigen as set forth in SEQ ID NO:29. In one embodiment, the sequence for expression in a non-human primate is operably linked to a leader sequence having an amino acid sequence as set forth in SEQ ID NO:16. In one embodiment, a nucleotide sequence encoding a consensus UIS3 antigen for expression in non-human primates is set forth in SEQ ID NO:30. In one embodiment, a nucleotide sequence encoding a consensus UIS3 antigen operably linked to a leader sequence for expression in non-human primates is set forth in SEQ ID NO:31.

In one embodiment, the UIS3 antigen is designed for expression in mice. In one embodiment, a nucleotide sequence encoding a consensus UIS3 antigen for expression in mice encodes a UIS3 antigen as set forth in SEQ ID NO:44. In one embodiment, the sequence for expression in mice is operably linked to a leader sequence having an amino acid sequence as set forth in SEQ ID NO:16. In one embodiment, a nucleotide sequence encoding a consensus UIS3 antigen for expression in mice is set forth in SEQ ID NO:45. In one embodiment, a nucleotide sequence encoding a consensus UIS3 antigen operably linked to a leader sequence for expression in mice is set forth in SEQ ID NO:46.

In one embodiment, the amino acid sequence of the consensus UIS3 antigen is operably linked to an HA tag. In one embodiment, the nucleic acid sequence encodes a consensus UIS3 antigen operably linked to an HA tag.

7. UIS10 Antigen

In one embodiment, the immunogenic composition of the present invention can comprise an UIS10 antigen, a fragment thereof, a variant thereof, or a combination thereof. In various embodiment, the nucleic acid encoding the consensus UIS10 antigen can be codon and RNA optimized for expression in humans, non-human primates or mouse. In one embodiment, a nucleotide sequence encodes a UIS10 antigen as set forth in SEQ ID NO:47. In one embodiment, a nucleotide sequence encodes a UIS10 antigen as set forth in SEQ ID NO:47 operably linked to an IgE leader sequence. In one embodiment, an IgE leader sequence comprises an amino acid sequence as set forth in SEQ ID NO:16. In one a nucleotide sequence encoding a consensus UIS10 antigen is set forth in SEQ ID NO:48. In one a nucleotide sequence encoding a consensus UIS10 antigen operably linked to a sequence encoding an IgE leader sequence is set forth in SEQ ID NO:49.

In one embodiment, the amino acid sequence of the consensus UIS10 antigen is operably linked to an HA tag. In one embodiment, the nucleic acid sequence encodes a consensus UIS10 antigen operably linked to an HA tag.

8. SPECT1 Antigen

In one embodiment, the immunogenic composition of the present invention can comprise a SPECT1 antigen, a fragment thereof, a variant thereof, or a combination thereof. In various embodiment, the nucleic acid encoding the consensus SPECT1 antigen can be codon and RNA optimized for expression in humans, non-human primates or mouse. In one embodiment, a nucleotide sequence encodes a SPECT1 antigen as set forth in SEQ ID NO:80. In one embodiment, a nucleotide sequence encodes a SPECT1 antigen as set forth in SEQ ID NO:80 operably linked to an IgE leader sequence. In one embodiment, an IgE leader sequence comprises an amino acid sequence as set forth in SEQ ID NO:16. In one a nucleotide sequence encoding a consensus SPECT1 antigen is set forth in SEQ ID NO:81. In one a nucleotide sequence encoding a consensus SPECT1 antigen is operably linked to a sequence encoding an IgE leader sequence.

In one embodiment, the amino acid sequence of the consensus SPECT1 antigen is operably linked to an HA tag. In one embodiment, the nucleic acid sequence encodes a consensus SPECT1 antigen operably linked to an HA tag.

9. SPECT2 Antigen

In one embodiment, the immunogenic composition of the present invention can comprise a SPECT2 antigen, a fragment thereof, a variant thereof, or a combination thereof. In various embodiment, the nucleic acid encoding the consensus SPECT2 antigen can be codon and RNA optimized for expression in humans, non-human primates or mouse. In one embodiment, a nucleotide sequence encodes a SPECT2 antigen as set forth in SEQ ID NO:82. In one embodiment, a nucleotide sequence encodes a SPECT2 antigen as set forth in SEQ ID NO:82 operably linked to an IgE leader sequence. In one embodiment, an IgE leader sequence comprises an amino acid sequence as set forth in SEQ ID NO:16. In one a nucleotide sequence encoding a consensus SPECT2 antigen is set forth in SEQ ID NO:83. In one a nucleotide sequence encoding a consensus SPECT2 antigen is operably linked to a sequence encoding an IgE leader sequence.

In one embodiment, the amino acid sequence of the consensus SPECT2 antigen is operably linked to an HA tag. In one embodiment, the nucleic acid sequence encodes a consensus SPECT2 antigen operably linked to an HA tag.

10. RON2 Antigen

In one embodiment, the immunogenic composition of the present invention can comprise a RON2 antigen, a fragment thereof, a variant thereof, or a combination thereof. In various embodiment, the nucleic acid encoding the consensus RON2 antigen can be codon and RNA optimized for expression in humans, non-human primates or mouse. In one embodiment, a nucleotide sequence encodes a RON2 antigen as set forth in SEQ ID NO:53. In one embodiment, a nucleotide sequence encodes a RON2 antigen as set forth in SEQ ID NO:53 operably linked to an IgE leader sequence. In one embodiment, an IgE leader sequence comprises an amino acid sequence as set forth in SEQ ID NO:16. In one a nucleotide sequence encoding a consensus RON2 antigen is set forth in SEQ ID NO:54. In one a nucleotide sequence encoding a consensus RON2 antigen operably linked to a sequence encoding an IgE leader sequence is set forth in SEQ ID NO:55.

In one embodiment, the amino acid sequence of the consensus RON2 antigen is operably linked to an HA tag. In one embodiment, the nucleic acid sequence encodes a consensus RON2 antigen operably linked to an HA tag.

11. Fusion Antigen

In some embodiments, fusion proteins are provided which comprise a combination of at least one of the LS proteins set forth herein with at least one other amino acid sequence. In one embodiment, fusion proteins may comprise one of EXP1, EXP2, EXP23, ICP, TMP21, UIS3, UIS10, SPECT1, SPECT2 and RON2 linked directly adjacent to another amino acid sequence. In one embodiment, fusion proteins may comprise two or more of EXP1, EXP2, EXP23, ICP, TMP21, UIS3, UIS10, SPECT1, SPECT2 and RON2 linked directly adjacent to each other or linked with a spacer or one or more amino acids in between.

In some embodiments the fusion protein comprises at least 1, 2, 3, 4, 5, 6, 7, 8, 9, 10 or more than 10 LS immunogens. Non-limiting, exemplary fusion proteins with two LS immunogens may comprise: EXP1 and EXP2; EXP1 and EXP23; EXP1 and ICP; EXP1 and TMP21; EXP1 and UIS3; EXP2 and EXP23; EXP2 and ICP; EXP2 and TMP21; EXP2 and UIS3; EXP23 and ICP; EXP23 and TMP21; EXP23 and UIS3; ICP and TMP21; ICP and UIS3; or TMP21 and UIS3. Non-limiting, exemplary fusion proteins with three LS immunogens may comprise: EXP1, EXP2 and EXP23; EXP1, EXP2 and ICP; EXP1, EXP2 and TMP21; EXP1, EXP2 and UIS3; EXP1, EXP23 and ICP; EXP1, EXP23 and TMP21; EXP1, EXP23 and UIS3; EXP1, ICP and TMP21; EXP1, ICP and UIS3; EXP1, TMP21 and UIS3; EXP2, EXP23 and ICP; EXP2, EXP23 and TMP21; EXP2, EXP23 and UIS3; EXP2, ICP and TMP21; EXP2, ICP and UIS3; EXP2, TMP21 and UIS3; EXP23, ICP and TMP21; EXP23, ICP and UIS3; EXP23, TMP21 and UIS3; or ICP, TMP21 and UIS3.

In some embodiments, a fusion protein may comprise one or more amino acid sequence selected from SEQ ID NO:1, SEQ ID NO:4, SEQ ID NO:7, SEQ ID NO:10, SEQ ID NO:13, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:68, SEQ ID NO:70, SEQ ID NO:72, SEQ ID NO:74, SEQ ID NO:76, SEQ ID NO:78, SEQ ID NO:80, SEQ ID NO:82 or homologs or fragments thereof. In one embodiment, a fusion protein comprises at least 1, 2, 3, 4, 5, 6, 7, 8, 9, 10 or more than 10 sequences selected from SEQ ID NO:1, SEQ ID NO:4, SEQ ID NO:7, SEQ ID NO:10, SEQ ID NO:13, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:68, SEQ ID NO:70, SEQ ID NO:72, SEQ ID NO:74, SEQ ID NO:76, SEQ ID NO:78, SEQ ID NO:80, SEQ ID NO:82 or homologs or fragments thereof.

In one embodiment, a fusion protein may comprise one or more amino acid sequences encoding one or more LS immunogens selected from: EXP1, EXP2, EXP23, ICP, TMP21, UIS3, UIS10, SPECT1, SPECT2 and RON2 fused with another *Plasmodium* spp. antigen. *Plasmodium* spp. antigens that are appropriate for fusion with the malaria LS immunogens of the invention are provided in PCT application no. PCT/US2011/53541 and corresponding U.S. application Ser. No. 13/876,148, the contents of which are fully incorporated by reference. Therefore, in one embodiment, a fusion protein of the invention may comprise one or more amino acid sequences encoding one or more LS immunogens selected from: EXP1, EXP2, EXP23, ICP, TMP21, UIS3, UIS10, SPECT1, SPECT2 and RON2 and one or more amino acid sequences encoding one or more PS. immunogens selected from: CSP, LSA1, TRAP, CelTOS and Ama1. In one embodiment, a fusion protein of the invention may comprise one or more amino acid sequences encoding a fragment of one or more LS immunogens selected from: EXP1, EXP2, EXP23, ICP, TMP21, UIS3, UIS10, SPECT1, SPECT2 and RON2 and one or more amino acid sequences encoding a fragment of one or more PS. immunogens selected from: CSP, LSA1, TRAP, CelTOS and Ama1. In one embodiment, a fusion protein of the invention may comprise one or more amino acid sequences encoding a protein greater than 98% or greater than 99% homologous to one or more LS immunogens selected from: EXP1, EXP2, EXP23, ICP, TMP21, UIS3, UIS10, SPECT1, SPECT2 and RON2 and one or more amino acid sequences encoding a protein greater than 98% or greater than 99% homologous to one or more P.f. immunogens selected from: CSP, LSA1, TRAP, CelTOS and Ama1.

In some embodiments, the fusion proteins comprise a signal peptide linked to the N terminus. In some embodiments, the fusion proteins comprises multiple signal peptides linked to the N terminal of each LS immunogen. In some embodiments, a spacer may be included between LS immunogens of a fusion protein. In some embodiments, the spacer between LS immunogens of a fusion protein may be a proteolyic cleavage site. In some embodiments, the spacer may be a proteolyic cleavage site recognized by a protease found in cells to which the immunogenic composition is intended to be administered and/or taken up. In some embodiments, a spacer may be included between LS immunogens of a fusion protein wherein the spacer is a proteolyic cleavage site recognized by a protease found in cells to which the immunogenic composition is intended to be administered and/or taken up and the fusion proteins comprises multiple signal peptides linked to the N terminal of each LS immunogen such that, upon cleavage, the signal peptide of each LS immunogen translocates the immunogen to outside the cell.

a. EXP1_EXP2 Fusion Antigen

In one embodiment, the immunogenic composition of the present invention can comprise a fusion EXP1_EXP2 antigen, a fragment thereof, a variant thereof, or a combination thereof. The nucleic acid encoding the consensus fusion EXP1_EXP2 antigen can be codon and RNA optimized for expression in humans. In one embodiment, a nucleotide sequence encodes a fusion EXP1_EXP2 antigen as set forth in SEQ ID NO:1. In one embodiment, a nucleotide sequence encodes a fusion EXP1_EXP2 antigen as set forth in SEQ ID NO:1 operably linked to an IgE leader sequence. In one embodiment, an IgE leader sequence comprises an amino acid sequence as set forth in SEQ ID NO:16. In one a nucleotide sequence encoding a consensus fusion EXP1_EXP2 antigen is set forth in SEQ ID NO:2. In one a nucleotide sequence encoding a consensus fusion EXP1_EXP2 antigen operably linked to a sequence encoding an IgE leader sequence is set forth in SEQ ID NO:3.

In one embodiment, the fusion EXP1_EXP2 antigen is designed for expression in non-human primates. In one embodiment, a nucleotide sequence encoding a consensus fusion EXP1_EXP2 antigen for expression in non-human primates encodes a fusion EXP1_EXP2 antigen as set forth in SEQ ID NO:17. In one embodiment, the sequence for expression in a non-human primate is operably linked to a leader sequence having an amino acid sequence as set forth in SEQ ID NO:16. In one embodiment, a nucleotide sequence encoding a consensus fusion EXP1_EXP2 antigen for expression in non-human primates is set forth in SEQ ID NO:18. In one embodiment, a nucleotide sequence encoding a consensus fusion EXP1_EXP2 antigen operably linked to a leader sequence for expression in non-human primates is set forth in SEQ ID NO:19.

In one embodiment, the fusion EXP1_EXP2 antigen is designed for expression in mice. In one embodiment, a nucleotide sequence encoding a consensus fusion EXP1_EXP2 antigen for expression in mice encodes a fusion EXP1_EXP2 antigen as set forth in SEQ ID NO:32. In one embodiment, the sequence for expression in mice is operably linked to a leader sequence having an amino acid sequence as set forth in SEQ ID NO:16. In one embodiment, a nucleotide sequence encoding a consensus fusion EXP1_EXP2 antigen for expression in mice is set forth in SEQ ID NO:33. In one embodiment, a nucleotide sequence encoding a consensus fusion EXP1_EXP2 antigen operably linked to a leader sequence for expression in mice is set forth in SEQ ID NO:34.

In one embodiment, the amino acid sequence of the consensus fusion EXP1_EXP2 antigen is operably linked to an HA tag. In one embodiment, the nucleic acid sequence encodes a consensus fusion EXP1_EXP2 antigen operably linked to an HA tag.

b. SPECT1 SPECT2 Fusion Antigen

In one embodiment, the immunogenic composition of the present invention can comprise a SPECT1 SPECT2 fusion antigen, a fragment thereof, a variant thereof, or a combination thereof. In various embodiment, the nucleic acid encoding the consensus SPECT1 SPECT2 fusion antigen can be codon and RNA optimized for expression in humans, non-human primates or mouse. In one embodiment, a nucleotide sequence encodes a SPECT1_SPECT2 fusion antigen as set forth in SEQ ID NO:50. In one embodiment, a nucleotide sequence encodes a SPECT1_SPECT2 fusion antigen as set forth in SEQ ID NO:50 operably linked to an IgE leader sequence. In one embodiment, an IgE leader sequence comprises an amino acid sequence as set forth in SEQ ID NO:16. In one a nucleotide sequence encoding a consensus SPECT1_SPECT2 fusion antigen is set forth in SEQ ID NO:51. In one a nucleotide sequence encoding a consensus SPECT1_SPECT2 fusion antigen operably linked to a sequence encoding an IgE leader sequence is set forth in SEQ ID NO:52.

In one embodiment, the amino acid sequence of the consensus SPECT1_SPECT2 fusion antigen is operably linked to an HA tag. In one embodiment, the nucleic acid sequence encodes a consensus SPECT1 SPECT2 fusion antigen operably linked to an HA tag.

3. Protein Coding Sequences

Provided herein are nucleic acid sequences that encode the LS immunogens. Administration of nucleic acid molecules comprising the nucleic acid sequences when taken up and expressed by cells results in a broad immune response against a *Plasmodium* spp. Coding sequences for LS proteins may encode EXP1, EXP2, EXP23, ICP, TMP21, UIS3, UIS10, SPECT1, SPECT2 and RON2, a fusion thereof, a fragment thereof, or a homolog thereof as described herein, a homologous variant amino acid sequence as described herein, or a fragment of a homologous variant amino acid sequence. In some embodiments, the coding sequences that encode EXP1, EXP2, EXP23, ICP, TMP21, UIS3, UIS10, SPECT1, SPECT2 and RON2 may be a DNA sequence. In some embodiments, the coding sequences that encode EXP1, EXP2, EXP23, ICP, TMP21, UIS3, UIS10, SPECT1, SPECT2 and RON2 may be an RNA sequence. In one embodiment, a coding sequence may be a DNA or RNA molecule encoding one or more amino acid sequence selected from SEQ ID NO:1, SEQ ID NO:4, SEQ ID NO:7, SEQ ID NO:10, SEQ ID NO:13, SEQ ID NO:17, SEQ ID NO:20, SEQ ID NO:23, SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, SEQ ID NO:53, SEQ ID NO:68, SEQ ID NO:70, SEQ ID NO:72, SEQ ID NO:74, SEQ ID NO:76, SEQ ID NO:78, SEQ ID NO:80, SEQ ID NO:82 or homologs or fragments thereof. In one embodiment, the coding sequence further encodes an IgE leader sequence as set forth in SEQ ID NO:16. In one embodiment, the coding sequence further encodes an HA tag.

4. Plasmid

Provided herein is a vector that is capable of expressing a LS immunogen or a fragment thereof in the cell of a mammal in a quantity effective to elicit an immune response in the mammal. The vector may comprise heterologous nucleic acid encoding the LS immunogen or a fragment thereof. The vector may be a plasmid. The plasmid may be useful for transfecting cells with nucleic acid encoding the LS immunogen or a fragment thereof, which the transformed host cell is cultured and maintained under conditions wherein expression of the LS immunogen or a fragment thereof takes place.

Plasmids may comprise DNA constructs which comprise one or more coding sequences encoding LS immunogens as disclosed herein. The coding sequences encoding LS immunogens as disclosed herein are preferable operably linked to regulatory elements.

In some embodiments, a plasmid has DNA constructs that include coding sequence for at least one LS immunogen, i.e. one of EXP1, EXP2, EXP23, ICP, TMP21, UIS3, UIS10, SPECT1, SPECT2 and RON2.

In some embodiments, a plasmid has DNA constructs that include coding sequence for multiple LS immunogens. In some embodiments, for a plasmid that has DNA constructs that include coding sequence for multiple LS immunogens, the constructs may be separate expression cassettes wherein each LS immunogen comprises a separate set of regulatory elements or two or more coding sequences may be incorporated into a single expression cassette in which coding sequences are separated by an IRES sequence.

In some embodiments, a plasmid has DNA constructs that include coding sequence for two LS immunogens. Such plasmids may comprise DNA constructs that include coding sequence for at least two of EXP1, EXP2, EXP23, ICP, TMP21, UIS3, UIS10, SPECT1, SPECT2 and RON2. In some embodiments, a plasmid has DNA constructs that include coding sequence for at least three of EXP1, EXP2, EXP23, ICP, TMP21, UIS3, UIS10, SPECT1, SPECT2 and RON2. In some embodiments, a plasmid has DNA constructs that include coding sequence for more than three LS immunogens. In some embodiments, a plasmid has DNA constructs that include coding sequence for 4, 5, 6, 7, 8, 9, 10 or more than 10 LS immunogens. In some embodiments, a plasmid has DNA constructs that include coding sequence for 4, 5, 6, 7, 8, 9 or 10 of EXP1, EXP2, EXP23, ICP, TMP21, UIS3, UIS10, SPECT1, SPECT2 and RON2.

In some embodiments, a plasmid having DNA constructs that include coding sequence for one or more LS immunogen, i.e. one or more of EXP1, EXP2, EXP23, ICP, TMP21, UIS3, UIS10, SPECT1, SPECT2 and RON2, further comprises coding sequence for one or more additional *Plasmodium* spp. antigen. Exemplary *Plasmodium* spp. antigens that may be encoded on a plasmid of the invention include, but are not limited to CSP, LSA1, TRAP, CelTOS and Ama1, or fragments thereof or homologs thereof, as disclosed in PCT application no. PCT/US2011/53541 and corresponding U.S. application Ser. No. 13/876,148.

The plasmid may comprise a nucleic acid encoding a protein that comprises the LS immunogen or a fragment thereof linked to an Ig signal peptide sequence at its N terminus. The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence. The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human (3-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig signal peptide sequence. The coding sequence of the signal peptide sequence may be 5' of the coding sequence. The antigens encoded by this sequence may comprise an N-terminal Ig signal peptide followed by a antigen protein. The N-terminal Ig signal peptide may be IgE or IgG. U.S. Pat. No. 6,733, 994, which is incorporated herein by reference, discloses constructs which comprise optimized RNA sequences and IgE signal peptide sequence. PCT application no. PCT/US04/18962 and corresponding U.S. application Ser. No. 10/560,650, which are both incorporated herein by reference, also disclose constructs which comprise IgE signal peptide sequences.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA1 or pcDNA3 (Invitrogen, San Diego, Calif.), which may be used for protein production in mammalian cells such as Chinese hamster ovary (CHO) cells.

Compositions are provided which comprise plasmids. The compositions may comprise a plurality of copies of a single nucleic acid molecule such as a single plasmid, a plurality of copies of a two or more different nucleic acid molecules such as two or more different plasmids. For example a compositions may comprise plurality of one, two, three, four, five, six, seven, eight, nine or ten or more different nucleic acid molecules. Such a compositions may comprise plurality of one, two, three, four, five, six, seven, eight, nine or ten or more different plasmids. Compositions may comprise coding sequences for one or more of EXP1, EXP2, EXP23, ICP, TMP21, UIS3, UIS10, SPECT1, SPECT2 and RON2. Compositions may comprise nucleic acid molecules, such as plasmids, that collectively contain coding sequence for at least 1, 2, 3, 4, 5, 6, 7, 8, 9, 10 or more than 10 LS immunogen, coding sequence for two LS immunogens. Compositions comprising coding sequence for at least 1, 2, 3, 4, 5, 6, 7, 8, 9, 10 or more than 10 LS immunogens may be on a single nucleic acid molecule such as a single plasmid or the compositions may comprise two or more different nucleic acid molecule. In some embodiments, a composition comprises a plurality of different nucleic acid molecules, such as 2, 3, 4, 5, 6, 7, 8, 9, 10 or more than 10 plasmids, which collectively comprising coding sequence for 2, 3, 4, 5, 6, 7, 8, 9, 10 or more than 10 different LS immunogens.

In one embodiment, one or more nucleic acid molecules are DNA molecules. In one embodiment, one or more nucleic acid molecules are RNA molecules.

In some embodiments, a composition further comprises one or more plasmids comprising coding sequence for one or more additional *Plasmodium* spp. antigen. In one embodiment, a single plasmid encodes at least 1, 2, 3, 4, 5, 6, 7, 8, 9, 10 or more than 10 LS immunogens and further encodes one or more additional antigens. In one embodiment, one or more additional antigen is selected from CSP, LSA1, TRAP, CelTOS and Ama1, or fragments thereof, or homologs thereof.

In one embodiment the nucleotide sequence encoding TRAP comprises an amino acid sequence as set forth in SEQ ID NO:56, SEQ ID NO:59 or SEQ ID NO:65. In one embodiment the nucleotide sequence encoding CSP comprises an amino acid sequence as set forth in SEQ ID NO:62. In one embodiment the nucleotide sequence encoding CelTOS comprises an amino acid sequence as set forth in SEQ ID NO:56.

In one embodiment the nucleotide sequence encoding TRAP comprises is set forth in SEQ ID NO:57, SEQ ID NO:58, SEQ ID NO:60, SEQ ID NO:61, SEQ ID NO:66 or SEQ ID NO:67. In one embodiment the nucleotide sequence encoding CSP comprises SEQ ID NO:63 or SEQ ID NO:64. In one embodiment the nucleotide sequence encoding Cel-TOS comprises SEQ ID NO:57 or SEQ ID NO:58.

In some embodiments, a composition further comprises coding sequence for one or more adjuvant. Adjuvants include, but are not limited to, IL-12, IL-15, IL-28B, IL-33 and RANTES. Coding sequence for IL-12, IL-15, IL-28B, IL-33 and/or RANTES may be included on one or more nucleic acid molecules that comprise coding sequence for one or more LS immunogens. Coding sequence for IL-12, IL-15, IL-28B, IL-33 and/or RANTES may be included on a separate nucleic acid molecules such as a separate plasmid.

5. Immunogenic Composition Formulation

Provided herein are immunogenic compositions capable of generating in a mammal an immune response against a *Plasmodium* spp., and preferably against malaria. The immunogenic composition may comprise one or more plasmid as discussed above. The immunogenic composition may comprise a plurality of the plasmids, or combinations thereof. The immunogenic composition may be provided to induce a therapeutic or prophylactic immune response against a *Plasmodium* spp.

The immunogenic composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the immunogenic composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid immunogenic compositions may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the immunogenic composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the immunogenic composition. The one or more adjuvants may be proteins and/or nucleic acid molecules that encode proteins selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or a combination thereof. In some embodiments adjuvant may be one or more proteins and/or nucleic acid molecules that encode proteins selected from the group consisting of: IL-12, IL-15, IL-28, IL-33 CTACK, TECK, MEC or RANTES. Examples of IL-12 constructs and sequences are disclosed in PCT application no. PCT/US1997/019502 and corresponding U.S. application Ser. No. 08/956,865, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/US10/048827, which are each incorporated herein by reference. Examples of IL-28 constructs and sequences are disclosed in PCT application no. PCT/US09/039648 and corresponding U.S. application Ser. No. 12/936, 192, which are each incorporated herein by reference. Examples of IL-33 constructs and sequences are disclosed in PCT application no. PCT/US14/58727 and corresponding U.S. application Ser. No. 15/026,162, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

The immunogenic composition may further comprise a genetic immunogenic composition facilitator agent as described in U.S. Ser. No. 021,579 filed Apr. 1, 1994, which is fully incorporated by reference.

The immunogenic composition may comprise the antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the antigen or plasmid thereof.

The immunogenic composition may be formulated according to the mode of administration to be used. An injectable immunogenic composition pharmaceutical composition may be sterile, pyrogen free and particulate free. An isotonic formulation or solution may be used. Additives for isotonicity may include sodium chloride, dextrose, mannitol, sorbitol, and lactose. The immunogenic composition may comprise a vasoconstriction agent. The isotonic solutions may include phosphate buffered saline. Immunogenic composition may further comprise stabilizers including gelatin and albumin. The stabilizing may allow the formulation to be stable at room or ambient temperature for extended periods of time such as LGS or polycations or polyanions to the immunogenic composition formulation.

In addition to using genetic immunogenic compositions such as DNA immunogenic compositions, coding sequences and or proteins may be incorporated into to attenuated live immunogenic compositions, recombinant vectors or subunit immunogenic compositions. Examples of attenuated live immunogenic compositions and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference.

6. Methods of Delivery the Immunogenic Composition

Provided herein is a method for delivering the immunogenic composition for providing genetic constructs and proteins of the antigen which comprise epitopes that make them particular effective against immunogens of malaria against which an immune response can be induced. The method of delivering the immunogenic composition or vaccination may be provided to induce a therapeutic and prophylactic immune response. The vaccination process may generate in the mammal an immune response against malaria. The immunogenic composition may be delivered to an individual to modulate modulate the activity of the mammal's immune system and enhance the immune response. The delivery of the immunogenic composition may be the transfection of the antigen as a nucleic acid molecule that is expressed in the cell and delivered to the surface of the cell upon which the immune system recognized and induces a cellular, humoral, or cellular and humoral response. The delivery of the immunogenic composition may be use to induce or elicit and immune response in mammals against malaria by administering to the mammals the immunogenic composition as discussed above.

Upon delivery of the immunogenic composition and plasmid into the cells of the mammal, the transfected cells will express and secrete antigens for each of the plasmids injected from the immunogenic composition. These proteins will be recognized as foreign by the immune system and antibodies will be made against them. These antibodies will be maintained by the immune system and allow for an effective response to subsequent malaria infections.

The immunogenic composition may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

a. Combination Treatments

The immunogenic composition may be administered in combination with other proteins and/or genes encoding .alpha.-interferon, .gamma.-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, MHC, CD80, CD86, IL-28, IL-1, IL-2, IL-4, IL-5, IL-6, IL-10, IL-18, IL-33, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. In some embodiments, the immunogenic composition is administered in combination with one or more of the following nucleic acid molecules and/or proteins: nucleic acid molecules selected from the group consisting of nucleic acid molecules comprising coding sequence that encode one or more of IL-12, IL-15, IL-28, IL-33, CTACK, TECK, MEC and RANTES or functional fragments thereof, and proteins selected from the group consisting of: IL-12 protein, IL-15 protein, IL-28 protein, IL-33 protein, CTACK protein, TECK protein, MEC protein or RANTES protein or functional fragments thereof.

The immunogenic composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The immunogenic composition may be administered by traditional syringes, needleless injection devices, "microprojectile bombardment gone guns", or other physical methods such as electroporation ("EP"), "hydrodynamic method", or ultrasound.

The plasmid of the immunogenic composition may be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The antigen may be delivered via DNA injection and along with in vivo electroporation.

b. Electroporation

Administration of the immunogenic composition via electroporation of the plasmids of the immunogenic composition may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (VGX Pharmaceuticals, Blue Bell, Pa.) or Elgen electroporator (Genetronics, San Diego, Calif.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA immunogenic compositions of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA immunogenic compositions include those provided in and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

c. Protein Boost

In some embodiments, one or more LS immunogen may be delivered as protein as part of immunogenic composition protocol. In some embodiments, subsequent to the initial immunization vaccination in which plasmid DNA compositions as disclosed herein are administered, protein immunogens are delivered as a boost. In some embodiments, boosts are combinations of plasmid DNA immunogenic composition and protein. In some embodiments, multiple boosts are administered. In some embodiments, multiple boosts are administered wherein one or more boosts are protein administration and one or more boosts a DNA immunogenic composition administration. Boosts employing viral vectors and/or killed or attenuated pathogen may also be employed. One or more vaccinations may be administered, independent with respect to all times other than the initial or most recent, within one day, one week, two weeks, three weeks, four weeks, six weeks, eight weeks, twelve weeks, six months, one year apart.

Proteins used in protein boosts may be produced by routine methods using the information disclosed herein and well known methodology. For example, recombinant vectors that include coding sequences for the proteins may be produced and used to generate large quantities of protein. Recombinant expression vectors that comprises a nucleotide sequence that encodes proteins of the invention can be produced routinely. As used herein, the term "recombinant expression vector" is meant to refer to a plasmid, phage, viral particle or other vector which, when introduced into an appropriate host, contains the necessary genetic elements to direct expression of a coding sequence. One having ordinary skill in the art can isolate or synthesize a nucleic acid molecule that encodes a protein of the invention and insert it into an expression vector using standard techniques and readily available starting materials. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. The recombinant expression vectors of the invention are useful for transforming hosts.

Host cells that comprise the recombinant expression vector can be used to produce the protein. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

In some embodiments, for example, one having ordinary skill in the art can, using well known techniques, insert DNA molecules into a commercially available expression vector for use in well known expression systems. For example, the commercially available plasmid pSE420 (Invitrogen, San Diego, Calif.) may be used for production of a protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA1 or pcDNA3 (Invitrogen, San Diego, Calif.) may, for example, be used for production in mammalian cells such as Chinese Hamster Ovary cells. One having ordinary skill in the art can use these commercial expression vectors and systems or others to produce proteins of the invention using routine techniques and readily available starting materials. (See e.g., Sambrook et al., Molecular Cloning a Laboratory Manual, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., Molecular Cloning a Laboratory Manual, Second Ed. Cold Spring Harbor Press (1989).

The expression vector including the DNA that encodes a protein is used to transform the compatible host which is then cultured and maintained under conditions wherein expression of the foreign DNA takes place. The protein of the invention thus produced is recovered from the culture, either by lysing the cells or from the culture medium as appropriate and known to those in the art. One having ordinary skill in the art can, using well known techniques, isolate the protein of the invention that is produced using such expression systems. The methods of purifying proteins of the invention from natural sources using antibodies which specifically bind to such protein are routine as is the methods of generating such antibodies (See: Harlow, E. and Lane, E., Antibodies: A Laboratory Manual, 1988, Cold Spring Harbor Laboratory Press which is incorporated herein by reference). Such antibodies may be used to purifying proteins produced by recombinant DNA methodology or natural sources.

Examples of genetic constructs include coding sequences which encode a protein of the invention and which are operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes proteins of the invention from readily available starting materials. Such gene constructs are useful for the production of proteins of the invention.

In addition to producing proteins of the invention by recombinant techniques, automated peptide synthesizers may also be employed to produce proteins of the invention. Such techniques are well known to those having ordinary skill in the art and are useful if derivatives which have substitutions not provided for in DNA-encoded protein production. For example, the proteins of the invention may be prepared by any of the following known techniques. Conveniently, the proteins of the invention may be prepared using the solid-phase synthetic technique initially described by Merrifield, in J. Am. Chem. Soc., 15:2149-2154 (1963) which is incorporated herein by reference. Other protein synthesis techniques may be found, for example, in M. Bodanszky et al., (1976) Peptide Synthesis, John Wiley & Sons, 2d Ed. which is incorporated herein by reference; Kent and Clark-Lewis in Synthetic Peptides in Biology and Medicine, p. 295-358, eds. Alitalo, K., et al. Science Publishers, (Amsterdam, 1985) which is incorporated herein by reference; as well as other reference works known to those skilled in the art. A summary of synthesis techniques may be found in J. Stuart and J. D. Young, Solid Phase Peptide Synthelia, Pierce Chemical Company, Rockford, Ill. (1984) which is incorporated herein by reference. Synthesis by solution methods may also be used, as described in The Proteins, Vol. II, 3d Ed., p. 105-237, Neurath, H. et al., Eds., Academic Press, New York, N.Y. (1976) which is incorporated herein by reference. Appropriate protective groups for use in such syntheses will be found in the above texts, as well as in J. F. W. McOmie, Protective Groups in Organic Chemistry, Plenum Press, New York, N.Y. (1973) which is incorporated herein by reference. In general, these synthetic methods involve the sequential addition of one or more amino acid residues or suitable protected amino acid residues to a growing peptide chain. Normally, either the amino or carboxyl group of the first amino acid residue is protected by a suitable, selectively-removable protecting group. A different, selectively removable protecting group is utilized for amino acids containing a reactive side group, such as lysine.

Proteins may be formulated for administration to a mammal by well known methods using readily available materials. One skilled in the art would readily comprehend the multitude of pharmaceutically acceptable media that may be used in the present invention. Suitable pharmaceutical carriers are described in Remington's Pharmaceutical Sciences, A. Osol, a standard reference text in this field, which is incorporated herein by reference. Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral, intravenous, intrathecal or intraventricular administration may include sterile aqueous solutions which may also contain buffers, diluents and other suitable additives and are preferably sterile and pyrogen free. Pharmaceutical compositions which are suitable for intravenous administration according to the invention are sterile and pyrogen free. For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions comprising protein according to the present invention may be administered as a single dose or in multiple doses. Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Formulation of therapeutic compositions and their subsequent administration is believed to be within the skill of those in the art. Usually, the dosage of peptide can be about 1 micrograms to 1000 milligrams or more; 10 micrograms to 1000 milligrams; preferably 50 micrograms to 500 milligrams; more preferably 100 micrograms to 400 milligrams. In some embodiments, dosages are in the rage of 10-250 micrograms. In some embodiments, dosages are higher, for example 250 micrograms-1 milligram, or higher such as 1-50 milligrams. In some embodiments, dosages are higher still, for example 50-500 milligrams.

d. Method of Preparing DNA Plasmids

Provided herein is methods for preparing the DNA plasmids that comprise the DNA immunogenic compositions discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1: Small Liver Stage Exported Proteins as Promising Novel Malaria DNA Immunogenic Compositions Malaria vaccines so far that elicited sterile protection in human and animal models are live attenuated sporozoites. This sterile protection is mainly mediated by CD8+ CTL, which is directed against hepatocytes infected with growth-arrested liver stages (LS). The invention is based on the discovery that proteins exported at or beyond the parasitophorous vacuolar membrane at the parasite-host interface could be displayed on MHC I molecules on the surface of infected hepatocytes (FIG. 1).

The materials and methods are now described

Construction and Design of Optimized LS Immunogens

A panel of plasmids expressing EXP1 and EXP2, EXP23, ICP, TMP21 and UIS3 were constructed using the pVAX1 backbone (Invitogen). All sequences were obtained from GenBank. Inserts were RNA and codon optimized to increased expression and cloned into pVAX1 using either BamHI/XhoI or BamHI/EcoRI.

Immune Response in Vaccinated Mice

For cellular immunogenicity studies, 30 μg of each antigen-encoding plasmid was delivered to the tibialis anterior muscle of Balb/c mice by intramuscular injection followed by electroporation using the CELLECTRA™ adaptive constant current electroporation device (Inovio Pharmaceuticals, Blue Bell Pa.). For all studies in which IL-12 was provided as an adjuvant, 11 μg of IL-12 encoding plasmid was co-delivered. For all studies in which IL-33 was provided as an adjuvant, 25 μg of IL-33 encoding plasmid was co-delivered. For the initial study, mice received 3 immunizations at weeks 0, 4 and 8. Cellular and responses were assessed 6 weeks after the last immunization (week 14) (FIG. 3A). For the second study, mice received 4 immunizations at weeks 0, 3, 6 and 9. Cellular and responses were assessed by ELISpot 6 weeks after the last immunization (week 14), and the mice were challenged with sporozoites at week 18 then monitored daily for 10 days for signs of BS disease (FIG. 4A). For a third study, mice received 4 immunizations at weeks 0, 3, 6 and 9. Cellular and responses were assessed 9 weeks after the last immunization (week 18) via ELISpot on one group of mice and a parallel group was challenged with sporozoites and monitored for an additional 10 days for signs of BS disease (FIG. 7A). ELISpots were carried out per manufacturer's instructions (R&D Systems) using 96-well plates (Millipore). $2 \times 10^5$ splenocytes from each immunized mouse were added to each well of the plates and stimulated overnight at 37° C., 5% $CO_2$, in the presence of R10 (negative control), concanavalin A (positive control), or peptide pools specific to each antigen. Peptide pools are composed of 15-mer peptides spanning the entire protein, overlapping by 11 amino acids.

Mouse Studies Using Multi-Antigen pDNA Immunogenic Composition Candidates Delivered Via In Vivo Electroporation Improved DNA immunogenic compositions for malaria through a multi-antigen immunogenic composition approach are the subject of studies. A multi-antigen DNA immunogenic composition candidate was delivered by intramuscular injection (i.m.) and electroporation (EP), which targets the liver-stage of Plasmodium spp. infection was assessed in initial mouse studies. This immunogenic composition candidate incorporated six important malaria LS antigens: EXP1, EXP2, EXP23, ICP, TMP21 and UIS3. The immunogenic composition antigens were designed based on *Plasmodium yoelii* sequences with several modifications to improve expression including codon and RNA optimization and the addition of a highly efficient IgE leader sequence.

Prior to immunogenicity studies in Balb/c mice, antigen expression was confirmed by in vitro translation, western blotting and immunohistochemistry. In mice, the immunogenic compositions elicited strong, antigen-specific cellular and humoral responses that were similar to, or surpassed, those induced by other vector systems. Specifically, interferon-gamma (IFNγ) spot forming cells per $10^6$ splenocytes (SFU) were quantified by ELISpot.

Current evidence supports that a malaria immunogenic composition candidate that elicits both strong humoral and cellular responses to multiple liver-stage antigens may be able to confer protection to malaria. Thus, the end goal of this immunogenic composition approach is to induce cellular and humoral responses to multiple liver-stage antigens simultaneously. Several studies were carried out in the mouse model to further optimize immunogenic composition design and delivery and to further characterize immunogenic composition-induced immune responses.

The Results are Now Described

Small LS exported proteins that are conserved in all *Plasmodium* species were selected (FIG. 2) and used in different combinations as DNA immunogenic compositions (FIGS. 3B, 4B and 7B). First, groups of BALB/c mice were immunized with intramuscular injections of synthetic DNA immunogenic composition constructs encoding six different small LS exported proteins (EXP1, EXP2, EXP23, UIS3, TLP21 and ICP). The nucleic acid molecules were introduced via electroporation, with or without different cytokines as adjuvants. Sterile protection against sporozoite challenges was observed in most immunization groups with combinations of different LS exported antigens with cytokines that bias immune responses toward Th1. Collectively, our data demonstrate the potential of using different combinations of small LS exported proteins in DNA immunogenic compositions against malaria parasite infection.

Figure 8:
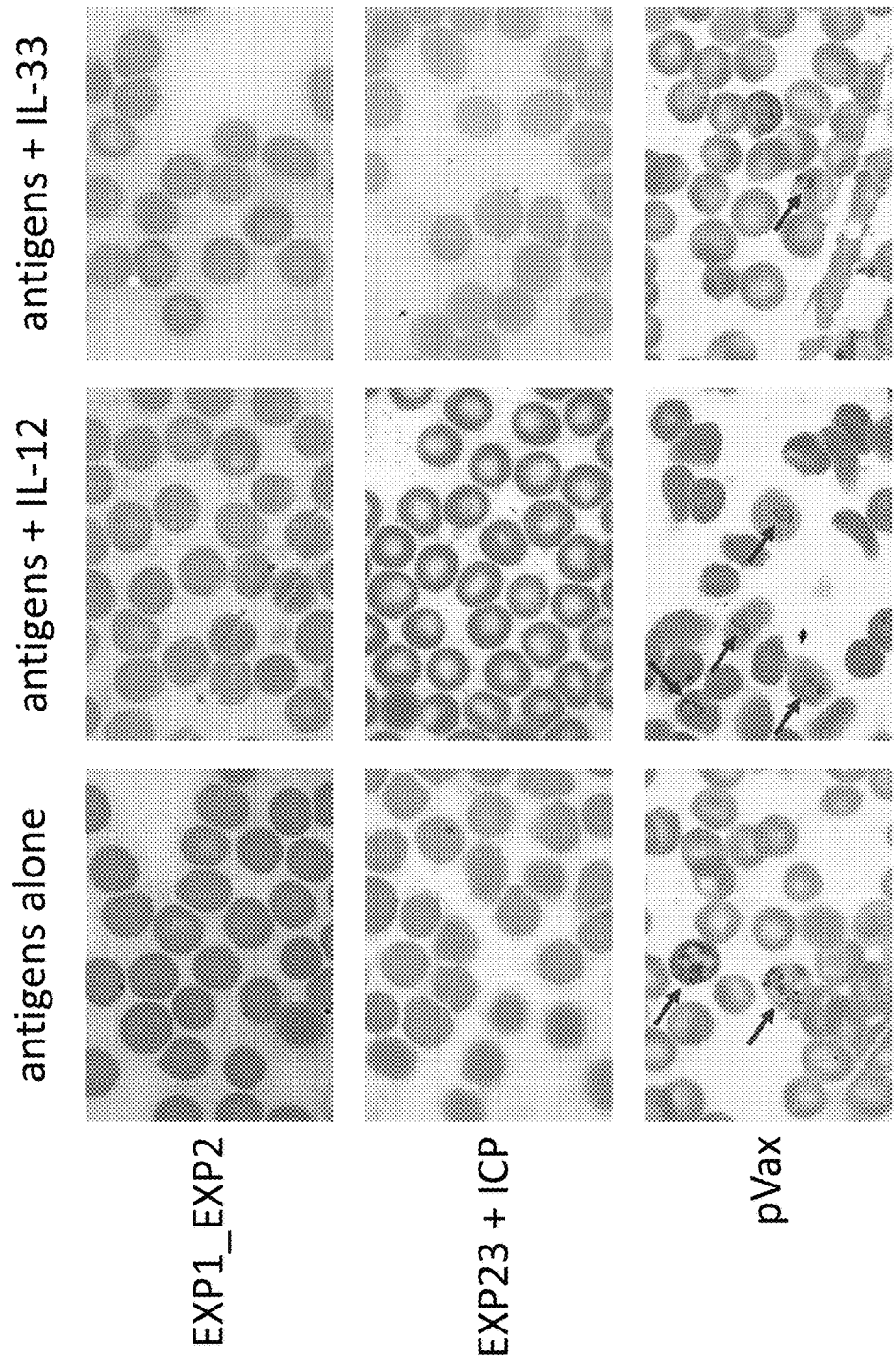
FIG. 8 depicts representative images of blood from mice immunized with EXP_1 and EXP2 antigens, EXP23 and ICP antigens or pVAX alone or in combination with an adjuvant (IL-12 or IL-33). Red arrows indicate development of BS disease.
Figure 9:
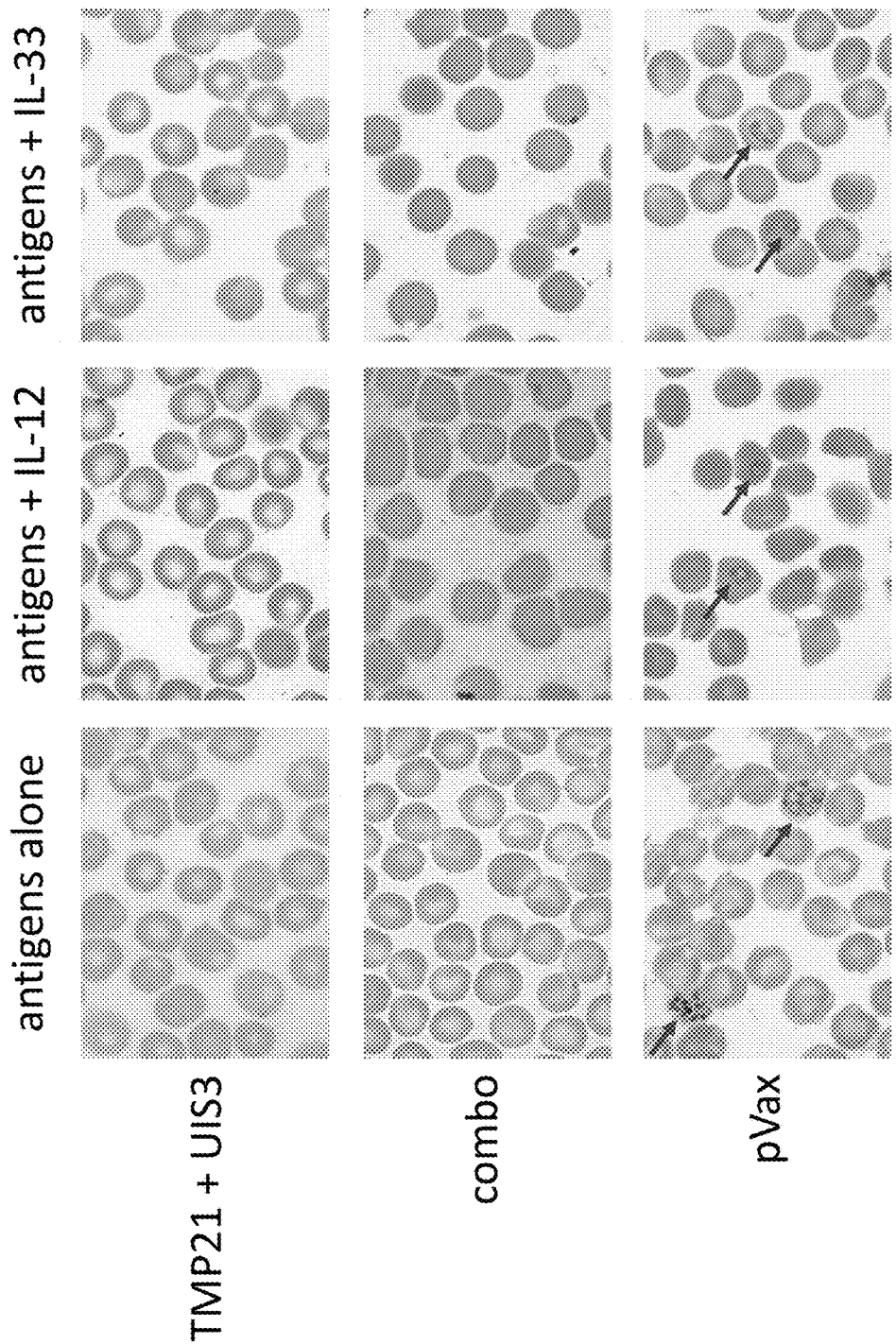
FIG. 9 depicts representative images of blood from mice immunized with TMP21 and UIS3 antigens, or a combination immunogenic composition (combo) comprising EXP1_EXP2, EXP23, ICP, TMP21 and UIS3 antigens or pVAX alone or in combination with an adjuvant (IL-12 or IL-33). Red arrows indicate development of BS disease.
Figure 10:
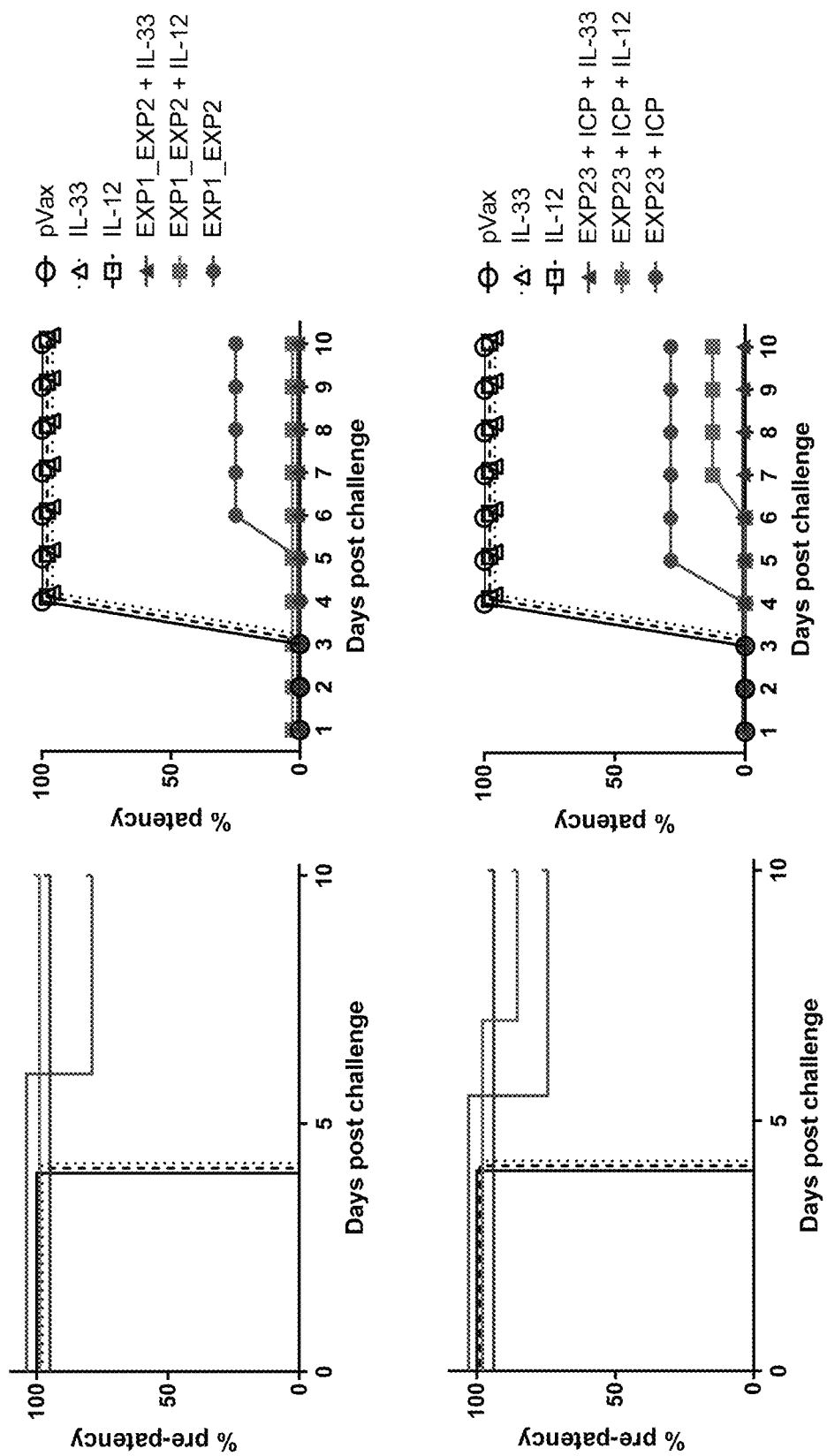
FIG. 10 depicts the percentage of mice having pre-patency and patency when immunized with EXP1_EXP2 (upper panels) or EXP23+ICP (lower panels), with or without adjuvant therapy (IL-12 or IL-33) over the course of 10 days post challenge.
Figure 11:
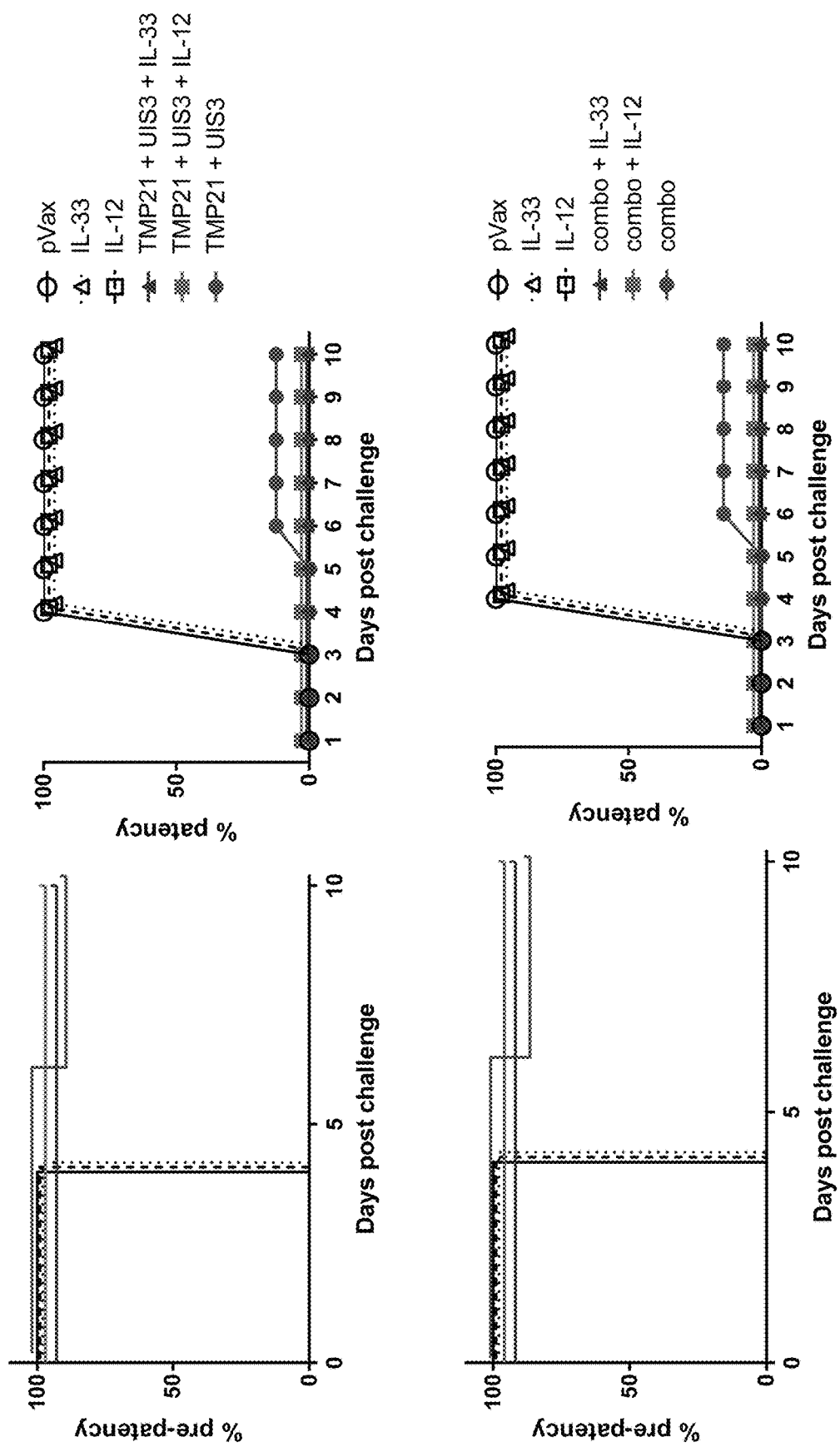
FIG. 11 depicts the percentage of mice having pre-patency and patency when immunized with TMP21 and UIS3 antigens (upper panels), or a combination immunogenic composition (combo) comprising EXP1_EXP2, EXP23, ICP, TMP21 and UIS3 antigens (lower panels), with or without adjuvant therapy (IL-12 or IL-33) over the course of 10 days post challenge.
Figure 12:
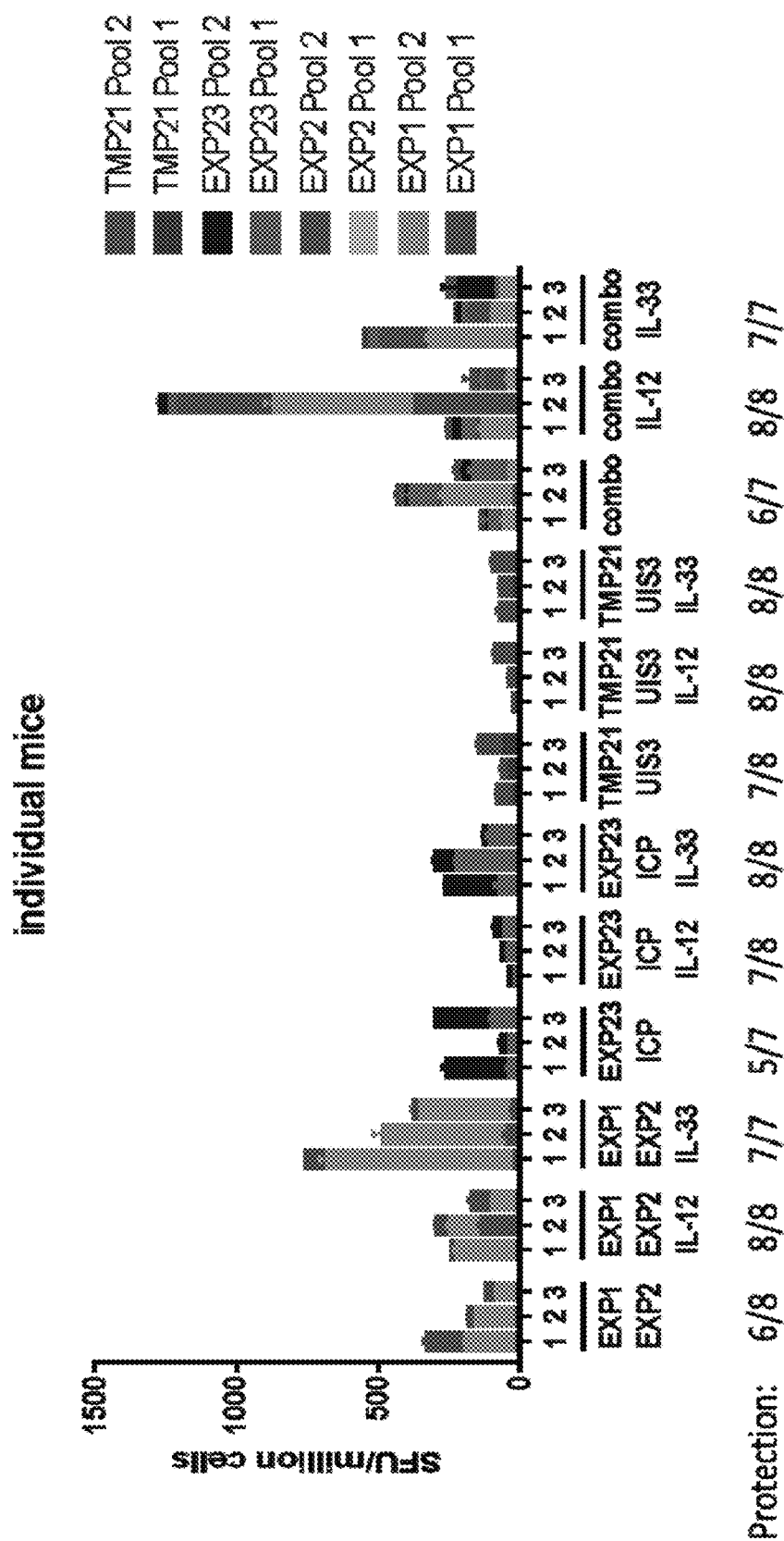
FIG. 12 depicts IFNγ ELISPOT assay results showing mice immunized with combinations of LS immunogens, with and without adjuvant treatment with IL-12 or IL-33 showed an increase in immune response as compared to mice treated with control vector (pVax) 18 weeks after the first immunization.
Figure 13:
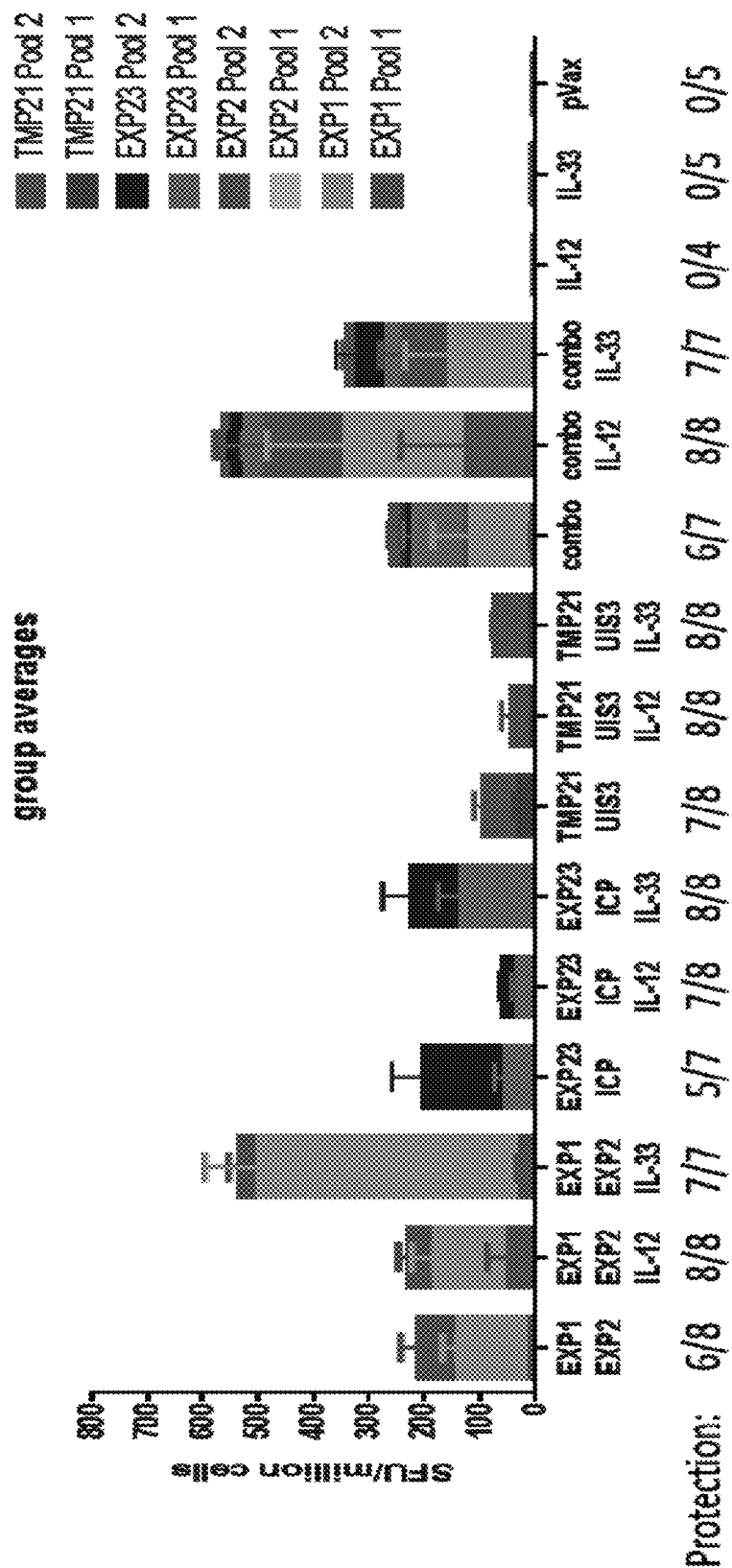
FIG. 13 depicts the average of the IFNγ ELISPOT assay results from FIG. 12, showing mice immunized with combinations of LS immunogens, with and without adjuvant treatment with IL-12 or IL-33 showed an increase in immune response as compared to mice treated with control vector (pVax).
Figure 15:
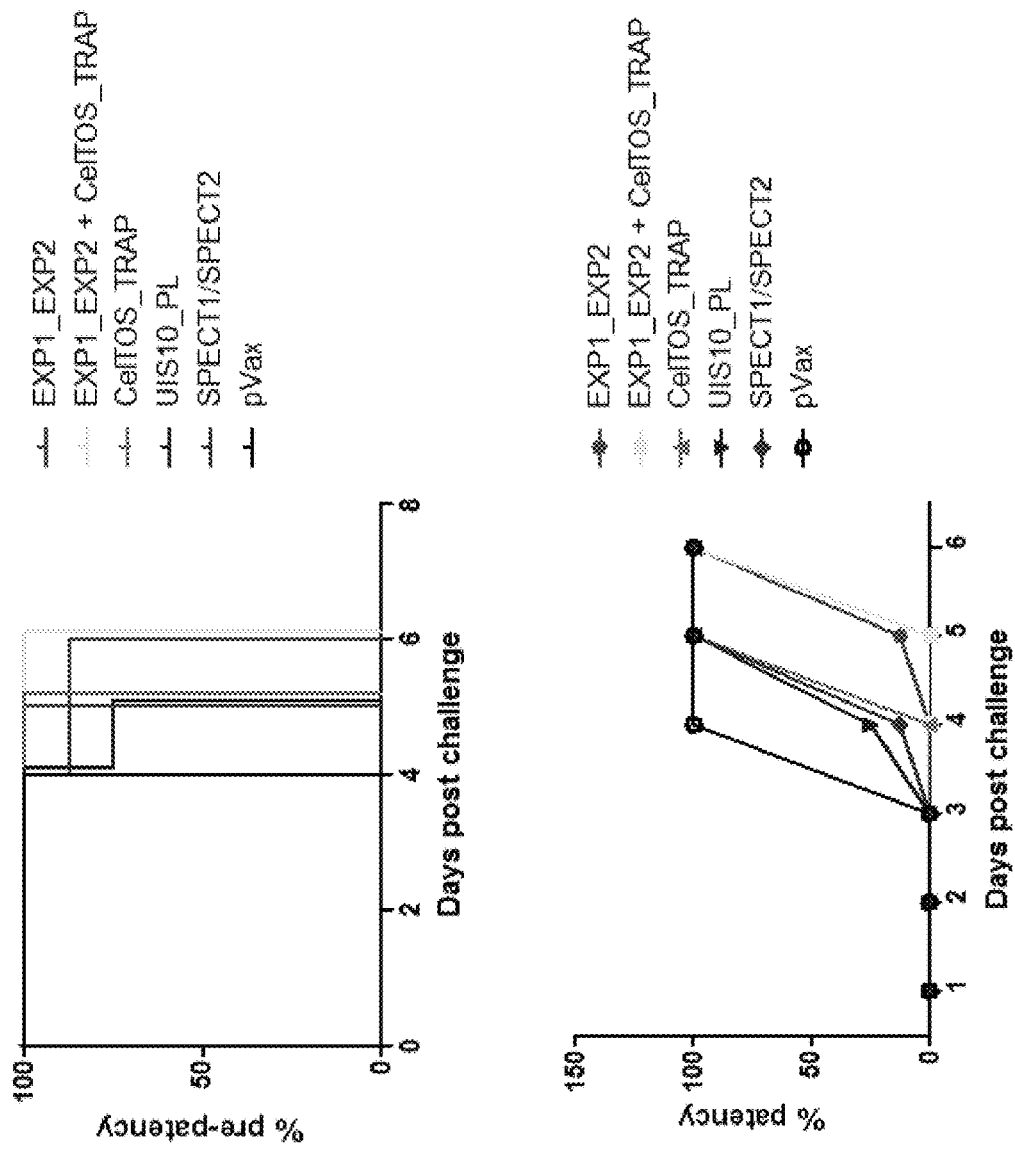
FIG. 15 depicts exemplary experimental results demonstrating the percentage of mice having pre-patency and patency when immunized with EXP1_EXP2, EXP1_EXP2 in combination with CelTOS_TRAP, CelTOS_TRAP, UIS10_PL, or SPECT1/SPECT2 over the course of several days post challenge.
Figure 16:
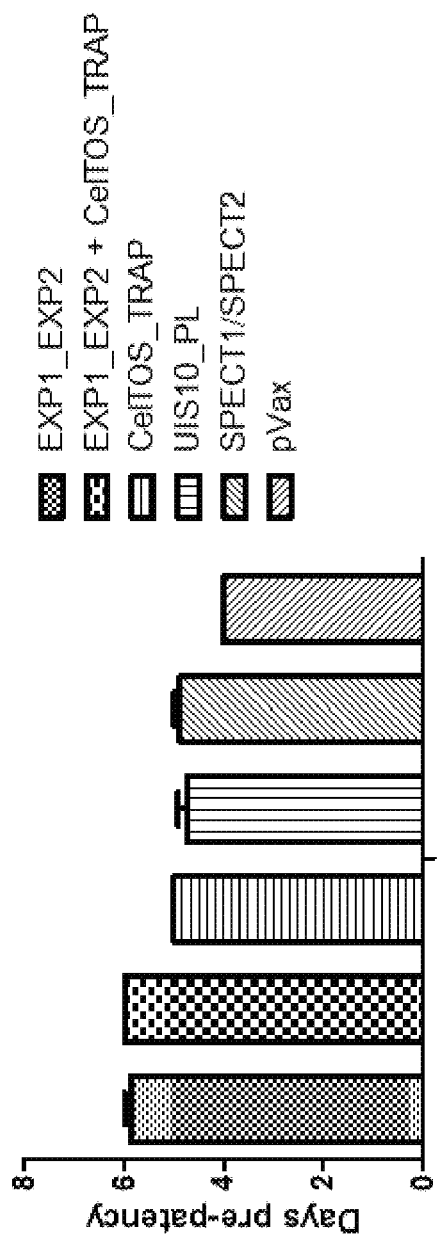
FIG. 16 depicts exemplary experimental results demonstrating the number of days of pre-patency for mice challenged with sporozoites following immunization with EXP1_EXP2, EXP1_EXP2 in combination with CelTOS_TRAP, CelTOS_TRAP, UIS10_PL, or SPECT1/SPECT2.
Figure 17:
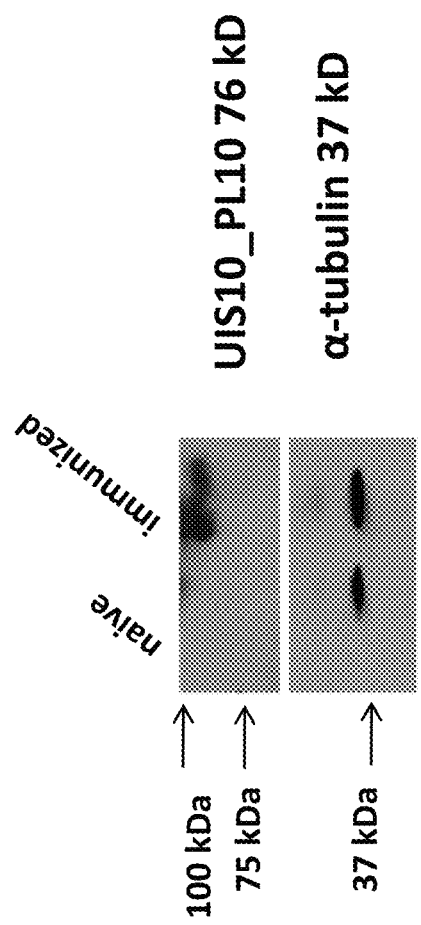
FIG. 17 depicts exemplary experimental results demonstrating that UIS10_PL10 is detected in serum from mice immunized with the UIS10_PL10 antigen.

Cellular immunogenicity of the antigens were determined by INF-γ ELISpot cellular immunogenicity analysis. Cellular immunogenicity of the LS antigens is shown in FIGS. 3 through 11. All immunogenic compositions induced a robust IFN-γ response as determined by ELISpot (FIGS. 5, 6, 12 and 13). Each of the antigens, adjuvants or combinations thereof were injected by hydrodynamic tail vein injection to allow for overexpression in the liver. Blood from the mice was analyzed for signs for development of Blood Stage infection (FIGS. 8 and 9).

Co-administration of EXP1_EXP2 with consensus P.f. immunogens TRAP and CelTOS showed a similar level of protection from the blood stage disease as EXP1_EXP2 (FIG. 14), indicating that co-administration of the immunogenic composition with other P.f. immunogens did not result in significant cross-reactivity.

Example 2: Non-Human Primates Immunized with LS Consensus Antigens Induce Potent Cellular and Humoral Responses Rhesus T cell immunity is much closer to human T cell immunity serving as a highly relevant model for immunotherapeutic vaccine development. Therefore, Rhesus macaques can serve as a model of for evaluating the potential effect of an LS antigen vaccine on human immune response.

To demonstrate immunogenicity of consensus LS antigens in a non-human primate (NHP) model, rhesus macaques (RhMs) are immunized with one or more of pGX7039, pGX7040, pGX7041, pGX7042, and pGX7043. Vaccination with consensus LS antigens is capable of generating robust LS antigen-specific CTLs in rhesus macaques. The non-human primates (NHP) received LS antigens formulated alone or with an adjuvant and delivered ID followed by electroporation.

mented with 10% FBS and Penicillin/Streptomycin). Monkey PBMCs are added in triplicates at an input cell number of $2\times10^5$ cells per well resuspended in R10. A set of peptides, (e.g., each containing 15 amino acid residues overlapping by 8 amino acids) representing the entire LS antigen was synthesized from GenScript. This set of peptides is pooled into multiple peptide pools. Concavalin A at 2.5 µg/ml is used as positive control and R10 medium is used as negative control, respectively. Plates are incubated for 24 hours at 37° C., in a 5% CO2 atmosphere incubator. Then, a biotinylated IFN-γ detection antibody is added, and plates are incubated for 2 hours at room temperature. The plates are washed, and color development was followed according to the manufacturer's instructions. The spots on the plates are counted using an automated ELISPOT reader (Cellular Technology, Shaker Heights, Ohio). Antigen-specific responses are determined by subtracting the number of spots in the negative control wells from the wells containing peptides. After subtracting the negative control, the mean value in the wells with the PBMCs collected post vaccination has to exceed 50 SFU/106 PBMCs and be at least four times higher than pre-vaccination reactivity to be considered as a positive response. The prebleed blood samples are studied to establish the background level of immune response of each individual animal in the study.

Without being bound by a particular theory, the results are expected to show that the LS antigen-immunized monkeys exhibited very low background level of immune response with a dramatic increase in vaccine-induced responses following each immunization, with the average numbers of IFN-γ producing cells increasing after the first, second, third and fourth immunizations. These results will demonstrate that immunization with one or a combination of LS antigens

TABLE 1

Exemplary NHP study design

| Study | Animal Model | Vaccine | Adjuvant | Regimen | Endpoint |
| --- | --- | --- | --- | --- | --- |
| LS antigen Immunogenicity study in NHP | Rhesus macaques | pGX7039 pGX7040 pGX7041 pGX7042 pGX7043 | None | Four immunizations, 6 weeks apart | ELISpot Physiological parameters |
| LS antigen + Adjuvant (IL-12) study in NHP | Rhesus macaques | pGX7039 pGX7040 pGX7041 pGX7042 pGX7043 | pGX6018 (Non-opt RhIL-12) | Four immunizations, 4 weeks apart | ELISpot |
| LS antigen immunogenicity study with increased dose in NHP | Rhesus macaques | pGX7039 pGX7040 pGX7041 pGX7042 pGX7043 | None | Four immunizations, 4 weeks apart | ELIspot |

Briefly, rhesus macaques are vaccinated with an LS antigen, four times intramuscularly followed by EP using CELLECTRA® adaptive constant current EP device (0.5 Amp constant current, 3 pulses, 52 msec pulse width, 0.2 sec between pulses), six weeks apart, at 2 mg DNA/each immunization. Blood is collected two weeks post each immunization and PBMCs are isolated by standard Ficoll-Hypaque density gradient centrifugation. Monkey pre-coated IFNγ ELISpot kit (Mabtech) is used to evaluate LS antigen-specific cellular responses two weeks after each immunization. Briefly, plates are washed with PBS and blocked for 2 hours at room temperature with R10 (RPMI 1640 supplecould elicit strong LS antigen-specific cellular responses. Epitope mapping may also be performed to investigate the diversity of the observed immune responses in rhesus macaques.

In order to examine if there is any CTL-mediated host toxicity, a number of physiological parameters are assessed in immunized monkeys. Briefly, weight is monitored while the animals are under anesthesia. Blood Chemistry and CBC panels are run on vaccinated animals starting 2 weeks after their final immunization and running out to three months after completion of the vaccination protocol by IDEXX Laboratories Without being bound by a particular theory, it is held that a well tolerated vaccine is one in which no significant weight loss is observed and WBC counts remain within normal range. No elevation of alkaline phosphatase (ALK P), alanine aminotransferase (ALT), aspartate aminotransferase (AST) and total bilirubin (TBIL) indicate that induction of an LS antigen-specific immune response did not cause significant damage to the liver. Without being bound by a particular theory, it is held that a well tolerated vaccine is one in which no evidence of impaired kidney function is seen, and Creatinine and Blood Urea Nitrogen (BUN) remain within normal limits. Without being bound by a particular theory, it is held that a well tolerated vaccine is one in which no significant changes in CPK are detected after the vaccination procedure.

Example 3: Expression of Consensus LS Antigens in Human Cells

Figure 19:
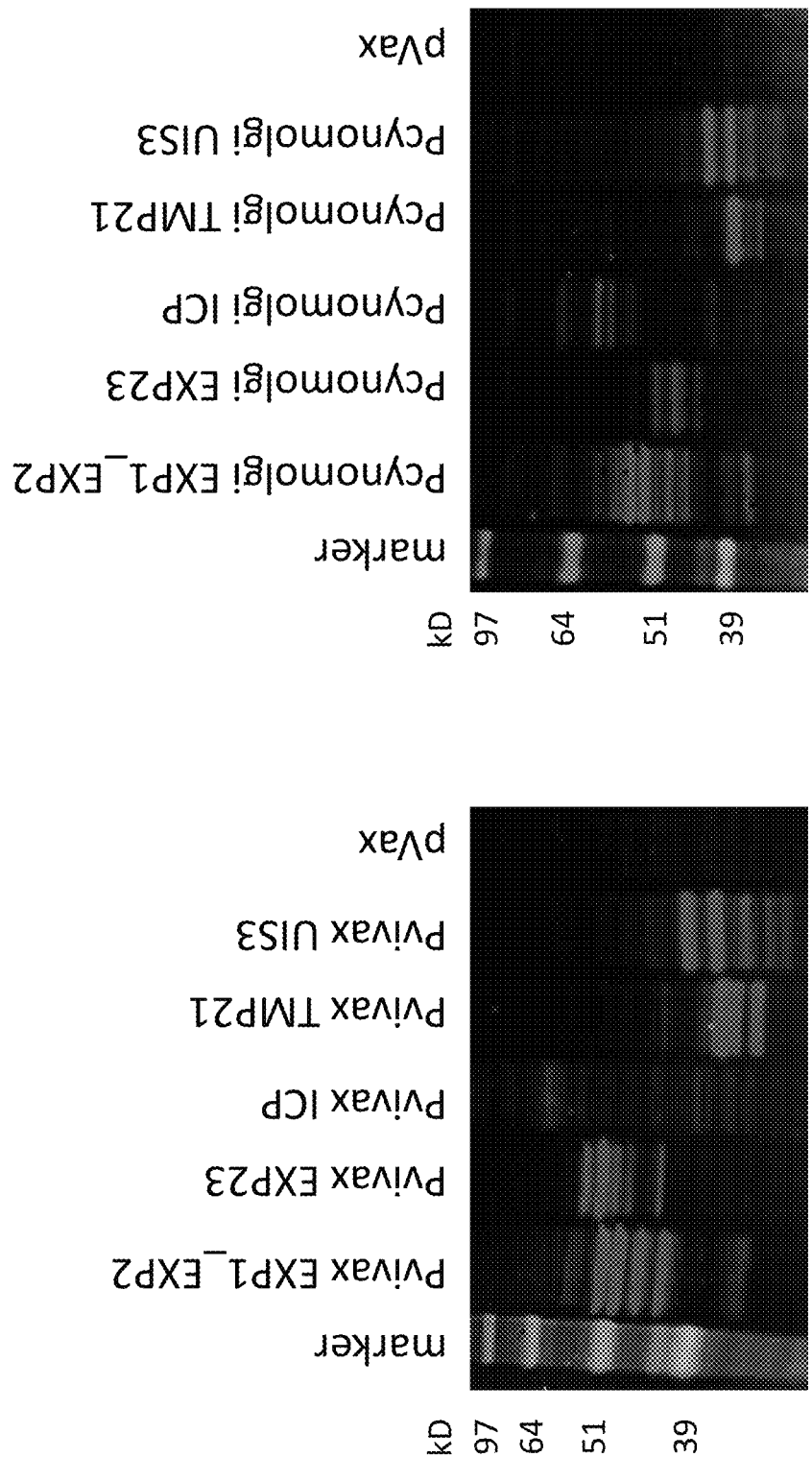
FIG. 19 depicts exemplary experimental results demonstrating expression of Pvivax and Pcynomolgi constructs.

Optimized consensus LS antigens for were developed for use in humans and non-human primates. FIG. 19 shows the results of experiments confirming that the optimized consensus LS antigens were able to express in a human cell line. 293T cells were transfected with the indicated construct. Cell lysates were run on a Bis-Tris gel and transferred to nitrocellulose membrane. The membrane was probed with an anti-HA primary antibody and an IRDye 680RD secondary antibody and imaged on an Odyssey reader.

Example 4: Sequence Information

TABLE 2

Optimized consensus Plasmodium spp. LS antigen sequences for expression in human

| SEQ ID NO | Sequence Type | Name | Description |
|---|---|---|---|
| 1 | Amino acid | pGX7034/ PGX7029 | Pvivax EXP1-EXP2 |
| 2 | Nucleotide | pGX7034/ PGX7029 | Pvivax EXP1-EXP2 |
| 3 | Nucleotide | pGX7034/ pGX7029 | Pvivax EXP1-EXP2 operably linked to IgE leader sequence |
| 4 | Amino acid | pGX7035/ pGX7030 | Pvivax EXP23 |
| 5 | Nucleotide | pGX7035/ pGX7030 | Pvivax EXP23 |
| 6 | Nucleotide | pGX7035/ pGX7030 | Pvivax EXP23 operably linked to IgE leader sequence |
| 7 | Amino acid | pGX7036/ PGX7031 | Pvivax ICP |
| 8 | Nucleotide | pGX7036/ PGX7031 | Pvivax ICP |
| 9 | Nucleotide | pGX7036/ pGX7031 | Pvivax ICP operably linked to IgE leader sequence |
| 10 | Amino acid | pGX7037/ PGX7032 | Pvivax TMP21 |
| 11 | Nucleotide | pGX7037/ PGX7032 | Pvivax TMP21 |
| 12 | Nucleotide | pGX7037/ pGX7032 | Pvivax TMP21 operably linked to IgE leader sequence |
| 13 | Amino acid | pGX7038/ PGX7033 | Pvivax UIS3 |
| 14 | Nucleotide | pGX7038/ PGX7033 | Pvivax UIS3 |
| 15 | Nucleotide | pGX7038/ pGX7033 | Pvivax UIS3 operably linked to IgE leader sequence |
| 16 | Amino acid | | IgE leader sequence |
| 17 | Amino acid | pGX7039 | Pcynomolgi EXP1-EXP2 |
| 18 | Nucleotide | pGX7039 | Pcynomolgi EXP1-EXP2 |
| 19 | Nucleotide | pGX7039 | Pcynomolgi EXP1-EXP2 operably linked to IgE leader sequence |
| 20 | Amino acid | pGX7040 | Pcynomolgi EXP23 |
| 21 | Nucleotide | pGX7040 | Pcynomolgi EXP23 |
| 22 | Nucleotide | pGX7040 | Pcynomolgi EXP23 operably linked to IgE leader sequence |
| 23 | Amino acid | pGX7041 | Pcynomolgi ICP |
| 24 | Nucleotide | pGX7041 | Pcynomolgi ICP |
| 25 | Nucleotide | pGX7041 | Pcynomolgi ICP operably linked to IgE leader sequence |
| 26 | Amino acid | pGX7042 | Pcynomolgi TMP21 |
| 27 | Nucleotide | pGX7042 | Pcynomolgi TMP21 |
| 28 | Nucleotide | pGX7042 | Pcynomolgi TMP21 operably linked to IgE leader sequence |
| 29 | Amino acid | pGX7043 | Pcynomolgi UIS3 |
| 30 | Nucleotide | pGX7043 | Pcynomolgi UIS3 |
| 31 | Nucleotide | pGX7043 | Pcynomolgi UIS3 operably linked to IgE leader sequence |
| 32 | Amino acid | pGX7021 | Py EXP1-EXP2 |
| 33 | Nucleotide | pGX7021 | Py EXP1-EXP2 |
| 34 | Nucleotide | pGX7021 | Py EXP1-EXP2 operably linked to IgE leader sequence |
| 35 | Amino acid | pGX7024 | Py EXP23 |
| 36 | Nucleotide | pGX7024 | Py EXP23 |
| 37 | Nucleotide | pGX7024 | Py EXP23 operably linked to IgE leader sequence |
| 38 | Amino acid | pGX7027 | Py ICP |
| 39 | Nucleotide | pGX7027 | Py ICP |
| 40 | Nucleotide | pGX7027 | Py ICP operably linked to IgE leader sequence |
| 41 | Amino acid | pGX7025 | Py TMP21 |
| 42 | Nucleotide | pGX7025 | Py TMP21 |
| 43 | Nucleotide | pGX7025 | Py TMP21 operably linked to IgE leader sequence |
| 44 | Amino acid | | Py UIS3 |
| 45 | Nucleotide | | Py UIS3 |
| 46 | Nucleotide | | Py UIS3 operably linked to IgE leader sequence |
| 47 | Amino acid | pGX7022 | Py UIS10 PL |
| 48 | Nucleotide | pGX7022 | Py UIS10 PL |
| 49 | Nucleotide | pGX7022 | Py UIS10 PL operably linked to IgE leader sequence |
| 50 | Amino acid | pGX7020 | Py SPECT1__SPECT2 |
| 51 | Nucleotide | pGX7020 | Py SPECT1__SPECT2 |
| 52 | Nucleotide | pGX7020 | Py SPECT1__SPECT2 operably linked to IgE leader sequence |
| 53 | Amino acid | pGX7026 | Py RON2 |
| 54 | Nucleotide | pGX7026 | Py RON2 |
| 55 | Nucleotide | pGX7026 | Py RON2 operably linked to IgE leader sequence |
| 56 | Amino acid | pGX7019 | PyCelTOS__TRAP |
| 57 | Nucleotide | pGX7019 | PyCelTOS__TRAP |
| 58 | Nucleotide | pGX7019 | PyCelTOS__TRAP operably linked to IgE leader sequence |
| 59 | Amino acid | pGX7008 | Pf TRAP 3D7 |
| 60 | Nucleotide | pGX7008 | Pf TRAP 3D7 |
| 61 | Nucleotide | pGX7008 | Pf TRAP 3D7 operably linked to IgE leader sequence |
| 62 | Amino acid | pGX7010 | Pf CSP 3D7 |
| 63 | Nucleotide | pGX7010 | Pf CSP 3D7 |
| 64 | Nucleotide | pGX7010 | Pf CSP 3D7 operably linked to IgE leader sequence |
| 65 | Amino acid | pGX7014 | 3D7TRAP-6 |
| 66 | Nucleotide | pGX7014 | 3D7TRAP-6 |
| 67 | Nucleotide | pGX7014 | 3D7TRAP-6 operably linked to IgE leader sequence |
| 68 | Amino acid | | Pvivax EXP1 |
| 69 | Nucleotide | | Pvivax EXP1 |
| 70 | Amino acid | | Pvivax EXP2 |
| 71 | Nucleotide | | Pvivax EXP2 |
| 72 | Amino acid | | Pcynomolgi EXP1 |
| 73 | Nucleotide | | Pcynomolgi EXP1 |
| 74 | Amino acid | | Pcynomolgi EXP2 |

TABLE 2-continued

Optimized consensus Plasmodium spp. LS antigen sequences for expression in human

| SEQ ID NO | Sequence Type | Name | Description |
|---|---|---|---|
| 75 | Nucleotide | | Pcynomolgi EXP2 |
| 76 | Amino acid | | Py EXP1 |
| 77 | Nucleotide | | Py EXP1 |
| 78 | Amino acid | | Py EXP2 |
| 79 | Nucleotide | | Py EXP2 |
| 80 | Amino acid | | Py SPECT1 |
| 81 | Nucleotide | | Py SPECT1 |
| 82 | Amino acid | | Py SPECT2 |
| 83 | Nucleotide | | Py SPECT2 |

What is claimed:

1. A nucleic acid molecule comprising one or more nucleic acid sequence that encodes one or more consensus Plasmodium spp. liver stage (LS) immunogen selected from the group consisting of EXP1 (export protein 1), EXP2 (export protein 2), EXP23 (export protein 23), ICP (inhibitor of cysteine protease), TMP21 (transmembrane protein 21), UIS3 (upregulated in infective sporozoites-3), UIS10 (up-regulated in infective sporozoites-10), SPECT1 (sporozoite microneme protein essential for cell traversal 1), SPECT2 (sporozoite microneme protein essential for cell traversal 2) and RON2 (rhoptry neck protein 2), wherein the nucleic acid sequence is selected from the group consisting of:

a) a nucleotide sequence encoding an amino acid sequence selected from the group consisting of SEQ ID NO: 1, SEQ ID NO: 4, SEQ ID NO: 7, SEQ ID NO: 10, SEQ ID NO: 13, SEQ ID NO:17, SEQ ID NO: 20, SEQ ID NO: 23, SEQ ID NO: 29, SEQ ID NO: 32, SEQ ID NO: 35, SEQ ID NO: 38, and SEQ ID NO: 50;

b) a nucleic acid sequence that encodes an amino acid sequence comprising a fragment comprising at least 90% of the full length of the amino acid sequence selected from the group consisting of SEQ ID NO: 1, SEQ ID NO: 4, SEQ ID NO: 7, SEQ ID NO: 10, SEQ ID NO: 13, SEQ ID NO: 17, SEQ ID NO: 20, SEQ ID NO: 23, SEQ ID NO: 29, SEQ ID NO: 32, SEQ ID NO: 35, SEQ ID NO: 38, and SEQ ID NO: 50;

c) a nucleic acid sequence that encodes the amino acid sequence comprising at least 90% homology to the amino acid sequence selected from the group consisting of SEQ ID NO: 1, SEQ ID NO: 4, SEQ ID NO: 7, SEQ ID NO: 10, SEQ ID NO: 13, SEQ ID NO: 17, SEQ ID NO: 20, SEQ ID NO: 23, SEQ ID NO: 29, SEQ ID NO: 32, SEQ ID NO: NO: 35, SEQ ID NO: 38, and SEQ ID NO: 50;

d) the nucleotide sequence selected from the group consisting of SEQ ID NO: 2, SEQ ID NO: 3, SEQ ID NO: 5, SEQ ID NO: 6, SEQ ID NO: 8, SEQ ID NO: 9, SEQ ID NO: 11, SEQ ID NO: 12, SEQ ID NO: 14, SEQ ID NO: 15, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 54, and SEQ ID NO: 55;

e) a nucleotide sequence comprising a fragment comprising at least 90% of the full length of the nucleotide sequence selected from the group consisting of SEQ ID NO: 2, SEQ ID NO: 3, SEQ ID NO: 5, SEQ ID NO: 6, SEQ ID NO: 8, SEQ ID NO: 9, SEQ ID NO: 11, SEQ ID NO: 12, SEQ ID NO: 14, SEQ ID NO: 15, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 54, and SEQ ID NO: 55; and f) a nucleotide sequence comprising at least 90% identity to the nucleotide sequence selected from the group consisting of SEQ ID NO: 2, SEQ ID NO: 3, SEQ ID NO: 5, SEQ ID NO: 6, SEQ ID NO: 8, SEQ ID NO: 9, SEQ ID NO: 11, SEQ ID NO: 12, SEQ ID NO: 14, SEQ ID NO: 15, SEQ ID NO: 18, SEQ ID NO: 19, SEQ ID NO: 21, SEQ ID NO: 22, SEQ ID NO: 24, SEQ ID NO: 25, SEQ ID NO: 27, SEQ ID NO: 28, SEQ ID NO: 30, SEQ ID NO: 31, SEQ ID NO: 33, SEQ ID NO: 34, SEQ ID NO: 36, SEQ ID NO: 37, SEQ ID NO: 39, SEQ ID NO: 40, SEQ ID NO: 42, SEQ ID NO: 43, SEQ ID NO: 45, SEQ ID NO: 46, SEQ ID NO: 48, SEQ ID NO: 49, SEQ ID NO: 51, SEQ ID NO: 52, SEQ ID NO: 54, and SEQ ID NO: 55.

2. The nucleic acid molecule of claim 1, wherein the nucleic acid sequence encodes an IgE leader sequence of SEQ ID NO: 16.

3. The nucleic acid molecule of claim 1, wherein said nucleic acid molecule is a plasmid.

4. The nucleic acid molecule of claim 1 further comprising one or more nucleotide sequences encoding one or more malaria antigen selected from the group consisting of: CSP (circumsporozoite protein), LSA1 (liver stage antigen 1), TRAP (hrombospondin-related anonymous protein), CelTOS (cell traversal protein for Plasmodium ookinetes and sporozoites), and Amal (apical membrane antigen 1).

5. The nucleic acid molecule of claim 4 wherein the nucleotide sequence is selected from the group consisting of: a nucleic acid sequence encoding an amino acid sequence selected from the group consisting of SEQ ID NO:56, SEQ ID NO:59, SEQ ID NO:62, and SEQ ID NO:65; and a nucleotide sequence selected from the group consisting of SEQ ID NO:60, SEQ ID NO:61, SEQ ID NO:63, SEQ ID NO:64, SEQ ID NO:66 and SEQ ID NO:67.

6. An immunogenic composition comprising at least one nucleic acid molecule of claim 1.

7. The immunogenic composition of claim 6 further comprising one or more nucleotide sequences encoding one or more malaria antigen selected from the group consisting of: CSP, LSA1, TRAP, CelTOS, and Ama1.

8. The immunogenic composition of claim 6 further comprising a nucleotide sequences that encodes IL-12, IL-15, IL-28B, IL-33 or RANTES.

9. The immunogenic composition of claim 6 wherein said nucleotide sequences are incorporated into one or more plasmids.

10. A method of immunizing a mammal against malaria comprising the step of administering an immunogenic composition comprising at least one nucleic acid molecule comprising one or more nucleic acid sequence that encodes one or more consensus Plasmodium spp. liver stage (LS) immunogen selected from the group consisting of: EXP1 (export protein 1), EXP2 (export protein 2), EXP23 (export protein 23), ICP (inhibitor of cysteine protease), TMP21 (transmembrane protein 21), UIS3 (upregulated in infective sporozoites-3), UIS10 (upregulated in infective sporozoites-10), SPECT1 (sporozoite microneme protein essential for cell traversal 1), SPECT2 (sporozoite microneme protein essential for cell traversal 2) and RON2 (rhoptry neck protein 2) wherein the nucleic acid sequence is selected from the group consisting of:
  a) a nucleotide sequence encoding the amino acid sequence selected from the group consisting of SEQ ID NO:1, SEQ ID NO:4, SEQ ID NO:7, SEQ ID NO:10, SEQ ID NO:13, SEQ ID NO:17, SEQ ID NO:20, SEQ ID NO:23, SEQ ID NO:26, SEQ ID NO:29, SEQ ID NO:41, SEQ ID NO:32, SEQ ID NO:35, SEQ ID NO:38, SEQ ID NO:44, SEQ ID NO:47, SEQ ID NO:50, and SEQ ID NO:53,
  b) a nucleic acid sequence that encodes an amino acid sequence comprising a fragment comprising at least 90% of the full length of the amino acid sequence selected from the group consisting of SEQ ID NO:1, SEQ ID NO:4, SEQ ID NO:7, SEQ ID NO:10, SEQ ID NO:13, SEQ ID NO:17, SEQ ID NO:20, SEQ ID NO:23, SEQ ID NO:26, SEQ ID NO:29, SEQ ID NO:41, SEQ ID NO:32, SEQ ID NO:35, SEQ ID NO:38, SEQ ID NO:44, SEQ ID NO:47, SEQ ID NO:50, and SEQ ID NO:53,
  c) a nucleic acid sequence that encodes the amino acid sequence comprising at least 90% homology to the amino acid sequence selected from the group consisting of SEQ ID NO:1, SEQ ID NO:4, SEQ ID NO:7, SEQ ID NO:10, SEQ ID NO:13, SEQ ID NO:17, SEQ ID NO:20, SEQ ID NO:23, SEQ ID NO:26, SEQ ID NO:29, SEQ ID NO:41, SEQ ID NO:32, SEQ ID NO:35, SEQ ID NO:38, SEQ ID NO:44, SEQ ID NO:47, SEQ ID NO:50, and SEQ ID NO:53;
  d) the nucleotide sequence selected from the group consisting of SEQ ID NO:2, SEQ ID NO:3, SEQ ID NO:5, SEQ ID NO:6, SEQ ID NO:8, SEQ ID NO:9, SEQ ID NO:11, SEQ ID NO:12, SEQ ID NO:14, SEQ ID NO:15, SEQ ID NO: 18, SEQ ID NO: 19, SEQ ID NO:21, SEQ ID NO:22, SEQ ID NO:24, SEQ ID NO:25, SEQ ID NO:27, SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:42, SEQ ID NO:43, SEQ ID NO:45, SEQ ID NO:46, SEQ ID NO:48, SEQ ID NO:49, SEQ ID NO:51, SEQ ID NO:52, SEQ ID NO:54, and SEQ ID NO:55,
  e) a nucleotide sequence comprising a fragment comprising at least 90% of the full length of the nucleotide sequence selected from the group consisting of SEQ ID NO:2, SEQ ID NO:3, SEQ ID NO:5, SEQ ID NO:6, SEQ ID NO:8, SEQ ID NO:9, SEQ ID NO:11, SEQ ID NO:12, SEQ ID NO:14, SEQ ID NO:15, SEQ ID NO: 18, SEQ ID NO: 19, SEQ ID NO:21, SEQ ID NO:22, SEQ ID NO:24, SEQ ID NO:25, SEQ ID NO:27, SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:42, SEQ ID NO:43, SEQ ID NO:45, SEQ ID NO:46, SEQ ID NO:48, SEQ ID NO:49, SEQ ID NO:51, SEQ ID NO:52, SEQ ID NO:54, and SEQ ID NO:55, and
  f) a nucleotide sequence comprising at least 90% identity to the nucleotide sequence selected from the group consisting of SEQ ID NO:2, SEQ ID NO:3, SEQ ID NO:5, SEQ ID NO:6, SEQ ID NO:8, SEQ ID NO:9, SEQ ID NO:11, SEQ ID NO:12, SEQ ID NO:14, SEQ ID NO:15, SEQ ID NO: 18, SEQ ID NO: 19, SEQ ID NO:21, SEQ ID NO:22, SEQ ID NO:24, SEQ ID NO:25, SEQ ID NO:27, SEQ ID NO:28, SEQ ID NO:30, SEQ ID NO:31, SEQ ID NO:33, SEQ ID NO:34, SEQ ID NO:36, SEQ ID NO:37, SEQ ID NO:39, SEQ ID NO:40, SEQ ID NO:42, SEQ ID NO:43, SEQ ID NO:45, SEQ ID NO:46, SEQ ID NO:48, SEQ ID NO:49, SEQ ID NO:51, SEQ ID NO:52, SEQ ID NO:54, and SEQ ID NO:55 to the tissue of the mammal.

11. The method of claim 10 comprising the steps of:
  a) administering the immunogenic composition to the tissue of the mammal, and
  b) electroporating cells of the tissue with a pulse of energy at a constant current effective to permit entry of the nucleic acid molecules into the cells.

12. The method of claim 10 wherein the immunogenic composition is administered by intramuscular or intradermal injection.

* * * * *

SEQUENCE LISTING

<160> NUMBER OF SEQ ID NOS: 83

<210> SEQ ID NO 1
<211> LENGTH: 326
<212> TYPE: PRT
<213> ORGANISM: Artificial sequence
<220> FEATURE:
<223> OTHER INFORMATION: pGX7034/pGX7029 Pvivax EXP1-EXP2

<400> SEQUENCE: 1

```
Lys Leu Leu Ala Ala Val Phe Leu Leu Phe Cys Ala Ile Leu Cys Asn
 1               5                  10                  15

His Ala Leu Gly Asp Asn Val Asn Gly Leu Gly Ala Gly Asn Pro Lys
            20                  25                  30

Lys Lys Ser Pro Lys Ser Lys Ser Pro Glu Pro Leu Ile Asp Val His
        35                  40                  45

Glu Leu Ile Ser Glu Ile Val Arg Lys Glu Glu Leu Val Asn Met
    50                  55                  60

Thr Lys Lys Lys Ser Asn Tyr Lys Leu Ala Thr Thr Val Leu Ala Ser
 65                  70                  75                  80

Ala Leu Gly Val Val Ser Ala Val Leu Leu Gly Gly Ala Gly Leu Val
                85                  90                  95

Phe Tyr Asn Ala Gly Asn Gly Arg His Pro Phe Ser Leu Gly Gly Gly
            100                 105                 110

Lys Gly Gly Asp Ala Ala Pro Thr Glu Pro Thr Pro Ala Pro Thr Ala
        115                 120                 125

Pro Ser Ala Thr Gly Leu Asn Asp Asp Gly Ser Ser Ser Gly Thr Glu
    130                 135                 140

Ser Thr Ser Arg Gly Arg Lys Arg Arg Ser Ala Glu Glu Glu Tyr Ser
145                 150                 155                 160

Trp Asp Ser Tyr Leu Asn Asp Arg Leu Leu Ala Thr Asn Gln Val Ser
                165                 170                 175

Ala Ala Gly Leu Ala Ser Glu Glu Asp Gly Val Val Tyr Ala Cys Val
            180                 185                 190

Ala Gln Ala Asp Glu Asn Asp Ala Glu Phe Asp Lys Trp Thr Leu Phe
        195                 200                 205

Tyr Lys Glu Asp Tyr Glu Ile Glu Val Glu Asp Glu Asn Gly Asn Lys
    210                 215                 220

Ser Gln Lys Thr Ile Asn Glu Gly Gln Thr Leu Leu Thr Val Phe Lys
225                 230                 235                 240

Glu Gly Tyr Ala Pro Asp Gly Val Trp Leu Gly Gly Thr Lys Tyr Gln
                245                 250                 255

Phe Ile Asn Ile Glu Arg Asp Leu Glu Phe Glu Gly Tyr Thr Phe Asp
            260                 265                 270
```

```
Val Ala Thr Cys Ala Lys Leu Lys Gly Gly Leu His Leu Ile Lys Val
        275                 280                 285

Pro Gly Gly Asn Ile Leu Val Val Leu Tyr Asp Glu Glu Lys Glu His
    290                 295                 300

Asp Arg Gly Asn Ser Lys Ile Ala Ala Leu Thr Phe Ser Lys Glu Leu
305                 310                 315                 320

Ala Glu Ser Gly Gly Gln
                325

<210> SEQ ID NO 2
<211> LENGTH: 978
<212> TYPE: DNA
<213> ORGANISM: Artificial sequence
<220> FEATURE:
<223> OTHER INFORMATION: pGX7034/pGX7029 Pvivax EXP1-EXP2

<400> SEQUENCE: 2
aagctgctgg ccgccgtgtt cctgctgttt tgcgcaatcc tgtgcaacca cgcactgggc    60
gacaacgtga atggcctggg agcaggcaat cccaagaaga gagccccaa gagcaagtcc    120 cccgagcctc tgatcgatgt gcacgagctg atctccgaga tcgtgcggaa ggaggaggag    180
ctggtgaaca tgaccaagaa gaagagcaat tacaagctgg ccaccacagt gctggccagc    240
gccctgggcg tggtgtccgc cgtgctgctg ggcggcgccg gcctggtgtt ctataacgcc    300
ggcaatggcc gccacccctt tagcctgggc ggcggcaagg gcggcgacgc agcacctacc    360
gagccaacac ccgcccctac cgcaccatcc gccacaggcc tgaacgacga tggcagctcc    420
tctggcaccg agtctacaag ccggggcagg aagaggagat ctgccgagga ggagtactcc    480
tgggactctt atctgaacga taggctgctg ccaccaatc aggtgtctgc cgcaggcctg    540
gcaagcgagg aggacggagt ggtgtacgca tgcgtggcac aggccgacga aatgatgcc    600 gagttcgata gtggacccct gttttacaag gaggactatg agatcgaggt ggaggatgag    660
aacggcaata agtcccagaa gacaatcaac gagggccaga ccctgctgac agtgttcaag    720
gagggctacg caccagatgg cgtgtggctg ggcggcacca gtatcagttt atcaatatc    780 gagagggacc tggagttcga gggctacacc tttgatgtgg ccacatgtgc caagctgaag    840
ggcggcctgc acctgatcaa ggtgcctggc ggcaacatcc tggtggtgct gtatgacgag    900
gagaaggagc acgatagagg caattccaag atcgccgccc tgacattttc caaggagctg    960
gccgagtctg gcggccag                                                 978

<210> SEQ ID NO 3
<211> LENGTH: 1032
<212> TYPE: DNA
<213> ORGANISM: Artificial sequence
<220> FEATURE:
<223> OTHER INFORMATION: pGX7034/pGX7029 Pvivax EXP1-EXP2 operably
      linked to IgE leader sequence

<400> SEQUENCE: 3
atggactgga cctggattct gttcctggtg gcagcagcaa caagggtgca cagcaagctg    60
ctggccgccg tgttcctgct gttttgcgca atcctgtgca accacgcact gggcgacaac    120
gtgaatggcc tgggagcagg caatcccaag aagagagccc caagagcaa gtcccccgag    180 cctctgatcg atgtgcacga gctgatctcc gagatcgtgc ggaaggagga ggagctggtg    240
aacatgacca agaagaagag caattacaag ctggccacca cagtgctggc cagcgccctg    300
ggcgtggtgt ccgccgtgct gctgggcggc gccggcctgg tgttctataa cgccggcaat    360
```

```
ggccgccacc cctttagcct gggcggcggc aagggcggcg acgcagcacc taccgagcca    420
acacccgccc ctaccgcacc atccgccaca ggcctgaacg acgatggcag ctcctctggc    480
accgagtcta caagccgggg caggaagagg agatctgccg aggaggagta ctcctgggac    540
tcttatctga acgataggct gctggccacc aatcaggtgt ctgccgcagg cctggcaagc    600
gaggaggacg gagtggtgta cgcatgcgtg gcacaggccg acgagaatga tgccgagttc    660
gataagtgga ccctgtttta caaggaggac tatgagatcg aggtggagga tgagaacggc    720
aataagtccc agaagacaat caacgagggc cagaccctgc tgacagtgtt caaggagggc    780
tacgcaccag atggcgtgtg gctgggcggc accaagtatc agtttatcaa tatcgagagg    840
gacctggagt tcgagggcta cacctttgat gtggccacat gtgccaagct gaagggcggc    900
ctgcacctga tcaaggtgcc tggcggcaac atcctggtgg tgctgtatga cgaggagaag    960
gagcacgata gaggcaattc caagatcgcc gccctgacat tttccaagga gctggccgag   1020
tctggcggcc ag                                                       1032

<210> SEQ ID NO 4
<211> LENGTH: 272
<212> TYPE: PRT
<213> ORGANISM: Artificial sequence
<220> FEATURE:
<223> OTHER INFORMATION: pGX7035/pGX7030 Pvivax EXP23

<400> SEQUENCE: 4

Lys Val Ser Tyr Ile Leu Ser Leu Phe Phe Phe Leu Ile Ile Tyr Lys
1               5                   10                  15

Asn Thr Thr Thr Asn Val Val Glu Cys Gly Gly Tyr Ser Asp Leu Ala
                20                  25                  30

Ala Thr Ser Ala Leu Thr Thr Ile Val Lys Asp Pro Ile Ser Leu Thr
            35                  40                  45

Ile Lys Asp Leu Tyr Glu His Gly Val Lys Asp Pro Ile Thr Lys Leu
        50                  55                  60

Ile His Lys Ile Lys Lys Val Val Arg Tyr Arg Lys Val Leu Arg Trp
65                  70                  75                  80

Ser Arg Ile Trp Trp Val Leu Leu Val Arg Glu Ile Val Gly Asp Asn
                85                  90                  95

Ala Ile Glu Arg Lys Thr Glu Lys Ala Leu Arg Glu Ile Trp Asp Gln
            100                 105                 110

Cys Thr Ile Ala Val Tyr Asn Asn Thr Leu Tyr Ala Ile Glu Ser Lys
        115                 120                 125

Pro Leu Leu Phe Leu His Gly Ile Leu Asn Glu Cys Lys Asn Asn Phe
    130                 135                 140

Ser Thr Lys Leu Arg Gln Asp Pro Gly Leu Ile Val Ala Lys Ile Asp
145                 150                 155                 160

Gln Ile Leu Lys Ser Gln Ile Tyr Arg Phe Trp Val Ser Glu Pro Tyr
                165                 170                 175

Leu Lys Ile Gly Lys Ser Ser Ile Phe Tyr Thr Arg Ile Asn Ser Lys
            180                 185                 190

Asn Val Pro Pro Leu Pro Lys Glu Cys Thr Leu Lys His Leu Ser Ser
        195                 200                 205

Tyr Met Glu Glu Lys Leu Lys Ser Met Glu Ser Lys Lys Asn Ile Glu
    210                 215                 220

Ser Gly Lys Tyr Glu Phe Asp Val Glu Ser Thr Lys Ser Thr Thr Asp
225                 230                 235                 240
```

Asp Gly Gln Ala Asp Asp Glu Asp Asp Glu Asn Glu Glu Asp Ala
            245                 250                 255

Phe Glu Glu Glu Thr Phe Glu Glu Lys Lys Ser Glu Glu Lys Lys Asp
            260                 265                 270

<210> SEQ ID NO 5
<211> LENGTH: 816
<212> TYPE: DNA
<213> ORGANISM: Artificial sequence
<220> FEATURE:
<223> OTHER INFORMATION: pGX7035/pGX7030 Pvivax EXP23

<400> SEQUENCE: 5

```
aaggtgtctt acatcctgtc tctgttcttt ttcctgatca tctataagaa caccacaacc      60
aatgtggtgg agtgcggcgg atactccgat ctggccgcca catctgccct gacaaccatc     120
gtgaaggacc ccatcagcct gaccatcaag gacctgtacg agcacggcgt gaaggacccc     180
atcacaaagc tgatccacaa gatcaagaag gtggtgaggt atagaaaggt gctgcggtgg     240
tcccgcatct ggtgggtgct gctggtgagg agatcgtgg gcgacaacgc catcgagagg      300
aagaccgaga aggccctgag agagatctgg gatcagtgca aatcgccgt gtacaacaat      360
accctgtatg ccatcgagtc taagcctctg ctgtttctgc acggcatcct gaatgagtgt     420
aagaacaatt tcagcaccaa gctgaggcag gacccaggcc tgatcgtggc caagatcgat     480
cagatcctga agagccagat ctaccggttt tgggtgtccg agccctatct gaagatcggc     540
aagagctcca tcttctatac ccgcatcaac tccaagaatg tgcccctct gcctaaggag      600
tgtacactga agcacctgtc tagctacatg gaggagaagc tgaagagcat ggagtccaag     660
aagaacatcg agtctggcaa gtatgagttc gacgtggagt ctaccaagag cacaaccgac     720
gatggccagg ccgacgatga ggacgatgac gagaatgagg aggacgcctt tgaggaggag     780
acattcgagg agaagaagtc cgaggagaag aaggat                              816
```

<210> SEQ ID NO 6
<211> LENGTH: 870
<212> TYPE: DNA
<213> ORGANISM: Artificial sequence
<220> FEATURE:
<223> OTHER INFORMATION: pGX7035/pGX7030 Pvivax EXP23 operably linked to
      IgE leader sequence

<400> SEQUENCE: 6

```
atggactgga catggattct gttcctggtg gcagcagcaa ccagagtgca ctccaaggtg      60
tcttacatcc tgtctctgtt cttttttcctg atcatctata agaacaccac aaccaatgtg    120
gtggagtgcg gcggatactc cgatctggcc gccacatctg ccctgacaac catcgtgaag    180
gaccccatca gcctgaccat caaggacctg tacgagcacg gcgtgaagga ccccatcaca    240
aagctgatcc acaagatcaa gaaggtggtg aggtatagaa aggtgctgcg gtggtcccgc    300
atctggtggg tgctgctggt gagggagatc gtgggcgaca acgccatcga ggaagacc     360
gagaaggccc tgagagagat ctgggatcag tgcacaatcg ccgtgtacaa caataccctg    420
tatgccatcg agtctaagcc tctgctgttt ctgcacggca tcctgaatga gtgtaagaac    480
aatttcagca ccaagctgag gcaggaccca ggcctgatcg tggccaagat cgatcagatc    540
ctgaagagcc agatctaccg gttttgggtg tccgagccct atctgaagat cggcaagagc    600
tccatcttct atacccgcat caactccaag aatgtgcccc tctgcctaa ggagtgtaca    660
ctgaagcacc tgtctagcta catggaggag aagctgaaga gcatggagtc caagaagaac    720
```

-continued

```
atcgagtctg gcaagtatga gttcgacgtg gagtctacca agagcacaac cgacgatggc     780
caggccgacg atgaggacga tgacgagaat gaggaggacg cctttgagga ggagacattc     840
gaggagaaga agtccgagga gaagaaggat                                       870
```

<210> SEQ ID NO 7
<211> LENGTH: 363
<212> TYPE: PRT
<213> ORGANISM: Artificial sequence
<220> FEATURE:
<223> OTHER INFORMATION: pGX7036/pGX7031 Pvivax ICP

<400> SEQUENCE: 7

```
Lys Leu Ser Ser Leu Phe Cys Leu Val Val Cys Ser Ser Val Ala His
1               5                   10                  15

Leu Ser Ser Cys Ser Asp Gln Asn Thr Tyr Ser Phe Asp Ile Val Asn
            20                  25                  30

Arg Asn Thr Trp Tyr Ser Ile Ala Lys Lys Ile Phe Gln Gly Thr Thr
        35                  40                  45

Pro Cys Asn Phe Thr Val Ile Pro Ser Ser Tyr Val Asn Asn Ser Asp
    50                  55                  60

Gly Val Ser Thr Ser Asp Asp Ser Val Leu Leu Ile Arg Lys Lys Leu
65                  70                  75                  80

Lys Asp Pro Ser Glu Ala Gly Leu Asp Gly Ser Ser Val Ser Gly Ser
                85                  90                  95

Ser Ser Ser Gly Asn Ser His Ser Gly Ser Ala Pro Cys Cys Asp Lys
            100                 105                 110

Gly Thr Pro Ala Lys Glu Ala Glu Leu Lys Phe Ser Thr Lys Phe Glu
        115                 120                 125

Gly Asp Asp Tyr Ala Lys Leu Arg Asp Ser Leu Ser Ile Asp Lys
    130                 135                 140

Ser Leu Arg Glu Glu Ser Ser Ser Glu Asp Ser Lys Met Glu Asp
145                 150                 155                 160

Ser Gln Val Gly Glu Val Thr His Glu Glu Thr Ile Thr Tyr Asn Met
                165                 170                 175

Pro Glu Glu Tyr Met Pro Gln Asn Ile Ser Glu Val Leu Ile Gly Ala
            180                 185                 190

Ala Glu Glu Asp Arg Thr Tyr Ala Leu Lys Gly Asp Glu Pro Cys Asp
        195                 200                 205

Val Tyr Leu Lys Leu Gly Glu Ile Ile Asn Gly Thr Asn Glu Lys Thr
    210                 215                 220

Ile Glu Tyr Ser Leu Gln Lys Asn Lys Ile Leu Cys Val Gln Leu Glu
225                 230                 235                 240

Ala Ile Gly Gly Asn Gly Tyr Leu Trp Ala Leu Leu Gly Val His Lys
                245                 250                 255

Glu Lys Pro Gln Ile Asn Pro Glu Glu Phe Pro Arg Lys Lys Ile Thr
            260                 265                 270

Lys Ser Phe Phe Thr Asn Glu Ile Ser Val Thr Gln Pro Lys Ala Val
        275                 280                 285

Gln Lys Asn Lys Ser Asn Asn Gly Gly Glu Ser Ser Asn Ser Pro
    290                 295                 300

Gly Tyr Gly Lys Pro Pro Ala Ser Glu Gln Leu Gly Gly Phe Val Gly
305                 310                 315                 320

Gly Thr Ser Met Leu Gln Ser Ile Val Lys Ala His Lys Glu Gly Thr
                325                 330                 335
```

Phe Phe Val Val Tyr Ser Tyr Tyr Arg Pro Phe Asp Pro Thr Ala Asn
              340                 345                 350

Ala Asn Thr Lys Ile Leu Lys Leu Thr Val Ser
              355                 360

<210> SEQ ID NO 8
<211> LENGTH: 1089
<212> TYPE: DNA
<213> ORGANISM: Artificial sequence
<220> FEATURE:
<223> OTHER INFORMATION: pGX7036/pGX7031 Pvivax ICP

<400> SEQUENCE: 8

| | | | | | |
|---|---|---|---|---|---|
| aagctgagct | ccctgttttg | cctggtggtg | tgcagcagcg | tggcacacct | gtcctcttgc | 60 |
| tccgaccaga | acacctactc | tttcgatatc | gtgaaccgca | atacatggta | tagcatcgcc | 120 |
| aagaagatct | tccagggcac | cacaccctgt | aacttcaccg | tgatccctag | ctcctacgtg | 180 |
| aacaattctg | acggcgtgtc | tacaagcgac | gatagcgtgc | tgctgatccg | aagaagctg | 240 |
| aaggacccca | gcgaggcagg | cctggatggc | tctagcgtgt | ccggctcctc | tagctccgga | 300 |
| aactcccact | ctggcagcgc | cccatgctgt | gataagggaa | ccccagcaaa | ggaggcagag | 360 |
| ctgaagttct | ctacaaagtt | tgagggcgac | gattatgcca | agctgaggga | ctccctgtct | 420 |
| ctgatcgata | gagcctgag | agaggagtct | agctccgagg | aggactctaa | gatgaggat | 480 |
| agccaagtgg | gcgaggtgac | ccacgaggag | acaatcacat | acaacatgcc | tgaggagtat | 540 |
| atgccacaga | atatctccga | ggtgctgatc | ggagcagcag | aggaggacag | gacatacgcc | 600 |
| ctgaagggcg | acgagccttg | cgacgtgtac | ctgaagctgg | gcgagatcat | caacggcacc | 660 |
| aatgagaaga | caatcgagta | cagcctgcag | aagaacaaga | tcctgtgcgt | gcagctggag | 720 |
| gcaatcggcg | gaaatggcta | tctgtgggcc | ctgctgggcg | tgcacaagga | gaagcctcag | 780 |
| atcaacccag | aggagtttcc | cagaaagaag | atcaccaaga | gcttctttac | aaatgagatc | 840 |
| tccgtgaccc | agcctaaggc | cgtgcagaag | aacaagagca | caatggcgg | cgagtctagc | 900 |
| tccaattccc | caggatacgg | caagccccct | gcatctgagc | agctgggcgg | cttcgtgggc | 960 |
| ggcaccagca | tgctgcagtc | catcgtgaag | gcccacaagg | agggcacatt | ctttgtggtg | 1020 |
| tattcctact | atcgcccatt | tgatcccacc | gccaacgcca | atacaaagat | cctgaagctg | 1080 |
| accgtgtct | | | | | | 1089 |

<210> SEQ ID NO 9
<211> LENGTH: 1143
<212> TYPE: DNA
<213> ORGANISM: Artificial sequence
<220> FEATURE:
<223> OTHER INFORMATION: pGX7036/pGX7031 Pvivax ICP operably linked to
      IgE leader sequence

<400> SEQUENCE: 9

| | | | | | |
|---|---|---|---|---|---|
| atggactgga | cctggattct | gttcctggtg | gcagcagcaa | cacgggtgca | ctccaagctg | 60 |
| agctccctgt | tttgcctggt | ggtgtgcagc | agcgtggcac | acctgtcctc | ttgctccgac | 120 |
| cagaacacct | actctttcga | tatcgtgaac | cgcaatacat | ggtatagcat | cgccaagaag | 180 |
| atcttccagg | gcaccacacc | ctgtaacttc | accgtgatcc | ctagctccta | cgtgaacaat | 240 |
| tctgacggcg | tgtctacaag | cgacgatagc | gtgctgctga | tccggaagaa | gctgaaggac | 300 |
| cccagcgagg | caggcctgga | tggctctagc | gtgtccggct | cctctagctc | cggaaactcc | 360 |
| cactctggca | gcgcccatg | ctgtgataag | ggaaccccag | caaaggaggc | agagctgaag | 420 |

```
ttctctacaa agtttgaggg cgacgattat gccaagctga gggactccct gtctctgatc    480
gataagagcc tgagagagga gtctagctcc gaggaggact ctaagatgga ggatagccaa    540
gtgggcgagg tgacccacga ggagacaatc acatacaaca tgcctgagga gtatatgcca    600
cagaatatct ccgaggtgct gatcggagca gcagaggagg acaggacata cgccctgaag    660
ggcgacgagc cttgcgacgt gtacctgaag ctgggcgaga tcatcaacgg caccaatgag    720
aagacaatcg agtacagcct gcagaagaac aagatcctgt gcgtgcagct ggaggcaatc    780
ggcggaaatg gctatctgtg ggccctgctg ggcgtgcaca aggagaagcc tcagatcaac    840
ccagaggagt tcccagaaaa gaagatcacc aagagcttct ttacaaatga gatctccgtg    900
acccagccta aggccgtgca agaacaag agcaacaatg gcggcgagtc tagctccaat    960
tccccaggat acggcaagcc ccctgcatct gagcagctgg gcggcttcgt gggcggcacc    1020
agcatgctgc agtccatcgt gaaggcccac aaggagggca cattctttgt ggtgtattcc    1080
tactatcgcc catttgatcc caccgccaac gccaatacaa agatcctgaa gctgaccgtg    1140
tct                                                                 1143
```

<210> SEQ ID NO 10
<211> LENGTH: 213
<212> TYPE: PRT
<213> ORGANISM: Artificial sequence
<220> FEATURE:
<223> OTHER INFORMATION: pGX7037/pGX7032 Pvivax TMP21

<400> SEQUENCE: 10

```
Gly Arg Leu Ala Arg Leu Ala Ala Leu Leu Val Val Leu Thr Leu Gln
1               5                   10                  15

Cys Leu Arg Thr Gly Ala Ile Glu Val Tyr Val Thr Val Arg Pro Asn
            20                  25                  30

Lys Ile Lys Cys Leu Lys Glu Arg Ile Asn Lys Asp Thr Leu Val Val
        35                  40                  45

Gly Lys Phe Lys Thr Asp Ser Lys Asn Ser Pro Ile Ser Ile Phe Ile
    50                  55                  60

Tyr Asp Ala Asp Val Asn Glu Arg Thr Phe Asn Phe Gln Lys Lys Leu
65                  70                  75                  80

Pro Ile Phe Glu Thr Ile Asn Glu His Asp Ile Lys Thr Ala Phe Thr
                85                  90                  95

Thr Phe Tyr Ser Thr Ser Tyr Ser Phe Cys Ala Tyr Asn Ser Thr Asn
            100                 105                 110

Lys Ile Leu Asp Val Phe Phe Glu Ile Lys His Gly Thr Glu Ala Arg
        115                 120                 125

Asp Tyr Ala Gln Ile Ala Lys Ser Glu His Leu Asn Glu Ala Thr Met
    130                 135                 140

Tyr Leu Asn Gln Ile Leu Asp Gln Met Asn Asn Phe His Leu Asn Leu
145                 150                 155                 160

Lys Arg Ile Lys Ala Ser Glu Glu Asn Glu Lys Lys Ser Ser Asp Lys
                165                 170                 175

Leu Asn Asp Thr Leu Met Trp Phe Ser Leu Met Asn Ile Leu Ile Ile
            180                 185                 190

Ile Val Ala Ala Ile Ile Gln Asp Phe Tyr Phe Lys Arg Phe Phe Thr
        195                 200                 205

Ser Lys Lys Ile Ile
    210
```

<210> SEQ ID NO 11
<211> LENGTH: 639
<212> TYPE: DNA
<213> ORGANISM: Artificial sequence
<220> FEATURE:
<223> OTHER INFORMATION: pGX7037/pGX7032 Pvivax TMP21

<400> SEQUENCE: 11

```
ggcaggctgg caagactggc cgccctgctg gtggtgctga ccctgcagtg cctgagaaca      60
ggcgccatcg aggtgtacgt gacagtgcgg cccaacaaga tcaagtgtct gaaggagcgc     120
atcaataagg acaccctggt ggtgggcaag ttcaagacag attctaagaa cagccccatc     180
tccatcttta tctatgacgc cgatgtgaac gagaggacct tcaattttca gaagaagctg     240
cctatcttcg agacaatcaa cgagcacgat atcaagacag ccttcaccac cttctactct     300
accagctatt cctttgcgc ctacaactcc acaaataaga tcctggacgt gttctttgag      360
atcaagcacg gaaccgaggc ccgggattac gcacagatcg ccaagtctga gcacctgaac     420
gaggccacca tgtatctgaa tcagatcctg accagatga acaatttcca cctgaacctg      480
aagcgcatca aggcctctga ggagaacgag aagaagagct ccgacaagct gaatgataca     540
ctgatgtggt ttagcctgat gaatatcctg atcatcatcg tggccgccat catccaggac     600
ttctacttca gaggttcttc acctccaag aagatcatc                             639
```

<210> SEQ ID NO 12
<211> LENGTH: 693
<212> TYPE: DNA
<213> ORGANISM: Artificial sequence
<220> FEATURE:
<223> OTHER INFORMATION: pGX7037/pGX7032 Pvivax TMP21 operably linked to IgE leader sequence

<400> SEQUENCE: 12

```
atggactgga catggattct gttcctggtg gcagcagcaa ccagggtgca cagcggcagg      60
ctggcaagac tggccgccct gctggtggtg ctgaccctgc agtgcctgag aacaggcgcc     120
atcgaggtgt acgtgacagt gcggcccaac aagatcaagt gtctgaagga gcgcatcaat     180
aaggacaccc tggtggtggg caagttcaag acagattcta agaacagccc catctccatc     240
tttatctatg acgccgatgt gaacgagagg accttcaatt ttcagaagaa gctgcctatc     300
ttcgagacaa tcaacgagca cgatatcaag acagccttca ccaccttcta ctctaccagc     360
tattcctttt gcgcctacaa ctccacaaat aagatcctgg acgtgttctt tgagatcaag     420
cacggaaccg aggcccggga ttacgcacag atcgccaagt ctgagcacct gaacgaggcc     480
accatgtatc tgaatcagat cctggaccag atgaacaatt tccacctgaa cctgaagcgc     540
atcaaggcct ctgaggagaa cgagaagaag agctccgaca agctgaatga tacactgatg     600
tggtttagcc tgatgaatat cctgatcatc atcgtggccg ccatcatcca ggacttctac     660
ttcagaggt tcttcacctc caagaagatc atc                                   693
```

<210> SEQ ID NO 13
<211> LENGTH: 212
<212> TYPE: PRT
<213> ORGANISM: Artificial sequence
<220> FEATURE:
<223> OTHER INFORMATION: pGX7038/pGX7033 Pvivax UIS3

<400> SEQUENCE: 13

```
Asn Ile Ser Lys Ile Phe Ala Phe Phe Phe Leu Leu Cys Ala Thr Glu
1               5                   10                  15
```

```
Lys Leu Leu Ile Val Cys Ala Ser Arg Ile Leu Ser Ser Ile Glu Lys
         20                  25                  30

Asp Leu Ala Pro Leu Lys Asn Ile Asp Asp Thr Leu Ala Glu Lys Asn
     35                  40                  45

Arg Lys Lys Lys Ile Tyr Tyr Ser Leu Ile Ser Ser Gly Ile Phe Val
 50                  55                  60

Phe Val Ala Ile Ala Leu Gly Ile Gly Phe Tyr Ile Asn Glu Lys Glu
65                  70                  75                  80

Glu Glu Tyr Tyr Phe Lys Lys Tyr Ala Leu Phe Arg Asp Lys Arg Phe
                 85                  90                  95

Gln Phe Glu Asn Pro Arg Asp Gly Gln Val Pro Ser Thr Ser Arg Glu
            100                 105                 110

Tyr Val Glu Pro Pro Gly Ile Asn Lys Val Asn Ile Lys Gly Pro Leu
        115                 120                 125

Val Glu Asn Thr Asn Glu Asn Asp Val Pro Ile Lys Lys Phe Asn Ile
130                 135                 140

Phe Leu Asp Asn Ala Arg Ile Ala Met Arg His His Phe Ser Asn Leu
145                 150                 155                 160

Ser Gln Pro Gln Gln Glu Tyr Tyr Leu Asn Asp Arg Asp Tyr Ile Arg
                165                 170                 175

Lys Val Val Gln Ser Leu Glu Glu Arg Arg Asn Val His Leu Ser Arg
            180                 185                 190

Met Gln Glu Asp Met Ala Val Leu Asn Met Glu Asp Phe Leu Gln Lys
        195                 200                 205

Ile Ser Lys Glu
    210

<210> SEQ ID NO 14
<211> LENGTH: 636
<212> TYPE: DNA
<213> ORGANISM: Artificial sequence
<220> FEATURE:
<223> OTHER INFORMATION: pGX7038/pGX7033 Pvivax UIS3

<400> SEQUENCE: 14
aatatctcca agatcttcgc cttcttttc ctgctgtgcg ccaccgagaa gctgctgatc      60
gtgtgcgcca gcagaatcct gagcagcatc gagaaggatc tggcccctct gaagaatatc    120
gacgatacac tggccgagaa gaacaggaag aagaagatct actattccct gatctctagc    180
ggcatcttcg tgttcgtggc catcgccctg gcatcggct tttacatcaa tgagaaggag     240
gaggagtact acttcaagaa gtatgccctg ttccgggaca gaggttcca gttcgagaac     300
ccaagggatg gccaggtgcc ctccacctct agagagtacg tggagccccc tggcatcaat    360
aaggtgaaca tcaagggccc tctggtggag aacacaaatg agaacgacgt gccaatcaag    420
aagtttaata tcttcctgga taacgccagg atcgccatga gacaccactt ttctaatctg    480
agccagcctc agcaggagta ctatctgaac gaccgggatt atatccgcaa ggtggtgcag    540
tccctggagg agaggagaaa tgtgcacctg tctagaatgc aggaggacat ggccgtgctg    600
aacatggagg atttcctgca gaagatctct aaggag                              636

<210> SEQ ID NO 15
<211> LENGTH: 690
<212> TYPE: DNA
<213> ORGANISM: Artificial sequence
<220> FEATURE:
<223> OTHER INFORMATION: pGX7038/pGX7033 Pvivax UIS3 operably linked to
```

IgE leader sequence

<400> SEQUENCE: 15
atggactgga cctggattct gttcctggtg gcagcagcaa caagggtgca cagcaatatc    60
tccaagatct tcgccttctt tttcctgctg tgcgccaccg agaagctgct gatcgtgtgc   120
gccagcagaa tcctgagcag catcgagaag gatctggccc ctctgaagaa tatcgacgat   180
acactggccg agaagaacag gaagaagaag atctactatt ccctgatctc tagcggcatc   240
ttcgtgttcg tggccatcgc cctgggcatc ggcttttaca tcaatgagaa ggaggaggag   300
tactacttca gaagtatgc cctgttccgg gacaagaggt tccagttcga gaacccaagg   360
gatggccagg tgcctccac ctctagagag tacgtggagc cccctggcat caataaggtg   420
aacatcaagg gccctctggt ggagaacaca aatgagaacg acgtgccaat caagaagttt   480
aatatcttcc tggataacgc caggatcgcc atgagacacc acttttctaa tctgagccag   540
cctcagcagg agtactatct gaacgaccgg gattatatcc gcaaggtggt gcagtccctg   600
gaggagagga gaaatgtgca cctgtctaga atgcaggagg acatggccgt gctgaacatg   660
gaggatttcc tgcagaagat ctctaaggag                                    690

<210> SEQ ID NO 16
<211> LENGTH: 18
<212> TYPE: PRT
<213> ORGANISM: Artificial sequence
<220> FEATURE:
<223> OTHER INFORMATION: IgE leader sequence

<400> SEQUENCE: 16

Met Asp Trp Thr Trp Ile Leu Phe Leu Val Ala Ala Thr Arg Val
1               5                   10                  15

His Ser

<210> SEQ ID NO 17
<211> LENGTH: 311
<212> TYPE: PRT
<213> ORGANISM: Artificial sequence
<220> FEATURE:
<223> OTHER INFORMATION: pGX7039 Pcynomolgi EXP1-EXP2

<400> SEQUENCE: 17

Lys Leu Leu Thr Ala Val Phe Leu Leu Phe Cys Ala Ile Leu Cys Asp
1               5                   10                  15

Pro Ala Leu Gly Asp Asn Val Asn Gly Leu Gly Gly Pro Ser Lys
            20                  25                  30

Lys Lys Thr Pro Lys Ser Lys Ser Pro Glu Pro Leu Ile Asp Val His
        35                  40                  45

Glu Leu Ile Gly Glu Met Val Arg Lys Glu Glu Leu Ile Asn Ala
    50                  55                  60

Asn Lys Lys Lys Ser Lys Tyr Lys Leu Ala Thr Thr Ile Leu Ala Ser
65                  70                  75                  80

Ala Leu Gly Val Val Ser Ala Val Leu Leu Gly Gly Ala Gly Leu Val
                85                  90                  95

Phe Tyr Asn Ala Gly Asn Gly Arg His Pro Phe Ser Leu Gly Gly Gly
            100                 105                 110

Lys Gly Gly Asp Ala Thr Pro Ser Glu Pro Ala Pro Ala Ala Gly Glu
        115                 120                 125

Pro Val Gly Lys Arg Gly Arg Lys Arg Arg Ser Ala Glu Glu Glu Tyr
    130                 135                 140

```
Ser Trp Asp Ser Tyr Leu Asn Asp Arg Leu Leu Ala Thr Asn Gln Val
145                 150                 155                 160

Ser Ala Ala Gly Leu Ala Ser Glu Glu Asp Gly Val Val Tyr Ala Cys
            165                 170                 175

Val Ala Gln Ala Asp Glu Asn Asn Pro Glu Phe Asp Lys Trp Ser Leu
        180                 185                 190

Phe Tyr Lys Glu Asp Phe Glu Ile Glu Val Glu Asp Glu Asn Gly Asn
    195                 200                 205

Lys Ser Lys Lys Thr Ile Asn Glu Gly Gln Thr Leu Leu Thr Val Phe
210                 215                 220

Lys Glu Gly Tyr Ala Pro Asp Gly Val Trp Leu Gly Thr Lys Tyr
225                 230                 235                 240

Gln Phe Ile Asn Ile Glu Arg Asp Leu Glu Phe Glu Gly Tyr Thr Phe
                245                 250                 255

Asp Val Ala Thr Cys Ala Lys Leu Lys Gly Gly Leu His Leu Ile Lys
            260                 265                 270

Val Pro Gly Gly Asn Ile Leu Val Val Leu Tyr Asp Glu Glu Lys Glu
        275                 280                 285

His Asp Arg Gly Asn Ser Lys Val Ala Ala Leu Thr Phe Ser Lys Glu
    290                 295                 300

Leu Ala Glu Ser Gly Gly Gln
305                 310

<210> SEQ ID NO 18
<211> LENGTH: 933
<212> TYPE: DNA
<213> ORGANISM: Artificial sequence
<220> FEATURE:
<223> OTHER INFORMATION: pGX7039 Pcynomolgi EXP1-EXP2

<400> SEQUENCE: 18
aagctgctga cagccgtgtt cctgctgttt tgcgcaatcc tgtgcgaccc tgccctgggc      60
gataacgtga atggcctggg cggccctccc agcaagaaga agaccccaaa gagcaagtcc     120
ccagagcccc tgatcgatgt gcacgagctg atcggcgaga tggtgcggaa ggaggaggag     180
ctgatcaacg ccaacaagaa gaagagcaag tacaagctgg caaccacaat cctggcatcc     240
gccctgggag tggtgtctgc cgtgctgctg ggcggcgccg gcctggtgtt ctataacgcc     300
ggcaatggcc gccacccatt ttccctgggc ggcggcaagg gcggcgacgc aaccccatct     360
gagcctgcac cagcagcagg agagccagtg ggcaagcggg gccgcaagag agatctgcc      420
gaggaggagt actcttggga cagctatctg aacgatagg tgctggccac aaatcaggtg     480
agcgccgcag gcctggcatc cgaggaggat ggagtggtgt acgcatgcgt ggcacaggca     540
gacgagaaca atcccgagtt cgataagtgg agcctgttct ataaggagga ctttgagatc     600
gaggtggagg atgagaacgg caataagtcc aagaagacca tcaacgaggg ccagaccctg     660
ctgacagtgt tcaaggaggg ctacgcacca gacggcgtgt ggctgggcgg cacaaagtat     720
cagtttatca atatcgagag ggacctggag ttcgagggct acacctttga tgtggccaca     780
tgtgccaagc tgaagggcgg cctgcacctg atcaaggtgc ctggcggcaa catcctggtg     840
gtgctgtatg acgaggagaa ggagcacgat agaggcaata gcaaggtggc cgccctgacc     900
ttttctaagg agctggcaga gagcggcggc cag                                  933

<210> SEQ ID NO 19
<211> LENGTH: 987
```

<212> TYPE: DNA
<213> ORGANISM: Artificial sequence
<220> FEATURE:
<223> OTHER INFORMATION: pGX7039 Pcynomolgi EXP1-EXP2 operably linked to IgE leader sequence

<400> SEQUENCE: 19

```
atggactgga cctggattct gttcctggtg gcagcagcaa ccagggtgca ctctaagctg     60
ctgacagccg tgttcctgct gttttgcgca atcctgtgcg accctgccct gggcgataac    120
gtgaatggcc tgggcggccc tcccagcaag aagaagaccc caaagagcaa gtccccagag    180
cccctgatcg atgtgcacga gctgatcggc gagatggtgc ggaaggagga ggagctgatc    240
aacgccaaca agaagaagag caagtacaag ctggcaacca caatcctggc atccgccctg    300
ggagtggtgt ctgccgtgct gctgggcggc gccggcctgg tgttctataa cgccggcaat    360
ggccgccacc cattttccct gggcggcggc aagggcggcg acgcaacccc atctgagcct    420
gcaccagcag caggagagcc agtgggcaag cggggccgca agaggagatc tgccgaggag    480
gagtactctt gggacagcta tctgaacgat aggctgctgg ccacaaatca ggtgagcgcc    540
gcaggcctgg catccgagga ggatggagtg gtgtacgcat gcgtggcaca ggcagacgag    600
aacaatcccg agttcgataa gtggagcctg ttctataagg aggactttga gatcgaggtg    660
gaggatgaga acggcaataa gtccaagaag accatcaacg agggccagac cctgctgaca    720
gtgttcaagg agggctacgc accagacggc gtgtggctgg gcggcacaaa gtatcagttt    780
atcaatatcg agagggacct ggagttcgag ggctacacct ttgatgtggc cacatgtgcc    840
aagctgaagg gcggcctgca cctgatcaag gtgcctggcg gcaacatcct ggtggtgctg    900
tatgacgagg agaaggagca cgatagaggc aatagcaagg tggccgccct gaccttttct    960
aaggagctgg cagagagcgg cggccag                                        987
```

<210> SEQ ID NO 20
<211> LENGTH: 305
<212> TYPE: PRT
<213> ORGANISM: Artificial sequence
<220> FEATURE:
<223> OTHER INFORMATION: pGX7040 Pcynomolgi EXP23

<400> SEQUENCE: 20

```
Lys Val Ser Tyr Ile Phe Ser Leu Leu Phe Phe Leu Ile Ile Tyr Lys
1               5                   10                  15

Asn Thr Thr Thr Asn Val Val His Cys Gly Gly Tyr Ser Asp Leu Ala
            20                  25                  30

Ala Thr Ser Ala Leu Thr Thr Ile Val Lys Asp Pro Ile Arg Leu Thr
        35                  40                  45

Ile Lys Asp Leu Tyr Glu His Gly Val Lys Asp Pro Ile Thr Lys Leu
    50                  55                  60

Ile His Lys Ile Lys Lys Val Val Arg Tyr Arg Lys Val Leu Arg Trp
65                  70                  75                  80

Ser Arg Ile Trp Trp Val Leu Leu Val Arg Glu Ile Val Gly Asp Asn
                85                  90                  95

Ala Ile Glu Arg Lys Thr Glu Lys Ala Leu Arg Glu Ile Trp Asp Gln
            100                 105                 110

Cys Thr Ile Ala Val Tyr Asn Asn Thr Leu Tyr Ala Ile Glu Ser Lys
        115                 120                 125

Pro Leu Leu Phe Leu His Gly Ile Leu Asn Glu Cys Lys Asn Asn Phe
    130                 135                 140
```

| | | | | | | | | | | | | | | |
|---|---|---|---|---|---|---|---|---|---|---|---|---|---|---|
|Ser|Thr|Lys|Leu|Arg|Gln|Asp|Pro|Gly|Leu|Ile|Val|Ala|Lys|Ile|Asp|
|145| | | | |150| | | | |155| | | | |160|

| | | | | | | | | | | | | |
|---|---|---|---|---|---|---|---|---|---|---|---|---|
|Gln|Ile|Leu|Lys|Ser|Gln|Ile|Tyr|Arg|Phe|Trp|Val|Ser|Glu|Pro|Tyr|
| | | | |165| | | | |170| | | | |175| |

Leu Lys Ile Gly Lys Ser Ser Ile Phe Tyr Thr Arg Ile Asn Ser Asn
            180                 185                 190

Asn Val Pro Pro Leu Pro Lys Glu Cys Thr Leu Lys His Leu Ser Ser
        195                 200                 205

Tyr Met Glu Glu Lys Leu Lys Ser Met Glu Ser Lys Lys Asn Ile Glu
    210                 215                 220

Ser Gly Lys Tyr Glu Phe Asp Val Glu Ser Thr Lys Asn Thr Thr Asp
225                 230                 235                 240

Asp Ser Gln Ala Asp Glu Glu Asp Asp Glu Asn Glu Glu Asp Ala
            245                 250                 255

Phe Glu Glu Glu Ser Phe Glu Glu Lys Lys Ser Glu Glu Lys Lys Asp
            260                 265                 270

Asp Asp Gly Gln Ala Asp Asp Glu Asp Asp Glu Asn Glu Glu Asp
        275                 280                 285

Ala Phe Glu Glu Glu Thr Phe Glu Glu Lys Lys Ser Glu Glu Lys Lys
    290                 295                 300

Asp
305

<210> SEQ ID NO 21
<211> LENGTH: 915
<212> TYPE: DNA
<213> ORGANISM: Artificial sequence
<220> FEATURE:
<223> OTHER INFORMATION: pGX7040 Pcynomolgi EXP23

<400> SEQUENCE: 21

```
aaggtgtctt acatcttttc tctgctgttc tttctgatca tctataagaa caccacaacc      60
aatgtggtgc actgcggcgg atactctgat ctggccgcca caagcgccct gacaaccatc     120
gtgaaggacc ccatcaggct gaccatcaag gacctgtacg agcacggcgt gaaggacccc     180
atcacaaagc tgatccacaa gatcaagaag gtggtgaggt atagaaaggt gctgcggtgg     240
tcccgcatct ggtgggtgct gctggtgaga gagatcgtgg gcgacaatgc catcgagagg     300
aagaccgaga aggccctgag agagatctgg gatcagtgca aatcgccgt gtacaacaat     360
accctgtatg ccatcgagtc caagcccctg ctgttcctgc acggcatcct gaacgagtgt     420
aagaacaatt tttctacaaa gctgaggcag gaccctggcc tgatcgtggc caagatcgat     480
cagatcctga gagccagat ctaccggttc tgggtgtccg agccatatct gaagatcggc     540
aagagctcca tcttttacac ccgcatcaat agcaacaatg tgccccctct gcccaaggag     600
tgtacactga agcacctgtc tagctacatg gaggagaagc tgaagagcat ggagtccaag     660
aagaacatcg agtccggcaa gtatgagttc gacgtggagt ctaccaagaa tacaaccgac     720
gatagccagg ccgacgagga ggacgatgac gagaacgagg aggatgcctt cgaggaggag     780
tcctttgagg agaagaagtc tgaggagaag aaggatgacg atggccaggc cgacgatgaa     840
gatgacgatg agaacgagga ggacgccttc gaggaggaga cattcgagga agaagagc     900
gaggagaaga aggat                                                     915
```

<210> SEQ ID NO 22
<211> LENGTH: 969
<212> TYPE: DNA

<213> ORGANISM: Artificial sequence
<220> FEATURE:
<223> OTHER INFORMATION: pGX7040 Pcynomolgi EXP23 operably linked to IgE
      leader sequence

<400> SEQUENCE: 22

```
atggactgga catggattct gttcctggtg gcagcagcaa cccgggtgca ctccaaggtg     60
tcttacatct tttctctgct gttctttctg atcatctata agaacaccac aaccaatgtg    120
gtgcactgcg gcggatactc tgatctggcc gccacaagcg ccctgacaac catcgtgaag    180
gaccccatca ggctgaccat caaggacctg tacgagcacg gcgtgaagga ccccatcaca    240
aagctgatcc acaagatcaa gaaggtggtg aggtatagaa aggtgctgcg gtggtcccgc    300
atctggtggg tgctgctggt gagagagatc gtgggcgaca atgccatcga gaggaagacc    360
gagaaggccc tgagagagat ctgggatcag tgcacaatcg ccgtgtacaa caataccctg    420
tatgccatcg agtccaagcc cctgctgttc ctgcacggca tcctgaacga gtgtaagaac    480
aatttttcta caaagctgag gcaggaccct ggcctgatcg tggccaagat cgatcagatc    540
ctgaagagcc agatctaccg gttctgggtg tccgagccat atctgaagat cggcaagagc    600
tccatctttt acacccgcat caatagcaac aatgtgcccc ctctgcccaa ggagtgtaca    660
ctgaagcacc tgtctagcta catggaggag aagctgaaga gcatggagtc caagaagaac    720
atcgagtccg gcaagtatga gttcgacgtg gagtctacca agaatacaac cgacgatagc    780
caggccgacg aggaggacga tgacgagaac gaggaggatg ccttcgagga ggagtccttt    840
gaggagaaga agtctgagga gaagaaggat gacgatggcc aggccgacga tgaagatgac    900
gatgagaacg aggaggacgc cttcgaggag gagacattcg aggagaagaa gagcgaggag    960
aagaaggat                                                            969
```

<210> SEQ ID NO 23
<211> LENGTH: 358
<212> TYPE: PRT
<213> ORGANISM: Artificial sequence
<220> FEATURE:
<223> OTHER INFORMATION: pGX7041 Pcynomolgi ICP

<400> SEQUENCE: 23

```
Lys Val Ser Ser Leu Phe Cys Leu Ile Val Cys Ser Ser Val Ala His
1               5                   10                  15

Val Ser Trp Cys Ser Asp Gln Asn Thr Tyr Ser Phe Asp Ile Val Asn
            20                  25                  30

Lys Asn Thr Trp Tyr Ser Ile Ala Lys Lys Ile Phe Glu Ser Thr Thr
        35                  40                  45

Pro Cys Asn Phe Thr Val Ile Pro Ser Ser Tyr Val Asn Asn Ser Asp
    50                  55                  60

Glu Val Ser Ser Gly Asp Asp Ser Val Leu Leu Ile Arg Lys Lys Leu
65                  70                  75                  80

Lys Asp Pro Ser Glu Ala Gly Val Glu Gly Ile Gly Glu Gly Ser Ile
                85                  90                  95

Lys Gly Ser Ser Ser Ser Ser Ala Ser Gly Lys Glu Thr Leu Glu Lys
            100                 105                 110

Glu Ala Gln Leu Asn Phe Ser Thr Asn Phe Glu Gly Asp Asp Tyr Ala
        115                 120                 125

Lys Leu Gln Asn Ser Leu Ser Leu Ile Asp Lys Ser Leu Arg Glu Glu
    130                 135                 140

Ser Ala Ser Asn Glu Asn Thr Lys Met Glu Asp Gly Lys Val Gly Asp
```

```
        145                 150                 155                 160
Val Asn Glu Glu Thr Ile Thr Met Asn Met Pro Glu Tyr Met
                165                 170                 175
Pro Gln Asn Ile Ser Glu Ile Leu Met Gly Ala Ala Glu Asp Arg
            180                 185                 190
Thr Tyr Ala Leu Lys Asp Asp Glu Pro Cys Asp Tyr Leu Lys Leu
        195                 200                 205
Gly Asp Ile Ile Asn Gly Thr Asn Glu Lys Thr Ile Glu Phe Ser Leu
    210                 215                 220
Gln Lys Asn Lys Val Leu Cys Val Gln Leu Glu Ala Ile Gly Gly Asn
225                 230                 235                 240
Gly Tyr Leu Trp Thr Leu Leu Gly Val His Lys Gln Lys Pro Gln Ile
                245                 250                 255
Asn Pro Glu Glu Phe Pro Arg Lys Lys Ile Thr Lys Ser Phe Phe Thr
                260                 265                 270
Tyr Glu Ile Ser Val Thr Gln Pro Lys Ala Ile Gln Lys Asn Lys Val
        275                 280                 285
Asn Asn Gly Asn Glu Leu Ser Ser Asn Ser Leu Gly Tyr Gly Lys Pro
    290                 295                 300
Gln Ala Arg Glu His Leu Gly Gly Phe Val Gly Gly Thr Ser Thr Leu
305                 310                 315                 320
Gln Ser Leu Val Lys Ala Arg Lys Ala Gly Thr Phe Phe Ile Val Tyr
                325                 330                 335
Ser Tyr Tyr Arg Pro Phe Asp Pro Thr Ala Asn Ser Asn Thr Lys Ile
                340                 345                 350
Leu Lys Leu Thr Val Ser
        355

<210> SEQ ID NO 24
<211> LENGTH: 1074
<212> TYPE: DNA
<213> ORGANISM: Artificial sequence
<220> FEATURE:
<223> OTHER INFORMATION: pGX7041 Pcynomolgi ICP

<400> SEQUENCE: 24
aaggtgagct ccctgttttg cctgatcgtg tgcagcagcg tggcccacgt gtcctggtgc      60
tctgaccaga acacctacag cttcgatatc gtgaacaaga atacatggta ttccatcgcc     120
aagaagatct tcgagtctac cacaccctgt aacttcaccg tgatccctta ctcttacgtg     180
aacaatagcg acgaggtgag ctccggcgac gattccgtgc tgctgatcag gaagaagctg     240
aaggacccct ccgaggcagg agtggaggga atcggcgagg gctctatcaa gggctctagc     300
tcctctagcg ccagcggcaa ggagacactg gagaaggagg cccagctgaa cttcagcaca     360
aattttgagg gcgacgatta cgccaagctg cagaacagcc tgtccctgat cgacaagtcc     420
ctgagggagg agtctgccag caacgagaat accaagatgg aggacggcaa ggtcggcgat     480
gtgaacaatg aggagacaat cacaatgaac atgcctgagg agtatatgcc acagaatatc     540
tccgagatcc tgatgggagc agcagaggag gatagaacct acgccctgaa ggacgatgag     600
ccctgcgaca catatctgaa gctgggcgat atcatcaacg gcaccaatga aagacaatc      660
gagttcagcc tgcagaagaa caaggtgctg tgcgtgcagc tggaggcaat cggcggaaat     720
ggctacctgt ggaccctgct gggcgtgcac aagcagaagc cacagatcaa ccccgaggag     780
tttcctcgga agaagatcac caagtctttc tttacatacg agatcagcgt gacacagcca     840
```

```
aaggccatcc agaagaataa ggtgaacaat ggcaacgagc tgtcctctaa ttccctggga      900
tatggcaagc cacaggcccg cgagcacctg ggcggcttcg tgggcggcac cagcacactg      960
cagtccctgg tgaaggccag gaaggccggc accttcttta tcgtgtactc ttactataga     1020 cccttttgatc ctaccgccaa ctccaataca aagatcctga agctgacagt gtct           1074
```

<210> SEQ ID NO 25
<211> LENGTH: 1128
<212> TYPE: DNA
<213> ORGANISM: Artificial sequence
<220> FEATURE:
<223> OTHER INFORMATION: pGX7041 Pcynomolgi ICP operably linked to IgE
      leader sequence

<400> SEQUENCE: 25
atggactgga cctggattct gttcctggtg gcagcagcaa cacgggtgca ctctaaggtg 60
agctccctgt tttgcctgat cgtgtgcagc agcgtggccc acgtgtcctg gtgctctgac 120
cagaacacct acagcttcga tatcgtgaac aagaatacat ggtattccat cgccaagaag 180
atcttcgagt ctaccacacc ctgtaacttc accgtgatcc cttcctctta cgtgaacaat 240
agcgacgagg tgagctccgg cgacgattcc gtgctgctga tcaggaagaa gctgaaggac 300
ccctccgagg caggagtgga gggaatcggc gagggctcta tcaagggctc tagctcctct 360
agcgccagcg gcaaggagac actggagaag gaggcccagc tgaacttcag cacaaatttt 420
gagggcgacg attacgccaa gctgcagaac agcctgtccc tgatcgacaa gtccctgagg 480
gaggagtctg ccagcaacga gaataccaag atggaggacg gcaaggtcgg cgatgtgaac 540
aatgaggaga caatcacaat gaacatgcct gaggagtata tgccacagaa tatctccgag 600
atcctgatgg gagcagcaga ggaggataga acctacgccc tgaaggacga tgagccctgc 660
gacacatatc tgaagctggg cgatatcatc aacggcacca atgagaagac aatcgagttc 720
agcctgcaga agaacaaggt gctgtgcgtg cagctggagg caatcggcgg aaatggctac 780
ctgtggaccc tgctgggcgt gcacaagcag aagccacaga tcaaccccga ggagtttcct 840
cggaagaaga tcaccaagtc tttctttaca tacgagatca gcgtgacaca gccaaaggcc 900
atccagaaga ataaggtgaa caatggcaac gagctgtcct ctaattccct gggatatggc 960
aagccacagg cccgcgagca cctgggcggc ttcgtgggcg gcaccagcac actgcagtcc 1020
ctggtgaagg ccaggaaggc cggcaccttc tttatcgtgt actcttacta tagacccttt 1080
gatcctaccg ccaactccaa tacaaagatc ctgaagctga cagtgtct 1128

<210> SEQ ID NO 26
<211> LENGTH: 214
<212> TYPE: PRT
<213> ORGANISM: Artificial sequence
<220> FEATURE:
<223> OTHER INFORMATION: pGX7042 Pcynomolgi TMP21

<400> SEQUENCE: 26

Val Gly Arg Leu Ala Gln Leu Ala Ala Leu Leu Ile Val Leu Thr Leu
1 5 10 15

Gln Cys Leu Arg Thr Gly Ala Ile Glu Val Tyr Ile Thr Val Arg Pro
20 25 30

Asn Lys Ile Lys Cys Leu Lys Glu Arg Ile Asn Lys Asp Thr Leu Val
35 40 45

Val Gly Lys Phe Lys Thr Asn Asn Lys Asn Ser Pro Ile Ser Ile Phe
50 55 60

Ile Tyr Asp Thr Asp Ile Asn Glu Arg Thr Phe Asn Phe Lys Lys Lys
65                  70                  75                  80

Leu Pro Ile Phe Glu Thr Ile Asn Asp His Asp Ile Lys Thr Ala Phe
                85                  90                  95

Thr Thr Phe Tyr Ser Thr Ser Tyr Ser Phe Cys Ala Tyr Asn Ser Thr
            100                 105                 110

Asn Lys Val Leu Glu Val Phe Phe Glu Ile Lys His Gly Thr Glu Ala
        115                 120                 125

Arg Asp Tyr Thr Gln Ile Ala Lys Ser Glu His Leu Asn Glu Ala Thr
    130                 135                 140

Ile Tyr Leu Lys Gln Ile Val Asp Gln Met Asn Asn Phe His Leu Asn
145                 150                 155                 160

Leu Lys Arg Ile Lys Ala Ser Glu Glu Asn Glu Lys Lys Ser Ser Asp
                165                 170                 175

Lys Leu Asn Asp Thr Leu Met Trp Phe Ser Leu Met Asn Ile Phe Ile
            180                 185                 190

Ile Ile Val Ala Ala Ile Ile Gln Asp Phe Tyr Phe Lys Arg Phe Phe
        195                 200                 205

Thr Ser Lys Lys Ile Ile
            210

<210> SEQ ID NO 27
<211> LENGTH: 642
<212> TYPE: DNA
<213> ORGANISM: Artificial sequence
<220> FEATURE:
<223> OTHER INFORMATION: pGX7042 Pcynomolgi TMP21

<400> SEQUENCE: 27
gtgggcagac tggcacagct ggccgccctg ctgatcgtgc tgaccctgca gtgcctgagg      60
acaggagcaa tcgaggtgta catcaccgtg cggcccaaca agatcaagtg tctgaaggag     120
cgcatcaata aggataccct ggtggtgggc aagttcaaga caaacaataa gaactctcca     180
atcagcatct ttatctatga caccgatatc aacgagagga ccttcaactt caagaagaag     240
ctgcccatct tcgagacaat caacgaccac gatatcaaga cagccttcac caccttctac     300
tctaccagct attccttttg cgcctacaac agcacaaata aggtgctgga ggtgttcttt     360
gagatcaagc acggcaccga ggccagggac tacacacaga tcgccaagtc cgagcacctg     420
aacgaggcca ccatctatct gaagcagatc gtggatcaga tgaacaattt ccacctgaat     480
ctgaagagaa tcaaggcctc cgaggagaac gagaagaaga gctccgacaa gctgaatgat     540
acactgatgt ggttctctct gatgaacatc tttatcatca tcgtggccgc catcatccag     600
gacttctact ttaagaggtt ctttaccagc aagaagatca tc                        642

<210> SEQ ID NO 28
<211> LENGTH: 696
<212> TYPE: DNA
<213> ORGANISM: Artificial sequence
<220> FEATURE:
<223> OTHER INFORMATION: pGX7042 Pcynomolgi TMP21 operably linked to IgE
     leader sequence

<400> SEQUENCE: 28
atggactgga catggattct gttcctggtg gcagcagcaa ccagggtgca ctctgtgggc      60
agactggcac agctggccgc cctgctgatc gtgctgaccc tgcagtgcct gaggacagga     120
gcaatcgagg tgtacatcac cgtgcggccc aacaagatca gtgtctgaa ggagcgcatc     180

| aataaggata | ccctggtggt | gggcaagttc | aagacaaaca | ataagaactc | tccaatcagc | 240 |
| atctttatct | atgacaccga | tatcaacgag | aggaccttca | acttcaagaa | gaagctgccc | 300 |
| atcttcgaga | caatcaacga | ccacgatatc | aagacagcct | tcaccacctt | ctactctacc | 360 |
| agctattcct | tttgcgccta | caacagcaca | aataaggtgc | tggaggtgtt | ctttgagatc | 420 |
| aagcacggca | ccgaggccag | ggactacaca | cagatcgcca | agtccgagca | cctgaacgag | 480 |
| gccaccatct | atctgaagca | gatcgtggat | cagatgaaca | atttccacct | gaatctgaag | 540 |
| agaatcaagg | cctccgagga | gaacgagaag | aagagctccg | acaagctgaa | tgatacactg | 600 |
| atgtggttct | ctctgatgaa | catctttatc | atcatcgtgg | ccgccatcat | ccaggacttc | 660 |
| tactttaaga | ggttctttac | cagcaagaag | atcatc | | | 696 |

<210> SEQ ID NO 29
<211> LENGTH: 212
<212> TYPE: PRT
<213> ORGANISM: Artificial sequence
<220> FEATURE:
<223> OTHER INFORMATION: pGX7043 Pcynomolgi UIS3

<400> SEQUENCE: 29

```
Asn Ile Ser Lys Ile Phe Thr Phe Phe Leu Leu Cys Ala Thr Glu
1               5                   10                  15
Lys Leu Leu Ile Leu Cys Ala Ser Arg Ile Leu Ser Ser Thr Glu Lys
            20                  25                  30
Asp Leu Ala Pro Leu Lys Asn Ile Asp Asp Thr Leu Ala Ala Lys Asn
        35                  40                  45
Arg Lys Lys Lys Ile Tyr Tyr Ser Leu Ile Ser Ser Ser Ile Phe Val
    50                  55                  60
Phe Val Ala Ile Ala Leu Gly Ile Gly Phe Tyr Ile Asn Glu Lys Glu
65                  70                  75                  80
Lys Glu Tyr Tyr Phe Gln Lys Tyr Thr Leu Val Lys Asp Lys Arg Phe
                85                  90                  95
Gln Phe Glu Asn Pro Arg Asp Gly Gln Met Pro Ser Thr Ser Arg Glu
            100                 105                 110
Tyr Val Glu Pro Pro Gly Ile Asn Lys Val Asn Ile Lys Gly Pro Leu
        115                 120                 125
Val Glu Asn Thr Asn Glu Asn Asp Val Pro Leu Lys Lys Phe Asn Ile
    130                 135                 140
Phe Leu Asp Asn Ala Arg Ile Ala Met Arg His His Phe Ser Asn Leu
145                 150                 155                 160
Ser Thr Pro Gln Gln Glu Tyr Tyr Val Lys Asp Arg Asp Tyr Ile Arg
                165                 170                 175
Lys Ile Val Gln Ser Val Glu Glu Arg Arg Asn Ile Gln Leu Ser Arg
            180                 185                 190
Met Gln Glu Asp Leu Ala Val Leu Asn Met Glu Glu Phe Leu Gln Lys
        195                 200                 205
Ile Ser Lys Glu
    210
```

<210> SEQ ID NO 30
<211> LENGTH: 636
<212> TYPE: DNA
<213> ORGANISM: Artificial sequence
<220> FEATURE:
<223> OTHER INFORMATION: pGX7043 Pcynomolgi UIS3

<400> SEQUENCE: 30

```
aatatctcta agatcttcac cttctttttc ctgctgtgcg ccacagagaa gctgctgatc     60
ctgtgcgcca gcagaatcct gagcagcacc gagaaggatc tggccccact gaagaatatc    120
gacgatacac tggccgccaa gaacaggaag aagaagatct actattctct gatctctagc    180
tccatcttcg tgttcgtggc catcgccctg ggcatcggct tttacatcaa tgagaaggag    240
aaggagtact atttccagaa gtataccctg gtgaaggaca agcggtttca gttcgagaac    300
cctcgcgatg gccagatgcc atctacaagc cgggagtacg tggagccccc tggcatcaat    360
aaggtgaaca tcaagggccc cctggtggag aacaccaatg agaacgacgt gcctctgaag    420
aagtttaata tcttcctgga taacgcccgg atcgccatgc gccaccactt tagcaacctg    480
tccacacccc agcaggagta ctatgtgaag gacagggatt acatcagaaa gatcgtgcag    540
tctgtggagg agaggagaaa tatccagctg agccgcatgc aggaggacct ggccgtgctg    600
aacatggagg agttcctgca gaagatctcc aaggag                              636
```

```

<210> SEQ ID NO 31
<211> LENGTH: 690
<212> TYPE: DNA
<213> ORGANISM: Artificial sequence
<220> FEATURE:
<223> OTHER INFORMATION: pGX7043 Pcynomolgi UIS3 operably linked to IgE
      leader sequence

<400> SEQUENCE: 31
atggactgga cctggattct gttcctggtg gcagcagcaa caagggtgca ctccaatatc     60
tctaagatct tcaccttctt tttcctgctg tgcgccacag agaagctgct gatcctgtgc    120
gccagcagaa tcctgagcag caccgagaag gatctggccc cactgaagaa tatcgacgat    180
acactggccg ccaagaacag gaagaagaag atctactatt ctctgatctc tagctccatc    240
ttcgtgttcg tggccatcgc cctgggcatc ggcttttaca tcaatgagaa ggagaaggag    300
tactatttcc agaagtatac cctggtgaag gacaagcggt ttcagttcga gaaccctcgc    360
gatggccaga tgccatctac aagccgggag tacgtggagc cccctggcat caataaggtg    420
aacatcaagg gccccctggt ggagaacacc aatgagaacg acgtgcctct gaagaagttt    480
aatatcttcc tggataacgc ccggatcgcc atgcgccacc actttagcaa cctgtccaca    540
ccccagcagg agtactatgt gaaggacagg gattacatca gaaagatcgt gcagtctgtg    600
gaggagagga gaaatatcca gctgagccgc atgcaggagg acctggccgt gctgaacatg    660
gaggagttcc tgcagaagat ctccaaggag                                      690
```

```
<210> SEQ ID NO 32
<211> LENGTH: 348
<212> TYPE: PRT
<213> ORGANISM: Artificial sequence
<220> FEATURE:
<223> OTHER INFORMATION: pGX7021 Py EXP1-EXP2

<400> SEQUENCE: 32

Lys Ile Asn Ile Ala Ser Ile Ile Phe Ile Ile Phe Ser Leu Cys Leu
1               5                   10                  15

Val Asn Asp Ala Tyr Gly Lys Asn Lys Tyr Gly Lys Asn Gly Lys Tyr
            20                  25                  30

Gly Ser Gln Asn Val Ile Lys Lys His Gly Glu Pro Val Ile Asn Val
        35                  40                  45

Gln Asp Leu Ile Ser Asp Met Val Arg Lys Glu Glu Glu Ile Val Lys
    50                  55                  60
```

Leu Thr Lys Asn Lys Lys Ser Leu Arg Lys Ile Asn Val Ala Leu Ala
65                  70                  75                  80

Thr Ala Leu Ser Val Ser Ala Ile Leu Leu Gly Gly Ala Gly Leu
                85                  90                  95

Val Met Tyr Asn Thr Glu Lys Gly Arg Arg Pro Phe Gln Ile Gly Lys
            100                 105                 110

Ser Lys Lys Gly Gly Ser Ala Met Ala Arg Asp Ser Ser Phe Pro Met
            115                 120                 125

Asn Glu Glu Ser Pro Leu Gly Phe Ser Pro Glu Met Glu Ala Val
            130                 135                 140

Ala Ser Lys Phe Arg Glu Ser Met Leu Lys Asp Gly Val Pro Ala Pro
145                 150                 155                 160

Ser Asn Thr Pro Asn Val Gln Asn Arg Val Arg Arg Ala Lys Arg Glu
                165                 170                 175

Glu Tyr Ser Trp Glu Asn Phe Leu Asn Asp Lys Leu Leu Ala Thr Asn
            180                 185                 190

Gln Val Ser Ala Ala Gly Leu Ala Ser Glu Glu Asp Gly Val Val Tyr
            195                 200                 205

Glu Cys Val Ala Thr Pro Asp Glu Asn Asn Pro Asp Phe Asp Lys Trp
210                 215                 220

Ser Leu Phe Tyr Lys Glu Asp Tyr Asp Ile Glu Ile Glu Asp Glu Asn
225                 230                 235                 240

Gly Asn Lys Thr Thr Lys Thr Ile Thr Glu Gly Gln Thr Ile Leu Thr
                245                 250                 255

Met Phe Asn Glu Gly Tyr Ala Pro Asp Gly Ile Trp Leu Gly Gly Thr
            260                 265                 270

Lys Tyr Gln Phe Ile Asn Met Glu Lys Gly Leu Glu Tyr Glu Gly Tyr
            275                 280                 285

Ser Phe Asp Val Ala Thr Cys Ala Lys Leu Lys Gly Met His Ile
            290                 295                 300

Ile Lys Val Gly Gly Gly His Ile Leu Ile Val Leu Tyr Asp Glu Glu
305                 310                 315                 320

Lys Glu Gln Asp Arg Gly Asn Ser Lys Asn Ala Ala Leu Ala Phe Ser
                325                 330                 335

Lys Glu Leu Ala Glu Ser Thr Asp Ala Gly Ala Ala
            340                 345

<210> SEQ ID NO 33
<211> LENGTH: 1044
<212> TYPE: DNA
<213> ORGANISM: Artificial sequence
<220> FEATURE:
<223> OTHER INFORMATION: pGX7021 Py EXP1-EXP2

<400> SEQUENCE: 33
aagatcaata tcgcctcaat cattttatc atcttcagtc tgtgcctcgt gaacgacgcc      60
tacggcaaga acaagtatgg caagaacggc aaatacggaa gccagaatgt gatcaagaaa    120
cacggagagc ccgtgatcaa cgtccaggac ctgatttcag atatggtgag aaaggaggaa    180
gagatcgtca gctgaccaa aaataagaaa agcctccgga agattaacgt ggccctggct     240
acagcactct ctgtggtcag tgcaatcctg ctcggaggag caggactggt catgtataat    300
accgagaaag ggaggagacc ctttcagatc ggcaagtcaa agaaagggg tagcgccatg     360 gctcgcgata gctccttccc tatgaacgaa gagtccccac tgggattttc tcccgaagag    420

```
atggaggcag tggccagtaa gttccgagaa tcaatgctga agacggcgt ccccgctcct      480 tccaacacac caaatgtgca gaaccgagtc cggcgcgcca agagggaaga gtactcttgg      540
gagaattttc tcaacgataa gctgctcgct actaaccagg tgagcgcagc tggactggca      600
tccgaagagg acggagtggt ctatgagtgc gtcgctaccc ctgatgaaaa caatccagac      660
ttcgataagt ggtctctgtt ttacaaggag gactacgata tcgaaatcga ggacgaaaac      720
gggaataaga ccacaaaaac tatcaccgag ggtcagacaa ttctgactat gttcaatgaa      780
ggatacgcac cagacggtat ctggctcgga ggaacaaagt atcagttcat taacatggag      840
aaaggcctgg agtacgaagg atatagcttt gatgtggcta cttgtgcaaa gctgaaaggg      900
ggtatgcaca tcattaaggt cggcggaggg catatcctga ttgtcctcta cgacgaagag      960
aaggagcagg atcgggggaa ttccaaaaac gcagccctgg ccttttctaa ggagctcgcc     1020
gaaagtaccg acgctggcgc tgca                                             1044

<210> SEQ ID NO 34
<211> LENGTH: 1098
<212> TYPE: DNA
<213> ORGANISM: Artificial sequence
<220> FEATURE:
<223> OTHER INFORMATION: pGX7021 Py EXP1-EXP2 operably linked to IgE
      leader sequence

<400> SEQUENCE: 34
atggactgga cctggattct gttcctggtg gctgccgcaa ctagagtgca ttcaaagatc       60
aatatcgcct caatcatttt tatcatcttc agtctgtgcc tcgtgaacga cgcctacggc      120
aagaacaagt atggcaagaa cggcaaatac ggaagccaga atgtgatcaa gaaacacgga      180
gagcccgtga tcaacgtcca ggaccctgat tcagatatgg tgagaaagga ggaagagatc      240
gtcaagctga ccaaaaataa gaaaagcctc cggaagatta acgtggccct ggctacagca      300
ctctctgtgg tcagtgcaat cctgctcgga ggagcaggac tggtcatgta taataccgag      360
aaagggagga gacccttcca gatcggcaag tcaaagaaag ggggtagcgc catggctcgc      420
gatagctcct tccctatgaa cgaagagtcc ccactgggat tttctcccga agagatggag      480
gcagtggcca gtaagttccg agaatcaatg ctgaaagacg cgtccccgc tccttccaac      540 acaccaaatg tgcagaaccg agtccggcgc gccaagaggg aagagtactc ttgggagaat      600
tttctcaacg ataagctgct cgctactaac caggtgagcg cagctggact ggcatccgaa      660
gaggacggag tggtctatga gtgcgtcgct acccctgatg aaaacaatcc agacttcgat      720
aagtggtctc tgttttacaa ggaggactac gatatcgaaa tcgaggacga aaacgggaat      780
aagaccacaa aaactatcac cgagggtcag acaattctga ctatgttcaa tgaaggatac      840
gcaccagacg gtatctggct cggaggaaca agtatcagtt cattaacat ggagaaaggc      900 ctggagtacg aaggatatag ctttgatgtg gctacttgtg caaagctgaa aggggtatg      960 cacatcatta aggtcggcgg agggcatatc ctgattgtcc tctacgacga agagaaggag     1020
caggatcggg ggaattccaa aaacgcagcc ctggcctttt ctaaggagct cgccgaaagt     1080
accgacgctg gcgctgca                                                    1098

<210> SEQ ID NO 35
<211> LENGTH: 268
<212> TYPE: PRT
<213> ORGANISM: Artificial sequence
<220> FEATURE:
<223> OTHER INFORMATION: pGX7024 Py EXP23
```

<400> SEQUENCE: 35

Lys Ile Arg Tyr Phe Leu Ser Leu Phe Leu Phe Tyr Ala Thr Tyr Lys
1               5                   10                  15

His Thr Thr Asn Ile Val Lys Cys Asp Ala Tyr Ser Asp Leu Ala Ala
            20                  25                  30

Thr Thr Ala Leu Ser Thr Val Ile Arg Asp Pro Leu Ser Met Ser Leu
        35                  40                  45

Lys Asp Leu Tyr Asp His Gly Val Lys Val Pro Ile Thr Asp Ile Ile
    50                  55                  60

Asn Lys Leu Lys Lys Ala Val Arg Tyr Lys Lys Ile Leu Arg Trp Ser
65                  70                  75                  80

Arg Ile Trp Trp Val Leu Leu Val Arg Glu Ile Val Gly Asn Asn Lys
                85                  90                  95

Val Glu Glu Ala Thr Glu Cys Ile Leu Arg Asp Ile Trp Asp Gln Cys
            100                 105                 110

Thr Ile Ser Ile Tyr Asn Asn Thr Leu Tyr Ser Val Glu Ser Lys Pro
        115                 120                 125

Ile Leu Phe Leu His Gly Ile Leu Asn Glu Cys Lys Asn Ser Phe Ser
    130                 135                 140

Thr Lys Leu Arg His Asp Pro Gly Leu Ile Val Ser Lys Ile Asp Gln
145                 150                 155                 160

Ile Leu Lys Ser Gln Ile Tyr Arg Phe Trp Val Ser Glu Pro Tyr Leu
                165                 170                 175

Lys Leu Gly Arg Ser Asn Thr Phe Tyr Ala Asn Ile Thr Gln Lys Asn
            180                 185                 190

Val Pro Leu Leu Pro Lys Glu Cys Thr Leu Lys His Leu Ser Ser Tyr
        195                 200                 205

Met Glu Glu Lys Leu Lys Ser Met Glu Ser Lys Asn Ile Glu Ser
    210                 215                 220

Gly Lys Tyr Glu Phe Asp Val Asp Ser Glu Ser Ala Pro Asn Asp Ala
225                 230                 235                 240

Tyr Thr Glu Tyr Glu Asp Asp Gln Ser Glu Glu Ile Leu Asn Asp Gln
                245                 250                 255

Leu Phe Glu Asp Gln Glu Thr Asp Ala Asn Gly Ala
            260                 265

<210> SEQ ID NO 36
<211> LENGTH: 804
<212> TYPE: DNA
<213> ORGANISM: Artificial sequence
<220> FEATURE:
<223> OTHER INFORMATION: pGX7024 Py EXP23

<400> SEQUENCE: 36

```
aagattagat actttctgag cctgtttctg ttctacgcca cttataagca caccacaaat    60
atcgtgaaat gcgacgccta cagcgatctg gccgctacta ccgctctctc cacagtcatt   120
cgggacccta tgtctatgag tctgaaggac ctctacgatc atggggtgaa agtcccaatc   180
actgacatca ttaacaagct gaagaaagca gtgcgatata agaaaatcct gaggtggagc   240
agaatttggt gggtgctgct cgtcagggag atcgtggta acaataaggt cgaggaagcc   300
accgaatgca tcctgagaga catttgggat cagtgtacca tcagcatcta caacaataca   360
ctgtatagtg tggagtcaaa gcccatcctg ttcctccacg gcattctgaa cgaatgcaag   420
aatagcttca gcacaaaact gaggcatgac cctggactca tcgtgtctaa gatcgatcag   480
```

-continued

```
attctgaaaa gtcagatcta ccggttctgg gtctcagagc catatctgaa gctcggccgc    540
tccaacacat tttacgctaa tatcactcag aaaaacgtgc ccctgctccc taaggagtgt    600
acactgaaac acctcagctc ctacatggag gaaaagctga aaagcatgga gtccaagaaa    660
aatatcgagt ctggcaagta tgaattcgac gtcgattccg aatctgctcc caacgacgca    720
tacactgagt atgaagacga tcagagtgag gaaattctga tgatcagct ctttgaggac     780 caggaaaccg atgcaaacgg agcc                                           804
```

<210> SEQ ID NO 37
<211> LENGTH: 858
<212> TYPE: DNA
<213> ORGANISM: Artificial sequence
<220> FEATURE:
<223> OTHER INFORMATION: pGX7024 Py EXP23 operably linked to IgE leader
      sequence

<400> SEQUENCE: 37

```
atggactgga cctggattct gttcctcgtc gccgccgcca caagagtgca tagcaagatt     60
agatactttc tgagcctgtt tctgttctac gccacttata agcacaccac aaatatcgtg    120
aaatgcgacg cctacagcga tctggccgct actaccgctc tctccacagt cattcgggac    180
cctctgtcta tgagtctgaa ggacctctac gatcatgggg tgaaagtccc aatcactgac    240
atcattaaca agctgaagaa agcagtgcga tataagaaaa tcctgaggtg gagcagaatt    300
tggtgggtgc tgctcgtcag ggagatcgtg ggtaacaata aggtcgagga agccaccgaa    360
tgcatcctga gagacatttg ggatcagtgt accatcagca tctacaacaa tacactgtat    420
agtgtggagt caaagcccat cctgttcctc cacggcattc tgaacgaatg caagaatagc    480
ttcagcacaa aactgaggca tgaccctgga ctcatcgtgt ctaagatcga tcagattctg    540
aaaagtcaga tctaccggtt ctgggtctca gagccatatc tgaagctcgg ccgctccaac    600 acatttacg ctaatatcac tcagaaaaac gtgcccctgc tccctaagga gtgtacactg    660
aaacacctca gctcctacat ggaggaaaag ctgaaaagca tggagtccaa gaaaaatatc    720
gagtctggca gtatgaatt cgacgtcgat tccgaatctg ctcccaacga cgcatacact    780
gagtatgaag acgatcagag tgaggaaatt ctgaatgatc agctctttga ggaccaggaa    840
accgatgcaa acggagcc                                                  858
```

<210> SEQ ID NO 38
<211> LENGTH: 357
<212> TYPE: PRT
<213> ORGANISM: Artificial sequence
<220> FEATURE:
<223> OTHER INFORMATION: pGX7027 Py ICP

<400> SEQUENCE: 38

```
Lys Ser Ile Thr Phe Phe Val Phe Asn Ile Cys Ser Ile Leu Ala Leu
1               5                   10                  15

Leu Ser His Cys Glu Asp Arg Asp Leu Tyr Ser Phe Asp Ile Val Asn
            20                  25                  30

Glu Thr Ser Trp Leu Lys Ile Ala Lys Lys Ile Phe Lys Gly Lys Ser
        35                  40                  45

Pro Ser Asn Phe Thr Ile Ile Pro Phe Asn Asn Thr Gly Ser Ser Asp
    50                  55                  60

Asn Asn Glu Gly Asp Lys Glu Glu Ser Val Leu Leu Ile Arg Lys Lys
65                  70                  75                  80

Ile Lys Ser Asn Thr Lys His Gly Ser Asn Ile Ile Ser Asp Asp Ser
```

```
            85                  90                  95
Val Asn Asp Asp Ile Ser Asn Leu Ser Leu Asn Ser Thr Ala Ser Asn
            100                 105                 110

Phe Ser Asp Asn Asn Glu Glu Ile Glu Asp Asn Gln Lys Tyr Pro Thr
        115                 120                 125

Thr Ser Tyr Asn Ser Phe Asn Asp Pro Asn Ser Asn Ile Ser Phe Asn
    130                 135                 140

Glu Glu Ser Glu Phe Ser Glu Ile Asp Ser Glu Ser Asn Leu Glu Asn
145                 150                 155                 160

Asn Ile Lys Asp Ile Asn Ile Lys Asn Asn Leu Glu Glu Asn Asn Thr
                165                 170                 175

Met Asn Glu Ile Asp Asn Lys Val Asp Ser Lys Tyr Glu Leu Thr Gly
            180                 185                 190

Asp Glu Lys Cys Gly Asn Ser Leu Lys Leu Gly Asn Ile Ser Asn Gln
        195                 200                 205

Thr Ser Gln Glu Thr Ile Asn Gln Ser Leu Ser Val Gly Glu Thr Phe
    210                 215                 220

Cys Ile Asp Phe Glu Ala Asn Ala Gly Thr Gly Tyr Ile Trp Ala Leu
225                 230                 235                 240

Leu Gly Val His Lys Asn Glu Pro Ile Ile Asn Pro Glu Asn Phe Pro
                245                 250                 255

Thr Lys Leu Thr Lys Lys Pro Tyr Phe Ser Glu Glu Ile Ser Val Thr
            260                 265                 270

Gln Pro Lys Arg Tyr Lys Ile Asp Glu His Asp Ser Ser Lys Asn Val
        275                 280                 285

Asp Lys Glu Asn Glu Ser Gln Asp Gln Lys Glu Ser Asp Ser Lys Pro
    290                 295                 300

Lys Lys Pro Gln Met His Leu Leu Gly Gly Pro Asp Asn Met Arg Ser
305                 310                 315                 320

Val Ile Lys Gly His Lys Ala Gly Lys Tyr Tyr Ile Val Tyr Ser Tyr
                325                 330                 335

Tyr Arg Pro Phe Ser Pro Thr Ser Gly Ala Asn Thr Lys Ile Leu Tyr
            340                 345                 350

Val Thr Val Gln Pro
        355
```

<210> SEQ ID NO 39
<211> LENGTH: 1071
<212> TYPE: DNA
<213> ORGANISM: Artificial sequence
<220> FEATURE:
<223> OTHER INFORMATION: pGX7027 Py ICP

<400> SEQUENCE: 39

```
aaaagcatta ccttcttcgt cttcaacatc tgttccatcc tggctctgct ctctcactgc      60
gaggaccggg atctctacag cttcgacatt gtgaacgaaa ccagctggct gaagatcgca     120
aagaaaattt ttaagggcaa atcacccagc aacttcacta tcattccttt taacaatacc     180
ggcagctccg acaacaatga gggagataag gaggaaagcg tgctgctcat caggaagaag     240
atcaagagta cactaagca tggatctaat atcatttctg acgatagtgt caacgacgat     300
atctcaaacc tgagcctcaa ttccaccgcc tctaacttca gtgacaacaa tgaggaaatc     360
gaggataatc agaagtaccc aaccacatca tataacagct taatgaccc caactccaat     420
atctctttca cgaagagag tgagttttca gaaatcgact ccgagtctaa cctggaaaac     480
```

| aacatcaagg atatcaacat taagaacaac ctggaggaaa acaataccat gaacgagatc | 540 |
| gacaacaagg tggattccaa gtacgagctg acaggggacg aaaaatgcgg taactctctg | 600 |
| aagctcggga acatctctaa tcagacaagt caggagacta ttaatcagag tctgtcagtg | 660 |
| ggcgagacat tctgtatcga ttttgaagcc aacgctggga ctggttatat ttgggccctg | 720 |
| ctcggggtcc acaagaatga gcccatcatt aaccctgaaa atttcccaac taagctgacc | 780 |
| aagaaacctt acttttcaga ggaaatcagc gtgacacagc caaagaggta caagatcgac | 840 |
| gagcatgatt ctagtaagaa cgtcgacaag gagaatgaaa gccaggacca gaaagaaagc | 900 |
| gattccaagc caaagaaacc ccagatgcac ctgctcggcg acccgataaa catgaggagc | 960 |
| gtgatcaagg ccataaagc cggaaagtac tatattgtct actcctacta tagacctttc | 1020 |
| agcccaacct ccggagccaa cacaaagatc ctgtacgtga ctgtccagcc c | 1071 |

<210> SEQ ID NO 40
<211> LENGTH: 1125
<212> TYPE: DNA
<213> ORGANISM: Artificial sequence
<220> FEATURE:
<223> OTHER INFORMATION: pGX7027 Py ICP operably linked to IgE leader
      sequence

<400> SEQUENCE: 40

| atggactgga cttggattct cttcctcgtc gctgccgcaa ctcgcgtgca tagcaaaagc | 60 |
| attaccttct tcgtcttcaa catctgttcc atcctggctc tgctctctca ctgcgaggac | 120 |
| cgggatctct acagcttcga cattgtgaac gaaaccagct ggctgaagat cgcaaagaaa | 180 |
| attttaagg gcaaatcacc cagcaacttc actatcattc cttttaacaa taccggcagc | 240 |
| tccgacaaca atgagggaga taaggaggaa agcgtgctgc tcatcaggaa gaagatcaag | 300 |
| agtaacacta gcatggatc taatatcatt tctgacgata gtgtcaacga cgatatctca | 360 |
| aacctgagcc tcaattccac cgcctctaac ttcagtgaca acaatgagga aatcgaggat | 420 |
| aatcagaagt acccaaccac atcatataac agctttaatg accccaactc caatatctct | 480 |
| ttcaacgaag agagtgagtt ttcagaaatc gactccgagt ctaacctgga aaacaacatc | 540 |
| aaggatatca acattaagaa caacctggag gaaaacaata ccatgaacga gatcgacaac | 600 |
| aaggtggatt ccaagtacga gctgacaggg gacgaaaaat gcggtaactc tctgaagctc | 660 |
| gggaacatct ctaatcagac aagtcaggag actattaatc agagtctgtc agtgggcgag | 720 |
| acattctgta tcgattttga agccaacgct gggactggtt atatttgggc cctgctcggg | 780 |
| gtccacaaga atgagcccat cattaaccct gaaaatttcc caactaagct gaccaagaaa | 840 |
| ccttactttt cagaggaaat cagcgtgaca cagccaaaga ggtacaagat cgacgagcat | 900 |
| gattctagta agaacgtcga caaggagaat gaaagccagg accagaaaga aagcgattcc | 960 |
| aagccaaaga aaccccagat gcacctgctc ggcgacccga taacatgag gagcgtgatc | 1020 |
| aagggccata aagccggaaa gtactatatt gtctactcct actatagacc tttcagccca | 1080 |
| acctccggag ccaacacaaa gatcctgtac gtgactgtcc agccc | 1125 |

<210> SEQ ID NO 41
<211> LENGTH: 213
<212> TYPE: PRT
<213> ORGANISM: Artificial sequence
<220> FEATURE:
<223> OTHER INFORMATION: pGX7025 Py TMP21

<400> SEQUENCE: 41

Ala Lys Ile Ser Lys Leu Leu Thr Phe Phe Ile Ala Phe Ile Phe Gln
1               5                   10                  15

Ala Ser Ile Ile Asn Ser Leu Gln Ile Tyr Leu Ser Leu Lys Pro Asn
            20                  25                  30

Leu Pro Lys Cys Ile Lys Glu Arg Ile Ser Lys Asp Thr Leu Val Val
            35                  40                  45

Gly Lys Phe Lys Thr His Glu Lys Glu Ser Val Val Ser Ile Phe Ile
        50                  55                  60

Tyr Asp Ile Asp Val Asn Glu Lys Lys Ile Asn Ser Leu Asp Lys Leu
65                  70                  75                  80

Pro Ile Phe Glu Ala Ile Asp Glu His Asp Ile Lys Thr Ala Phe Thr
                85                  90                  95

Thr Phe Tyr Ser Gly Ser Tyr Ser Phe Cys Ala Tyr Asn Lys Ser Asn
                100                 105                 110

Lys Val Val Asp Ile Tyr Phe Glu Ile Lys His Gly Val Glu Ala Arg
            115                 120                 125

Asp Tyr Thr Lys Ile Ala Lys Ala Asp His Leu Asn Glu Ala Thr Ile
    130                 135                 140

Phe Leu Lys Gln Ile Leu Asn Ser Met Lys Thr Phe Gln Ser Asn Leu
145                 150                 155                 160

Lys Arg Ile Lys Ile Ser Glu Glu Lys Glu Lys Lys Ser Ser Glu Lys
                165                 170                 175

Leu Asn Asp Thr Leu Met Trp Phe Ser Ile Leu Thr Ile Ile Ile Ile
            180                 185                 190

Ile Ile Ala Ala Leu Thr Gln Asp Phe Tyr Tyr Lys Arg Phe Phe Thr
        195                 200                 205

Ser Lys Lys Ile Ile
        210

<210> SEQ ID NO 42
<211> LENGTH: 639
<212> TYPE: DNA
<213> ORGANISM: Artificial sequence
<220> FEATURE:
<223> OTHER INFORMATION: pGX7025 Py TMP21

<400> SEQUENCE: 42

```
gccaaaatta gcaagctcct gacattcttt attgctttca tctttcaggc atctatcatt    60
aacagtctgc agatctacct gtccctcaag cccaatctcc ctaagtgcat caaagagcgg   120
atttctaaag acactctggt ggtcgggaag ttcaaaaccc acgagaagga agcgtggtc    180 tccatcttca tctacgacat cgatgtgaac gaaaagaaaa ttaatagcct ggataagctc   240
cccatcttcg aggccattga cgaacatgat atcaagaccg cttttcaccac atttactct   300 ggcagttatt cattctgtgc ttacaacaag tccaacaagg tggtcgacat ctattttgag   360
attaagcacg gagtcgaagc aagggactac actaagatcg caaaagccga tcatctgaac   420
gaggccacca tcttcctgaa gcagattctc aactcaatga aacatttca gagcaatctg   480 aagagaatca aaattagtga ggaaaaggag aagaaaagct ccgaaaaact gaatgacaca   540
ctcatgtggt tctctatcct gactatcatc atcatcatca tcgccgctct cacccaggat   600
ttctactaca gaggttctt tacaagcaag aaaatcatc                          639
```

<210> SEQ ID NO 43
<211> LENGTH: 693
<212> TYPE: DNA
<213> ORGANISM: Artificial sequence
<220> FEATURE:
<223> OTHER INFORMATION: pGX7025 Py TMP21 operably linked to IgE leader
      sequence

<400> SEQUENCE: 43

```
atggactgga cctggattct gttcctcgtc gcagcagcaa ctagagtgca ttccgccaaa    60
attagcaagc tcctgacatt ctttattgct ttcatctttc aggcatctat cattaacagt   120
ctgcagatct acctgtccct caagcccaat ctccctaagt gcatcaaaga gcggatttct   180
aaagacactc tggtggtcgg aagttcaaa acccacgaga aggaaagcgt ggtctccatc    240
ttcatctacg acatcgatgt gaacgaaaag aaaattaata gcctggataa gctcccatc    300
ttcgaggcca ttgacgaaca tgatatcaag accgctttca ccacatttta ctctggcagt   360
tattcattct gtgcttacaa caagtccaac aaggtggtcg acatctattt tgagattaag   420
cacggagtcg aagcaaggga ctacactaag atcgcaaaag ccgatcatct gaacgaggcc   480
accatcttcc tgaagcagat tctcaactca atgaaaacat tcagagcaa tctgaagaga    540
atcaaaatta gtgaggaaaa ggagaagaaa agctccgaaa aactgaatga cacactcatg   600
tggttctcta tcctgactat catcatcatc atcatcgccg ctctcaccca ggatttctac   660
tacaagaggt tctttacaag caagaaaatc atc                                693
```

<210> SEQ ID NO 44
<211> LENGTH: 214
<212> TYPE: PRT
<213> ORGANISM: Artificial sequence
<220> FEATURE:
<223> OTHER INFORMATION: Py UIS3

<400> SEQUENCE: 44

```
Asn Thr Leu Lys Val Phe Phe Val Phe Tyr Val Leu Tyr Ile Thr Thr
1               5                   10                  15

Phe Phe Phe Asn Pro Cys Phe Cys Glu Asp Ala Asp Tyr Tyr Ser Glu
            20                  25                  30

Ile Asp Asp Gly Ala Leu Asp Ser Ile Asp Thr Ala Ile Lys Lys Lys
        35                  40                  45

Lys Lys Arg Lys Ser Val Ala Ile Ala Leu Leu Ser Ser Gly Leu Val
50                  55                  60

Ala Ser Val Ile Gly Val Leu Tyr Tyr Met Tyr Lys Ser His Asn Lys
65                  70                  75                  80

Gly Arg His Asp Trp Asn Lys Gly Phe Asn Phe Pro Phe Asn Lys
            85                  90                  95

Gln Thr Glu Tyr Lys Gln Pro Asp Gly Glu Lys Pro Ser Thr Ser Thr
            100                 105                 110

Lys Tyr Glu Glu Pro Leu Gly Val Asn Lys Val Asn Ile Lys Gly Lys
            115                 120                 125

Leu Lys Glu Asn Asn Asn Asp Ile Asp Val Pro Leu Lys Arg Phe Asn
130                 135                 140

Thr Phe Met Asp Asn Val Lys Leu Ala Ala Lys His His Phe Ser Asn
145                 150                 155                 160

Leu Ser Asn Glu Gln Gln Lys Tyr Leu Ile Lys Asp Tyr Asp Tyr Leu
            165                 170                 175

Arg Lys Ile Val Gln Thr Leu Asp Glu Asn Lys Asp Val Asn Ile Ser
            180                 185                 190

Arg Ala Gln Glu Asp Ile Ala Val Leu Gly Val Glu His Phe Leu Lys
            195                 200                 205
```

Glu Gln Tyr Gln Pro Lys
    210

<210> SEQ ID NO 45
<211> LENGTH: 642
<212> TYPE: DNA
<213> ORGANISM: Artificial sequence
<220> FEATURE:
<223> OTHER INFORMATION: Py UIS3

<400> SEQUENCE: 45

```
aataccctga aggtcttttt cgtgttttac gtgctgtaca tcaccacatt cttttttcaac      60 ccttgctttt gtgaggacgc agattactat tccgaaatcg acgatggggc cctggactct     120
atcgataccg ctattaagaa aagaaaaag cggaagagcg tggcaatcgc cctgctcagc     180
tccggactcg tggctagtgt cattggagtg ctgtactata tgtataagtc ccacaacaag     240 ggcgccatg actggaataa gggttttaac ttttttccat tcaacaagca gacagagtac      300
aaacagcccg atggtgaaaa gccttctact agtaccaaat atgaggaacc actcggcgtc     360
aataaggtga acatcaaagg aaagctgaaa gagaacaata cgacattga tgtccccctc      420 aagaggttta atacattcat ggacaacgtg aagctcgccg ctaaacacca tttctcaaat     480
ctgagcaacg aacagcagaa gtacctgatc aaagactacg attatctcag gaagattgtc     540
cagactctgg acgagaacaa ggatgtgaac atctctagag ctcaggaaga tattgcagtc     600
ctgggggtgg aacactttct caaggaacag taccagccta aa                        642
```

<210> SEQ ID NO 46
<211> LENGTH: 696
<212> TYPE: DNA
<213> ORGANISM: Artificial sequence
<220> FEATURE:
<223> OTHER INFORMATION: Py UIS3 operably linked to IgE leader sequence

<400> SEQUENCE: 46

```
atggactgga cttggattct gtttctggtc gccgcagcaa ctagagtgca tagcaatacc      60
ctgaaggtct ttttcgtgtt ttacgtgctg tacatcacca cattcttttt caacccttgc     120
ttttgtgagg acgcagatta ctattccgaa atcgacgatg gggccctgga ctctatcgat     180
accgctatta agaaaaagaa aaagcggaag agcgtggcaa tcgccctgct cagctccgga     240
ctcgtggcta gtgtcattgg agtgctgtac tatatgtata gtcccacaa caaggggcgc     300 catgactgga ataagggttt taactttttc ccattcaaca gcagacaga gtacaaacag     360 cccgatggtg aaaagccttc tactagtacc aaatatgagg aaccactcgg cgtcaataag     420
gtgaacatca aggaaagct gaaagagaac aataacgaca ttgatgtccc cctcaagagg     480
tttaatacat tcatggacaa cgtgaagctc gccgctaaac accatttctc aaatctgagc     540
aacgaacagc agaagtacct gatcaaagac tacgattatc tcaggaagat tgtccagact     600
ctggacgaga caaggatgt gaacatctct agagctcagg aagatattgc agtcctgggg     660
gtggaacact ttctcaagga acagtaccag cctaaa                               696
```

<210> SEQ ID NO 47
<211> LENGTH: 766
<212> TYPE: PRT
<213> ORGANISM: Artificial sequence
<220> FEATURE:
<223> OTHER INFORMATION: pGX7022 Py UIS10 PL

<400> SEQUENCE: 47

```
Gln Val Phe Leu Phe Ile Ile Ile Leu Tyr Asn Cys Ile Cys Leu Thr
1               5                   10                  15
Leu Ile Tyr Ser Phe Asn Pro Ser Ile Gly Ser Ile Ile Asn Val Leu
            20                  25                  30
Ile Lys Thr Pro Tyr Lys Leu Ser Phe Gly Glu Ser Asn Lys Asn Ser
            35                  40                  45
Glu Ile Ala Asn Leu Glu Gly Thr Gly Asn Phe Leu Asn Glu Thr Asn
50                  55                  60
Thr Glu Glu Thr Glu Gln Thr Val Glu Phe Ser Lys Glu Ser Lys
65                  70                  75                  80
Asn Asp Asp Gln Asn Val Leu Asn Ile Glu Ser Thr Pro Glu Ala Val
                85                  90                  95
Val Glu Tyr Glu Val Ala Asp Thr Lys Glu Ala Ile Val Glu Glu Ala
            100                 105                 110
Ser Ile Asp Lys Glu Thr Val Ile Glu Glu Thr Ala Asp Lys Asp Asp
            115                 120                 125
Pro Ser Val Glu Ile Lys Arg Val Lys Glu Val Thr Ala Glu Glu Ile
    130                 135                 140
Glu Lys Val Lys Glu Ser Ala Glu Lys Glu Ile Lys Lys Ile Lys Glu
145                 150                 155                 160
Thr Ala Ala Glu Glu Val Glu Lys Ile Lys Glu Thr Val Ala Glu Glu
            165                 170                 175
Ile Glu Ile Ala Lys Glu Ile Ile Ala Gly Ala Val Leu Glu Gln Lys
            180                 185                 190
Gln Lys Glu Lys Glu Tyr Val Ser Glu His Thr Glu Glu Asn Glu Glu
    195                 200                 205
Lys Lys Ile Glu Ser Glu Tyr Thr Glu Glu Asn Glu Glu Lys Glu Ile
    210                 215                 220
Glu Ser Lys Tyr Thr Glu Glu Asn Glu Glu Lys Lys Asn Glu Ser Glu
225                 230                 235                 240
Tyr Thr Glu Glu Asn Glu Glu Asp Thr Val Lys Glu Ile Glu Val Ser
            245                 250                 255
Lys Asn Val Asn Ile Glu Asn Glu Thr Ile Met Glu Glu Ile Asp Asn
            260                 265                 270
Ser Asp Val Glu Lys Leu Ser Glu Thr Glu Lys Glu Leu Lys Thr Asn
    275                 280                 285
Glu Met Ile Gln Glu Lys Tyr Gly Glu Phe Lys Arg Ala Glu Asp Ser
    290                 295                 300
Tyr Tyr Trp Glu Ser Lys Ser Thr Asp Val Glu Asp Gly Val Asp Asp
305                 310                 315                 320
Asp Val Asp Asp Asp Glu Ile Val Gly Leu Pro Lys Lys Ser Asn Asn
            325                 330                 335
Thr Ile Ile Asp Asn Thr Pro Lys Ser Ser Val Tyr Leu Val Pro Gly
            340                 345                 350
Leu Gly Gly Ser Thr Leu Ile Ala Glu Tyr Asn His Ala Gln Ile Asp
    355                 360                 365
Ser Cys Ser Ser Lys Ala Leu His Ser Lys Pro Tyr Arg Ile Trp Leu
    370                 375                 380
Ser Leu Ser Arg Leu Phe Ser Ile Arg Ser Asn Val Tyr Cys Leu Phe
385                 390                 395                 400
Asp Thr Leu Lys Leu Asp Tyr Asp Arg Lys Lys Met Tyr Arg Asn
            405                 410                 415
Lys Pro Gly Val Phe Ile Asn Val Glu His Tyr Gly Tyr Ile Lys Gly
```

```
                420             425             430
Val Ala Phe Leu Asp Tyr Ile Lys Asn Lys Pro Leu Arg Leu Thr Arg
            435             440             445

Tyr Tyr Gly Ile Leu Ala Asp Lys Phe Leu Glu Asn Gly Tyr Ile Asp
        450             455             460

Gly Lys Asp Ile Leu Ser Ala Pro Tyr Asp Trp Arg Phe Pro Leu Ser
465             470             475             480

Gln Gln Lys Tyr Glu Val Leu Lys Ser His Ile Glu Tyr Ile Tyr Gly
            485             490             495

Leu Lys Lys Gly Thr Lys Val Asp Leu Ile Gly His Ser Leu Gly Gly
            500             505             510

Leu Phe Ile Asn Tyr Phe Leu Ser Gln Phe Val Asp Glu Glu Trp Lys
        515             520             525

Lys Lys Tyr Ile Asn Ile Val Met His Ile Asn Val Pro Phe Ala Gly
        530             535             540

Ser Ile Lys Ala Ile Arg Ala Leu Leu Tyr Ser Ser Lys Asp Tyr Thr
545             550             555             560

Leu Phe Lys Leu Arg Asn Ile Leu Lys Val Ser Ile Ser Gly Ser Leu
            565             570             575

Met Lys Ala Ile Ser His Asn Met Gly Ser Pro Phe Asp Leu Ile Pro
            580             585             590

Tyr Arg Lys Tyr Asp Arg Asp Gln Ile Val Val Ile Ile Asn Met
            595             600             605

Gly Lys Leu Pro Ile Asp Glu Lys Leu Val Gln Ser Ile Val Thr Glu
        610             615             620

Cys Gly Ile Tyr Asn Glu Arg Cys Tyr Thr Asp Arg Glu Asp Val Asn
625             630             635             640

Leu Lys Thr Tyr Thr Leu Ser Asn Trp His Glu Leu Leu Ser Asp Asp
            645             650             655

Ile Arg Glu Lys Tyr Glu Asn Tyr Ile Gln Tyr Thr Asp Arg Phe Phe
            660             665             670

Ser Val Asp His Gly Ile Pro Thr Tyr Cys Leu Tyr Ser Thr Thr Arg
            675             680             685

Lys Arg Asn Thr Glu Tyr Met Leu Phe Tyr Gln Asp Val His Phe Asn
            690             695             700

His Asp Pro Ile Ile Tyr Tyr Gly Ile Gly Asp Gly Thr Ile Ser Leu
705             710             715             720

Glu Ser Leu Glu Ala Cys Lys Lys Leu Gln Asn Val Lys Glu Ala Lys
            725             730             735

His Phe Val Tyr Tyr Lys His Ile Gly Ile Leu Lys Ser Asp Ile Val
            740             745             750

Ser Asp Tyr Ile Tyr Asn Ile Ile Asn Gln Asn Arg Thr Asn
            755             760             765

<210> SEQ ID NO 48
<211> LENGTH: 2304
<212> TYPE: DNA
<213> ORGANISM: Artificial sequence
<220> FEATURE:
<223> OTHER INFORMATION: pGX7022 Py UIS10 PL

<400> SEQUENCE: 48
caggtcttcc tctttattat tattctctac aactgcatct gtctgacact catctactcc      60
tttaatccca gtattggttc aatcattaac gtgctgatca aaactcctta caagctctcc    120
```

|  |  |  |  |  | |
|---|---|---|---|---|---|
| ttcggcgagt | ctaacaagaa | tagtgagatc | gccaatctgg | aaggcaccgg | aaactttctc | 180 |
| aatgagacta | acaccgagga | aaccgaacag | acagtcgagt | tcgaaagcaa | agagtccaag | 240 |
| aacgacgatc | agaatgtgct | gaacatcgaa | agcactccg | aggctgtggt | cgagtacgaa | 300 |
| gtcgccgaca | ccaaggaggc | tatcgtggag | gaagcatcta | ttgacaagga | gactgtcatc | 360 |
| gaggaaaccg | cagataaaga | cgatcctagt | gtggagatca | gagggtgaa | ggaagtcaca | 420 |
| gctgaggaaa | tcgaaaaggt | gaaagagtcc | gcagagaaag | aaatcaagaa | aattaaggag | 480 |
| acagccgctg | aggaagtcga | aaagatcaaa | gagactgtgg | cagaggaaat | cgaaattgcc | 540 |
| aaggagatca | ttgcaggagc | cgtcctggag | cagaagcaga | aggagaagga | atacgtgagt | 600 |
| gagcacacag | aggaaaatga | ggaaaagaaa | atcgagtcag | aatacactga | ggaaaacgag | 660 |
| gaaaaagaga | tcgaaagcaa | gtataccgaa | gagaatgagg | aaaagaaaaa | cgagtccgaa | 720 |
| tacactgagg | aaaatgagga | agacaccgtg | aaagagattg | aagtgtctaa | gaacgtcaat | 780 |
| atcgagaatg | aaaccatcat | ggaggaaatt | gacaactccg | atgtggagaa | gctgtctgag | 840 |
| accgaaaaag | agctcaagac | aaacgaaatg | atccaggaga | aatacggcga | attcaagaga | 900 |
| gccgaggata | gctactattg | ggaatccaag | tctaccgacg | tggaggatgg | agtcgacgat | 960 |
| gacgtggatg | acgatgagat | cgtggggctg | ccaaagaaaa | gcaacaacac | aatcatcgac | 1020 |
| aacactccta | agagctccgt | gtatctggtc | ccaggactgg | gcggcagcac | cctgattgcc | 1080 |
| gagtacaacc | acgtcagat | cgatagctgc | tctagtaaag | ctctgcattc | caagccctat | 1140 |
| cggatttggc | tgagtctctc | acgactgttt | tctatcagga | gtaacgtgta | ctgtctgttc | 1200 |
| gacactctga | agctcgacta | tgataggaag | aaaaagatgt | acagaaacaa | gccaggtgtc | 1260 |
| tttattaacg | tggagcacta | cggatatatc | aaggggtgg | ccttcctgga | ctacatcaaa | 1320 |
| aataagcccc | tgcggctcac | ccgctactat | ggcatcctgg | ccgataagtt | cctggagaac | 1380 |
| ggttatatcg | acggcaaaga | tattctgtct | gccccatacg | actggagatt | cccctgtct | 1440 |
| cagcagaaat | atgaggtcct | caagagtcac | atcgaataca | tctacggact | gaaaaagggg | 1500 |
| acaaaggtgg | acctcattgg | acattcactg | ggcggcctct | tcatcaacta | ttttctgagc | 1560 |
| cagttcgtgg | atgaggaatg | gaaaagaaa | tacatcaaca | tcgtcatgca | catcaacgtg | 1620 |
| ccttttgctg | ggagcatcaa | ggctattcga | gcactgctct | attcaagcaa | agactacact | 1680 |
| ctgttcaagc | tccgcaatat | cctgaaagtg | agcatttccg | gttctctgat | gaaggccatt | 1740 |
| tcacataaca | tgggcagccc | cttgacctg | atccttaca | gaaagtacta | tgaccgggat | 1800 |
| cagattgtgg | tcatcattaa | tatgggaaag | ctgccaatcg | atgagaaact | cgtccagagc | 1860 |
| attgtgaccg | agtgcgggat | ctataacgaa | cgctgttaca | cagaccgaga | ggatgtgaat | 1920 |
| ctgaagacat | acactctcag | taactggcac | gagctgctct | cagacgatat | tcgggaaaag | 1980 |
| tacgagaact | atatccagta | cacagaccgc | ttctttttccg | tggatcatgg | catccccact | 2040 |
| tattgcctgt | actctaccac | aaggaagaga | ataccgagt | atatgctgtt | ttaccaggac | 2100 |
| gtgcacttca | accatgatcc | aatcatctac | tatgggatcg | tgacggcac | aatttcactg | 2160 |
| gaaagcctgg | aggcctgtaa | gaaactgcag | aacgtcaaag | aggctaagca | cttcgtgtac | 2220 |
| tataagcata | tcggcattct | gaaaagcgac | atcgtgagcg | actacatcta | caacattatt | 2280 |
| aaccagaatc | ggactaactg | ataa |  |  |  | 2304 |

<210> SEQ ID NO 49
<211> LENGTH: 2358
<212> TYPE: DNA
<213> ORGANISM: Artificial sequence
<220> FEATURE:
<223> OTHER INFORMATION: pGX7022 Py UIS10 PL operably linked to IgE leader sequence

<400> SEQUENCE: 49

| | | | | | |
|---|---|---|---|---|---|
| atggactgga | cttggattct | ctttctcgtc | gccgccgcta | ctagggtgca | ttcacaggtc | 60 |
| ttcctctta | ttattattct | ctacaactgc | atctgtctga | cactcatcta | ctcctttaat | 120 |
| cccagtattg | gttcaatcat | taacgtgctg | atcaaaactc | cttacaagct | ctccttcggc | 180 |
| gagtctaaca | agaatagtga | gatcgccaat | ctggaaggca | ccggaaactt | tctcaatgag | 240 |
| actaacaccg | aggaaaccga | acagacagtc | gagttcgaaa | gcaaagagtc | caagaacgac | 300 |
| gatcagaatg | tgctgaacat | cgaaagcact | cccgaggctg | tggtcgagta | cgaagtcgcc | 360 |
| gacaccaagg | aggctatcgt | ggaggaagca | tctattgaca | aggagactgt | catcgaggaa | 420 |
| accgcagata | aagacgatcc | tagtgtggag | atcaagaggg | tgaaggaagt | cacagctgag | 480 |
| gaaatcgaaa | aggtgaaaga | gtccgcagag | aaagaaatca | gaaaattaa | ggagacagcc | 540 |
| gctgaggaag | tcgaaaagat | caaagagact | gtggcagagag | aaatcgaaat | tgccaaggag | 600 |
| atcattgcag | gagccgtcct | ggagcagaag | cagaaggaga | aggaatacgt | gagtgagcac | 660 |
| acagaggaaa | atgaggaaaa | gaaaatcgag | tcagaataca | ctgaggaaaa | cgaggaaaaa | 720 |
| gagatcgaaa | gcaagtatac | cgaagagaat | gaggaaaaga | aaacgagtc | cgaatacact | 780 |
| gaggaaaatg | aggaagacac | cgtgaaagag | attgaagtgt | ctaagaacgt | caatatcgag | 840 |
| aatgaaacca | tcatggagga | aattgacaac | tccgatgtgg | agaagctgtc | tgagaccgaa | 900 |
| aaagagctca | agacaaacga | aatgatccag | gagaaatacg | gcgaattcaa | gagagccgag | 960 |
| gatagctact | attgggaatc | caagtctacc | gacgtggagg | atggagtcga | cgatgacgtg | 1020 |
| gatgacgatg | agatcgtggg | gctgccaaag | aaaagcaaca | acacaatcat | cgacaacact | 1080 |
| cctaagagct | ccgtgtatct | ggtcccagga | ctgggcggca | gcaccctgat | tgccgagtac | 1140 |
| aaccacgctc | agatcgatag | ctgctctagt | aaagctctgc | attccaagcc | ctatcggatt | 1200 |
| tggctgagtc | tctcacgact | gttttctatc | aggagtaacg | tgtactgtct | gttcgacact | 1260 |
| ctgaagctcg | actatgatag | gaagaaaaag | atgtacagaa | acaagccagg | tgtctttatt | 1320 |
| aacgtggagc | actacggata | tatcaagggg | gtggccttcc | tggactacat | caaaaataag | 1380 |
| cccctgcggc | tcacccgcta | ctatggcatc | ctggccgata | agttcctgga | gaacggttat | 1440 |
| atcgacggca | agatattct | gtctgcccca | tacgactgga | gattccccct | gtctcagcag | 1500 |
| aaatatgagg | tcctcaagag | tcacatcgaa | tacatctacg | gactgaaaaa | ggggacaaag | 1560 |
| gtggacctca | ttggacattc | actgggcggc | ctcttcatca | actatttct | gagccagttc | 1620 |
| gtggatgagg | aatggaaaaa | gaaatacatc | aacatcgtca | tgcacatcaa | cgtgcctttt | 1680 |
| gctgggagca | tcaaggctat | cgagcactg | ctctattcaa | gcaaagacta | cactctgttc | 1740 |
| aagctccgca | atatcctgaa | agtgagcatt | tccggttctc | tgatgaaggc | catttcacat | 1800 |
| aacatgggca | gccccttgga | cctgatccct | acagaaagt | actatgaccg | ggatcagatt | 1860 |
| gtggtcatca | ttaatatggg | aaagctgcca | atcgatgaga | aactcgtcca | gagcattgtg | 1920 |
| accgagtgcg | ggatctataa | cgaacgctgt | tacacagacc | gagaggatgt | gaatctgaag | 1980 |
| acatacactc | tcagtaactg | gcacgagctg | ctctcagacg | atattcggga | aaagtacgag | 2040 |
| aactatatcc | agtacacaga | ccgcttcttt | tccgtggatc | atggcatccc | cacttattgc | 2100 |
| ctgtactcta | ccacaaggaa | gagaaatacc | gagtatatgc | tgtttacca | ggacgtgcac | 2160 |
| ttcaaccatg | atccaatcat | ctactatggg | atcggtgacg | gcacaatttc | actggaaagc | 2220 |

```
ctggaggcct gtaagaaact gcagaacgtc aaagaggcta agcacttcgt gtactataag    2280
catatcggca ttctgaaaag cgacatcgtg agcgactaca tctacaacat tattaaccag    2340
aatcggacta actgataa                                                   2358
```

<210> SEQ ID NO 50
<211> LENGTH: 1061
<212> TYPE: PRT
<213> ORGANISM: Artificial sequence
<220> FEATURE:
<223> OTHER INFORMATION: pGX7020 Py SPECT1_SPECT2

<400> SEQUENCE: 50

```
Lys Ile Ser Ile Thr Ile Leu Val Leu Phe Ile Ile Leu Lys Cys Val
1               5                   10                  15

Leu Ser Phe Asn Leu Ser Ile Glu Pro Lys Gly Asn Asn Ile Thr Leu
            20                  25                  30

Asp Lys His Ile Lys Lys Glu Ser Asn Ile Asp His Ser Lys Asn Gln
        35                  40                  45

Ile Ile Glu Glu Phe Asp Lys Ile Ser Asp Asp Phe Ser Asp Asp Ile
    50                  55                  60

Asn Thr Thr Lys Gln Thr Ile Lys Asp Leu Phe Leu Asp Ile Glu Gly
65                  70                  75                  80

Ser Phe Glu Asp Thr Ser Asp Asp Val Val Lys Leu Leu Ser Lys Tyr
                85                  90                  95

Ser Phe Val Pro Glu Glu Lys Leu Asn Ile Ile Asp Gly Ile Leu Arg
            100                 105                 110

Ser Phe Ile Glu Asn Asn Lys Thr His Val Ile Asn Ser Ser Asn Ala
        115                 120                 125

Tyr Met Tyr Met Gln Lys Glu Lys Ile Lys Asn Val Cys Asp Phe Ile
    130                 135                 140

Leu Lys Lys Leu Asn Ser Leu Ile Gln Ile Asn Glu Leu Asn Lys Asn
145                 150                 155                 160

His Ile Ile Leu Lys Tyr Gly Lys Gly Glu Ala Lys Lys Gly Val Leu
                165                 170                 175

Glu Ser Ile Lys Asn Asn Asp Asn Ile Ser Lys Asn Leu Lys Ser Glu
            180                 185                 190

Leu Leu Lys Tyr Glu Asn Val Ser Asn Gln Asn Ile Arg Val Ser Glu
        195                 200                 205

Leu Ile Asn Phe Ile Thr Pro Ile Tyr Asp Asp Phe Ile Lys Lys Leu
    210                 215                 220

Ser Asp Leu Ile Asn Asp Leu Gln Ile Lys Leu Asn Asn Ile Ser Lys
225                 230                 235                 240

Arg Val Arg Arg Ala Lys Arg Lys Met Arg Asn Ile Lys Lys Ser Leu
                245                 250                 255

Pro Val Leu Phe Ile Leu Leu Cys Ile Tyr Gln Gln Ser Phe Ile Asn
            260                 265                 270

Ser Leu Arg Ile Ser Val Arg Asn Asn Lys Asn His Arg Asp Gly Asn
        275                 280                 285

Asn Glu Asn Lys Phe Asn Lys Asn Val Glu Leu Gly Thr Met Glu Lys
    290                 295                 300

Pro Ile Asn Ile Leu Cys Asn Asp Ile Ser Cys Asn Pro Gly Asn Asn
305                 310                 315                 320

Ile Ser Phe Val Asn Gln Lys Lys Lys Glu Ile Asp Ser Asp Asp Asp
                325                 330                 335
```

```
Leu Tyr Asp Met Leu Asp Asp Ala Ser Thr Ser Ala Gly Asp Asp
            340                 345                 350

Glu Asp Glu Asp Asp Tyr Asp Tyr Thr Asp Asp Lys Asn Thr Glu
        355                 360                 365

Ile Lys Asp Glu Glu Gln Asn Glu His Ile Asp Lys Thr Asp Gln Lys
370                 375                 380

Lys Asp Lys Lys Gly Thr Phe Ser Ile Lys Lys Gln Glu Glu Glu Ile
385                 390                 395                 400

Asn Glu Asn Lys Asn Arg Thr Glu Lys Phe Phe Lys Lys Tyr Lys Phe
                405                 410                 415

Asn Asp Ala Asp Asn Glu Gly Gly Asp Asp Glu Ser Glu Thr Asp Asp
            420                 425                 430

Glu Asn Leu Asp Asn Ser Thr Gln Asn Ser His Ala Glu Asn Lys Asn
        435                 440                 445

Pro Glu Ser Val Ile Asp Lys His Met Ser Val Phe Pro Gly Leu Tyr
            450                 455                 460

Phe Val Gly Ile Gly Tyr Asp Ile Leu Phe Gly Asn Pro Leu Gly Glu
465                 470                 475                 480

Thr Asp Ser Leu Ser Asp Pro Gly Tyr Arg Ala Gln Ile Tyr Leu Leu
                485                 490                 495

Asn Trp Glu Phe Ser Asn His Gly Ile Ala Asn Asp Leu His Thr Leu
            500                 505                 510

Gln Pro Ile Asn Ala Trp Ile Arg Lys Glu Asn Ala Cys Ser Arg Val
        515                 520                 525

Glu Ser Ile Asn Glu Cys Ser Ser Val Ser Glu Tyr Thr Lys Asn Leu
        530                 535                 540

Ser Val Asp Val Ser Val Ser Gly Ser Tyr Met Gly Phe Gly Ser Phe
545                 550                 555                 560

Ser Ala Ser Thr Gly Tyr Lys Lys Phe Ile Asn Glu Ile Ser Lys Arg
                565                 570                 575

Thr Ser Lys Thr Tyr Phe Ile Lys Ser Asn Cys Ile Lys Tyr Thr Ile
            580                 585                 590

Gly Leu Pro Pro Tyr Val Pro Trp Glu Gln Thr Thr Ala Tyr Met Asn
        595                 600                 605

Ala Val Asp Ile Leu Pro Arg Glu Phe Thr Gly Leu Asp Glu Asp Ser
        610                 615                 620

Glu Cys Thr Pro Asp Val Tyr Glu Gln Lys Lys Met Thr Lys Glu Cys
625                 630                 635                 640

Arg Asn Val Gln Leu Trp Ile Gln Phe Phe Lys Thr Tyr Gly Thr His
                645                 650                 655

Ile Ile Val Glu Ala Gln Leu Gly Gly Lys Ile Thr Lys Ile Ile Asn
            660                 665                 670

Val Ser Asn Thr Ser Val Asn Gln Met Lys Lys Asp Gly Val Ser Val
        675                 680                 685

Lys Ala Gln Ile Gln Ala Gln Phe Gly Phe Ala Ser Val Gly Gly Ser
        690                 695                 700

Thr Ser Val Ser Ser Asp Asn Ser Ser Lys Asn Asp Asn Ser Ser Tyr
705                 710                 715                 720

Asp Met Ser Glu Lys Leu Val Val Ile Gly Gly Asn Pro Ile Lys Asp
                725                 730                 735

Val Thr Lys Glu Glu Asn Leu Tyr Glu Trp Ser Lys Thr Val Ser Ser
            740                 745                 750
```

| Asn | Pro | Met | Pro | Ile | His | Ile | Lys | Leu | Leu | Pro | Ile | Tyr | Lys | Ser | Phe |
|  | 755 |  |  |  |  | 760 |  |  |  |  | 765 |  |  |  |  |

Asp Ser Glu Glu Leu Lys Glu Ser Tyr Glu Lys Ala Leu Leu Tyr Tyr
770             775             780

Thr Arg Leu Tyr Gly Ser Pro His Gly Thr Ile Gln Lys Asp Glu
785             790             795             800

Asn Asp Ile Ile Lys Ile Leu Thr Ala Ser Thr Thr Ile Thr Lys Ile
    805             810             815

Gly Ala Pro Pro Ile Thr Ala Glu Cys Pro His Asn Gln Val Val Leu
        820             825             830

Phe Gly Tyr Val Leu Lys Gln Asn Phe Trp Asp Asn Thr Ser Arg Leu
    835             840             845

Lys Gly Tyr Asp Ile Glu Ile Cys Glu Ser Gly Leu Asn Ser Cys Thr
850             855             860

Ser Lys Gln Gly Ser Thr Asn Lys Tyr Asp Val Ser Tyr Leu Tyr Ile
865             870             875             880

Glu Cys Gly Thr Gln Ala Met Pro Phe Ser Asp Gln Val Ile Thr Ser
            885             890             895

Thr Asn Ala Thr Tyr Asn Thr Ile Lys Cys Pro Asn Asp Tyr Thr Ile
        900             905             910

Ile Phe Gly Phe Gly Phe Ser Ser Ser Gly Lys Gly Val Ser Ala
    915             920             925

Met His Ser His Ile Thr Ser Cys Arg Pro Gly Met Lys Ser Cys Ser
        930             935             940

Leu Asn Met Gly Asn Ser Asn Asp Lys Asn Tyr Met Tyr Leu Val Cys
945             950             955             960

Val Asp Ala Thr Ile Trp Ser Gly Ile Asn Glu Leu Thr Thr Val Ala
            965             970             975

Lys Asp Asp Phe His Gly Ala Val Asn Arg Ser Lys Gln Phe Asn Asp
        980             985             990

Gly Gln Leu Val Leu Asn Cys Gln Glu Asn Gly Thr Ile Leu Thr Gly
    995             1000            1005

Phe Ala Gly Glu Thr His Thr Ser Ser Pro Tyr Val Lys Ser Pro
    1010            1015            1020

Phe Ser Lys Cys Leu Lys Asn Leu Lys Ser Cys Ser Val His Gly
    1025            1030            1035

Ser Gly Gln Ser Ile Gly Tyr Thr Asn Tyr Lys Ser Leu Phe Ala
    1040            1045            1050

Ile Ile Leu Cys Lys Asn Ser Glu
    1055            1060

<210> SEQ ID NO 51
<211> LENGTH: 3183
<212> TYPE: DNA
<213> ORGANISM: Artificial sequence
<220> FEATURE:
<223> OTHER INFORMATION: pGX7020 Py SPECT1_SPECT2

<400> SEQUENCE: 51
aaaatctcaa tcacaattct ggtgctgttc attatcctca agtgcgtgct gagtttcaac    60
ctctcaattg aacctaaagg aaacaatatc accctggaca agcacattaa gaaagagtca   120
aacatcgatc atagcaaaaa tcagatcatt gaggaatttg acaagatcag cgacgatttc   180
tccgacgata ttaacaccac aaaacagact atcaaggacc tgtttctcga tattgaaggg   240
tccttcgagg acacctctga cgatgtggtc aaactgctct ccaagtactc ttttgtgcca   300

```
gaggaaaagc tgaacatcat tgatggcatt ctccggagct tcatcgaaaa caataagaca      360
cacgtgatca atagctccaa cgcctacatg tatatgcaga aagagaagat caaaaacgtg      420
tgcgatttca ttctgaagaa actcaactcc ctgatccaga ttaatgagct gaacaagaac      480
catatcattc tcaagtatgg caaaggagaa gctaagaaag gcgtgctgga gtctattaag      540
aacaacgaca acatcagtaa gaacctgaaa tcagaactgc tcaagtacga aacgtctct       600 aaccagaata tcagggtgag tgagctgatc aattttatta ccccaatcta tgacgatttc      660
attaagaaac tctccgacct gattaacgat ctgcagatca aactcaacaa tatttctaag      720
agagtgagga gagccaagcg gaaaatgcgc aacatcaaga aaagcctccc cgtcctgttt      780
attctgctct gtatctacca gcagtctttc atcaatagtc tgcgaatttc agtgaggaac      840
aataagaacc accgcgacgg taacaacgag aataagtttta acaaaaacgt ggaactgggc     900
accatggaga agcctatcaa tattctctgc aacgatatca gctgtaaccc aggaaacaat      960
atttccttcg tgaatcagaa gaaaaaggag atcgactccg acgatgacct gtatgatatg     1020
ctcgatgacg atgccagcac atccgctggg gacgatgaag acgaggacga ttacgacgat     1080
tatactgacg ataaaaacac cgaaatcaag gacgaggaac agaatgagca tattgacaag     1140
acagatcaga aaaaggataa gaagggaact ttttctatca aaaagcagga ggaagagatt     1200
aacgaaaaca gaacaggac cgagaagttc tttaagaagt acaagttcaa tgacgctgat     1260
aacgaaggcg gagacgatga atccgagacc gacgatgaga atctggacaa cagcacacag     1320
aactcccacg cagaaaacaa gaaccccgag tcagtcatcg acaagcatat gagcgtgttt     1380
cctggcctgt acttcgtcgg gattggttat gatatcctgt ttgggaaccc actcggtgaa     1440
acagactctc tgagtgatcc cggatacaga gcacagatct atctgctcaa ttgggagttc     1500
tccaaccacg ggattgccaa tgatctccat actctgcagc ccattaacgc atggatcaga     1560
aaggaaaatg cctgctctcg ggtggaaagt atcaacgagt gttctagtgt ctccgagtac     1620
acaaagaatc tgtctgtgga cgtctcagtg agcggcagct acatgggctt tggatctttc     1680
agtgcctcaa ctgggtacaa gaagtttatt aacgagatct caaagcggac cagcaagaca     1740
tacttcatca aaagcaactg tattaagtac actatcggcc tgccccctta tgtgccttgg     1800
gaacagacta ccgcatatat gaacgccgtc gacatcctgc cacgcgagtt cactggactc     1860
gacgaagatt ccgagtgcac ccccgatgtg tacgaacaga aaaagatgac aaaggagtgt     1920
cgaaacgtcc agctgtggat tcagttcttt aagacttatg gcacccacat cattgtggag     1980
gctcagctgg ggggcaagat cactaagatc attaatgtca gtaacacctc agtgaaccag     2040
atgaaaaagg acggagtctc tgtgaaggct cagatccagg cacagttcgg gtttgcaagt     2100
gtcggcggaa gcacctccgt gtcaagcgat aattcctcta agaacgacaa cagttcatac     2160
gatatgtctg aaaagctggt ggtcatcggg ggtaacccca tcaaggacgt gaccaaggaa     2220
gagaatctgt acgagtggag caagacagtc agctccaacc ctatgccaat ccacatcaag     2280
ctgctcccca tctataagag ctttgactcc gaagagctga agaaagcta cgagaaggcc     2340 ctgctctact atacacgact gtatggctct agtcctcacg gaactatcca gaaagacgag     2400
aacgatatca ttaagattct gacagcttcc acaactatta ctaagatcgg tgcaccacca     2460
atcaccgctg agtgccccca taatcaggtg gtcctgtttg gctacgtgct caaacagaat     2520
ttctgggaca acacatcacg cctgaagggg tatgatatcg aaatttgcga gtccggtctc     2580
aactcttgta ccagtaaaaca gggcagtaca aataagtacg acgtgtcata cctgtatatc     2640
```

| | |
|---|---|
| gagtgcggca cccaggccat gcctttcagc gatcaggtca tcacttccac caatgctaca | 2700 |
| tacaacacta ttaagtgtcc aaacgactat actatcattt tcgggtttgg tttctcaagc | 2760 |
| tcctctggca agggagtgtc cgcaatgcac tctcatatca ccagttgccg gcccggaatg | 2820 |
| aagtcttgta gtctgaacat ggggaatagc aacgacaaga attacatgta tctggtctgc | 2880 |
| gtggatgcca caatttggtc cggtatcaac gagctgacca cagtggctaa agacgatttt | 2940 |
| cacggcgcag tcaaccgcag caagcagttc aatgacggtc agctggtgct caattgtcag | 3000 |
| gaaaacggca ccatcctgac aggctttgcc ggagagacac acactagttc accctacgtg | 3060 |
| aagtcacctt tcagcaagtg cctcaaaaac ctgaagtcat gtagcgtcca tgggtccggc | 3120 |
| cagtctatcg gctacaccaa ctataaatct ctgttcgcta tcattctctg taagaatagt | 3180 |
| gag | 3183 |

<210> SEQ ID NO 52
<211> LENGTH: 3237
<212> TYPE: DNA
<213> ORGANISM: Artificial sequence
<220> FEATURE:
<223> OTHER INFORMATION: pGX7020 Py SPECT1_SPECT2 operably linked to IgE leader sequence

<400> SEQUENCE: 52

| | |
|---|---|
| atggactgga catggattct gttcctggtc gccgccgcaa ctagagtgca ttcaaaaatc | 60 |
| tcaatcacaa ttctggtgct gttcattatc ctcaagtgcg tgctgagttt caacctctca | 120 |
| attgaaccta aggaaacaa tatcaccctg acaagcaca ttaagaaaga gtcaaacatc | 180 |
| gatcatagca aaaatcagat cattgaggaa tttgacaaga tcagcgacga tttctccgac | 240 |
| gatattaaca ccacaaaaca gactatcaag gacctgtttc tcgatattga agggtccttc | 300 |
| gaggacacct ctgacgatgt ggtcaaactg ctctccaagt actcttttgt gccagaggaa | 360 |
| aagctgaaca tcattgatgg cattctccgg agcttcatcg aaaacaataa gacacacgtg | 420 |
| atcaatagct ccaacgccta catgtatatg cagaaagaga agatcaaaaa cgtgtgcgat | 480 |
| ttcattctga gaaaactcaa ctccctgatc cagattaatg agctgaacaa gaaccatatc | 540 |
| attctcaagt atggcaaagg agaagctaag aaaggcgtgc tggagtctat taagaacaac | 600 |
| gacaacatca gtaagaacct gaaatcagaa ctgctcaagt acgagaacgt ctctaaccag | 660 |
| aatatcaggg tgagtgagct gatcaattt attaccccaa tctatgacga tttcattaag | 720 |
| aaactctccg acctgattaa cgatctgcag atcaaactca caatatttc taagagagtg | 780 |
| aggagagcca agcggaaaat gcgcaacatc aagaaaagcc tccccgtcct gtttattctg | 840 |
| ctctgtatct accagcagtc tttcatcaat agtctgcgaa tttcagtgag gaacaataag | 900 |
| aaccaccgcg acgtaacaa cgagaataag tttaacaaaa acgtggaact gggcaccatg | 960 |
| gagaagccta tcaatattct ctgcaacgat atcagctgta cccaggaaa caatatttcc | 1020 |
| ttcgtgaatc agaagaaaaa ggagatcgac tccgacgatg acctgtatga tatgctcgat | 1080 |
| gacgatgcca gcacatccgc tggggacgat gaagacgagg acgattacga cgattatact | 1140 |
| gacgataaaa acaccgaaat caaggacgag aacagaatg agcatattga caagacagat | 1200 |
| cagaaaaagg ataagaaggg aacttttct atcaaaaagc aggaggaaga gattaacgaa | 1260 |
| aacaagaaca ggaccgagaa gttctttaag aagtacaagt tcaatgacgc tgataacgaa | 1320 |
| ggcggagacg atgaatccga gaccgacgat gagaatctgg acaacagcac acagaactcc | 1380 |
| cacgcagaaa acaagaaccc cgagtcagtc atcgacaagc atatgagcgt gtttcctggc | 1440 |

```
ctgtacttcg tcgggattgg ttatgatatc ctgtttggga acccactcgg tgaaacagac    1500
tctctgagtg atcccggata cagagcacag atctatctgc tcaattggga gttctccaac    1560
cacgggattg ccaatgatct ccatactctg cagcccatta acgcatggat cagaaaggaa    1620
aatgcctgct ctcgggtgga aagtatcaac gagtgttcta gtgtctccga gtacacaaag    1680
aatctgtctg tggacgtctc agtgagcggc agctacatgg gctttggatc tttcagtgcc    1740
tcaactgggt acaagaagtt tattaacgag atctcaaagc ggaccagcaa gacatacttc    1800
atcaaaagca actgtattaa gtacactatc ggcctgcccc cttatgtgcc ttgggaacag    1860
actaccgcat atatgaacgc cgtcgacatc ctgccacgcg agttcactgg actcgacgaa    1920
gattccgagt gcacccccga tgtgtacgaa cagaaaaaga tgacaaagga gtgtcgaaac    1980
gtccagctgt ggattcagtt ctttaagact tatggcaccc acatcattgt ggaggctcag    2040
ctggggggca agatcactaa gatcattaat gtcagtaaca cctcagtgaa ccagatgaaa    2100
aaggacggag tctctgtgaa ggctcagatc caggcacagt tcgggtttgc aagtgtcggc    2160
ggaagcacct ccgtgtcaag cgataattcc tctaagaacg caacagttc atacgatatg    2220 tctgaaaagc tggtggtcat cgggggtaac cccatcaagg acgtgaccaa ggaagagaat    2280
ctgtacgagt ggagcaagac agtcagctcc aaccctatgc caatccacat caagctgctc    2340
cccatctata agagctttga ctccgaagag ctgaaagaaa gctacgagaa ggccctgctc    2400
tactatacac gactgtatgg ctctagtcct cacggaacta ccagaaaga cgagaacgat    2460 atcattaaga ttctgacagc ttccacaact attactaaga tcggtgcacc accaatcacc    2520
gctgagtgcc cccataatca ggtggtcctg tttggctacg tgctcaaaca gaatttctgg    2580
gacaacacat cacgcctgaa ggggtatgat atcgaaattt gcgagtccgg tctcaactct    2640
tgtaccagta acagggcag tacaaataag tacgacgtgt catacctgta tatcgagtgc    2700
ggcacccagg ccatgccttt cagcgatcag gtcatcactt ccaccaatgc tacatacaac    2760
actattaagt gtccaaacga ctatactatc attttcgggt ttggtttctc aagctcctct    2820
ggcaagggag tgtccgcaat gcactctcat atcaccagtt gccggcccgg aatgaagtct    2880
tgtagtctga acatggggaa tagcaacgac aagaattaca tgtatctggt ctgcgtggat    2940
gccacaattt ggtccggtat caacgagctg accacagtgg ctaaagacga ttttcacggc    3000
gcagtcaacc gcagcaagca gttcaatgac ggtcagctgg tgctcaattg tcaggaaaac    3060
ggcaccatcc tgacaggctt tgccggagag acacacacta gttcaccta cgtgaagtca    3120 cctttcagca agtgcctcaa aaacctgaag tcatgtagcg tccatgggtc cggccagtct    3180
atcggctaca ccaactataa atctctgttc gctatcattc tctgtaagaa tagtgag       3237
```

<210> SEQ ID NO 53
<211> LENGTH: 2231
<212> TYPE: PRT
<213> ORGANISM: Artificial sequence
<220> FEATURE:
<223> OTHER INFORMATION: pGX7026 Py RON2

<400> SEQUENCE: 53

```
Leu Lys Ala Thr Ile Gly Ile Ile Leu Phe Ile Cys Val Asn Ile Asp
1               5                   10                  15

Ile Ile Arg Thr Thr Ser Arg Asp Asn Val Val Asn Thr Lys Phe Val
                20                  25                  30

Arg Gln Lys Ser Pro Thr Tyr Asp Pro Asn Lys Lys Gly Asp Val Ile
            35                  40                  45
```

-continued

```
Phe Tyr Met Pro Glu His Lys Asp Glu Ile His Arg Ala Asn Asn Lys
     50                  55                  60
Ser Ala Asn Ile Asn Leu Lys Asn Asn Pro Pro Arg Asn Ile Asn Ile
 65                  70                  75                  80
Gly Tyr Asn Thr Ala Pro Gly Val Asn His Gly Phe Gly Gln Phe Ser
                 85                  90                  95
Gly Lys Ser Ser Asn Met Asn Asn Gly Ile Asn Thr Tyr Lys Asn Gln
                100                 105                 110
Pro Lys His Phe Gln Ser Met Asn Tyr Gln Lys Asn Gly Pro Phe Gly
            115                 120                 125
Asn Lys Leu Glu Gln Met Asn Ile Pro Ala Asn Leu Tyr Asn Asn Lys
        130                 135                 140
Asn Asn Ser Tyr Tyr Ser Gly Ser Asn Asn Gly Asn Asn Asn Ser Tyr
145                 150                 155                 160
Gly Leu His Gly Asn Ile Tyr Asp Lys Ile Asn Ser Ser Val Tyr Asn
                165                 170                 175
Asn Ser Lys Tyr Asn Asn Ser Asn Phe Asn Thr Asp Lys Asn Asn Asn
            180                 185                 190
Asp Asn Glu Asn Asn Lys Thr Tyr Lys Ser Tyr Leu Asn Leu Tyr Val
        195                 200                 205
Ser Asp Asn Lys Ile Ser Pro Ile Gly Asn Asn Gly Arg Pro Gly His
210                 215                 220
Leu Ile Ser His Phe Asn Asn Pro Asn Gln Lys Leu Glu Phe Leu His
225                 230                 235                 240
Gly Phe Asp Gly Leu Phe Asn Gln Asn Ile Pro Gly Met Asn His Lys
                245                 250                 255
Gly Asn Tyr Gly Phe Asn Gly Val Asn Ile Lys Gly Gln Gly Lys Asn
            260                 265                 270
Glu Lys Phe Asp Asn Tyr Gly Gln Asn Leu Gly Leu Asn Lys Thr Asn
        275                 280                 285
Glu Tyr Gln Gln Met Ile Asn Gly Asn Asn Met Gly Ser Asp His Ile
        290                 295                 300
Tyr Glu Ser Pro Asn Phe Val Asn Gly Asn Asn Met Gly Ser Asp Asn
305                 310                 315                 320
Ala Gly Glu Tyr Gln Arg Leu Val Asn Gly Asn Asn Met Gly Ser Asp
                325                 330                 335
His Ile Tyr Glu Ser Pro Asn Phe Val Asn Gly Asn Asn Met Gly Ser
                340                 345                 350
Asp Asn Ala Gly Glu Ser Gln Arg Leu Val Asn Gly Asn Asn Met Gly
            355                 360                 365
Ser Asp Asn Ala Gly Glu Ser Pro Lys Leu Val Asn Gly Asn Asn Met
        370                 375                 380
Gly Ser Asp Asn Ala Gly Glu Ser Pro Lys Leu Val Asn Gly Asn Asn
385                 390                 395                 400
Met Gly Ser Asp Asn Ala Gly Glu Ser Gln Arg Leu Val Asn Gly Asn
                405                 410                 415
Asn Met Gly Ser Asp Asn Ala Gly Glu Ser Pro Lys Leu Val Asn Gly
            420                 425                 430
Asn Asn Met Gly Ser Asp Asn Ala Gly Glu Ser Gln Arg Leu Val Asn
        435                 440                 445
Gly Asn Asn Met Gly Ser Asp Asn Ser Gly Glu Tyr Gln Arg Leu Val
450                 455                 460
Asn Gly Asn Asn Met Gly Ser Asp Asn Ser Gly Glu Tyr Gln Arg Leu
```

```
                465                 470                 475                 480
        Val Asn Gly Asn Asn Met Gly Ser Asp His Ile Tyr Glu Ser Pro Asn
                            485                 490                 495
        Phe Val Asn Gly Asn Asn Met Gly Ser Asp Asn Ala Gly Glu Tyr Gln
                            500                 505                 510
        Arg Leu Ile Asn Gly Asn Asn Met Gly Ser Asp Asn Ala Gly Glu Tyr
                            515                 520                 525
        Gln Arg Leu Ile Asn Gly Asn Asn Met Gly Ser Asp His Ile Tyr Glu
                    530                 535                 540
        Ser Pro Asn Phe Val Asn Gly Asn Asn Met Gly Ser Asp Asn Ala Gly
        545                 550                 555                 560
        Glu Tyr Gln Arg Leu Ile Asn Gly Asn Asn Met Gly Ser Asp Asn Ala
                            565                 570                 575
        Gly Glu Tyr Gln Arg Leu Ile Asn Gly Asn Asn Met Gly Ser Asp His
                        580                 585                 590
        Ile Tyr Glu Ser Pro Asn Phe Val Asn Gly Asn Asn Met Gly Ser Asp
                    595                 600                 605
        Asn Ala Gly Glu Tyr Gln Arg Leu Val Asn Gly Asn Asn Met Gly Ser
                610                 615                 620
        Asp Asn Ala Gly Glu Tyr Gln Arg Leu Val Asn Gly Asn Asn Met Gly
        625                 630                 635                 640
        Ser Asp His Ile Tyr Glu Ser Pro Asn Leu Val Asn Gly Asn Asn Met
                        645                 650                 655
        Gly Ser Asp Asn Ser Gly Glu Tyr Gln Arg Leu Val Asn Gly Asn Asn
                    660                 665                 670
        Met Gly Ser Asp Asn Ala Gly Glu Tyr Gln Arg Leu Val Asn Gly Asn
                675                 680                 685
        Asn Met Gly Ser Asp His Ile Tyr Glu Ser Pro Asn Leu Val Asn Gly
                    690                 695                 700
        Asn Asn Met Gly Ser Asp Asn Ser Gly Glu Tyr Gln Arg Leu Val Asn
        705                 710                 715                 720
        Gly Asn Asn Met Gly Ser Asp Asp Ser Gly Glu Tyr Gln Lys Leu Val
                            725                 730                 735
        Asn Gly Asn Asn Gly Val Ile Pro Asn Phe Thr Gly Asn Asp Gln Glu
                        740                 745                 750
        Ile Phe Lys Asn Ile Arg Gly Leu Arg Pro Val Asn His Glu Glu Leu
                    755                 760                 765
        Tyr Lys Asn Lys Met Asn Pro Leu Ile Tyr Asn Ala His Gly Met Gln
                770                 775                 780
        Ser Gly Asn Lys Asn Gly Ala Pro Asn Ser Thr Ser Asp Tyr Val Ser
        785                 790                 795                 800
        Asp Tyr Asn Ser Asp Ser Asp Thr Asp Ser Asp Ser Asp Ser Asp Ser
                            805                 810                 815
        Asp Leu Asp Tyr Asp Ser Glu Ser Asn Glu Ser Asn Val Tyr Lys Ile
                        820                 825                 830
        Lys Thr Asn Lys Leu Glu Asn Asp Asn Lys Asp Gly Asn Gly Asn Val
                    835                 840                 845
        Asn Asp Ala Asn Tyr Tyr Lys Asn Gln Ile Asp Ile Ala Asn Lys Asn
                850                 855                 860
        His Gly Asn Arg Tyr Asn Ser Glu Asn Asp Tyr Gly Asp Ser Met His
        865                 870                 875                 880
        Ser Asp Ser Ala Leu Ser Tyr Glu Arg Asp Leu Ser Ser Gly Asn Arg
                            885                 890                 895
```

-continued

His Val Lys Glu Gly Ser Asn Asp Glu Ile Asn Ile Phe Tyr Arg Asp
              900                 905                 910

Asn Ala Gln Asp Arg Glu Thr Lys Glu Lys Leu Met Asn Ser Ser Glu
      915                 920                 925

Ser Asp Lys Asp Val Glu Asn Pro Leu Asn Ile Thr Ile Pro Glu Glu
      930                 935                 940

Asn Val Asn Tyr His Phe Ser Asn Tyr Met Asn Phe Asp Lys Lys Asn
945                 950                 955                 960

Ile Leu Thr Ser Asn Glu Glu Leu Leu Lys Met Ile Gly Pro Asp
              965                 970                 975

Phe Ser Lys Glu Val Ser Asn Tyr Cys Ser Lys Lys Ser Ile Phe Pro
              980                 985                 990

Ser Asn Gly Lys Tyr Leu Asp Val Ser Phe Glu Tyr Ser Lys Glu Leu
              995                1000                1005

Gly Lys Leu Arg Glu Lys Met Met Ser Gly Leu Phe Lys Lys Lys
       1010                1015            1020

Gly Lys Leu Val Thr Lys Glu Asn Asn Ile Leu Lys Gln Ile Glu
       1025                1030            1035

Asn Ser Leu Lys Met Asp Tyr Leu Glu Arg Gln Gln Gly Tyr Val
       1040                1045            1050

Asn Tyr Gly Ser Lys Ser Asn Glu Leu Lys Asn Asp Glu Glu Ser
       1055                1060            1065

Met Leu Ser Asn Glu Tyr Asn Lys Leu Leu Glu Glu Tyr Ile Cys
       1070                1075            1080

His Ile Leu Ser Asn Asn Pro Gly Lys Thr Gln Phe Glu Lys Leu
       1085                1090            1095

Tyr Tyr His Asn Leu Ala Leu Gly Glu Ile Met Lys Pro Ile Lys
       1100                1105            1110

Thr Lys Tyr Lys Asn Ala Ala Thr Leu Ser Ile Ala Leu Asn Tyr
       1115                1120            1125

Glu Ile Tyr Ile Val Ser Ser Ser Asn Ile Tyr Leu Phe Gly His
       1130                1135            1140

Met Leu Leu Leu Ser Leu Ala Tyr Leu Ser Tyr Asn Ser Tyr Phe
       1145                1150            1155

Thr Lys Gly Thr Lys Ser Phe Tyr Ser Met Glu Thr Met Leu Leu
       1160                1165            1170

Ala Asn Ser Asp Tyr Ser Phe Phe Met Tyr Asn Glu Met Cys Asn
       1175                1180            1185

Val Tyr Tyr Arg Pro Asn Lys Ser Phe Lys Lys Asp Leu Thr Phe
       1190                1195            1200

Ile Pro Ile Glu Leu Arg Pro Gly Arg Tyr Thr Thr Tyr Val Gly
       1205                1210            1215

Glu Arg Lys Ile Ile Cys Asn Thr Leu Glu Leu Ile Leu Asn Ala
       1220                1225            1230

Ile Ser Leu Ile Asn Ile Asn Glu Ile Tyr Asn Val Phe His Lys
       1235                1240            1245

Asn Asn Val Tyr Gly Tyr Glu Asn Ser Val Ser Phe Ser Asn Asn
       1250                1255            1260

Ala Ile Arg Val Phe Ser Gln Val Cys Pro Arg Asn Met Glu Lys
       1265                1270            1275

Asn Ile Ile Asn Cys Ser Phe Glu Lys Ser Thr Leu Tyr Lys Ala
       1280                1285            1290

```
Asn Ala Pro Glu Asp Thr Asn   Gln Asn Glu Tyr   Gln Arg Gln Asn
    1295            1300              1305

Gln Ile Lys Asn Gln Asn Glu   Leu Lys Lys Ala   Phe Asp Leu Leu
    1310            1315              1320

Asn Thr Phe Ser Glu Ile Glu   Ser Phe Ser Asn   Asn Tyr Gln
    1325            1330              1335

Asn Ser Tyr Tyr Ile Lys Leu   Ile Met Glu Gln   Asn Leu Tyr Thr
    1340            1345              1350

Asp Phe Tyr Lys Tyr Leu Phe   Trp Tyr Asp Asn   Arg Glu Leu Ile
    1355            1360              1365

Lys Thr His Glu Ile Asn Gly   Lys Lys Asn Thr   Lys Lys Thr Ser
    1370            1375              1380

Asn Tyr Ile Tyr Asp Gln Tyr   Ile Lys Thr Asn   Arg Leu Leu Glu
    1385            1390              1395

Lys Lys Phe Asn Val Leu Ser   Lys His Asn Leu   Lys Ser Lys Gly
    1400            1405              1410

Leu Leu Ala Phe His Ser Leu   Ile Asp Arg Tyr   Ser Glu Phe Val
    1415            1420              1425

Lys Asn Lys Lys Ile Arg Asn   Leu Tyr Leu Lys   Phe Val Ser Tyr
    1430            1435              1440

Ala Arg His Phe Leu Phe Met   Asn Asn Thr Met   Lys Ser Leu Asn
    1445            1450              1455

Lys Ser Asp Leu Asp Phe Met   Lys Met Ile Phe   Glu Glu Leu Gln
    1460            1465              1470

Asn Glu Thr Lys Val Pro Leu   Lys Leu Ile Val   Arg Gly Asn Tyr
    1475            1480              1485

Met Lys Ser Met Asn Asp Ile   Ala Lys Lys Glu   Asn Leu Phe Phe
    1490            1495              1500

Ile Asn Leu Phe Ile Leu Ser   Leu Phe Ser Asn   Lys Asn Pro Val
    1505            1510              1515

Lys Asn Phe Tyr Asn Gly Lys   Arg Glu Met Leu   Lys Ala Ser Leu
    1520            1525              1530

Ser Glu Lys Phe Ala Thr Ser   Thr Ser Ala Phe   Ile Pro His Lys
    1535            1540              1545

Leu Arg Arg Ile Val Val Gly   Met Lys Lys Gly   Phe Leu Lys Arg
    1550            1555              1560

Lys Leu Leu Lys Thr Leu Met   Lys Asn Arg Leu   Leu Gln His Ile
    1565            1570              1575

Pro Ile Asp Leu Leu Glu Asn   Ile Met Thr Thr   Phe Arg Phe Thr
    1580            1585              1590

Thr His Ala Ile Ala Thr Ser   Glu Leu Ala Gln   Asn Ala His Arg
    1595            1600              1605

Thr Ser Lys Tyr Leu Asn Ser   Asn Asn Thr Ser   Lys Leu Glu Phe
    1610            1615              1620

Ala Lys Thr Ile Phe Ser Lys   Gly Gly Phe Pro   Gln Tyr Ala Asp
    1625            1630              1635

Lys Leu Met Glu Lys Trp Phe   Ser Lys Gly Phe   Glu Glu Tyr Lys
    1640            1645              1650

Lys Glu Lys Ile Asp Asn Gln   Asn Met Glu Asn   Glu Val Asp Lys
    1655            1660              1665

Glu Leu Asp Gln Ile Lys Glu   Met Phe Ile Pro   Gly Ser Asn Gly
    1670            1675              1680

Lys His Asn Ser Asn Thr Pro   Pro His Leu Ile   Glu Asn Ile Asn
```

|  |  |  | 1685 |  |  |  | 1690 |  |  |  | 1695 |  |
|---|---|---|---|---|---|---|---|---|---|---|---|---|
| Thr | Asp | Val | Asn | Asn | Ser | Leu | Asp | Asn | Gln | Asp | Lys | Tyr Asp Asn |
|  |  |  | 1700 |  |  |  | 1705 |  |  |  | 1710 |  |
| Thr | Leu | Gly | Lys | Gln | Arg | Val | Asp | Lys | Leu | Ile | Tyr | Asn Glu His |
|  |  |  | 1715 |  |  |  | 1720 |  |  |  | 1725 |  |
| Asp | Lys | Trp | Asp | His | Tyr | Ile | Asn | Lys | Glu | Tyr | Val | Lys Ala Leu |
|  |  |  | 1730 |  |  |  | 1735 |  |  |  | 1740 |  |
| Gly | Ala | Trp | Ile | Glu | Ile | His | Lys | Lys | Ser | Asn | Asn | Val Met Glu |
|  |  |  | 1745 |  |  |  | 1750 |  |  |  | 1755 |  |
| Asn | Ile | Leu | Gln | Ala | Val | Glu | Asp | Ser | Lys | Tyr | Leu | Leu Glu Asn |
|  |  |  | 1760 |  |  |  | 1765 |  |  |  | 1770 |  |
| Asn | Ile | Glu | Asp | Ser | Ile | Phe | Phe | Ser | Arg | Thr | Phe | Lys Ala Thr |
|  |  |  | 1775 |  |  |  | 1780 |  |  |  | 1785 |  |
| Lys | Gln | Ser | Ala | Phe | Arg | Asn | Val | Leu | Asn | Lys | Thr | Leu Ser Leu |
|  |  |  | 1790 |  |  |  | 1795 |  |  |  | 1800 |  |
| Gly | Lys | Met | Leu | Leu | Arg | Lys | Pro | Ser | Phe | Lys | Val | Asp His Ala |
|  |  |  | 1805 |  |  |  | 1810 |  |  |  | 1815 |  |
| Leu | Trp | Phe | Gly | Ala | Thr | Ile | Asn | Met | Lys | Lys | Gly | Phe Ala Leu |
|  |  |  | 1820 |  |  |  | 1825 |  |  |  | 1830 |  |
| Leu | Glu | Lys | Val | Ser | Glu | Leu | His | Lys | Leu | Ile | Arg | His Glu Asp |
|  |  |  | 1835 |  |  |  | 1840 |  |  |  | 1845 |  |
| Glu | Ser | Trp | Leu | Ile | Asn | Glu | Ala | Phe | Ile | Glu | Ile | Val Asp His |
|  |  |  | 1850 |  |  |  | 1855 |  |  |  | 1860 |  |
| Ile | Ile | Ala | Ile | Ser | Thr | Pro | Ser | Ser | Ile | Ser | Ser | Arg Ala Gly |
|  |  |  | 1865 |  |  |  | 1870 |  |  |  | 1875 |  |
| Tyr | Leu | Ser | Asn | Pro | Gly | Met | Phe | His | Ile | Asn | Pro | Phe Tyr His |
|  |  |  | 1880 |  |  |  | 1885 |  |  |  | 1890 |  |
| Arg | Leu | Ser | Asn | Glu | Glu | Arg | Leu | Lys | Glu | Leu | Gln | Gln Tyr Met |
|  |  |  | 1895 |  |  |  | 1900 |  |  |  | 1905 |  |
| Cys | Tyr | Asp | His | Cys | Ser | Ser | Leu | Trp | Lys | Met | Leu | Ser Thr Phe |
|  |  |  | 1910 |  |  |  | 1915 |  |  |  | 1920 |  |
| Ala | Leu | His | His | Leu | Lys | Asn | Pro | Asp | Ser | Leu | Gln | Thr Tyr Glu |
|  |  |  | 1925 |  |  |  | 1930 |  |  |  | 1935 |  |
| Asp | Lys | Phe | Ser | Lys | Asn | Ser | Leu | Gly | Asn | Lys | Met | Thr Asp Lys |
|  |  |  | 1940 |  |  |  | 1945 |  |  |  | 1950 |  |
| Asp | Phe | Val | Asn | Asn | Phe | Lys | Met | Ile | Leu | Gly | Gly | Asp Ala Ala |
|  |  |  | 1955 |  |  |  | 1960 |  |  |  | 1965 |  |
| Leu | His | Phe | Tyr | Asp | Asn | Leu | Leu | Pro | Lys | Ser | Met | Lys Lys Glu |
|  |  |  | 1970 |  |  |  | 1975 |  |  |  | 1980 |  |
| Leu | Lys | Ser | Met | Lys | Tyr | Gly | Val | Ser | Leu | Ser | Phe | Ser Phe Ser |
|  |  |  | 1985 |  |  |  | 1990 |  |  |  | 1995 |  |
| Leu | Lys | Leu | Ala | Lys | Met | Val | Phe | Gly | Glu | Met | Gln | Leu Pro His |
|  |  |  | 2000 |  |  |  | 2005 |  |  |  | 2010 |  |
| Leu | Ser | His | Met | Phe | Tyr | Ala | Gln | Ala | Pro | Tyr | Phe | Gly His Phe |
|  |  |  | 2015 |  |  |  | 2020 |  |  |  | 2025 |  |
| Ile | Gly | Lys | Trp | Gln | Lys | Glu | Arg | Gln | Gln | Gly | Arg | Leu Lys Glu |
|  |  |  | 2030 |  |  |  | 2035 |  |  |  | 2040 |  |
| Ile | Leu | Gly | Ala | Met | Thr | Leu | Gly | Thr | Leu | Ser | Thr | Tyr Thr Val |
|  |  |  | 2045 |  |  |  | 2050 |  |  |  | 2055 |  |
| Leu | Ser | Ala | Met | Asp | Ile | Thr | Gln | His | Ala | Thr | Asp | Ile Gly Met |
|  |  |  | 2060 |  |  |  | 2065 |  |  |  | 2070 |  |
| Gly | Pro | Ser | Thr | Ser | Cys | Tyr | Thr | Ser | Leu | Leu | Pro | Pro Pro Lys |
|  |  |  | 2075 |  |  |  | 2080 |  |  |  | 2085 |  |

| Ser | Ile | Cys | Ile | Gln | Gln | Thr | Val | Lys | Thr | Val | Leu | Thr | Asn | Ser |
| | 2090 | | | | 2095 | | | | 2100 | | | | | |

Thr Leu Ala Ser Met Lys Ser Val Phe Ser Val Gly Leu Phe Ala
    2105                2110                2115

Ala Ile Thr Pro Tyr Met Phe Ala Pro Met Ala Gly Leu Ala Val
    2120                2125                2130

Trp Ser Val Leu Lys Ser Gln Phe Lys Val Val Asn Arg Ile Asp
    2135                2140                2145

Met Ala Leu Lys Gly Ala Leu Lys Asn Met Trp Asn Lys Phe Met
    2150                2155                2160

Ser Leu Lys Gly Ile Arg Arg Leu Lys Asn Val Phe Lys Lys Ile
    2165                2170                2175

Lys Thr Ile Lys Lys Lys Met Ile Gln Lys Thr Glu Lys Asn Leu
    2180                2185                2190

Ala Glu Ile Gln Gln Asn Pro Glu Ala Glu Gln Asn His Lys Ala
    2195                2200                2205

Ala Val Asn Glu Ile His Asn Asn Thr Arg Gly Asn Tyr His Tyr
    2210                2215                2220

Ile Ser Tyr Ala Lys Ile Val Val
    2225                2230

<210> SEQ ID NO 54
<211> LENGTH: 6693
<212> TYPE: DNA
<213> ORGANISM: Artificial sequence
<220> FEATURE:
<223> OTHER INFORMATION: pGX7026 Py RON2

<400> SEQUENCE: 54

```
ctcaaagcaa ctattggtat tattctgttc atctgcgtga acatcgacat cattcgcacc      60
acatcccgag ataacgtggt caatactaaa tttgtgaggc agaagtctcc tacctatgac     120
ccaaacaaga aaggcgatgt catcttctac atgcctgaac acaaggacga gattcatcgg     180
gcaaacaata agagcgccaa tatcaacctg aaaaacaatc cccctcgcaa tatcaacatt     240
ggttacaata ccgctcctgg cgtgaaccat ggcttcggac agtttagcgg aaagagctcc     300
aacatgaaca acgggatcaa tacatacaag aaccagccaa agcactttca gtccatgaat     360
taccagaaga acggccccct cggaaacaaa ctggagcaga tgaatatccc tgccaacctg     420
tacaacaata agaacaactc ttactactct ggcagtaaca atggaaacaa taacagttat     480
gggctgcacg gtaatatcta cgacaagatt aactctagtg tgtacaacaa ctcaaagtac     540
aacaacagca atttcaacac cgataagaat aacaatgata cgagaacaa caagacatac     600 aagtcctatc tcaatctgta cgtgtccgat aacaagatct ctccaattgg caacaatgga     660
agacccgggc acctgatctc tcatttcaac aatcctaacc agaagctgga gttcctccat     720
ggttttgacg gcctgttcaa tcagaacatt ccaggcatga tcacaaagg aaactatggg     780 tttaacggtg tgaatatcaa ggggcagggt aaaaacgaaa agttcgataa ttatgggcag     840
aacctcggtc tgaacaagac caatgagtac cagcagatga ttaacggcaa caatatggga     900
agtgaccata tctacgaatc accaaacttt gtgaatggga caatatggg tagcgataac     960 gccggcgagt atcagaggct ggtcaatggc aacaatatgg aagcgaccaa catctacgaa    1020
tcccccaact tcgtcaacgg gaacaatatg ggttctgata acgccggaga gagtcagaga    1080
ctggtcaacg gtaataatat gggatcagac aatgctgggg aaagccccaa gctggtgaac    1140
```

```
ggcaataata tgggttccga taatgcaggc gagtctccta agctggtcaa cggtaacaac    1200
atgggaagtg acaatgccgg agaatcacag cggctggtga acggcaacaa catgggtagc    1260
gataatgctg gggagtcccc aaagctggtc aacggaaata atatgggatc tgacaatgca    1320
ggcgaaagtc agcgactggt gaacggcaac aatatgggta gtgataattc aggagagtac    1380
cagaggctgg tcaacggaaa caacatggga agcgacaatt ccggggaata tcagagactg    1440
gtgaacggta ataatatggg ttcagatcat atctacgaga gccctaactt cgtgaacggt    1500
aacaatatgg gcagcgacaa cgccggcgaa taccagcggc tgatcaacgg caataacatg    1560
ggttctgata tgctggaga gtatcagcgc ctgattaacg gtaataatat gggcagcgat    1620
catatctacg aatctccaaa cttcgtcaat ggtaataaca tgggtagcga taacgcaggg    1680
gagtaccagc gactgatcaa cggcaataat atgggcagcg ataatgccgg cgaatatcag    1740
aggctgatta acggtaacaa catgggtagt gatcatatct acgagtcacc caacttcgtg    1800
aatggtaata acatgggatc tgataacgct ggagaatacc agagactggt gaacggaaat    1860
aacatgggta gcgacaatgc aggggagtat cagcgcctcg tcaatggtaa taatatggga    1920
agcgatcata tctacgagtc ccctaacctg gtcaatggta acaacatggg ttctgataac    1980
agtggcgagt accagcgcct cgtcaatgga ataatatgg gaagcgacaa tgccggagaa    2040
tatcagcgac tcgtgaacgg aaataatatg ggttctgatc atatctacga gagtcctaac    2100
ctggtgaatg gtaacaacat gggatcagac aacagcgggg aatatcagcg gctggtcaat    2160
ggtaacaata tgggttccga cgattctggc gagtaccaga aactcgtcaa tggcaacaat    2220
ggagtcatcc caatttttac cggtaacgac caggagatct tcaagaacat tcgaggactg    2280
aggcctgtga atcatgagga actctataag aacaaaatga atccactgat ctacaacgcc    2340
cacggcatgc agagcggaaa taagaacggg gctcccaact caactagcga ctatgtgtcc    2400
gattacaatt ccgactctga taccgacagt gattcagaca gcgattccga cctggattat    2460
gactctgaaa gtaacgagtc caatgtgtac aagatcaaaa ccaacaagct ggagaatgat    2520
aacaaagacg gcaatggaaa cgtcaatgac gcaaattact ataagaacca gatcgatatt    2580
gccaacaaaa atcatggaaa ccgctataat tctgaaaacg attacgggga cagtatgcac    2640
tcagacagcg ctctgtctta tgagagagat ctctcaagcg gaaaccggca cgtgaaggaa    2700
gggagcaatg acgagatcaa catttttctac cgggacaacg cccaggatcg cgaaactaag    2760
gagaaactga tgaattcctc tgaaagcgat aaggacgtgg agaatcccct gaacatcacc    2820
attcctgagg aaaacgtcaa ctaccacttc agtaactaca tgaacttcga taagaaaaat    2880
atcctgacct caaacgagga agagctgctc aagatgatcg gcccagactt tagcaaagag    2940
gtgtccaact actgcagtaa gaaatcaatc tttccctcca atgggaagta tctggacgtc    3000
tctttcgaat acagtaaaga gctgggcaag ctccgggaga aaatgatgtc tggactgttc    3060
aagaaaaagg ggaagctcgt gacaaaagaa aacaatatcc tgaagcagat tgagaacagc    3120
ctgaaaatgg attacctgga gcgccagcag ggttacgtga attatggctc caaatctaat    3180
gaactcaaga cgacgaaga gagcatgctg tccaatgagt ataacaagct gctcgaagag    3240
tacatctgtc atattctcag caacaatccc ggcaaaactc agttcgaaaa gctgtactat    3300
cacaacctcg ccctgggaga gatcatgaag cctattaaga caaagtacaa gaacgccgct    3360
actctgagca ttgctctcaa ttacgagatc tatattgtga gttcaagcaa catctacctg    3420
ttcggacaca tgctgctcct gtccctggca tacctctctt ataacagtta ctttaccaaa    3480
ggcacaaagt cattctacag catggaaacc atgctcctgg ccaactccga ttactctttc    3540
```

```
tttatgtaca acgagatgtg caacgtgtac tatcggccaa acaagtcctt caaaaaggac   3600
ctgactttta tcccaattga gctcagaccc ggtcggtata ctacctacgt gggcgaacgc   3660
aagatcattt gtaacaccct ggagctgatc ctcaatgcta tctctctgat caacatcaac   3720
gaaatctaca acgtgttcca caagaacaat gtctacggct atgagaatag cgtgagcttc   3780
agcaacaatg ccatccgcgt gttcagccag gtctgcccac gaaacatgga aaagaatatc   3840
attaactgtt cattcgagaa aagcaccctg tataaggcaa acgccccga agatacaaac   3900 cagaatgagt accagagaca gaatcagatt aagaaccaga atgagctgaa aaaggccttc   3960
gacctcctga acacattttc cgaaatcgag tccttctcta caacaactaa ccagaactct   4020
tactacatca agctgattat ggagcagaat ctctataccg acttttacaa atatctcttc   4080
tggtacgata accgagaact gatcaagaca cacgagatta atggaaaaaa gaacactaaa   4140
aagaccagca actacatcta tgaccagtat attaagacca atagactcct ggagaaaaag   4200
tttaatgtgc tgtcaaagca taacctcaaa agcaagggcc tcctggcttt tcactccctg   4260
attgaccggt actctgagtt cgtgaaaaac aagaagatcc gcaacctgta tctcaagttc   4320
gtctcctacg cacgcacttt cctgtttatg aataacacaa tgaagtccct gaacaaatct   4380
gatctcgact ttatgaagat gatcttcgaa gagctgcaga cgagactaa ggtgcctctg   4440 aaactcattg tcaggggcaa ttatatgaag tctatgaacg acatcgctaa aaaggagaat   4500 ctgttctttta tcaacctctt tattctgagt ctcttctcaa acaagaaccc cgtgaagaac   4560
ttctacaacg gcaaaagaga aatgctgaag gccagtctct cagagaaatt tgctactagc   4620
acctccgcat tcatccctca taagctgagg agaattgtgg tcggtatgaa aaagggcttc   4680
ctcaaaagga agctcctgaa gaccctgatg aaaaacagac tcctgcagca catcccaatt   4740
gacctcctgg aaaacatcat gacaactttc aggtttacca cacatgctat cgcaactagt   4800
gagctggcac agaacgccca cagaacctca agtacctca atagtaataa cacctcaaaa   4860
ctggagtttg caaagacaat cttctccaaa ggcggatttc cccagtatgc cgataagctg   4920
atggaaaaat ggttttctaa gggcttcgaa gagtacaaaa aggagaagat cgacaaccag   4980
aatatggaaa acgaggtgga caaggaactg gatcagatca aagagatgtt cattcctggg   5040
agtaacggca agcacaactc aaatacacca ccccatctca tcgagaacat taatactgat   5100
gtgaataaca gcctggataa tcaggacaag tatgataaca ccctcggaaa gcagagggtc   5160
gacaaactga tctacaacga gcacgacaag tgggatcatt atatcaacaa ggaatacgtg   5220
aaggctctgg gcgcatggat cgagattcac aaaaagagta ataacgtgat ggaaaacatc   5280
ctgcaggccg tcgaggactc taagtacctc ctggaaaaca acatcgagga tagcattttc   5340
ttttccagga ccttcaaggc cactaagcag tccgctttca gaaatgtgct gaacaagaca   5400
ctgagcctcg gcaaaatgct cctgagaaaa ccatccttta aggtcgacca tgcactgtgg   5460
ttcggtgcca ctatcaacat gaaaaagggc tttgctctcc tggaaaaggt gtcagagctg   5520
cacaaactca tccggcatga agacgagagc tggctgatta cgaagctttt catcgagatt   5580
gtcgatcaca tcattgcaat cagtacaccc tcctctatta gttcacgcgc cggttatctg   5640
agcaaccctg gcatgttcca catcaatcca ttttaccatc gactgagcaa cgaagagagg   5700
ctgaaggagc tccagcagta tatgtgctac gaccactgta gctccctgtg gaaaatgctc   5760
tccacatttg ccctgcacca tctcaagaac ccagactctc tgcagactta cgaggataaa   5820
ttcagcaaga attccctggg caacaaaatg accgataagg actttgtgaa taacttcaag   5880
```

| | |
|---|---|
| atgatcctgg ggggtgacgc agccctccac ttctatgata acctcctgcc caagtcaatg | 5940 |
| aaaaaggagc tcaaaagcat gaagtacgga gtgtctctga gcttcagctt cagcctgaag | 6000 |
| ctcgctaaga tggtctttgg ggagatgcag ctgccacacc tctcccatat gttctatgcc | 6060 |
| caggctccct acttcggaca ttttattggg aaatggcaga aggaaaggca gcagggcaga | 6120 |
| ctgaaggaga tcctcggagc catgacactg gggactctca gcacatatac tgtgctgtcc | 6180 |
| gctatggaca tcacccagca cgcaacagat attgggatgg gtccctccac ttcttgctac | 6240 |
| acctccctcc tgcctccacc caagtctatc tgtattcagc agaccgtgaa acagtcctg | 6300 |
| actaactcca ccctcgcctc tatgaagagt gtgttctcag tcgggctgtt tgctgcaatc | 6360 |
| acaccttaca tgtttgcccc aatggctggc ctggcagtgt ggtctgtcct caaaagtcag | 6420 |
| ttcaaggtgg tcaaccggat tgacatggcc ctgaaaggag ctctcaagaa tatgtggaac | 6480 |
| aagtttatga gcctgaaagg catcaggcgc ctcaagaacg tgttcaaaaa gatcaaaacc | 6540 |
| atcaagaaga agatgattca gaaaactgaa aagaacctgg ccgagatcca gcagaatcct | 6600 |
| gaagctgagc agaaccacaa ggccgctgtg aatgagatcc ataataacac ccgcggcaac | 6660 |
| taccactata tctcctatgc taagattgtg gtc | 6693 |

<210> SEQ ID NO 55
<211> LENGTH: 6747
<212> TYPE: DNA
<213> ORGANISM: Artificial sequence
<220> FEATURE:
<223> OTHER INFORMATION: pGX7026 Py RON2 operably linked to IgE leader
      sequence

<400> SEQUENCE: 55

| | |
|---|---|
| atggactgga cctggattct cttcctcgtc gccgcagcaa ctcgcgtgca ttctctcaaa | 60 |
| gcaactattg gtattattct gttcatctgc gtgaacatcg acatcattcg caccacatcc | 120 |
| cgagataacg tggtcaatac taaatttgtg aggcagaagt ctcctaccta tgacccaaac | 180 |
| aagaaaggcg atgtcatctt ctacatgcct gaacacaagg acgagattca tcgggcaaac | 240 |
| aataagagcg ccaatatcaa cctgaaaaac aatcccccctc gcaatatcaa cattggttac | 300 |
| aataccgctc ctggcgtgaa ccatggcttc ggacagttta gcggaaagag ctccaacatg | 360 |
| aacaacggga tcaatacata caagaaccag ccaaagcact ttcagtccat gaattaccag | 420 |
| aagaacggcc ccttcggaaa caaactggag cagatgaata tccctgccaa cctgtacaac | 480 |
| aataagaaca actcttacta ctctggcagt aacaatggaa acaataacag ttatgggctg | 540 |
| cacggtaata tctacgacaa gattaactct agtgtgtaca caactcaaa gtacaacaac | 600 |
| agcaatttca caccgataa gaataacaat gataacgaga acaacaagac atacaagtcc | 660 |
| tatctcaatc tgtacgtgtc cgataacaag atctctccaa ttggcaacaa tggaagaccc | 720 |
| gggcacctga tctctcattt caacaatcct aaccagaagc tggagttcct ccatggtttt | 780 |
| gacggcctgt tcaatcagaa cattccaggc atgaatcaca aaggaaacta tgggtttaac | 840 |
| ggtgtgaata tcaaggggca gggtaaaaac gaaaagttcg ataattatgg gcagaacctc | 900 |
| ggtctgaaca agaccaatga gtaccagcag atgattaacg gcaacaatat gggaagtgac | 960 |
| catatctacg aatcaccaaa ctttgtgaat gggaacaata tgggtagcga taacgccggc | 1020 |
| gagtatcaga ggctggtcaa tgcaacaat atgggaagcg accacatcta cgaatccccc | 1080 |
| aacttcgtca acgggaacaa tatgggttct gataacgccg agagagtca gagactggtc | 1140 |
| aacggtaata atatgggatc agacaatgct ggggaaagcc ccaagctggt gaacggcaat | 1200 |

```
aatatgggtt ccgataatgc aggcgagtct cctaagctgg tcaacggtaa caacatggga    1260
agtgacaatg ccggagaatc acagcggctg gtgaacggca acaacatggg tagcgataat    1320
gctggggagt ccccaaagct ggtcaacgga aataatatgg gatctgacaa tgcaggcgaa    1380
agtcagcgac tggtgaacgg caacaatatg ggtagtgata attcaggaga gtaccagagg    1440
ctggtcaacg gaaacaacat gggaagcgac aattccgggg aatatcagag actggtgaac    1500
ggtaataata tgggttcaga tcatatctac gagagcccta acttcgtgaa cggtaacaat    1560
atgggcagcg acaacgccgg cgaataccag cggctgatca acggcaataa catgggttct    1620
gataatgctg gagagtatca cgcctgatt aacggtaata atatgggcag cgatcatatc    1680
tacgaatctc caaacttcgt caatggtaat aacatgggta gcgataacgc aggggagtac    1740
cagcgactga tcaacggcaa taatatgggc agcgataatg ccggcgaata tcagaggctg    1800
attaacggta caacatggg tagtgatcat atctacgagt cacccaactt cgtgaatggt    1860
aataacatgg gatctgataa cgctggagaa taccagagac tggtgaacgg aaataacatg    1920
ggtagcgaca atgcagggga gtatcagcgc ctcgtcaatg gtaataatat gggaagcgat    1980
catatctacg agtcccctaa cctggtcaat ggtaacaaca tgggttctga taacagtggc    2040
gagtaccagc gcctcgtcaa tggaaataat atgggaagcg acaatgccgg agaatatcag    2100
cgactcgtga acggaaataa tatgggttct gatcatatct acgagagtcc taacctggtg    2160
aatggtaaca catgggatc agacaacagc ggggaatatc agcggctggt caatggtaac    2220
aatatgggtt ccgacgattc tggcgagtac cagaaactcg tcaatggcaa caatggagtc    2280
atcccaaatt ttaccggtaa cgaccaggag atcttcaaga acattcgagg actgaggcct    2340
gtgaatcatg aggaactcta taagaacaaa atgaatccac tgatctacaa cgcccacggc    2400
atgcagagcg gaaataagaa cggggctccc aactcaacta gcgactatgt gtccgattac    2460
aattccgact ctgataccga cagtgattca gacagcgatt ccgacctgga ttatgactct    2520
gaaagtaacg agtccaatgt gtacaagatc aaaaccaaca agctggagaa tgataacaaa    2580
gacggcaatg gaaacgtcaa tgacgcaaat tactataaga accagatcga tattgccaac    2640
aaaaatcatg gaaaccgcta taattctgaa aacgattacg gggacagtat gcactcagac    2700
agcgctctgt cttatgagag agatctctca agcggaaacc ggcacgtgaa ggaagggagc    2760
aatgacgaga tcaacatttt ctaccgggac aacgcccagg atcgcgaaac taaggagaaa    2820
ctgatgaatt cctctgaaag cgataaggac gtggagaatc ccctgaacat caccattcct    2880
gaggaaaacg tcaactacca cttcagtaac tacatgaact tcgataagaa aaatatcctg    2940
acctcaaacg aggaagagct gctcaagatg atcggcccag actttagcaa agaggtgtcc    3000
aactactgca gtaagaaatc aatctttccc tccaatggga agtatctgga cgtctctttc    3060
gaatacagta aagagctggg caagctccgg gagaaaatga tgtctggact gttcaagaaa    3120
aaggggaagc tcgtgacaaa agaaaacaat atcctgaagc agattgagaa cagcctgaaa    3180
atggattacc tggagcgcca gcagggttac gtgaattatg gctccaaatc taatgaactc    3240
aagaacgacg aagagagcat gctgtccaat gagtataaca agctgctcga gagtacatc    3300 tgtcatattc tcagcaacaa tcccggcaaa actcagttcg aaaagctgta ctatcacaac    3360
ctcgccctgg gagagatcat gaagcctatt aagacaaagt acaagaacgc cgctactctg    3420
agcattgctc tcaattacga gatctatatt gtgagttcaa gcaacatcta cctgttcgga    3480
cacatgctgc tcctgtcct ggcataccta tcttataaca gttactttac caaaggcaca    3540
aagtcattct acagcatgga aaccatgctc ctggccaact ccgattactc tttctttatg    3600
```

```
tacaacgaga tgtgcaacgt gtactatcgg ccaaacaagt ccttcaaaaa ggacctgact    3660
tttatcccaa ttgagctcag acccggtcgg tatactacct acgtgggcga acgcaagatc    3720
atttgtaaca ccctggagct gatcctcaat gctatctctc tgatcaacat caacgaaatc    3780
tacaacgtgt tccacaagaa caatgtctac ggctatgaga atagcgtgag cttcagcaac    3840
aatgccatcc gcgtgttcag ccaggtctgc ccacgaaaca tggaaaagaa tatcattaac    3900
tgttcattcg agaaaagcac cctgtataag gcaaacgccc ccgaagatac aaaccagaat    3960
gagtaccaga gacagaatca gattaagaac cagaatgagc tgaaaaaggc cttcgacctc    4020
ctgaacacat tttccgaaat cgagtccttc tctaacaaca actaccagaa ctcttactac    4080
atcaagctga ttatggagca gaatctctat accgactttt acaaatatct cttctggtac    4140
gataaccgag aactgatcaa gacacacgag attaatggaa aaagaacac taaaaagacc     4200 agcaactaca tctatgacca gtatattaag accaatagac tcctggagaa aaagtttaat    4260
gtgctgtcaa agcataacct caaaagcaag ggcctcctgg cttttcactc cctgattgac    4320
cggtactctg agttcgtgaa aaacaagaag atccgcaacc tgtatctcaa gttcgtctcc    4380
tacgcacgac acttcctgtt tatgaataac acaatgaagt ccctgaacaa atctgatctc    4440
gactttatga agatgatctt cgaagagctg cagaacgaga ctaaggtgcc tctgaaactc    4500
attgtcaggg gcaattatat gaagtctatg aacgacatcg ctaaaaagga gaatctgttc    4560
tttatcaacc tctttattct gagtctcttc tcaaacaaga accccgtgaa gaacttctac    4620
aacggcaaaa gagaaatgct gaaggccagt ctctcagaga aatttgctac tagcaccctcc   4680 gcattcatcc ctcataagct gaggagaatt gtggtcggta tgaaaaaggg cttcctcaaa    4740
aggaagctcc tgaagaccct gatgaaaaac agactcctgc agcacatccc aattgacctc    4800
ctggaaaaca tcatgacaac tttcaggttt accacacatg ctatcgcaac tagtgagctg    4860
gcacagaacg cccacagaac ctcaaagtac ctcaatagta ataacacctc aaaactggag    4920
tttgcaaaga caatcttctc caaaggcgga tttccccagt atgccgataa gctgatggaa    4980
aaatggtttt ctaagggctt cgaagagtac aaaaaggaga agatcgacaa ccagaatatg    5040
gaaaacgagg tggacaagga actggatcag atcaaagaga tgttcattcc tgggagtaac    5100
ggcaagcaca actcaaatac accacccccat ctcatcgaga acattaatac tgatgtgaat    5160
aacagcctgg ataatcagga caagtatgat aacacccctcg gaaagcagag ggtcgacaaa    5220
ctgatctaca acgagcacga caagtgggat cattatatca caaggaata cgtgaaggct    5280 ctgggcgcat ggatcgagat tcacaaaaag agtaataacg tgatgaaaa catcctgcag    5340 gccgtcgagg actctaagta cctcctggaa aacaacatcg aggatagcat tttctttttcc    5400 aggaccttca aggccactaa gcagtccgct ttcagaaatg tgctgaacaa gacactgagc    5460
ctcggcaaaa tgctcctgag aaaaccatcc tttaaggtcg accatgcact gtggttcggt    5520
gccactatca acatgaaaaa gggctttgct ctcctggaaa aggtgtcaga gctgcacaaa    5580
ctcatccggc atgaagacga gagctggctg attaacgaag ctttcatcga gattgtcgat    5640
cacatcattg caatcagtac accctcctct attagttcac gcgccggtta tctgagcaac    5700
cctggcatgt tccacatcaa tccatttttac catcgactga gcaacgaaga gaggctgaag    5760
gagctccagc agtatatgtg ctacgaccac tgtagctccc tgtggaaaat gctctccaca    5820
tttgccctgc accatctcaa gaacccgac tctctgcaga cttacgagga taaattcagc    5880
aagaattccc tgggcaacaa aatgaccgat aaggactttg tgaataactt caagatgatc    5940
```

```
ctgggggtg acgcagccct ccacttctat gataacctcc tgcccaagtc aatgaaaaag      6000
gagctcaaaa gcatgaagta cggagtgtct ctgagcttca gcttcagcct gaagctcgct      6060
aagatggtct ttggggagat gcagctgcca cacctctccc atatgttcta tgcccaggct      6120
ccctacttcg acattttat tgggaaatgg cagaaggaaa ggcagcaggg cagactgaag       6180
gagatcctcg gagccatgac actggggact ctcagcacat atactgtgct gtccgctatg      6240
gacatcaccc agcacgcaac agatattggg atgggtccct ccacttcttg ctacacctcc      6300
ctcctgcctc cacccaagtc tatctgtatt cagcagaccg tgaaaacagt cctgactaac      6360
tccaccctcg cctctatgaa gagtgtgttc tcagtcgggc tgtttgctgc aatcacacct      6420
tacatgtttg ccccaatggc tggcctggca gtgtggtctg tcctcaaaag tcagttcaag      6480
gtggtcaacc ggattgacat ggccctgaaa ggagctctca agaatatgtg gaacaagttt      6540
atgagcctga aaggcatcag gcgcctcaag aacgtgttca aaagatcaa aaccatcaag       6600 aagaagatga ttcagaaaac tgaaaagaac ctggccgaga tccagcagaa tcctgaagct      6660
gagcagaacc acaaggccgc tgtgaatgag atccataata cacccgcgg caactaccac       6720 tatatctcct atgctaagat tgtggtc                                           6747
```

<210> SEQ ID NO 56
<211> LENGTH: 1017
<212> TYPE: PRT
<213> ORGANISM: Artificial sequence
<220> FEATURE:
<223> OTHER INFORMATION: pGX7019 PyCelTOS_TRAP

<400> SEQUENCE: 56

```
Asn Lys Leu Thr Lys Leu Ser Val Ile Ser Val Leu Val Phe Phe
1               5                   10                  15

Cys Phe Phe Asn Val Leu Cys Leu Arg Gly Lys Asn Gly Ser Glu Met
                20                  25                  30

Ser Lys Phe Leu Glu Gly Gly Val Glu Ser Ser Asn Arg Ile Lys Asn
            35                  40                  45

Ser Leu Ser Ser Phe Ile Ser Glu Ser Ala Ser Leu Asp Asp Ile Gly
        50                  55                  60

Asn Gly Leu Ala Glu Thr Ile Thr Asn Glu Ile Phe Ser Ala Phe Gln
65                  70                  75                  80

Gln Asp Ser Ser Ser Phe Leu Gln Thr Gln Phe Asp Ile Lys Lys His
                85                  90                  95

Ile Lys Glu Asn Ala Lys Lys Val Leu Ile Glu Ala Ile Arg Leu Gly
            100                 105                 110

Leu Glu Pro Val Glu Lys Ile Val Ala Lys Ser Ile Gln Pro Pro Lys
        115                 120                 125

Val Asn Arg His Thr Tyr Ser Leu Val Ser Pro Ile Val Lys Ala Leu
    130                 135                 140

Phe Asn Lys Ile Glu Asp Ala Val His Lys Pro Val Asn Asp Asn Ile
145                 150                 155                 160

Trp Glu Tyr Glu Gly Gly Asp Glu Glu Tyr Asp Glu Asn Glu Glu Glu
                165                 170                 175

Asn Phe Asp Asn Asp Phe Phe Asn Arg Val Arg Arg Ala Lys Arg Lys
            180                 185                 190

Leu Leu Gly Asn Ser Lys Tyr Ile Phe Val Val Leu Leu Leu Cys Ile
        195                 200                 205

Ser Val Phe Leu Asn Gly Gln Glu Thr Leu Asp Glu Ile Lys Tyr Ser
    210                 215                 220
```

-continued

```
Glu Glu Val Cys Thr Glu Gln Ile Asp Ile His Ile Leu Leu Asp Gly
225                 230                 235                 240

Ser Gly Ser Ile Gly Tyr Ser Asn Trp Lys Ala His Val Ile Pro Met
                245                 250                 255

Leu Asn Thr Leu Val Asp Asn Leu Asn Ile Ser Asn Asp Glu Ile Asn
            260                 265                 270

Val Ser Leu Thr Leu Phe Ser Thr Asn Ser Arg Glu Leu Ile Lys Leu
        275                 280                 285

Lys Gly Tyr Gly Ser Thr Ser Lys Asp Ser Leu Arg Phe Ile Leu Ala
    290                 295                 300

His Leu Gln Asn Asn Tyr Ser Pro Asn Gly Asn Thr Asn Leu Thr Ser
305                 310                 315                 320

Ala Leu Leu Val Val Asp Thr Leu Ile Asn Glu Arg Met Tyr Arg Pro
                325                 330                 335

Asp Ala Ile Gln Leu Ala Ile Ile Leu Thr Asp Gly Ile Pro Asn Asp
            340                 345                 350

Leu Pro Arg Ser Thr Ala Val Val His Gln Leu Lys Arg Lys His Val
        355                 360                 365

Asn Val Ala Ile Ile Gly Val Gly Ala Gly Val Asn Asn Glu Tyr Asn
    370                 375                 380

Arg Ile Leu Val Gly Cys Asp Arg Tyr Ala Pro Cys Pro Tyr Tyr Ser
385                 390                 395                 400

Ser Gly Ser Trp Asn Glu Ala Gln Asn Met Ile Lys Pro Phe Leu Thr
                405                 410                 415

Lys Val Cys Gln Glu Val Glu Arg Ile Ala His Cys Gly Lys Trp Glu
            420                 425                 430

Glu Trp Ser Glu Cys Ser Thr Thr Cys Asp Glu Gly Arg Lys Ile Arg
        435                 440                 445

Arg Arg Gln Ile Leu His Pro Gly Cys Val Ser Glu Met Thr Thr Pro
    450                 455                 460

Cys Lys Val Arg Asp Cys Pro Gln Ile Pro Ile Pro Pro Val Ile Pro
465                 470                 475                 480

Asn Lys Ile Pro Glu Lys Pro Ser Asn Pro Glu Glu Pro Val Asn Pro
                485                 490                 495

Asn Asp Pro Asn Asp Pro Asn Asn Pro Asn Asn Pro Asn Asn Pro Asn
            500                 505                 510

Asn Pro Asn Asn Pro Asn Asn Pro Asn Asn Pro Asn Asn Pro Asn Asn
        515                 520                 525

Pro Asn Asn Pro Asn Asn Pro Asn Asn Pro Asn Asn Pro Asn Asn Pro
    530                 535                 540

Asn Asn Pro Asn Asn Pro Asn Asn Pro Asn Asn Pro Asn Asn Pro Asn
545                 550                 555                 560

Asn Pro Asn Asn Pro Asn Asn Pro Asn Asn Asp Pro Ser Asn
                565                 570                 575

Pro Asn Asn Pro Asn Pro Lys Lys Arg Asn Pro Lys Arg Arg Asn Pro
        580                 585                 590

Asn Lys Pro Lys Pro Asn Lys Pro Asn Pro Lys Pro Asn Pro Asn
    595                 600                 605

Glu Pro Ser Asn Pro Asn Lys Pro Asn Pro Asn Glu Pro Ser Asn Pro
        610                 615                 620

Asn Lys Pro Asn Pro Asn Glu Pro Ser Asn Pro Asn Lys Pro Asn Pro
625                 630                 635                 640
```

Asn Glu Pro Ser Asn Pro Lys Pro Asn Pro Glu Pro Leu Asn
            645                 650                 655

Pro Asn Glu Pro Ser Asn Pro Asn Glu Pro Ser Asn Pro Asn Ala Pro
        660                 665                 670

Ser Asn Pro Asn Glu Pro Ser Asn Pro Asn Glu Pro Ser Asn Pro Asn
            675                 680                 685

Glu Pro Ser Asn Pro Asn Glu Pro Ser Asn Pro Asn Glu Pro Ser Asn
        690                 695                 700

Pro Lys Lys Pro Ser Asn Pro Asn Glu Pro Ser Asn Pro Asn Glu Pro
705                 710                 715                 720

Leu Asn Pro Asn Glu Pro Ser Asn Pro Asn Glu Pro Ser Asn Pro Asn
            725                 730                 735

Glu Pro Ser Asn Pro Glu Glu Pro Ser Asn Pro Lys Glu Pro Ser Asn
        740                 745                 750

Pro Asn Glu Pro Ser Asn Pro Glu Glu Pro Asn Pro Glu Glu Pro Ser
            755                 760                 765

Asn Pro Lys Glu Pro Ser Asn Pro Glu Glu Pro Ile Asn Pro Glu Glu
        770                 775                 780

Leu Asn Pro Lys Glu Pro Ser Asn Pro Glu Glu Ser Asn Pro Lys Glu
785                 790                 795                 800

Pro Ile Asn Pro Glu Glu Ser Asn Pro Lys Glu Pro Ile Asn Pro Glu
                805                 810                 815

Asp Asn Glu Asn Pro Leu Ile Ile Gln Asp Glu Pro Ile Glu Pro Arg
            820                 825                 830

Asn Asp Ser Asn Val Ile Pro Ile Leu Pro Ile Ile Pro Gln Lys Gly
        835                 840                 845

Asn Asn Ile Pro Ser Asn Leu Pro Glu Asn Pro Ser Asp Ser Glu Val
        850                 855                 860

Glu Tyr Pro Arg Pro Asn Asp Asn Gly Glu Asn Ser Asn Asn Thr Met
865                 870                 875                 880

Lys Ser Lys Lys Asn Ile Pro Asn Glu Pro Ile Pro Ser Pro Gly Asp
                885                 890                 895

Asn Pro Tyr Lys Gly His Glu Glu Arg Ile Pro Lys Pro His Arg Ser
        900                 905                 910

Asn Asp Asp Tyr Val Tyr Asp Asn Asn Val Asn Lys Asn Asn Lys Asp
    915                 920                 925

Glu Pro Glu Ile Pro Asn Asn Glu Tyr Glu Glu Asp Lys Asn Lys Asn
        930                 935                 940

Gln Ser Lys Ser Asn Asn Gly Tyr Lys Ile Ala Gly Gly Ile Ile Gly
945                 950                 955                 960

Gly Leu Ala Ile Leu Gly Cys Ala Gly Val Gly Tyr Asn Phe Ile Ala
                965                 970                 975

Gly Ser Ser Ala Ala Gly Leu Ala Gly Ala Glu Pro Ala Pro Phe Glu
            980                 985                 990

Asp Val Ile Pro Asp Asp Lys Asp Ile Val Glu Asn Glu Gln Phe
        995                 1000                1005

Lys Leu Pro Glu Asp Asn Asp Trp Asn
    1010                1015

<210> SEQ ID NO 57
<211> LENGTH: 3051
<212> TYPE: DNA
<213> ORGANISM: Artificial sequence
<220> FEATURE:
<223> OTHER INFORMATION: pGX7019 PyCelTOS_TRAP

<400> SEQUENCE: 57

```
aacaaactca caaaactcag cgtcatctct tctgtgctgg tcttcttttg cttctttaat     60
gtgctctgtc tgcgaggcaa gaacggctct gagatgagta aatttctcga aggcggagtg    120
gagagctcca ataggattaa gaactctctg tctagtttca tctccgagtc tgcaagtctc    180
gacgatatcg gcaatggact ggccgaaaca attactaacg agatcttcag cgcttttcag    240
caggattcaa gctccttcct gcagacacag tttgacatta agaaacacat caaggagaac    300
gctaagaaag tgctgattga agcaatcaga ctcggactgg aacctgtgga agagattgtc    360
gccaaatcta tccagccccc taaggtgaac cggcacactt actcactcgt gagccctatt    420
gtcaaggccc tgtttaacaa aatcgaggat gctgtgcata agccagtcaa cgacaatatc    480
tgggaatacg agggggggcga cgaggaatat gacgagaacg aggaagagaa tttcgataac    540
gacttcttta accgagtgag gagagcaaag aggaaactgc tcggtaacag caagtatatt    600
ttcgtggtcc tgctcctgtg catctccgtg tttctcaacg ggcaggaaac cctggatgag    660
atcaagtaca gcgaagaagt gtgtacagag cagatcgata ttcacatcct cctggacggg    720
tcaggtagca ttggctattc caactggaag gcccatgtga tccccatgct caacaccctg    780
gtcgataacc tgaacatctc taacgacgaa atcaacgtca gtctcactct gttttccacc    840
aactctcggg agctcatcaa gctgaaaggc tacggcagca cttctaagga ctccctgcgc    900
ttcatcctcg cccacctgca gaacaattat tcacccaacg ggaataccaa cctcacaagc    960
gctctcctgg tggtcgatac cctgattaac gagcggatgt accgccctga cgctatccag   1020
ctcgcaatca ttctgacaga tggcattccc aacgacctcc ctaggagcac tgctgtggtc   1080
caccagctga agagaaaaca tgtgaacgtc gcaatcattg gggtgggtgc cggcgtcaac   1140
aatgagtaca accgcatcct ggtgggatgc gaccgatatg caccttgtcc atactattct   1200
agtgggtcct ggaatgaggc ccagaacatg atcaagcctt tcctgacaaa agtgtgccag   1260
gaagtcgagc gcattgccca ctgtggaaaa tgggaagagt ggagtgagtg ctcaaccaca   1320
tgtgatgagg gtaggaagat tcggcgccga cagatcctgc atcctggctg cgtgtccgag   1380
atgactaccc catgcaaggt ccgcgactgt ccccagattc ctatcccacc cgtgattccc   1440
aacaagatcc cagagaaacc ctctaacccct gaagagccag tcaatcccaa cgatcctaac   1500
gacccaaaca atcccaacaa tccgaacaat cctaataacc ctaacaaccc taataatccc   1560
aataacccaa ataatcctaa caatccaaat aaccccaata accccaacaa tcccaataac   1620
cccaataatc caaataatcc caacaacccc aataaccccta ataacccaa taaccctaac   1680
aacccaaata tcccaataa tcccaacaat cctaatgacc caagcaatcc aaacaatccc   1740
aatcctaaga aagaaaccc aaagagaaga aatcccaaca gccaaaacc caacaagcca   1800
aatccaaaca accccaatcc taacgagcct tctaatccaa caagcctaa tcccaacgaa   1860
ccctctaacc caaacaaacc taatccaaac gagccaagta tcccaacaa gcccaatcct   1920
aacgaacctt caaatcctaa caaacctaac cccaacgaac cctgaatcc taacgagcca   1980
tctaatccca acgaacctag taatccaaac gctccctcaa atcctaacga gccaagcaat   2040
cccaacgaac cttccaatcc aaacgagccc tctaatccta acgaaccaag taatcccaac   2100
gagccttcta acccaaagaa acctagtaat cctaacgaac catccaatcc caacgagcct   2160
ctgaatccaa atgagccttc caatcctaat gaaccttcta accctaatga gccttcaaat   2220
ccagaagagc ccagcaaccc taaagagcca tcaaacccca cgaaccttc taatccagaa   2280
```

```
gagcctaacc cagaagagcc tagtaatcct aaggagccat caaaccccga agagcctatc    2340
aatccagaag agctgaaccc caaggagcct agcaatccag aagagtccaa ccccaaagaa    2400
cctatcaatc ctgaggagtc caaccccaag gagcctatta acccagaaga caatgagaac    2460
ccactgatca ttcaggatga acccatcgag cctagaaatg actctaacgt gattccaatc    2520
ctgcccatca ttcctcagaa gggcaacaat atccccagta atctgccaga gaaccccagt    2580
gattcagaag tggagtaccc ccggcctaat gacaacggag agaacagcaa caacaccatg    2640
aagtccaaga aaatatccc caacgagcca atccctccc ctggcgacaa cccttataag     2700
ggccacgaag agaatccc aaacccat cggtctaacg acgattacgt gtatgataac        2760
aatgtcaaca agaacaacaa ggacgaacct gagatcccaa caatgagta cgaagaggac     2820 aagaacaaga accagagcaa gtccaacaat ggctataaaa tcgccggcgg aatcattggg    2880
ggtctcgcca ttctgggatg tgctggagtg gggtacaact tcatcgctgg gtcaagcgca    2940
gctggactgg caggagcaga acctgcacca tttgaggatg tgattccaga cgatgacaag    3000
gacatcgtcg aaaacgagca gttcaaactg cccgaggata atgactggaa c            3051
```

<210> SEQ ID NO 58
<211> LENGTH: 3105
<212> TYPE: DNA
<213> ORGANISM: Artificial sequence
<220> FEATURE:
<223> OTHER INFORMATION: pGX7019 PyCelTOS_TRAP operably linked to IgE leader sequence

<400> SEQUENCE: 58

```
atggattgga cctggattct cttcctcgtc gccgccgcaa cccgcgtgca ctctaacaaa      60
ctcacaaaac tcagcgtcat ctcttctgtg ctggtcttct tttgcttctt taatgtgctc    120
tgtctgcgag gcaagaacgg ctctgagatg agtaaatttc tcgaaggcgg agtggagagc    180
tccaatagga ttaagaactc tctgtctagt ttcatctccg agtctgcaag tctcgacgat    240
atcggcaatg gactggccga acaattact aacgagatct cagcgctttt tcagcaggat     300
tcaagctcct tcctgcagac acagtttgac attaagaaac acatcaagga gaacgctaag    360
aaagtgctga ttgaagcaat cagactcgga ctggaacctg tggagaagat tgtcgccaaa    420
tctatccagc ccctaaggt gaaccggcac acttactcac tcgtgagccc tattgtcaag    480
gccctgttta caaaatcga ggatgctgtg cataagccag tcaacgacaa tatctgggaa    540 tacgagggg gcgacgagga atatgacgag aacgaggaag agaatttcga taacgacttc     600
tttaaccgag tgaggagagc aaagaggaaa ctgctcggta cagcaagta tattttcgtg    660 gtcctgctcc tgtgcatctc cgtgtttctc aacgggcagg aaaccctgga tgagatcaag    720
tacagcgaag aagtgtgtac agagcagatc gatattcaca tcctcctgga cgggtcaggt    780
agcattggct attccaactg gaaggcccat gtgatcccca tgctcaacac cctggtcgat    840
aacctgaaca tctctaacga cgaaatcaac gtcagtctca ctctgttttc caccaactct    900
cgggagctca tcaagctgaa aggctacggc agcacttcta aggactccct gcgcttcatc    960
ctcgcccacc tgcagaacaa ttattcaccc aacgggaata ccaacctcac aagcgctctc    1020
ctggtggtcg ataccctgat taacgagcgg atgtaccgcc tgacgctat ccagctcgca     1080 atcattctga cagatggcat tcccaacgac ctccctagga gcactgctgt ggtccaccag    1140
ctgaagagaa acatgtgaa cgtcgcaatc attggggtgg gtgccggcgt caacaatgag    1200
tacaaccgca tcctggtggg atgcgaccga tatgcacctt gtccatacta ttctagtggg    1260
```

```
tcctggaatg aggcccagaa catgatcaag cctttcctga caaaagtgtg ccaggaagtc    1320
gagcgcattg cccactgtgg aaaatgggaa gagtggagtg agtgctcaac cacatgtgat    1380
gagggtagga agattcggcg ccgacagatc ctgcatcctg gctgcgtgtc cgagatgact    1440
acccccatgca aggtccgcga ctgtccccag attcctatcc cacccgtgat tcccaacaag    1500
atcccagaga acccctctaa ccctgaagag ccagtcaatc caacgatcc taacgaccca     1560
aacaatccca acaatccgaa caatcctaat aaccctaaca accctaataa tcccaataac    1620
ccaaataatc ctaacaatcc aaataacccc aataacccca acaatcccaa taaccccaat    1680
aatccaaata atcccaacaa ccccaataac cctaataacc caataacccc taacaaccca    1740
aataatccca ataatcccaa caatcctaat gacccaagca atccaaacaa tcccaatcct    1800
aagaaaagaa acccaaagag aagaaatccc aacaagccaa acccaacaa gccaaatcca    1860
aacaaaccca atcctaacga gccttctaat ccaaacaagc ctaatcccaa cgaaccctct    1920
aacccaaaca aacctaatcc aaacgagcca agtaatccca acaagcccaa tcctaacgaa    1980
ccttcaaatc ctaacaaacc taaccccaac gaaccctga atcctaacga gccatctaat    2040
cccaacgaac ctagtaatcc aaacgctccc tcaaatccta acgagccaag caatcccaac    2100
gaaccttcca atccaaacga gccctctaat cctaacgaac caagtaatcc caacgagcct    2160
tctaacccaa agaaacctag taatcctaac gaaccatcca atcccaacga gcctctgaat    2220
ccaaatgagc cttccaatcc taatgaacct tctaacccta atgagccttc aaatccagaa    2280
gagcccagca accctaaaga gccatcaaac cccaacgaac cttctaatcc agaagagcct    2340
aacccagaag agcctagtaa tcctaaggag ccatcaaacc ccgaagagcc tatcaatcca    2400
gaagagctga accccaagga gcctagcaat ccagaagagt ccaaccccaa agaacctatc    2460
aatcctgagt agtccaaccc caaggagcct attaacccag aagacaatga gaacccactg    2520
atcattcagg atgaacccat cgagcctaga aatgactcta acgtgattcc aatcctgccc    2580
atcattcctc agaagggcaa caatatcccc agtaatctgc cagagaaccc cagtgattca    2640
gaagtggagt accccggcc taatgacaac ggagagaaca gcaacaacac catgaagtcc    2700
aagaaaaata tccccaacga gccaatcccc tcccctggcg acaaccctta taagggccac    2760
gaagagagaa tcccaaaacc ccatcggtct aacgacgatt acgtgtatga taacaatgtc    2820
aacaagaaca acaaggacga acctgagatc ccaaacaatg agtacgaaga ggacaagaac    2880
aagaaccaga gcaagtccaa caatggctat aaaatcgccg gcggaatcat tgggggtctc    2940
gccattctgg gatgtgctgg agtggggtac aacttcatcg ctgggtcaag cgcagctgga    3000
ctggcaggag cagaacctgc accatttgag gatgtgattc agacgatga caaggacatc    3060
gtcgaaaacg agcagttcaa actgcccgag gataatgact ggaac                    3105
```

<210> SEQ ID NO 59
<211> LENGTH: 573
<212> TYPE: PRT
<213> ORGANISM: Artificial sequence
<220> FEATURE:
<223> OTHER INFORMATION: pGX7008 Pf TRAP 3D7

<400> SEQUENCE: 59

```
Asn His Leu Gly Asn Val Lys Tyr Leu Val Ile Val Phe Leu Ile Phe
1               5                   10                  15

Phe Asp Leu Phe Leu Val Asn Gly Arg Asp Val Gln Asn Asn Ile Val
            20                  25                  30

Asp Glu Ile Lys Tyr Arg Glu Glu Val Cys Asn Asp Glu Val Asp Leu
```

```
                35                  40                  45
Tyr Leu Leu Met Asp Cys Ser Gly Ser Ile Arg Arg His Asn Trp Val
 50                  55                  60
Asn His Ala Val Pro Leu Ala Met Lys Leu Ile Gln Gln Leu Asn Leu
 65                  70                  75                  80
Asn Asp Asn Ala Ile His Leu Tyr Ala Ser Val Phe Ser Asn Asn Ala
                 85                  90                  95
Arg Glu Ile Ile Arg Leu His Ser Asp Ala Ser Lys Asn Lys Glu Lys
                100                 105                 110
Ala Leu Ile Ile Ile Lys Ser Leu Leu Ser Thr Asn Leu Pro Tyr Gly
                115                 120                 125
Lys Thr Asn Leu Thr Asp Ala Leu Leu Gln Val Arg Lys His Leu Asn
130                 135                 140
Asp Arg Ile Asn Arg Glu Asn Ala Asn Gln Leu Val Val Ile Leu Thr
145                 150                 155                 160
Asp Gly Ile Pro Asp Ser Ile Gln Asp Ser Leu Lys Glu Ser Arg Lys
                165                 170                 175
Leu Ser Asp Arg Gly Val Lys Ile Ala Val Phe Gly Ile Gly Gln Gly
                180                 185                 190
Ile Asn Val Ala Phe Asn Arg Phe Leu Val Gly Cys His Pro Ser Asp
                195                 200                 205
Gly Lys Cys Asn Leu Tyr Ala Asp Ser Ala Trp Glu Asn Val Lys Asn
210                 215                 220
Val Ile Gly Pro Phe Met Lys Ala Val Cys Val Glu Val Glu Lys Thr
225                 230                 235                 240
Ala Ser Cys Gly Val Trp Asp Glu Trp Ser Pro Cys Ser Val Thr Cys
                245                 250                 255
Gly Lys Gly Thr Arg Ser Arg Lys Arg Glu Ile Leu His Glu Gly Cys
                260                 265                 270
Thr Ser Glu Leu Gln Glu Gln Cys Glu Glu Arg Cys Leu Pro Lys
                275                 280                 285
Arg Glu Pro Leu Asp Val Pro Asp Glu Pro Glu Asp Asp Gln Pro Arg
290                 295                 300
Pro Arg Gly Asp Asn Phe Ala Val Glu Lys Pro Asn Glu Asn Ile Ile
305                 310                 315                 320
Asp Asn Asn Pro Gln Glu Pro Ser Pro Asn Pro Glu Glu Gly Lys Gly
                325                 330                 335
Glu Asn Pro Asn Gly Phe Asp Leu Asp Glu Asn Pro Glu Asn Pro Pro
                340                 345                 350
Asn Pro Pro Asn Pro Pro Asn Pro Pro Asn Pro Pro Asn Pro Pro Asn
                355                 360                 365
Pro Asp Ile Pro Glu Gln Glu Pro Asn Ile Pro Glu Asp Ser Glu Lys
                370                 375                 380
Glu Val Pro Ser Asp Val Pro Lys Asn Pro Glu Asp Asp Arg Glu Glu
385                 390                 395                 400
Asn Phe Asp Ile Pro Lys Lys Pro Glu Asn Lys His Asp Asn Gln Asn
                405                 410                 415
Asn Leu Pro Asn Asp Lys Ser Arg Tyr Ile Pro Tyr Ser Pro Leu
                420                 425                 430
Ser Pro Lys Val Leu Asp Asn Glu Arg Lys Gln Ser Asp Pro Gln Ser
                435                 440                 445
Gln Asp Asn Asn Gly Asn Arg His Val Pro Asn Ser Glu Asp Arg Glu
                450                 455                 460
```

```
Thr Arg Pro His Gly Arg Asn Asn Glu Asn Arg Ser Tyr Asn Arg Lys
465                 470                 475                 480

His Asn Asn Thr Pro Lys His Pro Glu Arg Glu Glu His Glu Lys Pro
            485                 490                 495

Asp Asn Asn Lys Lys Lys Ala Gly Ser Asp Asn Lys Tyr Lys Ile Ala
        500                 505                 510

Gly Gly Ile Ala Gly Gly Leu Ala Leu Leu Ala Cys Ala Gly Leu Ala
            515                 520                 525

Tyr Lys Phe Val Val Pro Gly Ala Ala Thr Pro Tyr Ala Gly Glu Pro
        530                 535                 540

Ala Pro Phe Asp Glu Thr Leu Gly Glu Glu Asp Lys Asp Leu Asp Glu
545                 550                 555                 560

Pro Glu Gln Phe Arg Leu Pro Glu Glu Asn Glu Trp Asn
                565                 570
```

<210> SEQ ID NO 60
<211> LENGTH: 1719
<212> TYPE: DNA
<213> ORGANISM: Artificial sequence
<220> FEATURE:
<223> OTHER INFORMATION: pGX7008 Pf TRAP 3D7

<400> SEQUENCE: 60

```
aatcatctgg gcaatgtcaa atatctggtc atcgtgttcc tgatcttctt tgacctgttt      60
ctggtcaatg gacgagacgt gcagaacaat attgtcgatg aaatcaaata ccgggaggaa     120
gtgtgcaacg atgaggtcga cctgtatctg ctgatggatt gtagcggctc catccggaga     180
cacaattggg tcaaccatgc cgtgcccctg ctatgaagc tgattcagca gctgaacctg     240
aatgacaacg ctatccatct gtacgcaagc gtgttcagca acaatgccag agaaatcatt     300
aggctgcact cagatgccag caaaaataag gagaaagctc tgatcattat caaatccctg     360
ctgtctacaa atctgcccta tggcaagacc aaccctgacag acgctctgct gcaggtgcgc     420
aagcatctga atgataggat taaccgcgaa atgccaacc agctggtggt catcctgacc     480
gatgggattc ctgactctat ccaggatagt ctgaaggagt cacggaaact gagcgacaga     540
ggagtcaaaa tcgccgtgtt cgggattgga cagggcatca atgtggcatt caaccggttt     600
ctggtcggat gccacccaag cgacggcaag tgtaacctgt acgctgattc cgcatgggag     660
aatgtcaaga acgtgattgg acccttatg aaagcagtgt gcgtcgaagt ggagaagact     720
gcctcctgtg gcgtgtggga tgagtggagt ccttgctcag tgacttgtgg aagggaacc     780
aggtctcgca acgagaaat cctgcatgag ggctgcacca gtgaactgca ggagcagtgc     840
gaggaagaga ggtgtctgcc taagcgcgag ccactggatg tgcctgacga accagaggac     900
gatcagcccc ggcctagagg ggacaatttc gccgtggaaa agccaaacga gaacatcatc     960
gataacaatc cccaggaacc aagccccaac cctgaagagg gcaaggggga gaatcctaac    1020
ggctttgacc tggatgaaaa tccagagaac ccccctaatc cacccaaccc tccaaatccc    1080
cctaacccac ccaatcctcc aaaccccgac attcctgaac aggagccaaa catccccgag    1140
gacagtgaaa agaggtccc ctcagatgtg cctaagaatc cagaagacga tagagaagag    1200
aactttgaca ttcccaagaa acctgagaac aagcacgata ccagaacaa tctgcctaat    1260
gataagtctg acaggtacat cccatatagc cccctgtccc ctaaggtgct ggacaacgag    1320
agaaaacagt ccgacccaca gtctcaggat aacaatggca ataggcatgt gcccaacagc    1380
gaagatcgag agacccggcc tcacgggcgc aacaatgaga atcgctccta caaccgaaag    1440
```

```
cacaacaata caccaaaaca tcccgaacgg gaagagcacg agaagccaga caacaataag    1500
aaaaaggccg gcagcgataa caagtataaa attgcaggag gaatcgcagg aggactggct    1560
ctgctggcat gtgcaggact ggcctacaaa ttcgtggtcc ccggggccgc tacaccttat    1620
gcaggagaac cagccccctt tgacgagact ctgggcgaag aggacaagga tctggacgaa    1680
cccgagcagt tccgcctgcc cgaagagaat gagtggaat                          1719
```

<210> SEQ ID NO 61
<211> LENGTH: 1773
<212> TYPE: DNA
<213> ORGANISM: Artificial sequence
<220> FEATURE:
<223> OTHER INFORMATION: pGX7008 Pf TRAP 3D7 operably linked to IgE
      leader sequence

<400> SEQUENCE: 61

```
atggactgga cctggattct gttcctggtg gctgctgcta cacgagtgca tagtaatcat      60
ctgggcaatg tcaaatatct ggtcatcgtg ttcctgatct tctttgacct gtttctggtc     120
aatggacgag acgtgcagaa caatattgtc gatgaaatca ataccgggag gaagtgtgc      180 aacgatgagg tcgacctgta tctgctgatg gattgtagcg gctccatccg agacacaat      240 tgggtcaacc atgccgtgcc cctggctatg aagctgattc agcagctgaa cctgaatgac     300
aacgctatcc atctgtacgc aagcgtgttc agcaacaatg ccagagaaat cattaggctg     360
cactcagatg ccagcaaaaa taaggagaaa gctctgatca ttatcaaatc cctgctgtct     420
acaaatctgc cctatggcaa gaccaacctg acagacgctc tgctgcaggt gcgcaagcat     480
ctgaatgata ggattaaccg gaaaatgcc aaccagctgg tggtcatcct gaccgatggg     540
attcctgact ctatccagga tagtctgaag gagtcacgga aactgagcga cagaggagtc     600
aaaatcgccg tgttcgggat tggacagggc atcaatgtgg cattcaaccg gtttctggtc     660
ggatgccacc caagcgacgg caagtgtaac ctgtacgctg attccgcatg ggagaatgtc     720
aagaacgtga ttggacccct tatgaaagca gtgtgcgtcg aagtggagaa gactgcctcc     780
tgtggcgtgt gggatgagtg gagtccttgc tcagtgactt gtgggaaggg aaccaggtct     840
cgcaaacgag aaatcctgca tgagggctgc accagtgaac tgcaggagca gtgcgaggaa     900
gagaggtgtc tgcctaagcg cgagccactg gatgtgcctg acgaaccaga ggacgatcag     960
ccccggccta gaggggacaa tttcgccgtg aaaagccaa acgagaacat catcgataac    1020 aatcccagg aaccaagccc caaccctgaa gagggcaagg gggagaatcc taacggcttt    1080
gacctggatg aaaatccaga gaacccccct aatccaccca accctccaaa tcccctaac     1140 ccacccaatc ctccaaaccc cgacattcct gaacaggagc caaacatccc cgaggacagt     1200 gaaaagagg tcccctcaga tgtgcctaag aatccagaag acgatagaga agagaacttt    1260
gacattccca gaaaacctga gaacaagcac gataaccaga caatctgcc taatgataag    1320 tctgacaggt acatcccata tagcccctg tcccctaagg tgctggacaa cgagagaaaa    1380
cagtccgacc cacagtctca ggataacaat ggcaataggc atgtgcccaa cagcgaagat    1440
cgagagaccc ggcctcacgg gcgcaacaat gagaatcgct cctacaaccg aaagcacaac    1500
aatacaccaa acatcccgaa cgggaagag cacgagaagc cagacaacaa taagaaaaag    1560
gccggcagcg ataacaagta taaaattgca ggaggaatcg caggaggact ggctctgctg    1620
gcatgtgcag gactggccta caaattcgtg gtccccgggg ccgctacacc ttatgcagga    1680
gaaccagccc cctttgacga gactctgggc gaagaggaca aggatctgga cgaacccgag    1740
```
cagttccgcc tgcccgaaga gaatgagtgg aat        1773

<210> SEQ ID NO 62
<211> LENGTH: 396
<212> TYPE: PRT
<213> ORGANISM: Artificial sequence
<220> FEATURE:
<223> OTHER INFORMATION: pGX7010 Pf CSP 3D7

<400> SEQUENCE: 62

Met Arg Lys Leu Ala Ile Leu Ser Val Ser Ser Phe Leu Phe Val Glu
1               5                   10                  15

Ala Leu Phe Gln Glu Tyr Gln Cys Tyr Gly Ser Ser Asn Thr Arg
            20                  25                  30

Val Leu Asn Glu Leu Asn Tyr Asp Asn Ala Gly Thr Asn Leu Tyr Asn
        35                  40                  45

Glu Leu Glu Met Asn Tyr Tyr Gly Lys Gln Glu Asn Trp Tyr Ser Leu
    50                  55                  60

Lys Lys Asn Ser Arg Ser Leu Gly Glu Asn Asp Asp Gly Asn Asn Glu
65                  70                  75                  80

Asp Asn Glu Lys Leu Arg Lys Pro Lys His Lys Lys Leu Lys Gln Pro
                85                  90                  95

Ala Asp Gly Asn Pro Asp Pro Asn Ala Asn Pro Asn Val Asp Pro Asn
            100                 105                 110

Ala Asn Pro Asn Val Asp Pro Asn Ala Asn Pro Asn Val Asp Pro Asn
        115                 120                 125

Ala Asn Pro Asn Ala Asn Pro Asn Ala Asn Pro Asn Ala Asn Pro Asn
    130                 135                 140

Ala Asn Pro Asn Ala Asn Pro Asn Ala Asn Pro Asn Ala Asn Pro Asn
145                 150                 155                 160

Ala Asn Pro Asn Ala Asn Pro Asn Ala Asn Pro Asn Ala Asn Pro Asn
                165                 170                 175

Ala Asn Pro Asn Ala Asn Pro Asn Ala Asn Pro Asn Ala Asn Pro Asn
            180                 185                 190

Ala Asn Pro Asn Val Asp Pro Asn Ala Asn Pro Asn Ala Asn Pro Asn
        195                 200                 205

Ala Asn Pro Asn Ala Asn Pro Asn Ala Asn Pro Asn Ala Asn Pro Asn
    210                 215                 220

Ala Asn Pro Asn Ala Asn Pro Asn Ala Asn Pro Asn Ala Asn Pro Asn
225                 230                 235                 240

Ala Asn Pro Asn Ala Asn Pro Asn Ala Asn Pro Asn Ala Asn Pro Asn
                245                 250                 255

Ala Asn Pro Asn Ala Asn Pro Asn Ala Asn Pro Asn Ala Asn Pro Asn
            260                 265                 270

Lys Asn Asn Gln Gly Asn Gly Gln Gly His Asn Met Pro Asn Asp Pro
        275                 280                 285

Asn Arg Asn Val Asp Glu Asn Ala Asn Ala Asn Ser Ala Val Lys Asn
    290                 295                 300

Asn Asn Asn Glu Glu Pro Ser Asp Lys His Ile Lys Glu Tyr Leu Asn
305                 310                 315                 320

Lys Ile Gln Asn Ser Leu Ser Thr Glu Trp Ser Pro Cys Ser Val Thr
                325                 330                 335

Cys Gly Asn Gly Ile Gln Val Arg Ile Lys Pro Gly Ser Ala Asn Lys
            340                 345                 350

```
Pro Lys Asp Glu Leu Asp Tyr Ala Asn Asp Ile Glu Lys Lys Ile Cys
        355                 360                 365

Lys Met Glu Lys Cys Ser Ser Val Phe Asn Val Asn Ser Ser Ile
    370                 375                 380

Gly Leu Ile Met Val Leu Ser Phe Leu Phe Leu Asn
385                 390                 395

<210> SEQ ID NO 63
<211> LENGTH: 1188
<212> TYPE: DNA
<213> ORGANISM: Artificial sequence
<220> FEATURE:
<223> OTHER INFORMATION: pGX7010 Pf CSP 3D7

<400> SEQUENCE: 63
atgagaaaac tggcaatcct gagcgtgtca tcattcctgt tgtcgaggc cctgttccag      60 gaataccagt gctatggcag ctcctctaac acccgggtgc tgaacgagct gaattacgat    120
aacgccggga ccaatctgta taacgagctg aaatgaatt actatggaaa gcaggagaac    180
tggtacagcc tgaagaaaaa ttctcggagt ctgggagaaa acgacgatgg caacaatgag    240
gacaacgaaa agctgagaaa gcccaaacac aagaaactga acagcctgc tgacggcaac    300 cccgatccta acgccaatcc taacgtggac ccaaatgcta accccaatgt cgatcctaat    360
gctaatccaa acgtggaccc caatgcaaac cctaatgcca tcctaatgc taatcctaac    420 gccaaccta tgccaatcc caatgctaat cctaacgcta ccctaatgc caatccaaac    480 gctaatccta acgcaaatcc taatgccaat ccaaatgcca tcctaacgc aaacccaaat    540 gccaatccaa atgcaaatcc taacgcaaac cccaatgcca cccaaacgt ggaccccaac    600 gccaacccta acgcaaatcc aaacgccaat cccaacgcca tccaaacgc caaccctaac    660 gccaatccca acgcaaaccc aaatgctaac ccaaacgcta ccccaacgc caatcctaat    720 gcaaacccta acgctaaccc caacgcaaac ccaaacgcca ccccaatgc taatcccaac    780 gccaatccta acgccaatcc aaatgctaat cccaacaaga caatcaggg caacgggcag    840 ggacacaata tgccaaacga ccccaatagg aacgtcgatg agaatgccaa cgctaatagt    900
gccgtgaaga acaataacaa tgaggaaccc tctgataagc atatcaaaga gtacctgaac    960
aagattcaga actcactgag caccgaatgg tcccctgct ctgtcacatg tggcaacggc   1020
atccaggtgc ggatcaagcc tggctccgcc aacaagccaa agacgaact ggattatgcc   1080 aacgacatcg agaagaaaat ttgcaagatg gaaagtgta gttcagtgtt taatgtggtc   1140
aacagctcca tcgggctgat tatggtcctg tccttcctgt tcctgaat               1188

<210> SEQ ID NO 64
<211> LENGTH: 1242
<212> TYPE: DNA
<213> ORGANISM: Artificial sequence
<220> FEATURE:
<223> OTHER INFORMATION: pGX7010 Pf CSP 3D7 operably linked to IgE
      leader sequence

<400> SEQUENCE: 64
atggactgga cctggattct gttcctggtc gccgccgcaa ctagagtgca ttcaatgaga     60
aaactggcaa tcctgagcgt gtcatcattc ctgtttgtcg aggccctgtt ccaggaatac    120
cagtgctatg gcagctcctc taacacccgg gtgctgaacg agctgaatta cgataacgcc    180
gggaccaatc tgtataacga gctggaaatg aattactatg gaaagcagga gaactggtac    240
agcctgaaga aaaattctcg gagtctggga gaaaacgacg atggcaacaa tgaggacaac    300
```

```
gaaaagctga gaaagcccaa acacaagaaa ctgaaacagc ctgctgacgg caaccccgat    360
cctaacgcca atcctaacgt ggacccaaat gctaaccccc atgtcgatcc taatgctaat    420
ccaaacgtgg acccccaatgc aaaccctaat gccaatccta atgctaatcc aacgccaac     480 cctaatgcca atcccaatgc taatcctaac gctaacccta atgccaatcc aaacgctaat    540
cctaacgcaa atcctaatgc caatccaaat gccaatccta acgcaaaccc aaatgccaat    600
ccaaatgcaa atcctaacgc aaaccccaat gccacccaaa acgtggaccc caacgccaac    660
cctaacgcaa atccaaacgc caatcccaac gccaatccaa acgccaaccc taacgccaat    720
cccaacgcaa acccaaatgc taacccaaac gctaaccccca acgccaatcc taatgcaaac    780
cctaacgcta accccaacgc aaacccaaac gccaaccccca atgctaatcc caacgccaat    840
cctaacgcca atccaaatgc taatcccaac aagaacaatc agggcaacgg gcagggacac    900
aatatgccaa acgaccccaa taggaacgtc gatgagaatg ccaacgctaa tagtgccgtg    960
aagaacaata acaatgagga accctctgat aagcatatca aagagtacct gaacaagatt   1020
cagaactcac tgagcaccga atggtccccc tgctctgtca catgtggcaa cggcatccag   1080
gtgcggatca gcctggctc cgccaacaag ccaaaagacg aactggatta tgccaacgac   1140
atcgagaaga aaatttgcaa gatggaaaag tgtagttcag tgtttaatgt ggtcaacagc   1200
tccatcgggc tgattatggt cctgtccttc ctgttcctga at                      1242
```

<210> SEQ ID NO 65
<211> LENGTH: 573
<212> TYPE: PRT
<213> ORGANISM: Artificial sequence
<220> FEATURE:
<223> OTHER INFORMATION: pGX7014 3D7TRAP-6

<400> SEQUENCE: 65

```
Asn His Leu Gly Asn Val Lys Tyr Leu Val Ile Val Phe Leu Ile Phe
1               5                   10                  15

Phe Asp Leu Phe Leu Val Asn Gly Arg Asp Val Gln Asn Asn Ile Val
            20                  25                  30

Asp Glu Ile Lys Tyr Arg Glu Glu Val Cys Asn Asp Glu Val Asp Leu
        35                  40                  45

Tyr Leu Leu Met Asp Cys Ser Gly Ser Ile Arg Arg His Asn Trp Val
    50                  55                  60

Asn His Ala Val Pro Leu Ala Met Lys Leu Ile Gln Gln Leu Asn Leu
65                  70                  75                  80

Asn Asp Asn Ala Ile His Leu Tyr Ala Ser Val Phe Ser Asn Asn Ala
                85                  90                  95

Arg Glu Ile Ile Arg Leu His Ser Asp Ala Ser Lys Asn Lys Glu Lys
            100                 105                 110

Ala Leu Ile Ile Ile Lys Ser Leu Leu Ser Thr Asn Leu Pro Tyr Gly
        115                 120                 125

Lys Thr Asn Leu Thr Asp Ala Leu Leu Gln Val Arg Lys His Leu Asn
    130                 135                 140

Asp Arg Ile Asn Arg Glu Asn Ala Asn Gln Leu Val Val Ile Leu Thr
145                 150                 155                 160

Asp Gly Ile Pro Asp Ser Ile Gln Asp Ser Leu Lys Glu Ser Arg Lys
                165                 170                 175

Leu Ser Asp Arg Gly Val Lys Ile Ala Val Phe Gly Ile Gly Gln Gly
            180                 185                 190
```

```
Ile Asn Val Ala Phe Asn Arg Phe Leu Val Gly Cys His Pro Ser Asp
            195                 200                 205
Gly Lys Cys Asn Leu Tyr Ala Asp Ser Ala Trp Glu Asn Val Lys Asn
210                 215                 220
Val Ile Gly Pro Phe Met Lys Ala Val Cys Val Glu Val Glu Lys Thr
225                 230                 235                 240
Ala Ser Cys Gly Val Trp Asp Glu Trp Ser Pro Cys Ser Val Thr Cys
                245                 250                 255
Gly Lys Gly Thr Arg Ser Arg Lys Arg Glu Ile Leu His Glu Gly Cys
                260                 265                 270
Thr Ser Glu Leu Gln Glu Gln Cys Glu Glu Arg Cys Leu Pro Lys
            275                 280                 285
Arg Glu Pro Leu Asp Val Pro Asp Glu Pro Glu Asp Asp Gln Pro Arg
290                 295                 300
Pro Arg Gly Asp Asn Phe Ala Val Glu Lys Pro Asn Glu Asn Ile Ile
305                 310                 315                 320
Asp Asn Asn Pro Gln Glu Pro Ser Pro Asn Pro Glu Glu Gly Lys Gly
                325                 330                 335
Glu Asn Pro Asn Gly Phe Asp Leu Asp Glu Asn Pro Glu Asn Pro Pro
                340                 345                 350
Asn Pro Pro Asn Pro Pro Asn Pro Pro Asn Pro Pro Asn Pro Pro Asn
                355                 360                 365
Pro Asp Ile Pro Glu Gln Glu Pro Asn Ile Pro Glu Asp Ser Glu Lys
            370                 375                 380
Glu Val Pro Ser Asp Val Pro Lys Asn Pro Glu Asp Asp Arg Glu Glu
385                 390                 395                 400
Asn Phe Asp Ile Pro Lys Lys Pro Glu Asn Lys His Asp Asn Gln Asn
                405                 410                 415
Asn Leu Pro Asn Asp Lys Ser Asp Arg Tyr Ile Pro Tyr Ser Pro Leu
                420                 425                 430
Ser Pro Lys Val Leu Asp Asn Glu Arg Lys Gln Ser Asp Pro Gln Ser
            435                 440                 445
Gln Asp Asn Asn Gly Asn Arg His Val Pro Asn Ser Glu Asp Arg Glu
450                 455                 460
Thr Arg Pro His Gly Arg Asn Asn Glu Asn Arg Ser Tyr Asn Arg Lys
465                 470                 475                 480
His Asn Asn Thr Pro Lys His Pro Glu Arg Glu His Glu Lys Pro
                485                 490                 495
Asp Asn Asn Lys Lys Lys Ala Gly Ser Asp Asn Lys Tyr Lys Ile Ala
                500                 505                 510
Gly Gly Ile Ala Gly Gly Leu Ala Leu Leu Ala Cys Ala Gly Leu Ala
            515                 520                 525
Tyr Lys Phe Val Val Pro Gly Ala Ala Thr Pro Tyr Ala Gly Glu Pro
530                 535                 540
Ala Pro Phe Asp Glu Thr Leu Gly Glu Glu Asp Lys Asp Leu Asp Glu
545                 550                 555                 560
Pro Glu Gln Phe Arg Leu Pro Glu Glu Asn Glu Trp Asn
                565                 570
```

<210> SEQ ID NO 66
<211> LENGTH: 1719
<212> TYPE: DNA
<213> ORGANISM: Artificial sequence
<220> FEATURE:
<223> OTHER INFORMATION: pGX7014 3D7TRAP-6

<400> SEQUENCE: 66

```
aaccacctgg gcaacgtgaa gtacctcgtg atcgtgttcc tgatcttctt cgacctgttt      60
ctcgtgaacg gccgggacgt gcagaacaac atcgtggacg agatcaagta ccgcgaggaa     120
gtgtgcaacg acgaggtgga cctgtacctg ctgatggact gcagcggcag catccggcgg     180
cacaactggg tcaaccatgc cgtgcctctg ccatgaagc tgatccagca gctgaacctg      240
aacgacaacc ccatccacct gtacgccagc gtgttcagca caacgccag agagatcatc      300
agactgcaca gcgacgccag caagaacaaa gagaaggccc tgatcatcat caagagcctg    360
ctgagcacca acctgcccta cggcaagacc aacctgaccg acgctctgct gcaagtgcgg    420
aagcacctga atgaccggat caacagagag aacgccaatc agctggtcgt gatcctgacc    480
gatggcatcc ccgacagcat ccaggacagc ctgaaagaga gccggaagct gagcgaccgg    540
ggcgtgaaga tcgccgtgtt tggcatcggc cagggcatca acgtggcctt caaccggttt    600
ctcgtgggct gccaccctag cgacggcaag tgcaatctgt acgccgacag cgcctgggag    660
aacgtgaaga atgtgatcgg ccctttcatg aaggccgtgt gcgtggaagt ggaaaagacc    720
gccagctgcg gcgtgtggga tgagtggtcc ccttgcagcg tgacctgcgg caagggcacc    780
agaagccgga agagagagat cctgcacgag ggctgcacca gcgagctgca ggaacagtgc    840
gaagaggaac ggtgcctgcc caagagggaa cccctggatg tgcccgacga gcccgaggac    900
gatcagccta gacccagagg cgacaacttc gccgtggaaa agcccaacga gaacatcatc    960
gacaacaacc cccaggaacc cagccccaac cccgaagagg gaaagggcga gaaccccaac   1020
ggcttcgatc tggacgagaa ccctgagaac ccccccaacc ctcccaatcc ccctaacccc   1080
ccaaatccac caaatcctcc caaccctgac atccccgagc aggaacctaa catccctgag   1140
gacagcgaga aagaggtgcc cagcgacgtg cccaagaacc ccgaggatga ccgggaagag   1200
aacttcgaca tccccaagaa gccagagaac aagcacgaca accagaacaa cctgcctaac   1260
gacaagtccg accggtacat cccctacagc cccctgagcc ccaaggtgct ggacaacgag   1320
agaaagcaga gcgaccccca gagccaggac aacaacggca acagacacgt gccaaacagc   1380
gaggacagag agacacggcc ccacggccgg aacaacgaga tcggagcta caaccggaag    1440
cacaacaaca cccccaagca ccctgagcgg gaagaacacg agaagcccga taacaacaag   1500
aagaaggccg gcagcgacaa caagtacaag attgccggcg gaatcgctgg cggcctggca   1560
ctgctggctt gtgccggact ggcctacaag ttcgtggtgc ctggcgccgc tacaccttat   1620
gccggcgaac ctgccccctt cgacgagaca ctgggcgagg aagataagga cctggacgag   1680
cctgagcagt tccggctgcc cgaagagaac gagtggaac                           1719
```

<210> SEQ ID NO 67
<211> LENGTH: 1773
<212> TYPE: DNA
<213> ORGANISM: Artificial sequence
<220> FEATURE:
<223> OTHER INFORMATION: pGX7014 3D7TRAP-6 operably linked to IgE leader sequence

<400> SEQUENCE: 67

```
atggactgga cctggattct gttcctggtg gccgctgcca cacgggtgca ctctaaccac      60
ctgggcaacg tgaagtacct cgtgatcgtg ttcctgatct tcttcgacct gtttctcgtg     120
aacgccggga cgtgcagaa caacatcgtg acgagatca agtaccgcga ggaagtgtgc       180
aacgacgagg tggacctgta cctgctgatg gactgcagcg gcagcatccg gcggcacaac    240
```

```
tgggtcaacc atgccgtgcc tctggccatg aagctgatcc agcagctgaa cctgaacgac    300
aacgccatcc acctgtacgc cagcgtgttc agcaacaacg ccagagagat catcagactg    360
cacagcgacg ccagcaagaa caaagagaag gccctgatca tcatcaagag cctgctgagc    420
accaacctgc cctacggcaa gaccaacctg accgacgctc tgctgcaagt gcggaagcac    480
ctgaatgacc ggatcaacag agagaacgcc aatcagctgg tcgtgatcct gaccgatggc    540
atccccgaca gcatccagga cagcctgaaa gagagccgga agctgagcga ccggggcgtg    600
aagatcgccg tgtttggcat cggccagggc atcaacgtgg ccttcaaccg gtttctcgtg    660
ggctgccacc ctagcgacgg caagtgcaat ctgtacgccg acagcgcctg ggagaacgtg    720
aagaatgtga tcggcccttt catgaaggcc gtgtgcgtgg aagtggaaaa gaccgccagc    780
tgcggcgtgt gggatgagtg gtccccttgc agcgtgacct gcggcaaggg caccagaagc    840
cggaagagag agatcctgca cgagggctgc accagcgagc tgcaggaaca gtgcgaagag    900
gaacggtgcc tgcccaagag ggaacccctg gatgtgcccg acgagcccga ggacgatcag    960
cctagaccca gaggcgacaa cttcgccgtg aaaagcccca cgagaacat catcgacaac   1020
aaccccagg aacccagccc caaccccgaa gagggaaagg gcgagaaccc caacggcttc   1080
gatctggacg agaaccctga gaacccccc aaccctccca tccccctaa cccccaaat   1140
ccaccaaatc ctcccaaccc tgacatcccc gagcaggaac ctaacatccc tgaggacagc   1200
gagaaagagg tgcccagcga cgtgcccaag aaccccgagg atgaccggga agagaacttc   1260
gacatcccca gaagccagaa gaacaagcac gacaaccaga acaacctgcc taacgacaag   1320
tccgaccggt acatccccta cagccccctg agccccaagg tgctggacaa cgagagaaag   1380
cagagcgacc cccagagcca ggacaacaac ggcaacagac acgtgccaaa cagcgaggac   1440
agagagacac ggccccacgg ccggaacaac gagaatcgga gctacaaccg gaagcacaac   1500
aacacccca gcaccctga gcgggaagaa cacgagaagc ccgataacaa caagaagaag   1560
gccggcagcg acaacaagta caagattgcc ggcggaatcg ctggcggcct ggcactgctg   1620
gcttgtgccg gactggccta caagttcgtg gtgcctggcg ccgctacacc ttatgccggc   1680
gaacctgccc ccttcgacga cactgggc gaggaagata aggacctgga cgagcctgag   1740
cagttccggc tgcccgaaga gaacgagtgg aac                                1773
```

<210> SEQ ID NO 68
<211> LENGTH: 147
<212> TYPE: PRT
<213> ORGANISM: Artificial sequence
<220> FEATURE:
<223> OTHER INFORMATION: Pvivax EXP1

<400> SEQUENCE: 68

```
Lys Leu Leu Ala Ala Val Phe Leu Leu Phe Cys Ala Ile Leu Cys Asn
1               5                   10                  15

His Ala Leu Gly Asp Asn Val Asn Gly Leu Gly Ala Gly Asn Pro Lys
            20                  25                  30

Lys Lys Ser Pro Lys Ser Lys Ser Pro Glu Pro Leu Ile Asp Val His
        35                  40                  45

Glu Leu Ile Ser Glu Ile Val Arg Lys Glu Glu Leu Val Asn Met
    50                  55                  60

Thr Lys Lys Lys Ser Asn Tyr Lys Leu Ala Thr Thr Val Leu Ala Ser
65                  70                  75                  80

Ala Leu Gly Val Val Ser Ala Val Leu Leu Gly Gly Ala Gly Leu Val
```

```
                  85                  90                  95

Phe Tyr Asn Ala Gly Asn Gly Arg His Pro Phe Ser Leu Gly Gly Gly
            100                 105                 110

Lys Gly Gly Asp Ala Ala Pro Thr Glu Pro Thr Pro Ala Pro Thr Ala
            115                 120                 125

Pro Ser Ala Thr Gly Leu Asn Asp Asp Gly Ser Ser Gly Thr Glu
            130                 135                 140

Ser Thr Ser
145

<210> SEQ ID NO 69
<211> LENGTH: 441
<212> TYPE: DNA
<213> ORGANISM: Artificial sequence
<220> FEATURE:
<223> OTHER INFORMATION: Pvivax EXP1

<400> SEQUENCE: 69
aagctgctgg ccgccgtgtt cctgctgttt tgcgcaatcc tgtgcaacca cgcactgggc        60
gacaacgtga atggcctggg agcaggcaat cccaagaaga gagccccaa gagcaagtcc       120 cccgagcctc tgatcgatgt gcacgagctg atctccgaga tcgtgcggaa ggaggaggag       180
ctggtgaaca tgaccaagaa gaagagcaat tacaagctgg ccaccacagt gctggccagc       240
gccctgggcg tggtgtccgc cgtgctgctg ggcggcgccg cctggtgtt ctataacgcc        300 ggcaatggcc gccacccctt tagcctgggc ggcggcaagg gcggcgacgc agcacctacc       360
gagccaacac ccgcccctac cgcaccatcc gccacaggcc tgaacgacga tggcagctcc       420
tctggcaccg agtctacaag c                                                 441

<210> SEQ ID NO 70
<211> LENGTH: 173
<212> TYPE: PRT
<213> ORGANISM: Artificial sequence
<220> FEATURE:
<223> OTHER INFORMATION: Pvivax EXP2

<400> SEQUENCE: 70

Ser Ala Glu Glu Tyr Ser Trp Asp Ser Tyr Leu Asn Asp Arg Leu
1               5                  10                  15

Leu Ala Thr Asn Gln Val Ser Ala Ala Gly Leu Ala Ser Glu Glu Asp
            20                  25                  30

Gly Val Val Tyr Ala Cys Val Ala Gln Ala Asp Glu Asn Asp Ala Glu
            35                  40                  45

Phe Asp Lys Trp Thr Leu Phe Tyr Lys Glu Tyr Glu Ile Glu Val
    50                  55                  60

Glu Asp Glu Asn Gly Asn Lys Ser Gln Lys Thr Ile Asn Glu Gly Gln
65                  70                  75                  80

Thr Leu Leu Thr Val Phe Lys Glu Gly Tyr Ala Pro Asp Gly Val Trp
                85                  90                  95

Leu Gly Gly Thr Lys Tyr Gln Phe Ile Asn Ile Glu Arg Asp Leu Glu
            100                 105                 110

Phe Glu Gly Tyr Thr Phe Asp Val Ala Thr Cys Ala Lys Leu Lys Gly
            115                 120                 125

Gly Leu His Leu Ile Lys Val Pro Gly Gly Asn Ile Leu Val Val Leu
            130                 135                 140

Tyr Asp Glu Glu Lys Glu His Asp Arg Gly Asn Ser Lys Ile Ala Ala
145                 150                 155                 160
```

```
Leu Thr Phe Ser Lys Glu Leu Ala Glu Ser Gly Gly Gln
            165                 170
```

<210> SEQ ID NO 71
<211> LENGTH: 519
<212> TYPE: DNA
<213> ORGANISM: Artificial sequence
<220> FEATURE:
<223> OTHER INFORMATION: Pvivax EXP2

<400> SEQUENCE: 71

```
tctgccgagg aggagtactc ctgggactct tatctgaacg ataggctgct ggccaccaat    60
caggtgtctg ccgcaggcct ggcaagcgag gaggacggag tggtgtacgc atgcgtggca   120
caggccgacg agaatgatgc cgagttcgat aagtggaccc tgttttacaa ggaggactat   180
gagatcgagg tggaggatga aacggcaat aagtcccaga agacaatcaa cgagggccag   240
accctgctga cagtgttcaa ggagggctac gcaccagatg gcgtgtggct gggcggcacc   300
aagtatcagt ttatcaatat cgagagggac ctggagttcg agggctacac ctttgatgtg   360
gccacatgtg ccaagctgaa gggcggcctg cacctgatca aggtgcctgg cggcaacatc   420
ctggtggtgc tgtatgacga ggagaaggag cacgatagag caattccaa gatcgccgcc    480
ctgacatttt ccaaggagct ggccgagtct ggcggccag                          519
```

<210> SEQ ID NO 72
<211> LENGTH: 132
<212> TYPE: PRT
<213> ORGANISM: Artificial sequence
<220> FEATURE:
<223> OTHER INFORMATION: Pcynomolgi EXP1

<400> SEQUENCE: 72

```
Lys Leu Leu Thr Ala Val Phe Leu Leu Phe Cys Ala Ile Leu Cys Asp
1               5                   10                  15
Pro Ala Leu Gly Asp Asn Val Asn Gly Leu Gly Pro Pro Ser Lys
            20                  25                  30
Lys Lys Thr Pro Lys Ser Lys Ser Pro Glu Pro Leu Ile Asp Val His
        35                  40                  45
Glu Leu Ile Gly Glu Met Val Arg Lys Glu Glu Leu Ile Asn Ala
    50                  55                  60
Asn Lys Lys Lys Ser Lys Tyr Lys Leu Ala Thr Thr Ile Leu Ala Ser
65                  70                  75                  80
Ala Leu Gly Val Val Ser Ala Val Leu Leu Gly Ala Gly Leu Val
                85                  90                  95
Phe Tyr Asn Ala Gly Asn Gly Arg His Pro Phe Ser Leu Gly Gly Gly
            100                 105                 110
Lys Gly Gly Asp Ala Thr Pro Ser Glu Pro Ala Pro Ala Ala Gly Glu
        115                 120                 125
Pro Val Gly Lys
    130
```

<210> SEQ ID NO 73
<211> LENGTH: 396
<212> TYPE: DNA
<213> ORGANISM: Artificial sequence
<220> FEATURE:
<223> OTHER INFORMATION: Pcynomolgi EXP1

<400> SEQUENCE: 73

```
aagctgctga cagccgtgtt cctgctgttt tgcgcaatcc tgtgcgaccc tgccctgggc    60
gataacgtga atggcctggg cggccctccc agcaagaaga agaccccaaa gagcaagtcc   120
ccagagcccc tgatcgatgt gcacgagctg atcggcgaga tggtgcggaa ggaggaggag   180
ctgatcaacg ccaacaagaa gaagagcaag tacaagctgg caaccacaat cctggcatcc   240
gccctgggag tggtgtctgc cgtgctgctg ggcggcgccg gcctggtgtt ctataacgcc   300
ggcaatggcc gccacccatt ttccctgggc ggcggcaagg gcggcgacgc aaccccatct   360
gagcctgcac cagcagcagg agagccagtg ggcaag                             396
```

<210> SEQ ID NO 74
<211> LENGTH: 173
<212> TYPE: PRT
<213> ORGANISM: Artificial sequence
<220> FEATURE:
<223> OTHER INFORMATION: Pcynomolgi EXP2

<400> SEQUENCE: 74

```
Ser Ala Glu Glu Glu Tyr Ser Trp Asp Ser Tyr Leu Asn Asp Arg Leu
1               5                   10                  15

Leu Ala Thr Asn Gln Val Ser Ala Ala Gly Leu Ala Ser Glu Glu Asp
            20                  25                  30

Gly Val Val Tyr Ala Cys Val Ala Gln Ala Asp Glu Asn Asn Pro Glu
        35                  40                  45

Phe Asp Lys Trp Ser Leu Phe Tyr Lys Glu Asp Phe Glu Ile Glu Val
    50                  55                  60

Glu Asp Glu Asn Gly Asn Lys Ser Lys Lys Thr Ile Asn Glu Gly Gln
65                  70                  75                  80

Thr Leu Leu Thr Val Phe Lys Glu Gly Tyr Ala Pro Asp Gly Val Trp
                85                  90                  95

Leu Gly Gly Thr Lys Tyr Gln Phe Ile Asn Ile Glu Arg Asp Leu Glu
            100                 105                 110

Phe Glu Gly Tyr Thr Phe Asp Val Ala Thr Cys Ala Lys Leu Lys Gly
        115                 120                 125

Gly Leu His Leu Ile Lys Val Pro Gly Gly Asn Ile Leu Val Val Leu
    130                 135                 140

Tyr Asp Glu Glu Lys Glu His Asp Arg Gly Asn Ser Lys Val Ala Ala
145                 150                 155                 160

Leu Thr Phe Ser Lys Glu Leu Ala Glu Ser Gly Gly Gln
                165                 170
```

<210> SEQ ID NO 75
<211> LENGTH: 519
<212> TYPE: DNA
<213> ORGANISM: Artificial sequence
<220> FEATURE:
<223> OTHER INFORMATION: Pcynomolgi EXP2

<400> SEQUENCE: 75

```
tctgccgagg aggagtactc ttgggacagc tatctgaacg ataggctgct ggccacaaat    60
caggtgagcg ccgcaggcct ggcatccgag gaggatggag tggtgtacgc atgcgtggca   120
caggcagacg agaacaatcc cgagttcgat aagtggagcc tgttctataa ggaggacttt   180
gagatcgagg tggaggatga gaacggcaat aagtccaaga agaccatcaa cgaggccag    240 accctgctga cagtgttcaa ggagggctac gcaccagacg gcgtgtggct gggcggcaca   300
aagtatcagt ttatcaatat cgagagggac ctggagttcg agggctacac ctttgatgtg   360
```

```
gccacatgtg ccaagctgaa gggcggcctg cacctgatca aggtgcctgg cggcaacatc      420
ctggtggtgc tgtatgacga ggagaaggag cacgatagag gcaatagcaa ggtggccgcc      480 ctgaccttt ctaaggagct ggcagagagc ggcggccag                              519

<210> SEQ ID NO 76
<211> LENGTH: 168
<212> TYPE: PRT
<213> ORGANISM: Artificial sequence
<220> FEATURE:
<223> OTHER INFORMATION: Py EXP1

<400> SEQUENCE: 76

Lys Ile Asn Ile Ala Ser Ile Ile Phe Ile Ile Phe Ser Leu Cys Leu
1               5                   10                  15

Val Asn Asp Ala Tyr Gly Lys Asn Lys Tyr Gly Lys Asn Gly Lys Tyr
            20                  25                  30

Gly Ser Gln Asn Val Ile Lys Lys His Gly Glu Pro Val Ile Asn Val
        35                  40                  45

Gln Asp Leu Ile Ser Asp Met Val Arg Lys Glu Glu Ile Val Lys
    50                  55                  60

Leu Thr Lys Asn Lys Lys Ser Leu Arg Lys Ile Asn Val Ala Leu Ala
65                  70                  75                  80

Thr Ala Leu Ser Val Val Ser Ala Ile Leu Leu Gly Gly Ala Gly Leu
                85                  90                  95

Val Met Tyr Asn Thr Glu Lys Gly Arg Arg Pro Phe Gln Ile Gly Lys
            100                 105                 110

Ser Lys Lys Gly Gly Ser Ala Met Ala Arg Asp Ser Ser Phe Pro Met
        115                 120                 125

Asn Glu Glu Ser Pro Leu Gly Phe Ser Pro Glu Glu Met Glu Ala Val
    130                 135                 140

Ala Ser Lys Phe Arg Glu Ser Met Leu Lys Asp Gly Val Pro Ala Pro
145                 150                 155                 160

Ser Asn Thr Pro Asn Val Gln Asn
                165

<210> SEQ ID NO 77
<211> LENGTH: 504
<212> TYPE: DNA
<213> ORGANISM: Artificial sequence
<220> FEATURE:
<223> OTHER INFORMATION: Py EXP1

<400> SEQUENCE: 77
aagatcaata tcgcctcaat cattttatc atcttcagtc tgtgcctcgt gaacgacgcc      60
tacggcaaga caagtatgg caagaacggc aaatacggaa gccagaatgt gatcaagaaa      120
cacggagagc ccgtgatcaa cgtccaggac ctgatttcag atatggtgag aaaggaggaa      180
gagatcgtca agctgaccaa aaataagaaa agcctccgga agattaacgt ggccctggct      240
acagcactct ctgtggtcag tgcaatcctg ctcggaggag caggactggt catgtataat      300
accgagaaag ggaggagacc ctttcagatc ggcaagtcaa agaaaggggg tagcgccatg      360
gctcgcgata gctccttccc tatgaacgaa gagtccccac tgggattttc tcccgaagag      420
atggaggcag tggccagtaa gttccgagaa tcaatgctga agacggcgt ccccgctcct      480 tccaacacac caaatgtgca gaac                                             504

<210> SEQ ID NO 78
```

<211> LENGTH: 173
<212> TYPE: PRT
<213> ORGANISM: Artificial sequence
<220> FEATURE:
<223> OTHER INFORMATION: Py EXP2

<400> SEQUENCE: 78

```
Glu Glu Tyr Ser Trp Glu Asn Phe Leu Asn Asp Lys Leu Leu Ala Thr
1               5                   10                  15
Asn Gln Val Ser Ala Ala Gly Leu Ala Ser Glu Glu Asp Gly Val Val
            20                  25                  30
Tyr Glu Cys Val Ala Thr Pro Asp Glu Asn Asn Pro Asp Phe Asp Lys
        35                  40                  45
Trp Ser Leu Phe Tyr Lys Glu Asp Tyr Asp Ile Glu Ile Glu Asp Glu
    50                  55                  60
Asn Gly Asn Lys Thr Thr Lys Thr Ile Thr Glu Gly Gln Thr Ile Leu
65                  70                  75                  80
Thr Met Phe Asn Glu Gly Tyr Ala Pro Asp Gly Ile Trp Leu Gly Gly
                85                  90                  95
Thr Lys Tyr Gln Phe Ile Asn Met Glu Lys Gly Leu Glu Tyr Glu Gly
            100                 105                 110
Tyr Ser Phe Asp Val Ala Thr Cys Ala Lys Leu Lys Gly Gly Met His
        115                 120                 125
Ile Ile Lys Val Gly Gly Gly His Ile Leu Ile Val Leu Tyr Asp Glu
    130                 135                 140
Glu Lys Glu Gln Asp Arg Gly Asn Ser Lys Asn Ala Ala Leu Ala Phe
145                 150                 155                 160
Ser Lys Glu Leu Ala Glu Ser Thr Asp Ala Gly Ala Ala
                165                 170
```

<210> SEQ ID NO 79
<211> LENGTH: 519
<212> TYPE: DNA
<213> ORGANISM: Artificial sequence
<220> FEATURE:
<223> OTHER INFORMATION: Py EXP2

<400> SEQUENCE: 79

```
gaagagtact cttgggagaa ttttctcaac gataagctgc tcgctactaa ccaggtgagc    60
gcagctggac tggcatccga agaggacgga gtggtctatg agtgcgtcgc tacccctgat   120
gaaaacaatc cagacttcga taagtggtct ctgttttaca aggaggacta cgatatcgaa   180
atcgaggacg aaaacgggaa taagaccaca aaaactatca ccgagggtca gacaattctg   240
actatgttca atgaaggata cgcaccagac ggtatctggc tcggaggaac aaagtatcag   300
ttcattaaca tggagaaagg cctggagtac gaaggatata gctttgatgt ggctacttgt   360
gcaaagctga aggggggtat gcacatcatt aaggtcggcg agggcatat cctgattgtc    420
ctctacgacg aagagaagga gcaggatcgg gggaattcca aaaacgcagc cctggccttt   480
tctaaggagc tcgccgaaag taccgacgct ggcgctgca                          519
```

<210> SEQ ID NO 80
<211> LENGTH: 240
<212> TYPE: PRT
<213> ORGANISM: Artificial sequence
<220> FEATURE:
<223> OTHER INFORMATION: Py SPECT1

<400> SEQUENCE: 80

Lys Ile Ser Ile Thr Ile Leu Val Leu Phe Ile Ile Leu Lys Cys Val
1               5                   10                  15

Leu Ser Phe Asn Leu Ser Ile Glu Pro Lys Gly Asn Asn Ile Thr Leu
            20                  25                  30

Asp Lys His Ile Lys Lys Glu Ser Asn Ile Asp His Ser Lys Asn Gln
        35                  40                  45

Ile Ile Glu Glu Phe Asp Lys Ile Ser Asp Asp Phe Ser Asp Asp Ile
    50                  55                  60

Asn Thr Thr Lys Gln Thr Ile Lys Asp Leu Phe Leu Asp Ile Glu Gly
65                  70                  75                  80

Ser Phe Glu Asp Thr Ser Asp Asp Val Val Lys Leu Leu Ser Lys Tyr
                85                  90                  95

Ser Phe Val Pro Glu Glu Lys Leu Asn Ile Ile Asp Gly Ile Leu Arg
            100                 105                 110

Ser Phe Ile Glu Asn Asn Lys Thr His Val Ile Asn Ser Ser Asn Ala
        115                 120                 125

Tyr Met Tyr Met Gln Lys Glu Lys Ile Lys Asn Val Cys Asp Phe Ile
    130                 135                 140

Leu Lys Lys Leu Asn Ser Leu Ile Gln Ile Asn Glu Leu Asn Lys Asn
145                 150                 155                 160

His Ile Ile Leu Lys Tyr Gly Lys Gly Glu Ala Lys Lys Gly Val Leu
                165                 170                 175

Glu Ser Ile Lys Asn Asn Asp Asn Ile Ser Lys Asn Leu Lys Ser Glu
            180                 185                 190

Leu Leu Lys Tyr Glu Asn Val Ser Asn Gln Asn Ile Arg Val Ser Glu
        195                 200                 205

Leu Ile Asn Phe Ile Thr Pro Ile Tyr Asp Asp Phe Ile Lys Lys Leu
    210                 215                 220

Ser Asp Leu Ile Asn Asp Leu Gln Ile Lys Leu Asn Asn Ile Ser Lys
225                 230                 235                 240

<210> SEQ ID NO 81
<211> LENGTH: 720
<212> TYPE: DNA
<213> ORGANISM: Artificial sequence
<220> FEATURE:
<223> OTHER INFORMATION: Py SPECT1

<400> SEQUENCE: 81
aaaatctcaa tcacaattct ggtgctgttc attatcctca agtgcgtgct gagtttcaac     60
ctctcaattg aacctaaagg aaacaatatc accctggaca agcacattaa gaaagagtca    120
aacatcgatc atagcaaaaa tcagatcatt gaggaatttg acaagatcag cgacgatttc    180
tccgacgata ttaacaccac aaaacagact atcaaggacc tgtttctcga tattgaaggg    240
tccttcgagg acacctctga cgatgtggtc aaactgctct ccaagtactc ttttgtgcca    300
gaggaaaagc tgaacatcat tgatggcatt ctccggagct tcatcgaaaa caataagaca    360
cacgtgatca atagctccaa cgcctacatg tatatgcaga agagaagat caaaaacgtg    420 tgcgatttca ttctgaagaa actcaactcc ctgatccaga ttaatgagct gaacaagaac    480
catatcattc tcaagtatgg caaggagaa gctaagaaag gcgtgctgga gtctattaag    540
aacaacgaca acatcagtaa gaacctgaaa tcagaactgc tcaagtacga gaacgtctct    600
aaccagaata tcagggtgag tgagctgatc aattttatta ccccaatcta tgacgatttc    660
attaagaaac tctccgacct gattaacgat ctgcagatca aactcaacaa tatttctaag    720

<210> SEQ ID NO 82
<211> LENGTH: 814
<212> TYPE: PRT
<213> ORGANISM: Artificial sequence
<220> FEATURE:
<223> OTHER INFORMATION: Py SPECT2

<400> SEQUENCE: 82

```
Lys Met Arg Asn Ile Lys Lys Ser Leu Pro Val Leu Phe Ile Leu Leu
1               5                   10                  15

Cys Ile Tyr Gln Gln Ser Phe Ile Asn Ser Leu Arg Ile Ser Val Arg
            20                  25                  30

Asn Asn Lys Asn His Arg Asp Gly Asn Glu Asn Lys Phe Asn Lys
        35                  40                  45

Asn Val Glu Leu Gly Thr Met Glu Lys Pro Ile Asn Ile Leu Cys Asn
    50                  55                  60

Asp Ile Ser Cys Asn Pro Gly Asn Asn Ile Ser Phe Val Asn Gln Lys
65                  70                  75                  80

Lys Lys Glu Ile Asp Ser Asp Asp Leu Tyr Asp Met Leu Asp Asp
            85                  90                  95

Asp Ala Ser Thr Ser Ala Gly Asp Glu Asp Glu Asp Tyr Asp
            100                 105                 110

Asp Tyr Thr Asp Asp Lys Asn Thr Glu Ile Lys Asp Glu Gln Asn
        115                 120                 125

Glu His Ile Asp Lys Thr Asp Gln Lys Lys Asp Lys Lys Gly Thr Phe
130                 135                 140

Ser Ile Lys Lys Gln Glu Glu Ile Asn Glu Asn Lys Asn Arg Thr
145                 150                 155                 160

Glu Lys Phe Phe Lys Lys Tyr Lys Phe Asn Asp Ala Asp Asn Glu Gly
            165                 170                 175

Gly Asp Asp Glu Ser Glu Thr Asp Asp Glu Asn Leu Asp Asn Ser Thr
        180                 185                 190

Gln Asn Ser His Ala Glu Asn Lys Asn Pro Glu Ser Val Ile Asp Lys
    195                 200                 205

His Met Ser Val Phe Pro Gly Leu Tyr Phe Val Gly Ile Gly Tyr Asp
    210                 215                 220

Ile Leu Phe Gly Asn Pro Leu Gly Glu Thr Asp Ser Leu Ser Asp Pro
225                 230                 235                 240

Gly Tyr Arg Ala Gln Ile Tyr Leu Leu Asn Trp Glu Phe Ser Asn His
            245                 250                 255

Gly Ile Ala Asn Asp Leu His Thr Leu Gln Pro Ile Asn Ala Trp Ile
        260                 265                 270

Arg Lys Glu Asn Ala Cys Ser Arg Val Glu Ser Ile Asn Glu Cys Ser
    275                 280                 285

Ser Val Ser Glu Tyr Thr Lys Asn Leu Ser Val Asp Val Ser Val Ser
    290                 295                 300

Gly Ser Tyr Met Gly Phe Gly Ser Phe Ser Ala Ser Thr Gly Tyr Lys
305                 310                 315                 320

Lys Phe Ile Asn Glu Ile Ser Lys Arg Thr Ser Lys Thr Tyr Phe Ile
            325                 330                 335

Lys Ser Asn Cys Ile Lys Tyr Thr Ile Gly Leu Pro Pro Tyr Val Pro
        340                 345                 350

Trp Glu Gln Thr Thr Ala Tyr Met Asn Ala Val Asp Ile Leu Pro Arg
    355                 360                 365
```

```
Glu Phe Thr Gly Leu Asp Glu Asp Ser Glu Cys Thr Pro Asp Val Tyr
370                 375                 380

Glu Gln Lys Lys Met Thr Lys Glu Cys Arg Asn Val Gln Leu Trp Ile
385                 390                 395                 400

Gln Phe Phe Lys Thr Tyr Gly Thr His Ile Ile Val Glu Ala Gln Leu
            405                 410                 415

Gly Gly Lys Ile Thr Lys Ile Ile Asn Val Ser Asn Thr Ser Val Asn
            420                 425                 430

Gln Met Lys Lys Asp Gly Val Ser Val Lys Ala Gln Ile Gln Ala Gln
            435                 440                 445

Phe Gly Phe Ala Ser Val Gly Ser Thr Ser Val Ser Ser Asp Asn
450                 455                 460

Ser Ser Lys Asn Asp Asn Ser Ser Tyr Asp Met Ser Glu Lys Leu Val
465             470                 475                 480

Val Ile Gly Gly Asn Pro Ile Lys Asp Val Thr Lys Glu Glu Asn Leu
                485                 490                 495

Tyr Glu Trp Ser Lys Thr Val Ser Asn Pro Met Pro Ile His Ile
            500                 505                 510

Lys Leu Leu Pro Ile Tyr Lys Ser Phe Asp Ser Glu Glu Leu Lys Glu
            515                 520                 525

Ser Tyr Glu Lys Ala Leu Leu Tyr Tyr Thr Arg Leu Tyr Gly Ser Ser
530                 535                 540

Pro His Gly Thr Ile Gln Lys Asp Glu Asn Asp Ile Ile Lys Ile Leu
545                 550                 555                 560

Thr Ala Ser Thr Thr Ile Thr Lys Ile Gly Ala Pro Pro Ile Thr Ala
                565                 570                 575

Glu Cys Pro His Asn Gln Val Val Leu Phe Gly Tyr Val Leu Lys Gln
            580                 585                 590

Asn Phe Trp Asp Asn Thr Ser Arg Leu Lys Gly Tyr Asp Ile Glu Ile
            595                 600                 605

Cys Glu Ser Gly Leu Asn Ser Cys Thr Ser Lys Gln Gly Ser Thr Asn
610                 615                 620

Lys Tyr Asp Val Ser Tyr Leu Tyr Ile Glu Cys Gly Thr Gln Ala Met
625                 630                 635                 640

Pro Phe Ser Asp Gln Val Ile Thr Ser Thr Asn Ala Thr Tyr Asn Thr
            645                 650                 655

Ile Lys Cys Pro Asn Asp Tyr Thr Ile Ile Phe Gly Phe Gly Phe Ser
            660                 665                 670

Ser Ser Ser Gly Lys Gly Val Ser Ala Met His Ser His Ile Thr Ser
            675                 680                 685

Cys Arg Pro Gly Met Lys Ser Cys Ser Leu Asn Met Gly Asn Ser Asn
690                 695                 700

Asp Lys Asn Tyr Met Tyr Leu Val Cys Val Asp Ala Thr Ile Trp Ser
705                 710                 715                 720

Gly Ile Asn Glu Leu Thr Thr Val Ala Lys Asp Phe His Gly Ala
            725                 730                 735

Val Asn Arg Ser Lys Gln Phe Asn Asp Gly Gln Leu Val Leu Asn Cys
            740                 745                 750

Gln Glu Asn Gly Thr Ile Leu Thr Gly Phe Ala Gly Thr His Thr
            755                 760                 765

Ser Ser Pro Tyr Val Lys Ser Pro Phe Ser Lys Cys Leu Lys Asn Leu
770                 775                 780

Lys Ser Cys Ser Val His Gly Ser Gly Gln Ser Ile Gly Tyr Thr Asn
```

Tyr Lys Ser Leu Phe Ala Ile Ile Leu Cys Lys Asn Ser Glu
            805                 810

<210> SEQ ID NO 83
<211> LENGTH: 2442
<212> TYPE: DNA
<213> ORGANISM: Artificial sequence
<220> FEATURE:
<223> OTHER INFORMATION: Py SPECT2

<400> SEQUENCE: 83

| | | | | |
|---|---|---|---|---|
| aaaatgcgca | acatcaagaa | aagcctcccc | gtcctgttta | ttctgctctg | tatctaccag | 60 |
| cagtctttca | tcaatagtct | gcgaatttca | gtgaggaaca | taagaaccca | ccgcgacggt | 120 |
| aacaacgaga | ataagtttaa | caaaaacgtg | gaactgggca | ccatggagaa | gcctatcaat | 180 |
| attctctgca | acgatatcag | ctgtaaccca | ggaaacaata | tttccttcgt | gaatcagaag | 240 |
| aaaaaggaga | tcgactccga | cgatgacctg | tatgatatgc | tcgatgacga | tgccagcaca | 300 |
| tccgctgggg | acgatgaaga | cgaggacgat | tacgacgatt | atactgacga | taaaaacacc | 360 |
| gaaatcaagg | acgaggaaca | gaatgagcat | attgacaaga | cagatcagaa | aaaggataag | 420 |
| aagggaactt | tttctatcaa | aaagcaggag | gaagagatta | cgaaaacaa | gaacaggacc | 480 |
| gagaagttct | ttaagaagta | caagttcaat | gacgctgata | cgaaggcgg | agacgatgaa | 540 |
| tccgagaccg | acgatgagaa | tctggacaac | agcacacaga | actcccacgc | agaaaacaag | 600 |
| aaccccgagt | cagtcatcga | caagcatatg | agcgtgtttc | ctggcctgta | cttcgtcggg | 660 |
| attggttatg | atatcctgtt | tgggaaccca | ctcggtgaaa | cagactctct | gagtgatccc | 720 |
| ggatacagag | cacagatcta | tctgctcaat | tgggagttct | ccaaccacgg | gattgccaat | 780 |
| gatctccata | ctctgcagcc | cattaacgca | tggatcagaa | aggaaaatgc | ctgctctcgg | 840 |
| gtggaaagta | tcaacgagtg | ttctagtgtc | tccgagtaca | caagaatct | gtctgtggac | 900 |
| gtctcagtga | gcggcagcta | catgggcttt | ggatctttca | gtgcctcaac | tgggtacaag | 960 |
| aagtttatta | cgagatctc | aaagcggacc | agcaagacat | acttcatcaa | aagcaactgt | 1020 |
| attaagtaca | ctatcggcct | gccccttat | gtgccttggg | aacagactac | cgcatatatg | 1080 |
| aacgccgtcg | acatcctgcc | acgcgagttc | actggactcg | acgaagattc | cgagtgcacc | 1140 |
| cccgatgtgt | acgaacagaa | aaagatgaca | aaggagtgtc | gaaacgtcca | gctgtggatt | 1200 |
| cagttctttta | agacttatgg | cacccacatc | attgtggagg | ctcagctggg | gggcaagatc | 1260 |
| actaagatca | ttaatgtcag | taacacctca | gtgaaccaga | tgaaaaagga | cggagtctct | 1320 |
| gtgaaggctc | agatccaggc | acagttcggg | tttgcaagtg | tcggcggaag | cacctccgtg | 1380 |
| tcaagcgata | ttcctctaa | gaacgacaac | agttcatacg | atatgtctga | aaagctggtg | 1440 |
| gtcatcgggg | gtaaccccat | caaggacgtg | accaaggaag | agaatctgta | cgagtggagc | 1500 |
| aagacagtca | gctccaaccc | tatgccaatc | cacatcaagc | tgctccccat | ctataagagc | 1560 |
| tttgactccg | aagagctgaa | agaaagctac | gagaaggccc | tgctctacta | tacacgactg | 1620 |
| tatggctcta | gtcctcacgg | aactatccag | aaagacgaga | cgatatcat | taagattctg | 1680 |
| acagcttcca | caactattac | taagatcggt | gcaccaccaa | tcaccgctga | gtgcccccat | 1740 |
| aatcaggtgg | tcctgtttgg | ctacgtgctc | aaacagaatt | tctgggacaa | cacatcacgc | 1800 |
| ctgaaggggt | atgatatcga | aatttgcgag | tccggtctca | actcttgtac | cagtaaacag | 1860 |
| ggcagtacaa | ataagtacga | cgtgtcatac | ctgtatatcg | agtgcggcac | ccaggccatg | 1920 |

```
cctttcagcg atcaggtcat cacttccacc aatgctacat acaacactat taagtgtcca    1980
aacgactata ctatcatttt cgggtttggt ttctcaagct cctctggcaa gggagtgtcc    2040
gcaatgcact ctcatatcac cagttgccgg cccggaatga agtcttgtag tctgaacatg    2100
gggaatagca acgacaagaa ttacatgtat ctggtctgcg tggatgccac aatttggtcc    2160
ggtatcaacg agctgaccac agtggctaaa gacgattttc acggcgcagt caaccgcagc    2220
aagcagttca atgacggtca gctggtgctc aattgtcagg aaaacggcac catcctgaca    2280
ggctttgccg gagagacaca cactagttca ccctacgtga agtcaccttt cagcaagtgc    2340
ctcaaaaacc tgaagtcatg tagcgtccat gggtccggcc agtctatcgg ctacaccaac    2400
tataaatctc tgttcgctat cattctctgt aagaatagtg ag                       2442
```